US010927070B2

(12) United States Patent
Freeman et al.

(10) Patent No.: US 10,927,070 B2
(45) Date of Patent: Feb. 23, 2021

(54) COMPOSITIONS AND METHODS FOR TREATING CANCER

(71) Applicant: Cedars-Sinai Medical Center, Los Angeles, CA (US)

(72) Inventors: Michael Freeman, West Hollywood, CA (US); Mirja Rotinen, Beverly Hills, CA (US); Ramachandran Murali, Beverly Hills, CA (US); Sungyong You, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 64 days.

(21) Appl. No.: 16/307,702

(22) PCT Filed: May 26, 2017

(86) PCT No.: PCT/US2017/034768
§ 371 (c)(1),
(2) Date: Dec. 6, 2018

(87) PCT Pub. No.: WO2017/213897
PCT Pub. Date: Dec. 14, 2017

(65) Prior Publication Data
US 2019/0194124 A1 Jun. 27, 2019

Related U.S. Application Data

(60) Provisional application No. 62/348,013, filed on Jun. 9, 2016, provisional application No. 62/421,733, filed on Nov. 14, 2016.

(51) Int. Cl.
| | |
|---|---|
| C07C 237/08 | (2006.01) |
| A61K 45/06 | (2006.01) |
| A61K 31/165 | (2006.01) |
| A61K 31/416 | (2006.01) |
| C07D 231/56 | (2006.01) |
| C07D 205/04 | (2006.01) |
| A61K 31/397 | (2006.01) |
| A61K 31/40 | (2006.01) |
| C07D 207/09 | (2006.01) |
| A61P 35/00 | (2006.01) |
| A61K 31/445 | (2006.01) |
| C07D 211/60 | (2006.01) |
| C07D 211/76 | (2006.01) |
| A61K 31/45 | (2006.01) |
| C07C 233/31 | (2006.01) |
| C07D 233/64 | (2006.01) |
| A61K 31/417 | (2006.01) |
| C12Q 1/68 | (2018.01) |
| C07C 237/22 | (2006.01) |
| A61K 31/4164 | (2006.01) |
| C07C 259/06 | (2006.01) |
| C12Q 1/6886 | (2018.01) |
| C07D 207/16 | (2006.01) |
| C07D 211/78 | (2006.01) |

(52) U.S. Cl.
CPC .......... *C07C 237/08* (2013.01); *A61K 31/165* (2013.01); *A61K 31/397* (2013.01); *A61K 31/40* (2013.01); *A61K 31/416* (2013.01); *A61K 31/417* (2013.01); *A61K 31/4164* (2013.01); *A61K 31/445* (2013.01); *A61K 31/45* (2013.01); *A61K 45/06* (2013.01); *A61P 35/00* (2018.01); *C07C 233/31* (2013.01); *C07C 237/22* (2013.01); *C07C 259/06* (2013.01); *C07D 205/04* (2013.01); *C07D 207/09* (2013.01); *C07D 207/16* (2013.01); *C07D 211/60* (2013.01); *C07D 211/76* (2013.01); *C07D 211/78* (2013.01); *C07D 231/56* (2013.01); *C07D 233/64* (2013.01); *C12Q 1/68* (2013.01); *C12Q 1/6886* (2013.01); *C07B 2200/07* (2013.01); *C12Q 2600/106* (2013.01); *C12Q 2600/158* (2013.01)

(58) Field of Classification Search
CPC ....... A61K 45/06; A61K 31/45; C07D 233/64
See application file for complete search history.

(56) References Cited

U.S. PATENT DOCUMENTS

| | | | |
|---|---|---|---|
| 4,394,389 A | | 7/1983 | Bartholomeus et al. |
| 8,367,677 B2 * | | 2/2013 | Kranich ................ C07C 235/34 514/255.01 |

(Continued)

FOREIGN PATENT DOCUMENTS

| | | |
|---|---|---|
| EP | 3468546 A1 | 4/2019 |
| WO | 2006/023778 A2 | 3/2006 |

(Continued)

OTHER PUBLICATIONS

CAS Registry Nos. RN 1565211-39-3 and RN 1542454-76-1 (2014) (Year: 2014).*

(Continued)

*Primary Examiner* — Mark L Shibuya
*Assistant Examiner* — Ebenezer O Sackey
(74) *Attorney, Agent, or Firm* — Haukaas Fortius PLLC; Michael H. Haukaas

(57) ABSTRACT

Provided herein are compositions and methods for treating, inhibiting and/or reducing the severity of cancer in subjects in need thereof. The methods include providing an agent that inhibits expression or activity of ONECUT2 and administering a therapeutically effective amount of the agent so as to treat, inhibit and/or reduce the severity of cancer in the subject.

16 Claims, 43 Drawing Sheets

(56) References Cited

U.S. PATENT DOCUMENTS

| | | |
|---|---|---|
| 8,377,930 B2 | 2/2013 | Cutshall et al. |
| 2010/0048709 A1 | 2/2010 | Wafa et al. |
| 2011/0263693 A1 | 10/2011 | Vinson-Hieronymus et al. |
| 2011/0265197 A1 | 10/2011 | Depinho et al. |
| 2012/0142921 A1 | 6/2012 | Shi |
| 2014/0206574 A1 | 7/2014 | Chapman et al. |
| 2014/0235479 A1 | 8/2014 | Depinho et al. |
| 2014/0314765 A1 | 10/2014 | Depinho et al. |
| 2016/0038444 A1 | 2/2016 | Alli et al. |

FOREIGN PATENT DOCUMENTS

| | | | |
|---|---|---|---|
| WO | WO-2011109393 A1 * | 9/2011 | ............. A61F 2/042 |
| WO | 2014/011713 A2 | 1/2014 | |
| WO | WO 2014/164730 A2 | 10/2014 | |
| WO | WO 2015/166295 A1 | 11/2015 | |
| WO | WO 2015/188130 A1 | 12/2015 | |
| WO | WO 2015/197909 A1 | 12/2015 | |
| WO | 2016/172545 A1 | 10/2016 | |
| WO | WO 2017/213897 A1 | 12/2017 | |
| WO | 2019/040647 A1 | 2/2019 | |

OTHER PUBLICATIONS

S. Ren et al., 45 Journal of Medicinal Chemistry, 410-419 (2002) (Year: 2002).*

El Hashash et al., Some Reactions with 2-Benzyl-4H-3,1-Benzoxazine-4-one, 6-Bromo-2-Methyl-4H-3,1-Benzoxazin-4-one and 2-Benzyl-3-Phenyl-4 (3H)-Quinazolinone, Egyptian Journal of Chemistry 1978, 21(2), pp. 115-131.

EP 17810721.5 European Partial Supplementary Search Report dated Nov. 26, 2019, 14 pages.

Kumar et al., Synthesis and Evaluation of Isonicotinoyl Hydrazone Derivatives as Antimycobacterial and Anticancer Agents, Med Chem Res, 2014, vol. 23, pp. 269-279.

Yusufi et al., Synthesis, Characterization and Anti-Tumor Activity of Novel Thymoquinone Analogs against Pancreatic Cancer, Bioorganic and Medicinal Chemistry Letters, 2013, vol. 23, pp. 3101-3104.

International Search Report and Written Opinion for PCT/US2017/034768 dated Oct. 13, 2017, 16 pages.

International Preliminary Report on Patentability for PCT/US2017/034768 dated Dec. 20, 2018, 10 pages.

International Search Report and Written Opinion for PCT/US2018/47569 dated Nov. 26, 2018, 14 pages.

Adam et al., Heparin-binding epidermal growth factor-like growth factor stimulates androgen-independent prostate tumor growth and antagonizes androgen receptor function. Endocrinology 2002, 143, pp. 4599-4608.

Aggarwal et al., Persistence of AR signaling in small cell neuroendocrine prostate cancer (SCNC) and intermediate atypical carcinoma (IAC): Results from the SU2C/PCF/AACR West Coast Prostate Cancer Dream Team (WCDT). J Clin Oncol 2016, 34 (suppl; abstr 5045).

Akamatsu et al., The Placental Gene PEG10 Promotes Progression of Neuroendocrine Prostate Cancer. Cell Rep, 2015, 12, pp. 922-936.

Arnold et al., The Swiss-Model workspace: a web-based environment for protein structure homology modelling. Bioinformatics, 2006, 22, pp. 195-201.

Bailey et al., Meme Suite: tools for motif discovery and searching. Nucleic Acids Research, 2009, 37, pp. W202-W208.

Baisch et al., An efficient chemo-enzymatic approach towards variably functionalized benzotropolones. Tetrahedron, 2010, 66, pp. 3742-3748.

Barretina et al., The Cancer Cell Line Encyclopedia enables predictive modelling of anticancer drug sensitivity. Nature, 2012, 483, pp. 603-607.

Beltran et al., Molecular characterization of neuroendocrine prostate cancer and identification of new drug targets. Cancer Discovery 2011, 1(6), pp. 487-495.

Beltran et al., Aggressive variants of castration-resistant prostate cancer. Clin Cancer Res, 2014, 20, pp. 2846-2850.

Beltran et al., Divergent clonal evolution of castration-resistant neuroendocrine prostate cancer. Nat Med 2016, 22, pp. 298-305.

Biasini et al., Swiss-Model: modelling protein tertiary and quaternary structure using evolutionary information. Nucleic Acids Research, 2014, 42, pp. W252-W258.

Bishop et al., The master neural transcription factor BRN2 is an androgen receptor-suppressed driver of neuroendocrine differentiation in prostate cancer. Cancer Discov 2017, 7, pp. 54-71.

Bolstad et al., A comparison of normalization methods for high density oligonucleotide array data based on variance and bias. Bioinformatics, 2003, 19, pp. 185-193.

Cai et al., Androgen receptor gene expression in prostate cancer is directly suppressed by the androgen receptor through recruitment of lysine-specific demethylase 1. Cancer Cell, 2011, 20, pp. 457-471.

Chang et al., Dihydrotestosterone synthesis bypasses testosterone to drive castration-resistant prostate cancer. Proc Natl Acad Sci U S A, 2011, 108, pp. 13728-13733.

Chembridge Corporation, Hit2Lead Compound retrieved from: http://www.hit2lead.com/result.asp?search=9122932 on Dec. 15, 2015.

Cleutjens et al., An androgen response element in a far upstream enhancer region is essential for high, androgen-regulated activity of the prostate-specific antigen promoter. Mol Endocrinol, 1997, 11, pp. 148-161.

D'Antonio et al., Longitudinal analysis of androgen deprivation of prostate cancer cells identifies pathways to androgen independence. Prostate, 2008, 68, pp. 698-714.

Epstein et al., Proposed morphologic classification of prostate cancer with neuroendocrine differentiation. Am J Surg Pathol, 2014, 38, pp. 756-767.

Espana et al., Onecut factors control development of the Locus Coeruleus and of the mesencephalic trigeminal nucleus. Mol Cell Neurosci, 2012, 50, pp. 93-102.

Fletcher et al., Master regulators of FGFR2 signalling and breast cancer risk. Nature Comm 2013, 4, pp. 2464.

Griffon et al., Integrative analysis of public ChIP-seq experiments reveals a complex multi-cell regulatory landscape. Nucleic Acids Res, 2015, 43, pp. e27.

Grozinsky-Glasberg et al., The role of cell lines in the study of neuroendocrine tumors. Neuroendocrinology, 2012, 96, pp. 173-187.

Gundem et al., The evolutionary history of lethal metastatic prostate cancer. Nature, 2015, 520, pp. 353-357.

Guo et al., Modulation of long noncoding RNAs by risk SNPs underlying genetic predispositions to prostate cancer. Nat Genet, 2016, 48, pp. 1142-1150.

Hu et al., Ligand-independent androgen receptor variants derived from splicing of cryptic exons signify hormone-refractory prostate cancer. Cancer Res, 2009, 69, pp. 16-22.

Hwang et al., A data integration methodology for systems biology. Proc Natl Acad Sci U S A, 2005,102, pp. 17296-17301.

Iyaguchi et al., DNA recognition mechanism of the ONECUT homeodomain of transcription factor HNF-6. Structure, 2007, 15, pp. 75-83.

Jacquemin et al., OC-2, a novel mammalian member of the ONECUT class of homeodomain transcription factors whose function in liver partially overlaps with that of hepatocyte nuclear factor-6, J Biol Chem, 1999, 274, pp. 2665-2671.

Jin et al., Cooperativity and equilibrium with FOXA1 define the androgen receptor transcriptional program. Nat Commun, 2014, 5, pp. 3972.

Kelsey, R., New Gene Panel For Aggressive Prostate Cancer, Nature Reviews Urology, 2015, vol. 12, p. 242.

Kharchenko et al., Design and analysis of ChIP-seq experiments for DNA-binding proteins. Nature Biotechnology, 2008, 26, pp. 1351-1359.

Kim et al., Activation of the Erk mitogen-activated protein kinase pathway stimulates neuroendocrine differentiation in LNCaP cells independently of cell cycle withdrawal and STAT3 phosphorylation. Cancer Res, 2002,62, pp. 1549-1554.

Kim et al., Involvement of cholesterol-rich lipid rafts in interleukin-6-induced neuroendocrine differentiation of LNCaP prostate cancer cells. Endocrinology, 2004 145, pp. 613-619.

(56) References Cited

OTHER PUBLICATIONS

Kim et al., FOXA1 inhibits prostate cancer neuroendocrine differentiation. Oncogene, 2017, 36, pp. 4072-4080.
Kumar et al., Substantial interindividual and limited intraindividual genomic diversity among tumors from men with metastatic prostate cancer. Nat Med, 2016, 22, pp. 369-378.
Lapuk et al., From sequence to molecular pathology, and a mechanism driving the neuroendocrine phenotype in prostate cancer. J Pathol, 2012, 227, pp. 286-297.
Latham et al., Prostate-specific antigen promoter/enhancer driven gene therapy for prostate cancer: construction and testing of a tissue-specific adenovirus vector. Cancer Res, 2000, 60, pp. 334-341.
Levine et al., Pathway and gene-set activation measurement from mRNA expression data: the tissue distribution of human pathways. Genome Biol, 2006, 7, pp. R93.
Leyten et al., Identification of a Candidate Gene Panel for the Early Diagnosis of Prostate Cancer, Clinical Cancer Research, 2015, vol. 21(13), pp. 3061-3071.
Li et al., Fast and accurate short read alignment with Burrows-Wheeler transform. Bioinformatics, 2009, 25, pp. 1754-1760.
Li et al., Measuring Reproducibility of High-Throughput Experiments Annals of Applied Statistics, 2011, 5, pp. 1752-1779.
Li et al., SRRM4 drives neuroendocrine transdifferentiation of prostate adenocarcinoma under androgen receptor pathway inhibition. Eur Urol 2017, 71, pp. 68-78.
Liberzon et al., The Molecular Signatures Database (MSigDB) hallmark gene set collection. Cell Syst, 2015, 1, pp. 417-425.
Margagliotti et al., The Onecut transcription factors HNF-6/OC-1 and OC-2 regulate early liver expansion by controlling hepatoblast migration. Dev Biol 2007, 311(2), pp. 579-589.
Martin et al., REST represses a subset of the pancreatic endocrine differentiation program. Dev Biol 2015, 405, pp. 316-327.
Morin et al., Collaboration gets the most out of software. Elife, 2013, 2, pp. e01456.
Mulholland et al., Pten loss and RAS/MAPK activation cooperate to promote EMT and metastasis initiated from prostate cancer stem/progenitor cells. Cancer Res, 2012, 72, pp. 1878-1889.
Naizhen et al., Co-expression of Achaete-Scute homologue-1 and calcitonin gene-related peptide during NNK-induced pulmonary neuroendocrine hyperplasia and carcinogenesis in hamsters. J Cancer 2016, 7, pp. 2124-2131.
Niu et al., Androgen receptor is a tumor suppressor and proliferator in prostate cancer. Proc Natl Acad Sci U S A, 2008, 105, pp. 12182-12187.
Nyquist et al., TALEN-engineered AR gene rearrangements reveal endocrine uncoupling of androgen receptor in prostate cancer. Proc Natl Acad Sci U S A, 2013, 110, pp. 17492-17497.
Qi et al., Siah2-dependent concerted activity of HIF and FoxA2 regulates formation of neuroendocrine phenotype and neuroendocrine prostate tumors. Cancer Cell 2010, 18, pp. 23-38.
Robinson et al., Integrative clinical genomics of advanced prostate cancer. Cell, 2015, 161, pp. 1215-1228.

Savci-Heijink et al., A novel gene expression signature for bone metastasis in breast carcinomas. Breast Cancer Res Treat, 2016, 156, pp. 249-259.
Sharma et al., The androgen receptor induces a distinct transcriptional program in castration-resistant prostate cancer in man. Cancer Cell, 2013, 23, pp. 35-47.
Shiau et al., IGRhCellID: integrated genomic resources of human cell lines for identification. Nucleic Acids Res, 2011, 39, pp. D520-524.
Smid et al., Subtypes of breast cancer show preferential site of relapse. Cancer Res, 2008, 68, pp. 3108-3114.
Storey et al., Statistical significance for genomewide studies. Proc Natl Acad Sci U S A, 2003, 100, pp. 9440-9445.
Sun et al., miR-429 Inhibits Cells Growth and Invasion and Regulates EMT-Related Marker Genes by Targeting Onecut2 in Colorectal Carcinoma, Mol. Cell Biochem, 2014, vol. 390, pp. 19-30.
Taylor et al., Integrative genomic profiling of human prostate cancer. Cancer Cell, 2010, 18, pp. 11-22.
Vanhorenbeeck et al., Role of the Onecut transcription factors in pancreas morphogenesis and in pancreatic and enteric endocrine differentiation. Dev Biol, 2007, 305, pp. 685-694.
Wong et al., Human neuroendocrine tumor cell lines as a three-dimensional model for the study of human neuroendocrine tumor therapy. J Vis Exp, 2012, pp. e4218.
Xu et al., EZH2 oncogenic activity in castration-resistant prostate cancer cells is Polycomb-independent. Science, 2012, 338, pp. 1465-1469.
Yang et al., Integration of proteomic and transcriptomic profiles identifies a novel PDGF-MYC network in human smooth muscle cells. Cell Commun Signal 2014, 12(1), pp. 44.
Yang et al., Current perspectives on FOXA1 regulation of androgen receptor signaling and prostate cancer. Genes Dis 2015, 2(2), pp. 144-151.
You et al., Integrated Classification of Prostate Cancer Reveals a Novel Luminal Subtype with Poor Outcome. Cancer Res, 2016, 76, pp. 4948-4958.
Yuan et al., Androgen receptor functions in castration-resistant prostate cancer and mechanisms of resistance to new agents targeting the androgen axis. Oncogene 2014, 33, pp. 2815-2825.
Zhang et al., Model-based analysis of ChIP-Seq (MACS). Genome Biol, 2009, 9, pp. R137.
Zhang et al., Comprehensive Profiling of Novel micro-RNA-9 Targets and a Tumor Suppressor Role of micro-RNA-9 via Targeting IGF2BP1 in a Hepatocellular Carcinoma, Oncotarget, 2015, vol. 6(39), pp. 42040-42052.
Zhang et al., SRRM4 Expression and the loss of REST activity may promote the emergence of the neuroendocrine phenotype in castration-resistant prostate cancer. Clin Cancer Res 2015, 21(20), pp. 4698-4708.
Zou et al., Transdifferentiation as a mechanism of treatment resistance in a mouse model of castration-resistant prostate cancer. Cancer Discov., 2017, 7, pp. 736-749.

\* cited by examiner

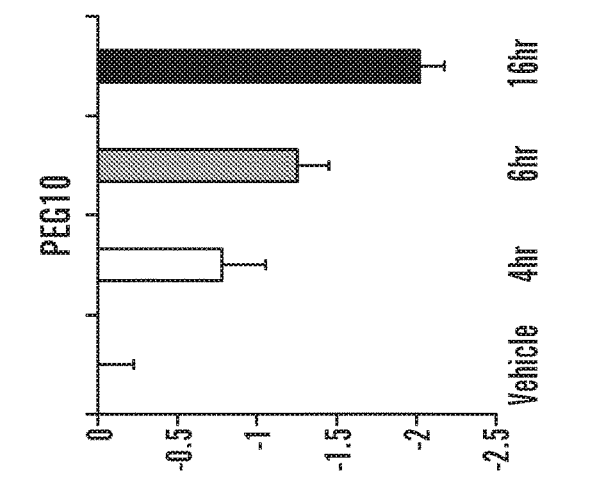
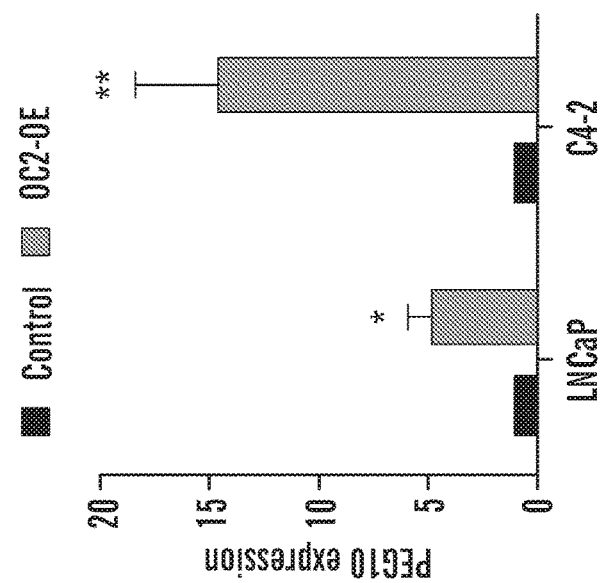
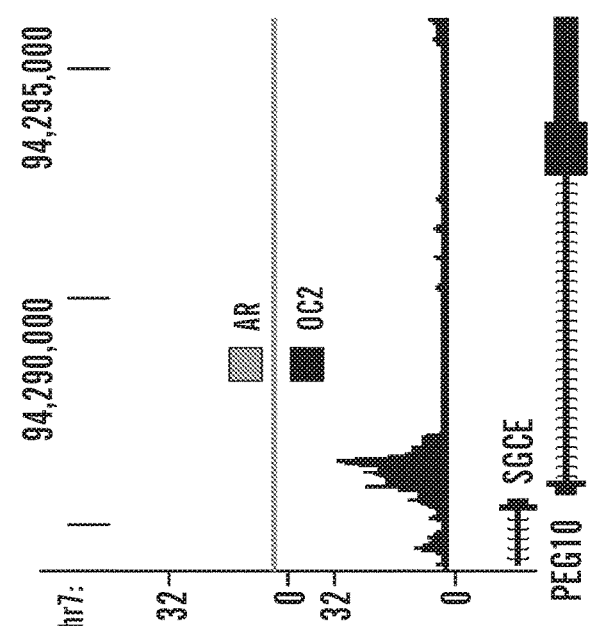
*FIG. 16A*
*FIG. 16B*
*FIG. 16C*

COMPOSITIONS AND METHODS FOR TREATING CANCER

This application is a National Phase of International Application No. PCT/US2017/034768 filed May 26, 2017, which designated the U.S. and that International Application was published under PCT Article 21(2) in English, which also includes a claim of priority under 35 U.S.C. § 119(e) to U.S. Provisional Patent Application No. 62/348,013, filed Jun. 9, 2016 and U.S. Provisional Patent Application No. 62/421,733, filed Nov. 14, 2016, the contents of each of which are incorporated herein by reference in their entirety.

STATEMENT REGARDING FEDERALLY SPONSORED RESEARCH OR DEVELOPMENT

This invention was made with government support under Grant Nos. DK087806 and CA143777 awarded by National Institutes of Health and Grant No. W81XWH-14-1-0152 awarded by Department of Defense. The government has certain rights in the invention.

TECHNICAL FIELD

The present disclosure relates generally to compositions and methods for treating cancers that overexpress ONE-CUT2. In some embodiments, the compositions include inhibitors of ONECUT2.

BACKGROUND

Prostate cancer is hormone-dependent in its initial stages. Hormonal therapy directed against the androgen receptor (AR) is generally effective; however, failure of therapy is frequent. The "castration resistant" form of prostate cancer progresses to end-stage, lethal disease, and there are very few options available to treat these patients, essentially none that substantially extend life. Approximately 25,000 men die from castration-resistance prostate cancer (CRPC) each year in the US. Because of widespread use of the next generation hormonal therapy drugs enzalutamide and abiraterone acetate, the number of patients that are failing these therapies is increasing.

Therapeutic failure in the castration-resistant phase of prostate cancer (CRPC) is essentially universal. We still lack a detailed understanding of the molecular and cellular basis of CRPC, resulting in no rational clinical options for these patients. The molecular mechanisms operating when treatment-resistant tumor variants emerge are not understood, and there is much controversy around terms for aggressive tumor subtypes, such as "anaplastic carcinoma" or tumors with "neuroendocrine" (NE) features. Although CRPC refers to acquired insensitivity to androgen receptor-(AR-) targeted therapy, the AR is believed to remain an oncogenic driver in most castration-resistant tumors. However, AR-negative clones appear in adenocarcinoma, and some cancers progress in the absence of indicators of AR activity, such as prostate-specific antigen (PSA) rise. AR expression as evaluated immunohistochemically is also heterogeneous, even in the setting of AR gene amplification. Currently, our understanding of the origin of aggressive prostate cancer (PC) variants is poor. In addition, there has only been limited progress in identifying lethal disease early in tumor evolution, and in adopting precision therapeutic approaches for individual patients.

The majority of attempts to improve prognosis in the face of a diagnosis of CRPC have been directed toward improving the effectiveness of targeting and inhibiting the action of the AR, which is believed to be the primary prostate cancer oncoprotein, even in the castration-resistant phase of the disease. Other approaches, including immunotherapy and directed agents against signal transduction mediators (e.g., SRC-family kinases). Most of these approaches have not moved forward into clinical practice. As such, there remains a need for compositions and methods for treating castration resistant prostate cancer.

SUMMARY

The following embodiments and aspects thereof are described and illustrated in conjunction with systems, compositions and methods which are meant to be exemplary and illustrative, not limiting in scope.

Embodiments of the various aspects disclosed herein are based on inventors' discovery that the ONECUT2 protein (also known as Hepatocyte nuclear factor-6-beta (HNF-6-beta)) is highly active in patients that have drug-resistant disease. Inventors have discovered inter alfa that ONECUT2 is a master regulator in a subset of CRPC patients. The inventors have shown that disabling the ONECUT-2 function either by silencing the gene using shRNA or by small molecule drug prevents metastasis in CRPC animal model. The inventors have identified drug-like small molecules that are designed to bind to the DNA-binding domain of the protein, thereby blocking the critical functional interaction between ONECUT2 and chromatin. One of the compounds (Compound CSRM617) replicate the effects of directed targeting of ONECUT2 using genetic silencing. The compounds disclosed herein may improve clinical efficacy in CRPC patients that have failed next generation hormonal therapy.

Studies by the inventors indicate that ONECUT2 is highly active in CRPC tumors and that it is co-expressed in human PC with the AR. ONECUT2 also interacts directly with the AR network by binding to chromatin sites that harbor the AR. ONECUT2 also forms a complex with the AR. However, data from experiments to functionally inhibit ONECUT2 indicate that it is an essential protein, required for survival and growth of PC cells that express the AR. Hence, the target is not the AR but a protein that can be as critical, or more critical, in the CRPC phase of the disease than the AR. Importantly, CRPC cells that express AR variants (AR-Vs) that in humans are biomarkers for failure of hormonal therapy are the most sensitive PC cells to ONE-CUT2 inhibition. These findings show that ONECUT2 is a viable therapeutic target in the enzalutamide-/abiraterone acetate-resistant disease phase. There is currently no effective treatment available for these patients. Thus, the present invention provides a major advancement in treatment for these patients.

Various embodiments of the invention provide a method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONE-CUT2 in the subject. In some embodiments, the agent is any one or more of small molecule, a peptide, an antibody or a fragment thereof, intrabody, aptamer, antisense construct, RNA interference agent, siRNA, shRNA, ribozyme, antibody-drug conjugate, or combination thereof. In some embodiments, the antibody is selected from the group consisting of monoclonal antibody or fragment thereof, a polyclonal antibody or a fragment thereof, chimeric antibodies, humanized antibodies, human antibodies, and a single chain antibody. In some embodiments, agents that target OC2 indirectly target OC2, for example by targeting OC2 interacting proteins like KDM5B. In some embodiments, the agent is Compound CSRM617 of structure:

COMPOUND CSRM617

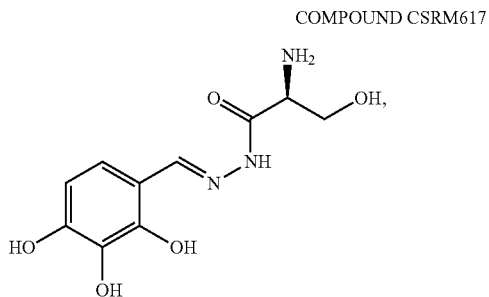 [SMILES: N[C@@H](CO)C(=O)N/N=C/c1ccc(O)c(O)c1O]

or a pharmacetucially acceptable salt thereof. In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the subject is human. In some embodiments, the agent is administered to the subject 1-3 times per day or 1-7 times per week. In some embodiments, the agent is administrated to the subject for 1-5 days, 1-5 weeks, 1-5 months, or 1-5 years. In some embodiments, the agent and the additional anti-cancer therapy are administered sequentially or simultaneously. In some embodiments, the cancer is castration resistant prostate cancer (CRPC), breast cancer, lung cancer, colon cancer, renal cancer, gastric cancer, brain cancer or medulloblastoma.

Various embodiments of the present invention provide a method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from a compound of Formula I:

(FORMULA I)

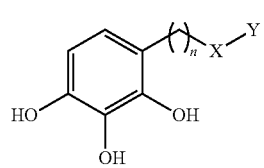

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof. In some embodiments, the compound of Formula I is not

COMPOUND CSRM617

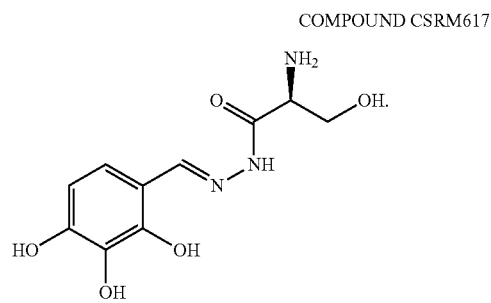

Various embodiments of the present invention provide a method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from a compound of Formula II:

(FORMULA II)

wherein: n is 0, 1, 2, 3, 4 or 5; X is NHC(O), C(O)NH, OC(O), C(O)O, or C(O); Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from a compound of Formula III:

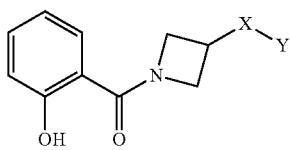

(FORMULA III)

wherein: X is NH, or O; Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from a compound of Formula IV:

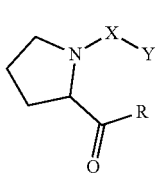

(FORMULA IV)

wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl; and any pharmaceutically acceptable salt thereof. In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from a compound of Formula V:

(FORMULA V)

wherein: Y is alkyl, heteroalkyl, cyclyl, heterocyclyl, aryl, or heteroaryl, each of which can be optionally substituted; and any pharmaceutically acceptable salt thereof. In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide a method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from:

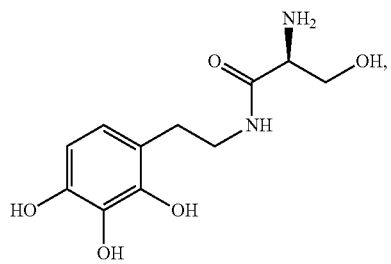

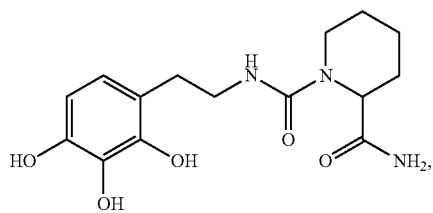

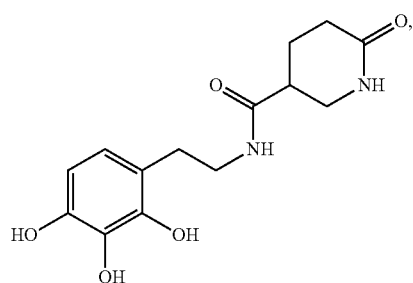

-continued

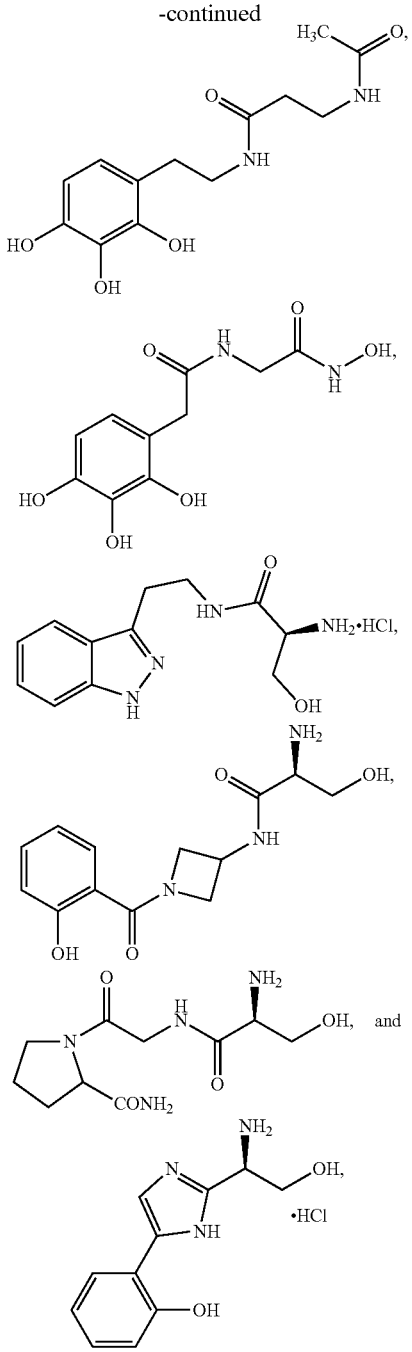

or a pharmaceutically acceptable salt thereof. In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

Various embodiments of the present invention provide an assay for determining the prognosis of cancer in a subject in need thereof comprising: obtaining a sample from the subject having or suspected of having cancer; assaying the sample to determine the expression level of ONECUT2; and determining that the subject has poor prognosis if the expression of ONECUT2 is increased relative to a reference value. In some embodiments, the sample is blood, plasma, urine, tissue or combinations thereof. In some embodiments, the sample is obtained before, during or after treatment for cancer. In some embodiments, the subject is human. In some embodiments, the reference value is the mean or median level of ONECUT2 expression in a population of subjects that do not have cancer. In some embodiments, the reference value is the mean or median level of ONECUT2 expression in a population of subjects that have cancer and have been treated for cancer. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have ONECUT2 overexpressing cancer and have undergone or are undergoing treatment for the ONECUT2 overexpressing cancer. In some embodiments, the expression of ONECUT2 is increased 2-fold, 3-fold, 4-fold, 5-fold, 10-fold, 20-fold, 50-fold, or 100-fold relative to a reference value.

Various embodiments of the present invention provide an assay for determining the likelihood of CRPC in a subject in need thereof comprising: obtaining a sample from the subject; assaying the sample to determine the expression level of ONECUT2; and determining that the subject has increased likelihood of CRPC if the expression of ONECUT2 is increased relative to a reference value. In some embodiments, the sample is blood, plasma, urine, tissue or combinations thereof. In some embodiments, the sample is obtained before, during or after treatment for CRPC. In some embodiments, the subject is human. In some embodiments, the reference value is the mean or median level of ONECUT2 expression in a population of subjects that do not have prostate cancer. In some embodiments, the reference value is the mean or median level of ONECUT2 expression in a population of subjects that have prostate cancer but do not have CRPC. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have CRPC but have not undergone or are not undergoing treatment for CRPC and the ONECUT2 expression in the sample is the same or similar to the ONECUT2 expression in the reference value. In some embodiments, the expression of ONECUT2 is increased 2-fold, 3-fold, 4-fold, 5-fold, 10-fold, 20-fold, 50-fold, or 100-fold relative to a reference value.

Various embodiments of the present invention provide an assay for selecting a subject for therapy targeting ONECUT2 comprising: obtaining a sample from the subject; assaying the sample to determine the expression level of ONECUT2; and selecting the subject for therapy that inhibits ONECUT2 if the expression of ONECUT2 is increased relative to a reference value. In some embodiments, the sample is blood, plasma, urine, tissue or combinations thereof. In some embodiments, the sample is obtained from the subject that has or is suspected of having cancer. In some embodiments, the sample is obtained from the subject that has or is suspected of having ONECUT2 overexpressing cancer. In some embodiments, the sample is obtained before, during or after treatment for cancer. In some embodiments, the sample is obtained before, during or after treatment for CRPC. In some embodiments, the subject is human. In some embodiments, the reference value is the mean or median level of ONECUT2 expression in a population of subjects that do not have cancer. In some embodiments, the reference value is the mean or median level of ONECUT2 expression in a population of subjects that have prostate cancer but do not have CRPC. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have ONECUT2 overexpressing cancer and have undergone or are undergoing treatment for ONECUT2 overexpressing cancer. In some embodiments, the expression of ONECUT2 is increased 2-fold, 3-fold, 4-fold, 5-fold, 10-fold, 20-fold, 50-fold, or 100-fold relative to a reference value.

In various embodiments of the methods and assays described herein, the cancer is CRPC, breast cancer, lung cancer, colon cancer, renal cancer, gastric cancer, brain cancer or medulloblastoma.

Various embodiments of the present invention provide a method for identifying inhibitors of ONECUT2 comprising: (i) contacting the ONECUT2 in a ONECUT2 positive cell with a molecule of interest; and (ii) determining whether the contact results in decreased expression of ONECUT2, a decrease in expression indicating that the molecule of interest is an inhibitor of ONECUT2. In some embodiments, the inhibitor (molecule of interest) is any one or more of small molecule, a peptide, an antibody or a fragment thereof, intrabody, aptamer, antisense construct, RNA interference agent, siRNA, shRNA, ribozyme, antibody-drug conjugate, or combination thereof. In some embodiments, the plurality of samples comprises more than about $10^4$ samples. In some embodiments, the plurality of samples comprises more than about $5 \times 10^4$ samples. In exemplary embodiments, the small molecule is a compound of Formula I:

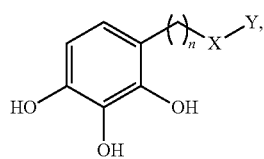

(FORMULA I)

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted provided that the compound of Formula I is not

COMPOUND CSRM617

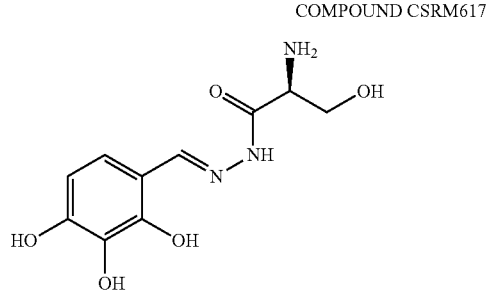 [SMILES: N[C@@H](CO)C(=O)N/N=C/c1ccc(O)c(O)c1O]

or a compound of Formula I as provided in Table I. In exemplary embodiments, the small molecule is a compound of Formula II:

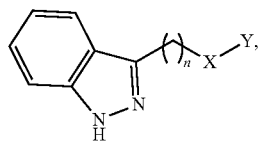

(FORMULA II)

wherein: n is 0, 1, 2, 3, 4 or 5; X is NHC(O), C(O)NH, OC(O), C(O)O, or C(O); Y is alkyl, heteroalkyl, cyclyl, heterocyclyl, aryl, or heteroaryl, each of which can be optionally substituted. In exemplary embodiments, the small molecule is a compound of Formula III:

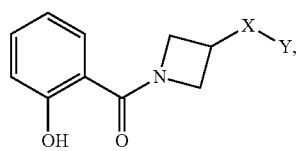

(FORMULA III)

wherein: X is NH, or O; Y is alkyl, heteroalkyl, cyclyl, heterocyclyl, aryl, or heteroaryl, each of which can be optionally substituted. In exemplary embodiments, the small molecule is a compound of Formula IV:

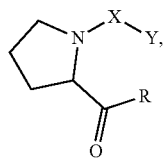

(FORMULA IV)

wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl. In exemplary embodiments, the small molecule is a compound of Formula V:

(FORMULA V)

wherein: Y is alkyl, heteroalkyl, cyclyl, heterocyclyl, aryl, or heteroaryl, each of which can be optionally substituted.

Various embodiments of the present invention provide a compound of Formula I:

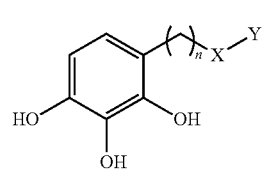

(FORMULA I)

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted; and any pharmaceutically acceptable salt thereof provided that the compound of Formula I is not

COMPOUND CSRM617

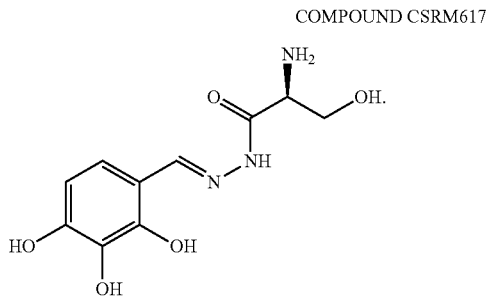 [SMILES: N[C@@H](CO)C(=O)N/N=C/c1ccc(O)c(O)c1O]

Various embodiments of the present invention provide compound of Formula II:

(FORMULA II)

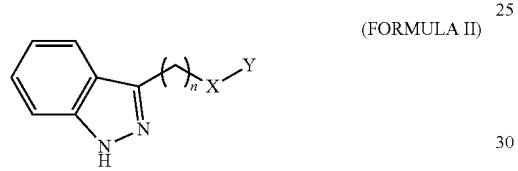

wherein: n is 0, 1, 2, 3, 4 or 5; X is NHC(O), C(O)NH, OC(O), C(O)O, or C(O); Y is alkyl, heteroalkyl, cyclyl, heterocyclyl, aryl, or heteroaryl, each of which can be optionally substituted; and any pharmaceutically acceptable salt thereof.

Various embodiments of the present invention provide a compound of Formula III:

(FORMULA III)

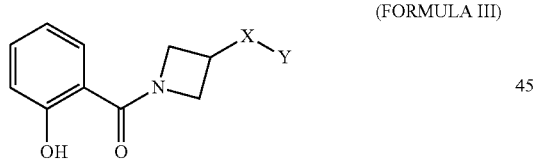

wherein: X is NH, or O; Y is alkyl, heteroalkyl, cyclyl, heterocyclyl, aryl, or heteroaryl, each of which can be optionally substituted; and any pharmaceutically acceptable salt thereof.

Various embodiments of the present invention provide a compound of Formula IV:

(FORMULA IV)

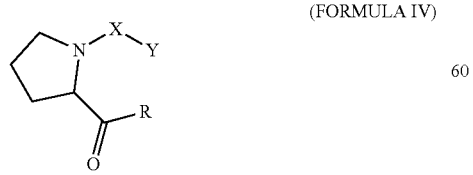

wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl; and any pharmaceutically acceptable salt thereof.

Various embodiments of the present invention provide a compound of Formula V:

(FORMULA V)

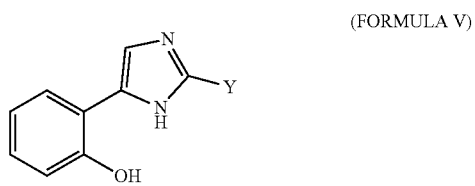

wherein: Y is alkyl, heteroalkyl, cyclyl, heterocyclyl, aryl, or heteroaryl, each of which can be optionally substituted; and any pharmaceutically acceptable salt thereof.

Various embodiments of the present invention provide a compound selected from:

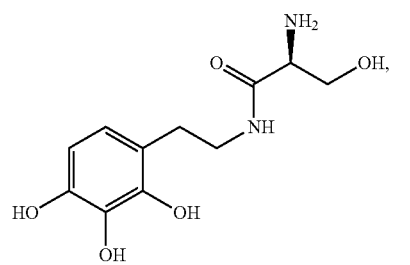

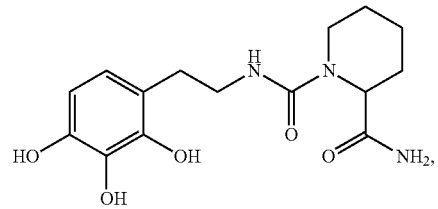

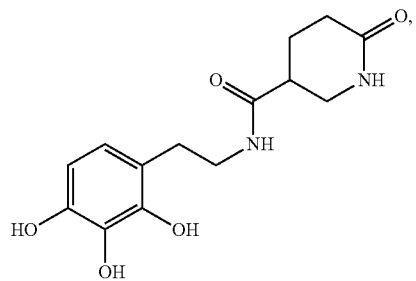

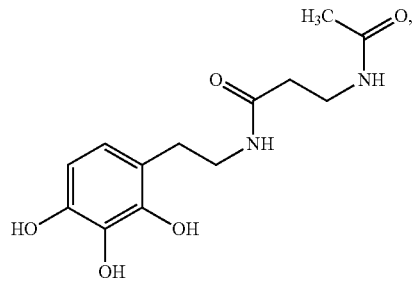

-continued

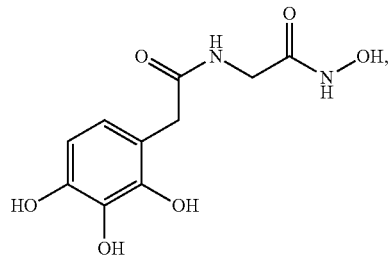

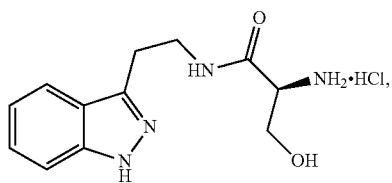

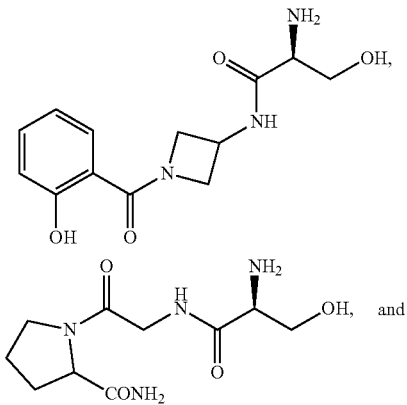

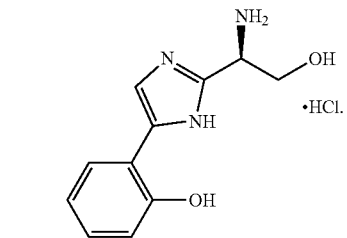

Various embodiments of the present invention provide a pharmaceutical composition comprising a compound of structure:

COMPOUND CSRM617

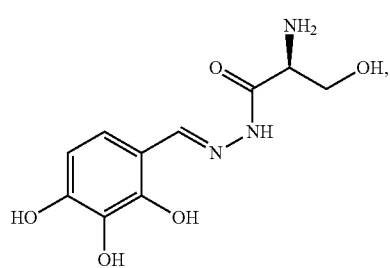

and a pharmaceutically acceptable excipient or carrier.

Various embodiments of the present invention provide a pharmaceutical composition comprising a compound of Formula I:

(FORMULA I)

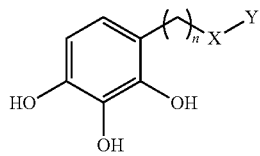

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier. In some embodiments, the compound of Formula (I) is not

COMPOUND CSRM617

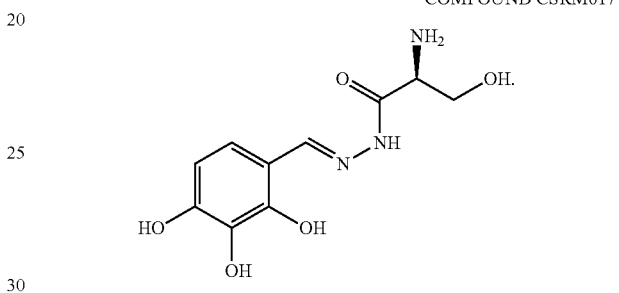

Various embodiments of the present invention provide a pharmaceutical composition comprising a compound of Formula II:

(FORMULA II)

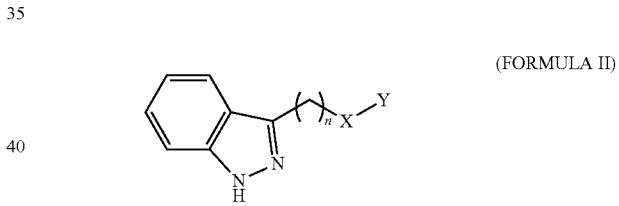

wherein: n is 0, 1, 2, 3, 4 or 5; X is NHC(O), C(O)NH, OC(O), C(O)O, or C(O); Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier.

Various embodiments of the present invention provide a pharmaceutical composition comprising a compound of Formula III:

(FORMULA III)

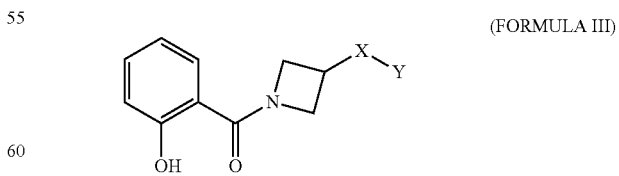

wherein: X is NH, or O; Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier.

Various embodiments of the present invention provide a pharmaceutical composition comprising a compound of Formula IV:

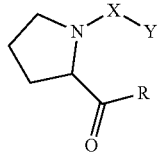
(FORMULA IV)

wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl; and any pharmaceutically acceptable salt thereof; and a pharmaceutically acceptable excipient or carrier.

Various embodiments of the present invention provide a pharmaceutical composition comprising a compound of Formula V:

(FORMULA V)

wherein: Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier.

Various embodiments of the present invention provide a pharmaceutical composition comprising a compound selected from:

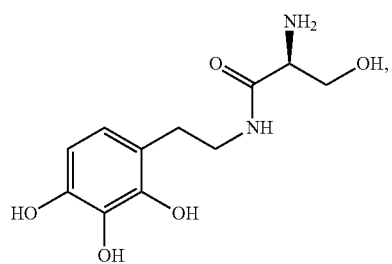

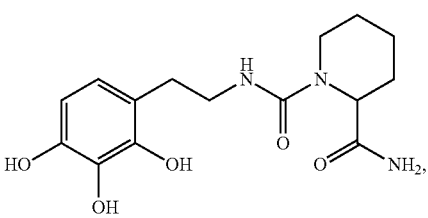

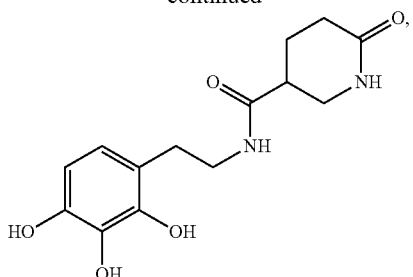

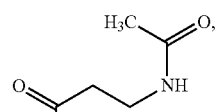

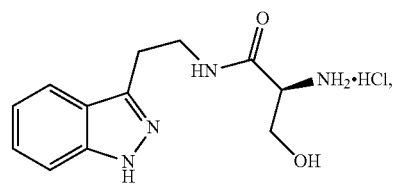

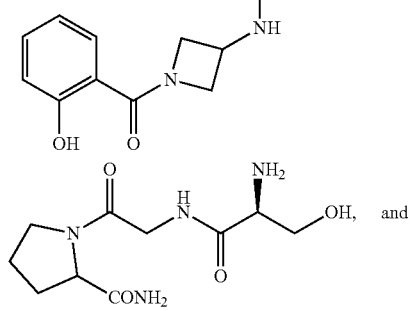

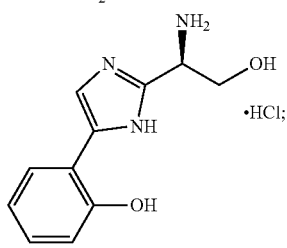

or a pharmaceutically acceptable salt thereof; and a pharmaceutically acceptable excipient or carrier.

Embodiments of the various aspects disclosed herein are based on inventors' discovery of small molecules capable of repressing OC2 activity by directly binding to the target, which inhibits metastatic progression of human CRPC cells in vivo.

BRIEF DESCRIPTION OF FIGURES

Exemplary embodiments are illustrated in referenced figures. It is intended that the embodiments and figures disclosed herein are to be considered illustrative rather than restrictive.

(FIG. 10B) Scatter plot of AR and OC2 expression levels measured by optical intensity from nuclei in 35 TMA cores of high-grade PC. Each dot represents one nucleus. (FIG. 10C) AR activation in mCRPC tumors with high and low OC2 expression. AR mRNA (FIG. 10D) and protein (FIG. 10E) in PC cell lines after enforced expression of OC2. Mean±SEM (n=3) is shown. ** P<0.01. OC2 can functionally oppose AR and nuclear OC2 and AR are inversely correlated.

(FIG. 11A) violin plot of OC2 gene expression combined from two cohorts (Beltran et al., Nature Medicine 2016, and Robinson et al., Cell 2015). Wilcoxon Rank-Sum test was performed to compare NE tumors and adenocarcinoma (Adeno). (FIG. 11B) NE activation score in mCRPC tumors with high and low OC2 expression from the DISC cohort. OC2 is associated with a neural/NE differentiation program.

FIG. 16A-FIG. 16C depict in accordance with various embodiments of the invention, that OC2 activates PEG10, a driver of transdifferentiation from adenocarcinoma to neuroendocrine cancer. OC2 binds to the PEG10 promoter (FIG. 16A), and ectopic OC2 increased PEG10 mRNA levels (FIG. 16B), indicating that OC2 is a direct upstream activator of PEG10 transcription. FIG. 16C: we have generated gene expression microarray data from 22Rv1 cells treated with the compound at a concentration of 10 µM for 4, 6 and 16 h. In response to CSRM617, PEG10 mRNA expression is downregulated in a time-dependent manner. By inhibiting OC2 with compound CSRM617 the expression levels of the NE driver PEG10 are reduced.

FIG. 17A: 22Rv1 cells were plated at a density of 1000 cells per well, in triplicate, in a 96 well plate. The next day cells were exposed to compound CSRM617, several derivatives or vehicle (1% DMSO) at a concentration of 25 µM. Viability was measured 48 hours post treatment using CellTiter-Glo Luminescent Cell Viability Assay (Promega). FIG. 17B: 22Rv1 cells were plated at a density of 1000 cells per well, in triplicate, in a 96 well plate. The next day, T0 reading was collected and cells were exposed to compound CSRM617, the derivatives or vehicle (1% DMSO) at 2-fold concentration ranging from 100 µM to 0.2 µM. Viability was measured 48 hours post treatment using CellTiter-Glo Luminescent Cell Viability Assay (Promega). IC$_{50}$ values were generated using GraphPad Prism version 6 Software and show that the potency of the derivatives is very similar to compound CSRM617. CSRM617 derivatives Compound 122, Compound 123, Compound 843, Compound 844, Compound 848 reduces cell viability in the castration resistant cell line 22Rv1 cell line. Their potency is similar to compound CSRM617 but its solubility is improved.

FIG. 18A: a network model describing activity and association of 10 TFs calculated to be highly active in 260 mCRPC tumors. TFs are identified as nodes; node size represents TF activity; node color represents the proportion of specimens with the TF up- or down-regulated, or unchanged; edges indicate the degree of interaction between the TFs; thickness of the edges represent the concordance in RNA expression. FIG. 18B: bar plot (top) showing the extent of summarized TF activation of the TFs in FIG. 18A (bottom). The heatmap shows activation patterns of individual TFs in each specimen distributed according to disease state. FIG. 18C: relative TF activity in mCRPC based on ranked expression of respective target genes.

FIG. 19A: representative images of OC2 expression in benign prostate, Gleason Grade 3 (G3) and Grade 4 (G4) PC tissues. Tissue sections were stained using a fluorescent antibody-based detection system and nuclei visualized with DAPI. Boxplots of OC2 staining intensity in TMA cores of benign, G3, and G4 PC tissues, quantified by digital imaging. Nuclear and cytoplasmic intensities were measured separately. FIG. 19B: double immunofluorescence staining with anti-O2 and anti-AR antibodies in 6 cases of high-grade PC. The heatmap plots fluorescent staining intensities of AR and OC2 in an unsupervised cluster analysis. The scatter plot (top middle) shows individual nuclei by intensity levels (natural log scale) of AR and OC2. Dot color corresponds to the cluster designation in the heat map. Pearson's rho=−0.4 for correlation of AR and OC2 nuclear intensity. Boxplots show intensity levels of AR and OC2 of cells in the C1 or C2 clusters in the heatmap.

FIG. 20A: effect of enforced OC2 expression on AR mRNA and protein and the AR-regulated genes PSA/KLK3, KLK2, and EHF. FIG. 20B: enrichment plot of an androgen response hall mark gene signature (n=101) in 22Rv1 and LNCaP cells in which OC2 expression was enforced.

FIG. 21A: ChIP-sequencing of endogenous OC2 in 22Rv1 cells indicates overlap with AR binding sites at only ~20% of OC2 sites. OC2 binding at KLK3/PSA enhancer and the FOXA1 promoter are shown. FIG. 21B: enforced OC2 suppresses FOXA1 protein. FIG. 21C: enforced OC2 suppresses FOXA1 gene expression.

FIG. 22A: enrichment plot showing downregulation of an NE differentiation gene signature in 22Rvl with OC2 depletion. FIG. 22B: sample-wise enrichment of an NE signature in 1,064 Cancer Cell Line Encyclopedia (CCLE) cell lines ranked by endogenous OC2 expression. FIG. 22C: upregulation of NE/neuronal genes in 22Rv1 cells following enforced expression of OC2.

FIG. 24A: Kaplan-Meier plots of the relationship between high and low OC2 expression and BCR-free survival in two PC cohorts. FIG. 24B: OC2 and AR mRNA expression levels in prostate needle biopsies from the Garraway cohort. M1=patients that progressed to metastasis and M0=patients that did now show metastatic progression with long-term follow-up.

FIG. 25A: (Left panel) representative sensorgram showing dose-dependent OC2-Compound CSRM617 interaction measured by surface plasmon resonance (SPR). Real-time binding was quantified by immobilizing biotinylated OC2 protein on the streptavidin biosensor with varying concentrations of Compound CSRM617 1.56-100 µm). (Right panel) OC2 binding to the experimentally determined OC2 binding site on the PEG10 promoter assayed by SPR. FIG. 25B: suppression of PEG10 protein expression in 22Rv1 tumors. FIG. 25C: suppression of PEG10 protein expression in 22Rv1 tumors.

DETAILED DESCRIPTION

Figure 1:
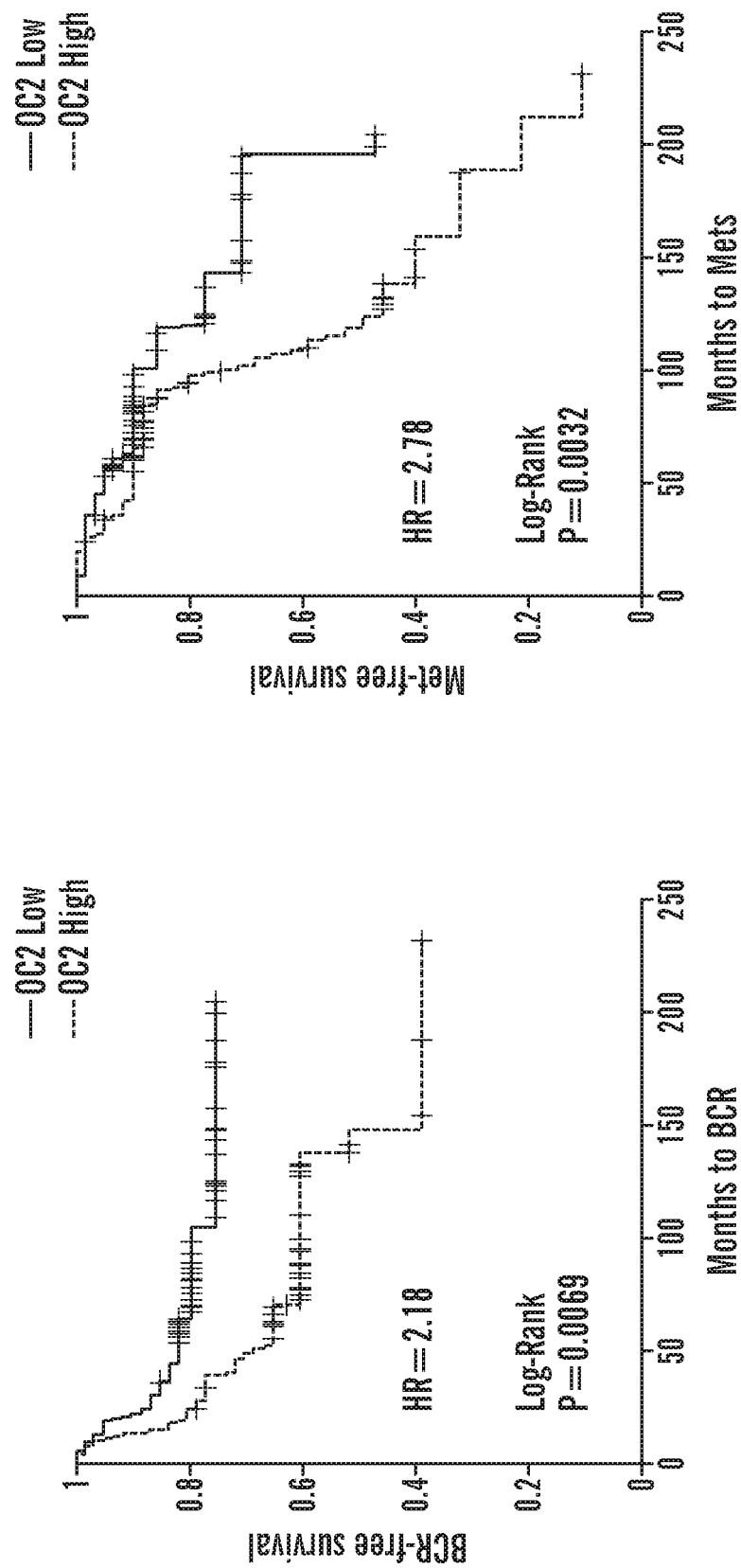
FIG. 1 depicts in accordance with various embodiments of the invention, that high ONECUT2 (OC2) expression is an indicator of likelihood of progression to lethal disease in prostate cancer.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: *The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar 24, 332(6162):323-7.

For references on pediatrics, see Schwartz et al., *The 5-Minute Pediatric Consult* $4^{th}$ ed., Lippincott Williams & Wilkins, (Jun. 16, 2005); Robertson et al., *The Harriet Lane Handbook: A Manual for Pediatric House Officers* $17^{th}$ ed., Mosby (Jun. 24, 2005); and Hay et al., *Current Diagnosis and Treatment in Pediatrics* (*Current Pediatrics Diagnosis & Treatment*)$18^{th}$ ed., McGraw-Hill Medical (Sep. 25, 2006).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

The term "effective amount" as used herein refers to the amount of a pharmaceutical composition comprising one or more peptides as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of cancers that overexpress ONECUT2, delay or slowing of cancers that overexpress ONECUT2, and amelioration or palliation of symptoms associated with cancers that overexpress ONECUT2.

"Diseases", "conditions" and "disease conditions," as used herein may include, but are in no way limited to any form of cancer that overexpresses ONECUT2. In exemplary embodiments, the disease is breast cancer, gastric cancer, colon cancer, renal cancer, brain cancer, lung cancer, prostate cancer or castration resistant prostate cancer.

"Overexpress" or "overexpression as used herein refers to excessive expression of a gene, for example ONECUT2, as that caused by, for example, increasing the frequency or level of transcription. In some embodiments, overexpression of ONECUT2 is determined relative to the level of ONECUT2 in control (healthy) subjects and/or subjects whose cancer is under remission and/or subjects with cancer not associated with overexpression of ONECUT2. In exemplary embodiments, cancers that may overexpress ONECUT2 include but are not limited to breast cancer, gastric cancer, colon cancer, renal cancer, brain cancer, lung cancer, prostate cancer or castration resistant prostate cancer. Methods for determining overexpression of ONECUT2 will be apparent to a person of skill in the art.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres, nanoparticles comprised of proteineous or non-proteineous components or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age. Thus, adult and newborn subjects, as well as fetuses, are intended to be included within the scope of this term.

A subject can be one who has been previously diagnosed with or identified as suffering from or having a condition in need of treatment (e.g., cancer that overexpresses ONECUT2) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

As used herein, the term "protein-drug conjugate," refers to complex molecules comprising proteins linked to a biologically active cytotoxic (anticancer) payload, drug, or drug-like small molecule. In some embodiments, a protein-drug conjugate, may be a complex molecule comprising a protein linked to a compound described herein, such as compound CSRM617, a compound of Formula I-V, or any pharmaceutically acceptable salt thereof. In some embodiments, the proteins are antibodies. Non-limiting examples of antibodies suitable for use in antibody-drug conjugates include a monoclonal antibody or fragment thereof, a polyclonal antibody or a fragment thereof, chimeric antibodies, humanized antibodies, human antibodies, or a single chain antibody that target prostate cancer cells, including but not limited to commercially available therapeutic antibodies.

As used herein, the term "photodynamic therapy", refers to a treatment that uses a drug, called a photosensitizer or photosensitizing agent, and light to kill cancer cells. The photosensitizers only work after they have been activated by certain wavelengths of light. Photodynamic therapy (PDT) may also be called photoradiation therapy, phototherapy, photochemotherapy.

"Diagnostic" means identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

By "at risk of" is intended to mean at increased risk of, compared to a normal subject, or compared to a control group, e.g. a patient population. Thus a subject carrying a particular marker may have an increased risk for a specific disease or disorder, and be identified as needing further testing. "Increased risk" or "elevated risk" mean any statistically significant increase in the probability, e.g., that the subject has the disorder. The risk is preferably increased by at least 10%, more preferably at least 20%, and even more preferably at least 50% over the control group with which the comparison is being made.

The term "diagnosis," or "dx," refers to the identification of the nature and cause of a certain phenomenon. As used herein, a diagnosis typically refers to a medical diagnosis, which is the process of determining which disease or condition explains a symptoms and signs. A diagnostic procedure, often a diagnostic test or assay, can be used to provide a diagnosis. A diagnosis can comprise detecting the presence of a disease or disorder or the risk of getting a disease or disorder.

The term "prognosis," or "px," as used herein refers to predicting the likely outcome of a current standing. For example, a prognosis can include the expected duration and course of a disease or disorder, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Sample" is used herein in its broadest sense. The term "biological sample" as used herein denotes a sample taken or isolated from a biological organism. A sample or biological sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Non-limiting examples of samples or biological samples include cheek swab; mucus; whole blood, blood, serum; plasma; urine; saliva; semen; lymph; fecal extract; sputum; other body fluid or biofluid; cell sample; and tissue sample etc. The term also includes a mixture of the above-mentioned samples or biological samples. The term "sample" also includes untreated or pretreated (or preprocessed) biological samples. In some embodiments, a sample or biological sample can comprise one or more cells from the subject. In some embodiments subject samples or biological samples comprise derivatives of blood products, including blood, plasma and serum.

Sample collection procedures and devices known in the art are suitable for use with various embodiment of the present invention. Examples of sample collection procedures and devices include but are not limited to: phlebotomy tubes (e.g., a vacutainer blood/specimen collection device for collection and/or storage of the blood/specimen), dried blood spots, Microvette CB300 Capillary Collection Device (Sarstedt), HemaX is blood collection devices (microfluidic technology, Hemaxis), Volumetric Absorptive Microsampling (such as CE-IVD Mitra microsampling device for accurate dried blood sampling (Neoteryx), HemaSpot™-HF Blood Collection Device.

Compounds

In some embodiments, the present invention provides a compound of structure:

COMPOUND CSRM617

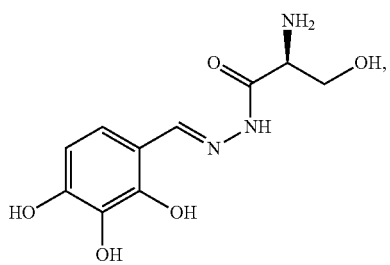

or a prodrug, isomer, dimer, enantiomer, derivative, or pharmaceutically acceptable salt thereof.

In some embodiments, the present invention provides a compound of structure:

COMPOUND CSRM617

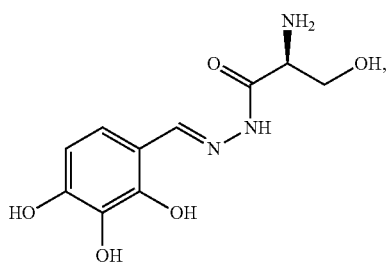

or any pharmaceutically acceptable salt thereof.

In some embodiments, the present invention provides a compound of structure:

COMPOUND CSRM617

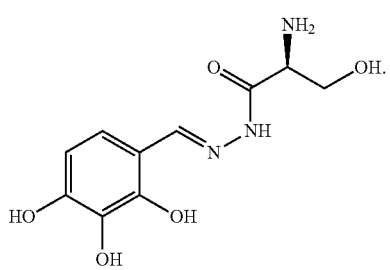

In some embodiments, the present invention provides a compound of Formula I:

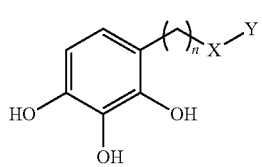
(FORMULA I)

or a prodrug, isomer, dimer, enantiomer, derivative, or pharmaceutically acceptable salt thereof, wherein:
n is 0, 1, 2, 3, 4 or 5;
X is NHC(O), C(O)NH, OC(O), C(O)O, C(O), or CH=N; and
Y is alkyl, heteroalkyl, cyclyl, heterocyclyl, aryl, or heteroaryl, each of which can be optionally substituted.

In some embodiments, the present invention provides a compound of Formula I:

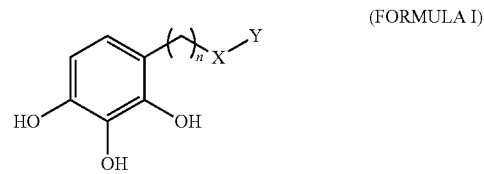
(FORMULA I)

wherein:
n is 0, 1, 2, 3, 4 or 5;
X is NHC(O), C(O)NH, OC(O), C(O)O, C(O), or CH=N;
Y is alkyl, heteroalkyl, cyclyl, heterocyclyl, aryl, or heteroaryl, each of which can be optionally substituted; and
any pharmaceutically acceptable salt thereof.

In some embodiments, the present invention provides a compound of Formula I:

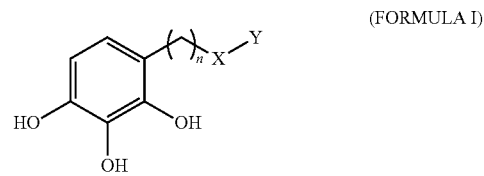
(FORMULA I)

wherein:
n is 0, 1, 2, 3, 4 or 5;
X is NHC(O), C(O)NH, OC(O), C(O)O, C(O), or CH=N; and
Y is alkyl, heteroalkyl, cyclyl, heterocyclyl, aryl, or heteroaryl, each of which can be optionally substituted.

In some embodiments, the present invention provides a compound of Formula I:

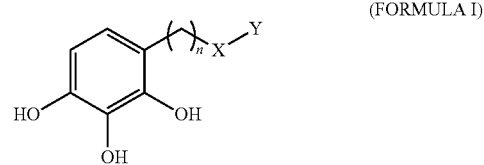
(FORMULA I)

or a prodrug, isomer, dimer, enantiomer, derivative, or pharmaceutically acceptable salt thereof, wherein:
n is 0, 1, 2, 3, 4 or 5;
X is NHC(O), C(O)NH, OC(O), C(O)O, C(O), or CH=N; and
Y is alkyl, heteroalkyl, cyclyl, heterocyclyl, aryl, or heteroaryl, each of which can be optionally substituted, provided the compound is not

COMPOUND CSRM617

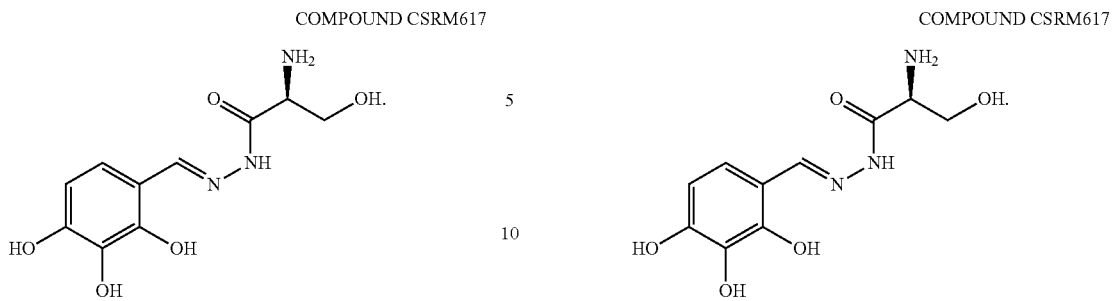

In some embodiments, the present invention provides a compound of Formula I:

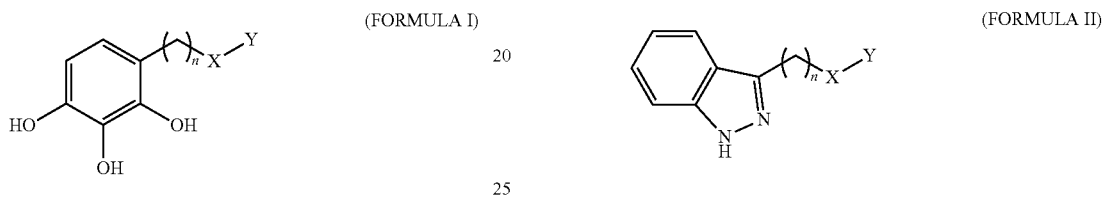

(FORMULA I)

wherein:
n is 0, 1, 2, 3, 4 or 5;
X is NHC(O), C(O)NH, OC(O), C(O)O, C(O), or CH=N;
Y is alkyl, heteroalkyl, cyclyl, heterocyclyl, aryl, or heteroaryl, each of which can be optionally substituted; and any pharmaceutically acceptable salt thereof, provided the compound is not

COMPOUND CSRM617

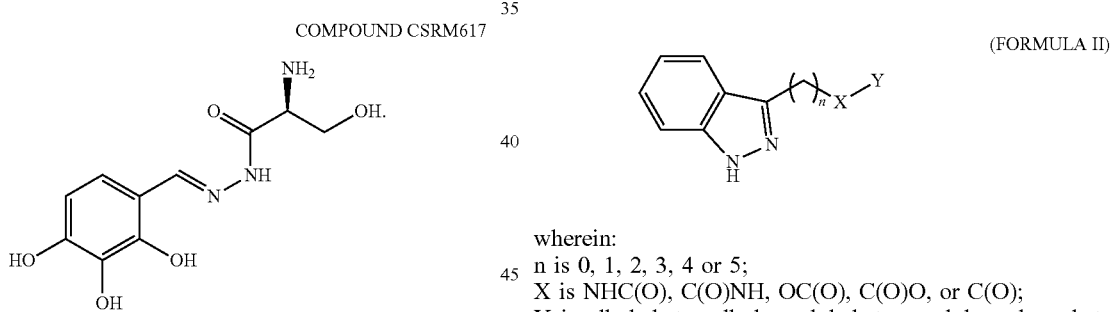

In some embodiments, the present invention provides a compound of Formula I:

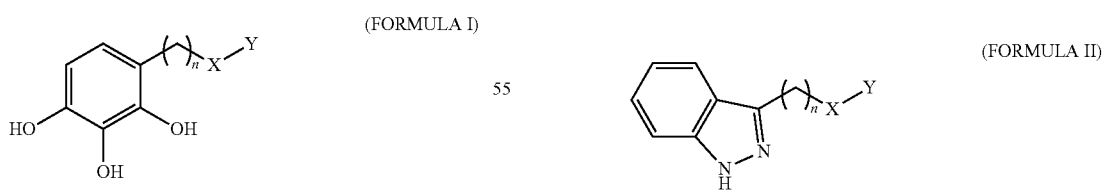

(FORMULA I)

wherein:
n is 0, 1, 2, 3, 4 or 5;
X is NHC(O), C(O)NH, OC(O), C(O)O, C(O), or CH=N; and
Y is alkyl, heteroalkyl, cyclyl, heterocyclyl, aryl, or heteroaryl, each of which can be optionally substituted, provided the compound is not

COMPOUND CSRM617

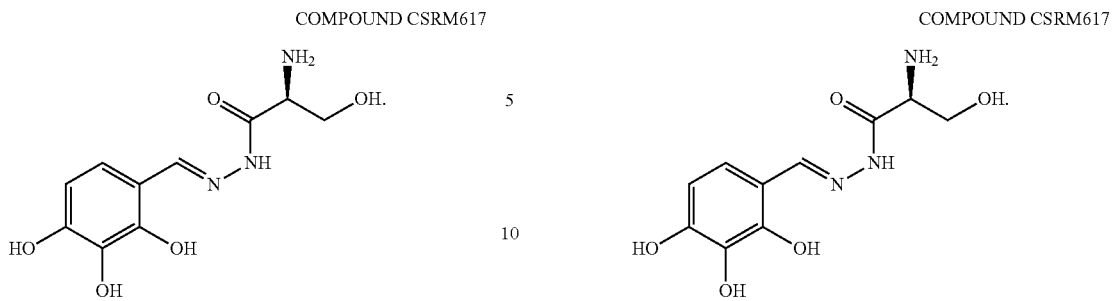

In some embodiments, the present invention provides a compound of Formula II:

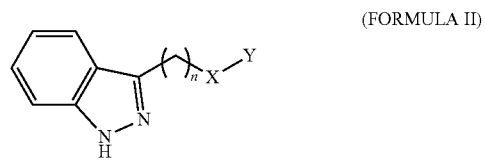

(FORMULA II)

or a prodrug, isomer, dimer, enantiomer, derivative, or pharmaceutically acceptable salt thereof, wherein:
n is 0, 1, 2, 3, 4 or 5;
X is NHC(O), C(O)NH, OC(O), C(O)O, or C(O); and
Y is alkyl, heteroalkyl, cyclyl, heterocyclyl, aryl, or heteroaryl, each of which can be optionally substituted.

In some embodiments, the present invention provides a compound of Formula II:

(FORMULA II)

wherein:
n is 0, 1, 2, 3, 4 or 5;
X is NHC(O), C(O)NH, OC(O), C(O)O, or C(O);
Y is alkyl, heteroalkyl, cyclyl, heterocyclyl, aryl, or heteroaryl, each of which can be optionally substituted; and
any pharmaceutically acceptable salt thereof.

In some embodiments, the present invention provides a compound of Formula II:

(FORMULA II)

wherein:
n is 0, 1, 2, 3, 4 or 5;
X is NHC(O), C(O)NH, OC(O), C(O)O, or C(O); and
Y is alkyl, heteroalkyl, cyclyl, heterocyclyl, aryl, or heteroaryl, each of which can be optionally substituted.

In some embodiments, the present invention provides a compound of Formula III:

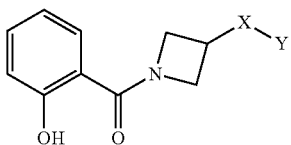

(FORMULA III)

or a prodrug, isomer, dimer, enantiomer, derivative, or pharmaceutically acceptable salt thereof, wherein:
X is NH, or O; and
Y is alkyl, heteroalkyl, cyclyl, heterocyclyl, aryl, or heteroaryl, each of which can be optionally substituted.

In some embodiments, the present invention provides a compound of Formula III:

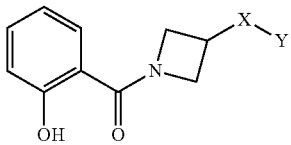

(FORMULA III)

wherein:
X is NH, or O;
Y is alkyl, heteroalkyl, cyclyl, heterocyclyl, aryl, or heteroaryl, each of which can be optionally substituted; and
any pharmaceutically acceptable salt thereof.

In some embodiments, the present invention provides a compound of Formula III:

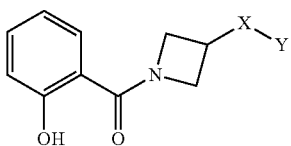

(FORMULA III)

wherein:
X is NH, or O;
Y is alkyl, heteroalkyl, cyclyl, heterocyclyl, aryl, or heteroaryl, each of which can be optionally substituted.

In some embodiments, the present invention provides a compound of Formula IV:

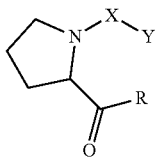

(FORMULA IV)

or a prodrug, isomer, dimer, enantiomer, derivative, or pharmaceutically acceptable salt thereof, wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5; and
R is H, CH$_3$, alkyl, NH$_2$, or OR', where R' is H, CH$_3$, or alkyl.

In some embodiments, the present invention provides a compound of Formula IV:

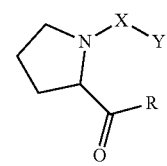

(FORMULA IV)

wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5;
R is H, CH$_3$, alkyl, NH$_2$, or OR', where R' is H, CH$_3$, or alkyl; and any pharmaceutically acceptable salt thereof.

In some embodiments, the present invention provides a compound of Formula IV:

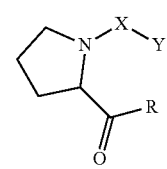

(FORMULA IV)

wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5; and
R is H, CH$_3$, alkyl, NH$_2$, or OR', where R' is H, CH$_3$, or alkyl.

In some embodiments, the present invention provides a compound of Formula V:

(FORMULA V)

or a prodrug, isomer, dimer, enantiomer, derivative, or pharmaceutically acceptable salt thereof, wherein:
Y is alkyl, heteroalkyl, cyclyl, heterocyclyl, aryl, or heteroaryl, each of which can be optionally substituted In some embodiments, the present invention provides a compound of Formula V:

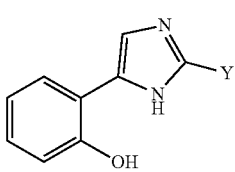

(FORMULA V)

wherein:
Y is alkyl, heteroalkyl, cyclyl, heterocyclyl, aryl, or heteroaryl, each of which can be optionally substituted; and any pharmaceutically acceptable salt thereof.

In some embodiments, the present invention provides a compound of Formula V:

(FORMULA V)

wherein:
Y is alkyl, heteroalkyl, cyclyl, heterocyclyl, aryl, or heteroaryl, each of which can be optionally substituted.

In some embodiments of compounds of Formula I or Formula II, n is 1, 2 or 3. In some embodiments of compounds of Formula I or Formula II, n is 2. In some embodiments of compounds of Formula I or Formula II, n is 1.

In some embodiments of compounds of Formula I or Formula II, X is NHC(O) or C(O)NH. In some embodiments of compounds of Formula I or Formula II, X is NHC(O). In some embodiments of compounds of Formula I or Formula II, X is C(O)NH.

In some embodiments of compounds of Formula I-Formula V, Y is an optionally substituted lower alkyl. In some embodiments of compounds of Formula I or II, Y is $C_1$-$C_6$ alkyl, 3-8 membered heterocyclyl, $C_6$-$C_8$ aryl, $C_3$-$C_8$ cyclyl, or 5-8 membered heteroaryl, each of which can be optionally substituted.

In some embodiments of compounds of Formula I-Formula V, Y can be an optionally substituted alkyl. In some embodiments, Y is alkyl optionally substituted with 1 or 2 substituents. In various embodiments, an optionally substituted alkyl is substituted with one or more substituents selected independently from the group consisting of amino, alkylamino, dialkylamino, hydroxyl, carbonyl (=O), NHOH, and amino substituted with an acyl group.

In some embodiments of compounds of Formula I-Formula V, Y can be an optionally substituted $C_1$-$C_4$ alkyl. In some embodiments, Y is $C_1$-$C_4$ alkyl optionally substituted with 1 or 2 substituents. In various embodiments, an optionally substituted $C_1$-$C_4$ alkyl is substituted with one or more substituents selected independently from the group consisting of amino, alkylamino, dialkylamino, hydroxyl, carbonyl (=O), NHOH, and amino substituted with an acyl group.

In various embodiments of compounds of Formula I-Formula V, Y is an ethyl, optionally substituted with two independently selected substituents.

In some embodiments of compounds of Formula I-Formula V, Y is an optionally substituted 6-membered heterocyclyl. In some embodiments, Y is a heterocyclyl optionally substituted with 1 or 2 substituents. In various embodiments, an optionally substituted heterocyclyl is substituted with one or more substituents selected independently from the group consisting of carbonyl (=O) and C(O)NH$_2$, halogen, carboxyl, and acyl. In some embodiments, Y is a heterocyclyl substituted with a carbonyl or C(O)NH$_2$ group.

In various embodiments of compounds of Formula I-Formula V, Y is a piperidine, optionally substituted with one substituent.

In various embodiments of compounds of Formula I-Formula V, Y is an optionally substituted aryl. Exemplary aryl for Y include, but are not limited to optionally substituted phenyl. In some embodiments, Y is an aryl optionally substituted with 1 or 2 substituents. In various embodiments, an optionally substituted aryl can be substituted with one or more substituents selected independently from the group consisting of C(O)NHOH, carbonyl (=O), C(O)NH$_2$, halogen, carboxyl, CF$_3$, hydroxyl, CH$_3$ and acyl. In some embodiments, Y is an aryl substituted with C(O)NHOH.

In various embodiments of compounds of Formula I-Formula V, Y is a phenyl, optionally substituted with one substituent.

In some embodiments of compounds of Formula I-Formula V, Y is —CH(NH$_2$)CH$_2$OH, —CH$_2$CH$_2$NHC(O)CH$_3$, —CH$_2$C(O)NHOH, piperidinecarbxamide, piperidone, or substituted phenyl.

In some embodiments of compounds of Formula I-Formula V, Y is

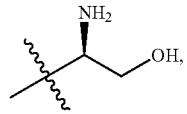

—CH$_2$CH$_2$NHC(O)CH$_3$, —CH$_2$C(O)NHOH,

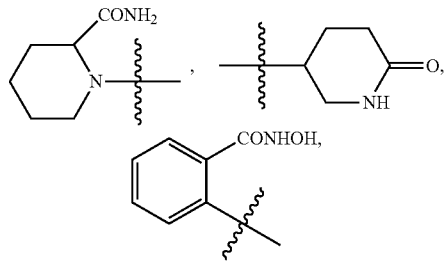

—NHC(O)CH(NH$_2$)CH2OH, —C(O)CH(NH$_2$)CH$_2$OH, —C(O)CH(NH$_2$)CH$_2$OH, or —CH(NH$_2$)CH$_2$OH.

In some embodiments of compounds of Formula I-Formula V, Y is

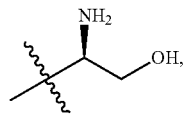

—CH$_2$CH$_2$NHC(O)CH$_3$, —CH$_2$C(O)NHOH,

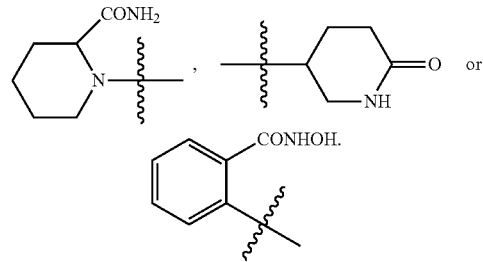

or

In some embodiments of compounds of Formula I-Formula V, Y is
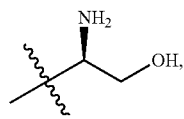 [SMILES: *[C@@H](N)CO]
—CH₂CH₂NHC(O)CH₃, —CH₂C(O)NHOH,
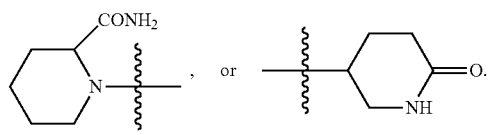 [SMILES: *N1CCCCC1C(N)=O ; *C1CCC(=O)NC1]
In some embodiments of compounds of Formula I, Y is
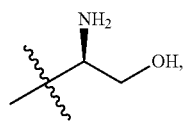 [SMILES: *[C@@H](N)CO]
CH₂CH₂NHC(O)CH₃, —CH₂C(O)NHOH,
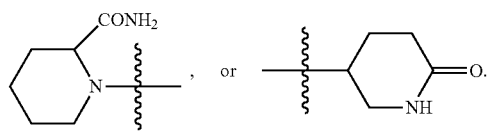
Various embodiments of the present invention provide a compound selected from:
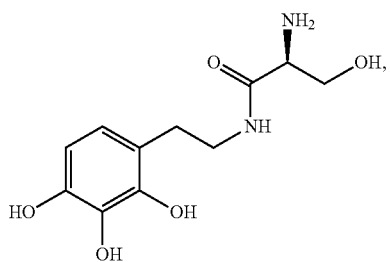 [SMILES: N[C@@H](CO)C(=O)NCCc1ccc(O)c(O)c1O]
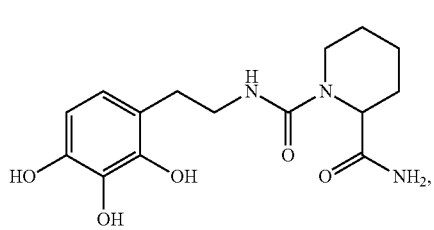
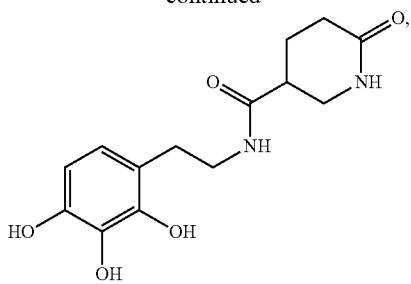
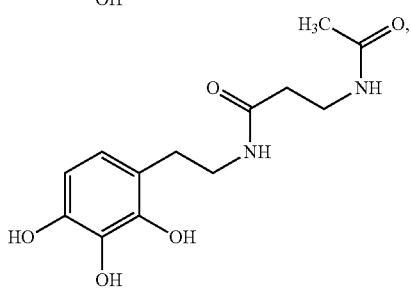
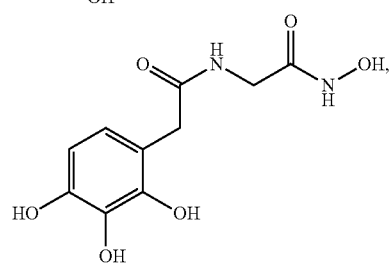
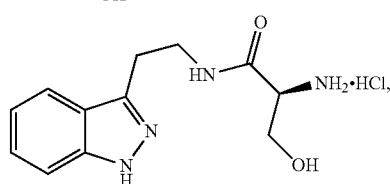
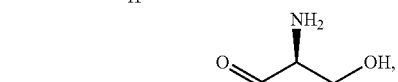
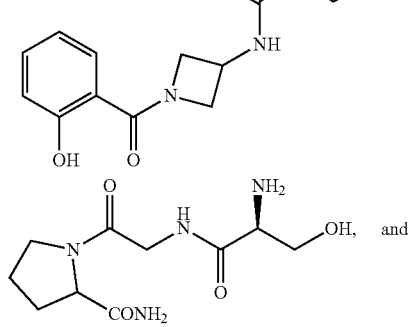
and
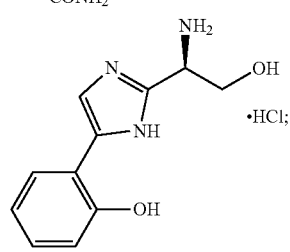
or a prodrug, an isomer, dimer, enantiomer, derivative, or pharmaceutically acceptable salt thereof.

Various embodiments of the present invention provide a compound selected from:
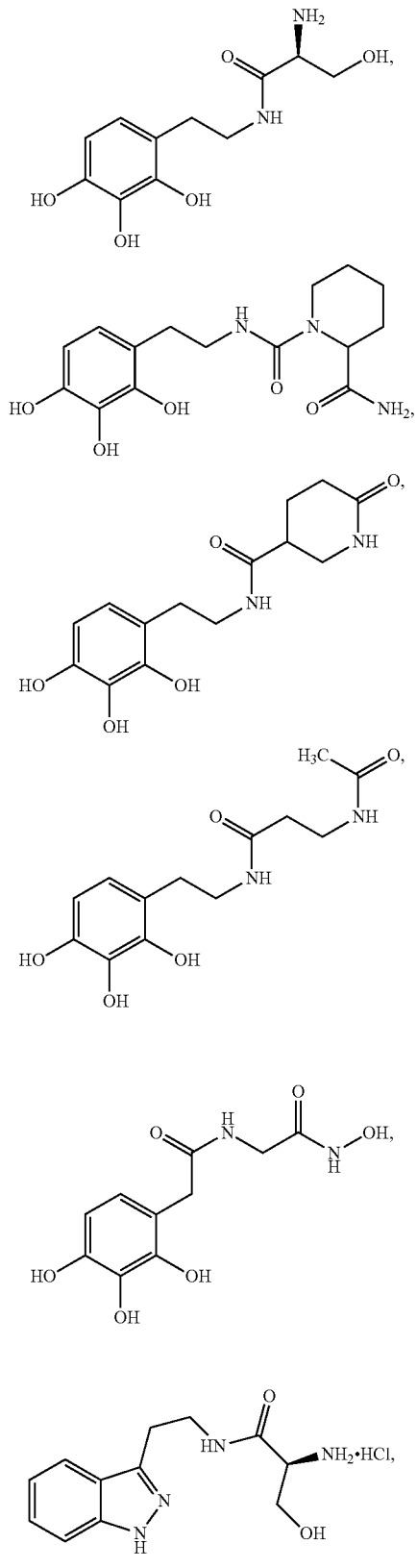
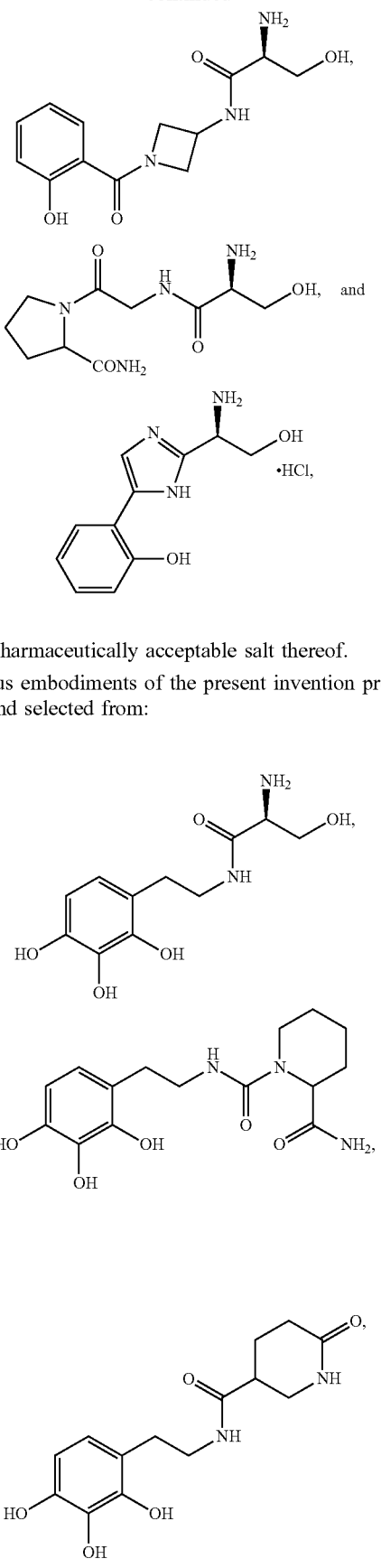
or any pharmaceutically acceptable salt thereof.
Various embodiments of the present invention provide a compound selected from:

39
-continued
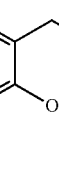
Various embodiments of the present invention provide a compound selected from:
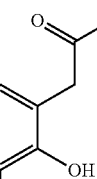
40
-continued
or a prodrug, an isomer, dimer, enantiomer, derivative, or pharmaceutically acceptable salt thereof.
Various embodiments of the present invention provide a compound selected from:

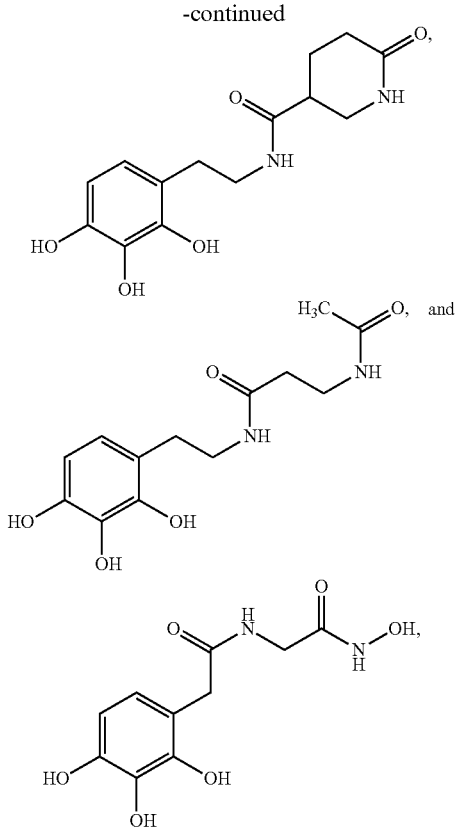

or any pharmaceutically acceptable salt thereof.

Various embodiments of the present invention provide a compound selected from:

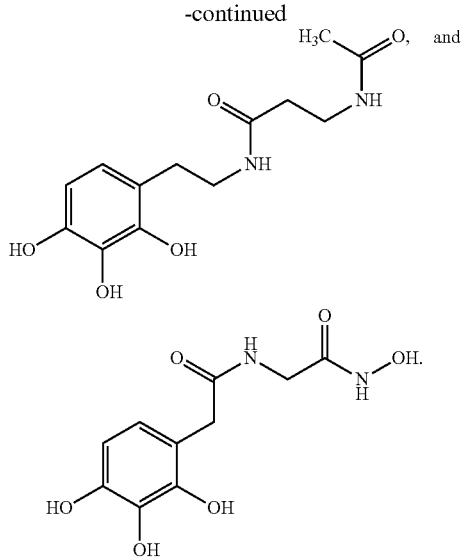

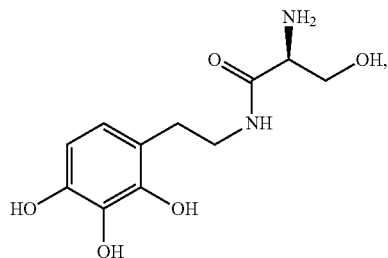

Various embodiments of the present invention provide a compound selected from:

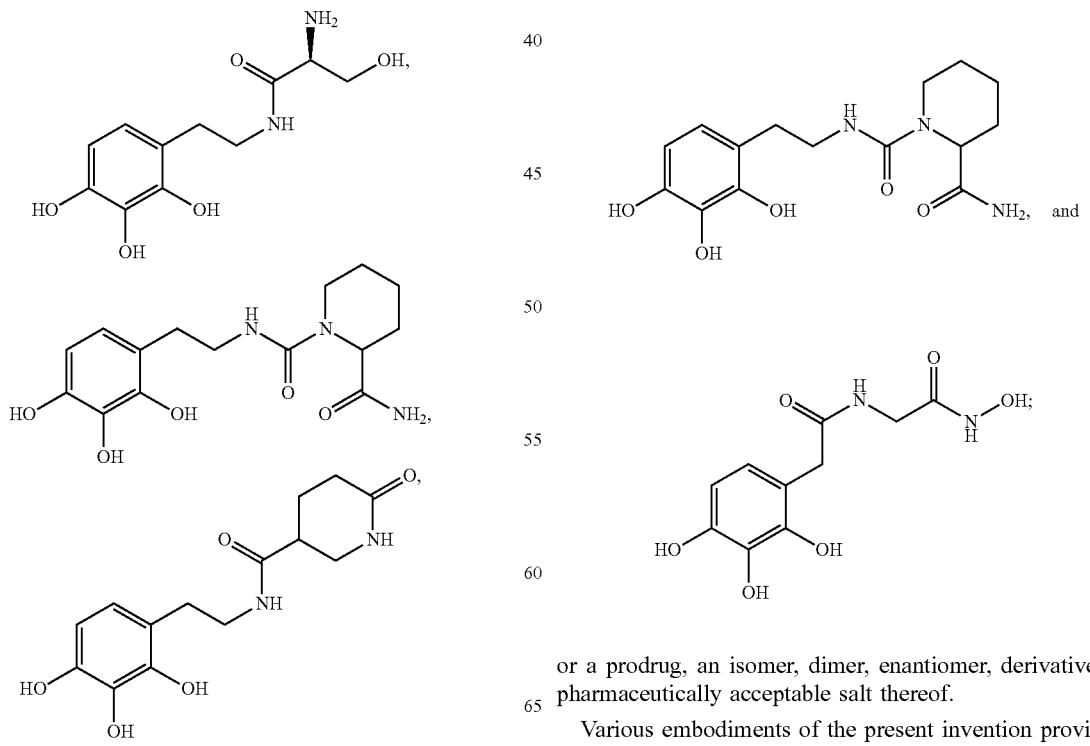

or a prodrug, an isomer, dimer, enantiomer, derivative, or pharmaceutically acceptable salt thereof.

Various embodiments of the present invention provide a compound selected from:

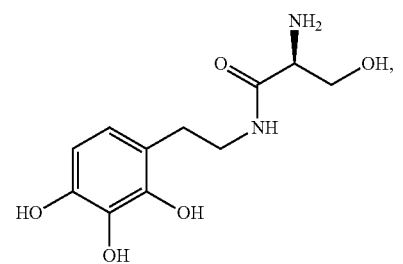 [SMILES: N[C@@H](CO)C(=O)NCCc1ccc(O)c(O)c1O]

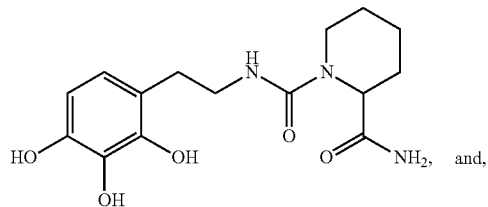

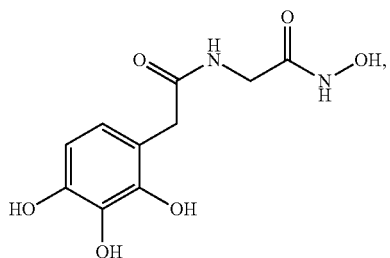

or any pharmaceutically acceptable salt thereof.

Various embodiments of the present invention provide a compound selected from:

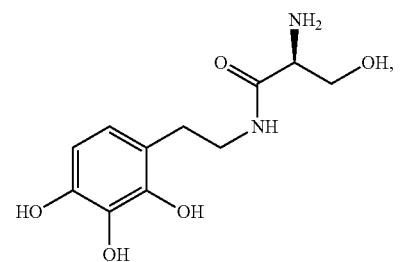

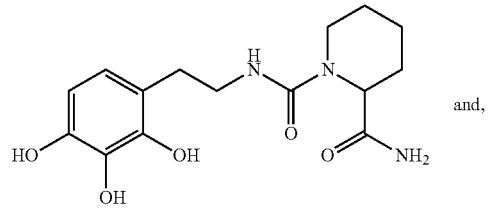

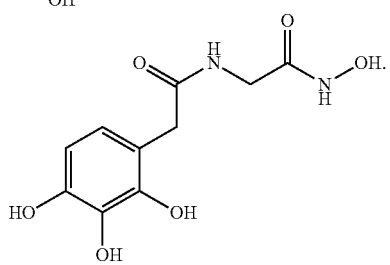

Various embodiments of the present invention provide a compound selected from:

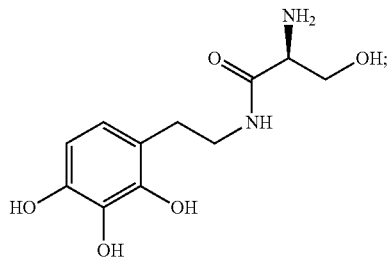

or a prodrug, an isomer, dimer, enantiomer, derivative, or pharmaceutically acceptable salt thereof.

Various embodiments of the present invention provide a compound selected from:

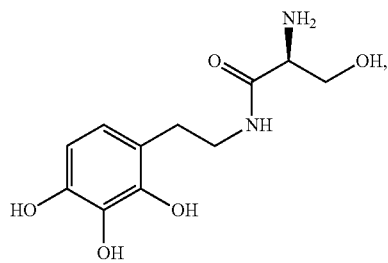

or any pharmaceutically acceptable salt thereof.

Various embodiments of the present invention provide a compound selected from:

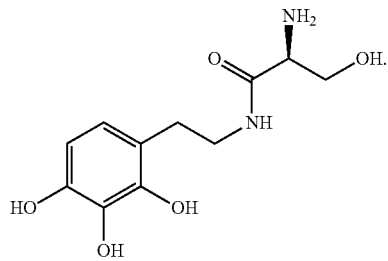 [SMILES: N[C@@H](CO)C(=O)NCCc1ccc(O)c(O)c1O]

Various embodiments of the present invention provide a compound selected from:

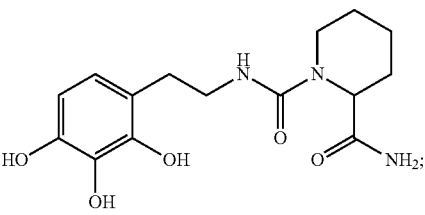 [SMILES: NC(=O)C1CCCCN1C(=O)NCCc1ccc(O)c(O)c1O]

or a prodrug, an isomer, dimer, enantiomer, derivative, or pharmaceutically acceptable salt thereof.

Various embodiments of the present invention provide a compound selected from:

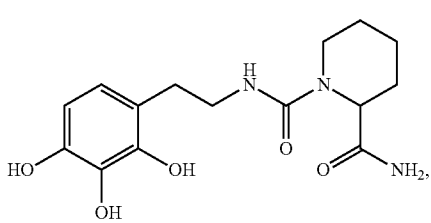

or any pharmaceutically acceptable salt thereof.

Various embodiments of the present invention provide a compound selected from:

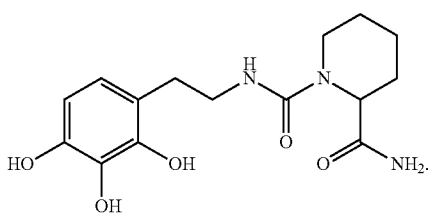 [SMILES: NC(=O)C1CCCCN1C(=O)NCCc1ccc(O)c(O)c1O]

Various embodiments of the present invention provide a compound selected from:

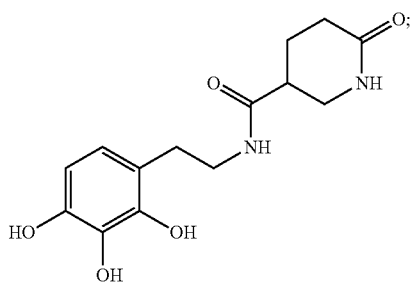 [SMILES: O=C1CCC(C(=O)NCCc2ccc(O)c(O)c2O)CN1]

or a prodrug, an isomer, dimer, enantiomer, derivative, or pharmaceutically acceptable salt thereof.

Various embodiments of the present invention provide a compound selected from:

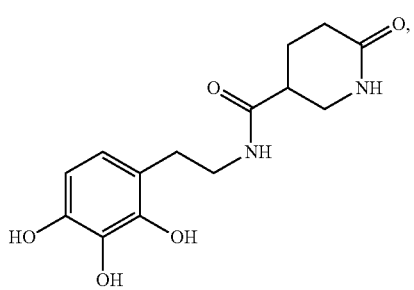 [SMILES: O=C1CCC(C(=O)NCCc2ccc(O)c(O)c2O)CN1]

or any pharmaceutically acceptable salt thereof.

Various embodiments of the present invention provide a compound selected from:

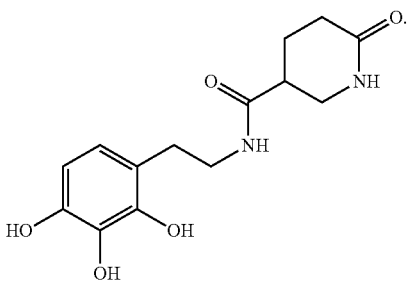 [SMILES: O=C1CCC(C(=O)NCCc2ccc(O)c(O)c2O)CN1]

Various embodiments of the present invention provide a compound selected from:

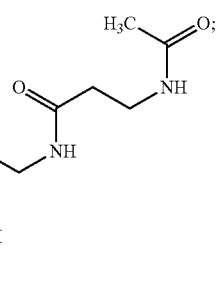

or a prodrug, an isomer, dimer, enantiomer, derivative, or pharmaceutically acceptable salt thereof.

Various embodiments of the present invention provide a compound selected from:

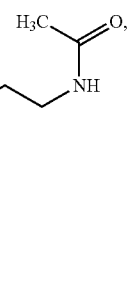

or any pharmaceutically acceptable salt thereof.

Various embodiments of the present invention provide a compound selected from:

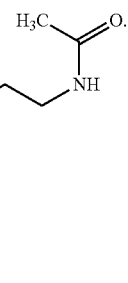

Various embodiments of the present invention provide a compound selected from:

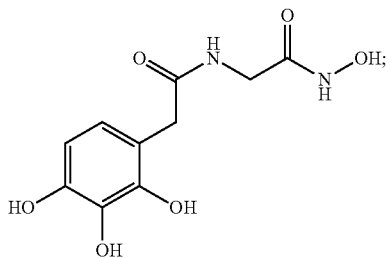 [SMILES: O=C(CNC(=O)Cc1ccc(O)c(O)c1O)NO]

or a prodrug, an isomer, dimer, enantiomer, derivative, or pharmaceutically acceptable salt thereof.

Various embodiments of the present invention provide a compound selected from:

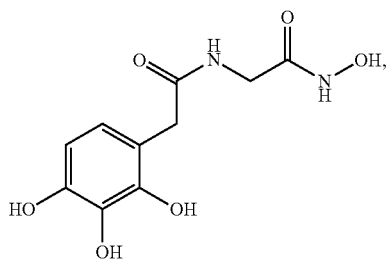 [SMILES: O=C(CNC(=O)Cc1ccc(O)c(O)c1O)NO]

or any pharmaceutically acceptable salt thereof.

Various embodiments of the present invention provide a compound selected from:

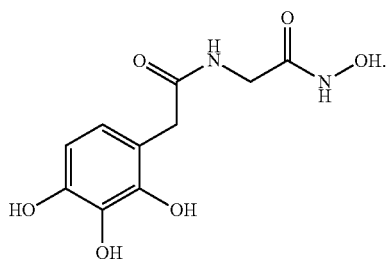 [SMILES: O=C(CNC(=O)Cc1ccc(O)c(O)c1O)NO]

Various embodiments of the present invention provide a compound selected from:

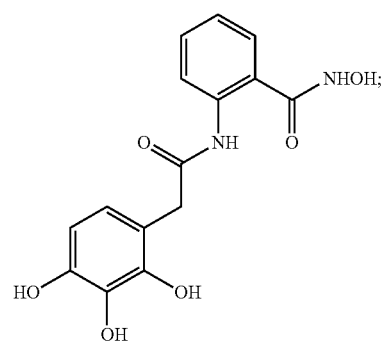

or a prodrug, isomer, dimer, enantiomer, derivative, or pharmaceutically acceptable salt thereof.

Various embodiments of the present invention provide a compound selected from:

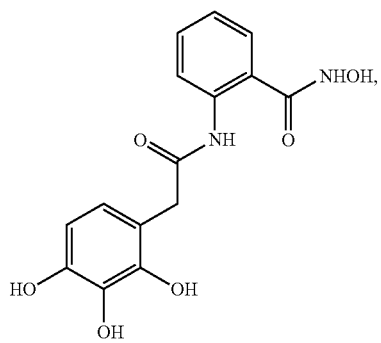

or any pharmaceutically acceptable salt thereof.

Various embodiments of the present invention provide a compound selected from:

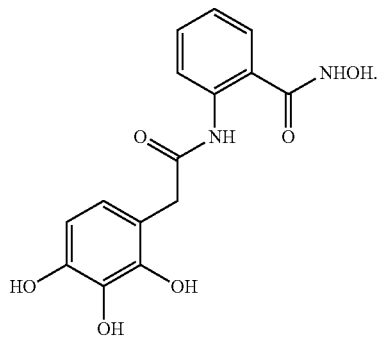

Various embodiments of the present invention provide a compound of Formula I, wherein the compound is selected from:

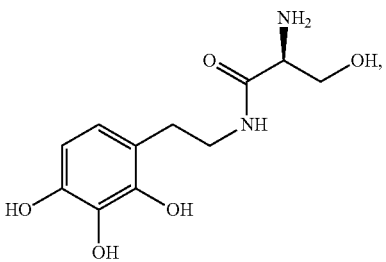 [SMILES: N[C@@H](CO)C(=O)NCCc1ccc(O)c(O)c1O]

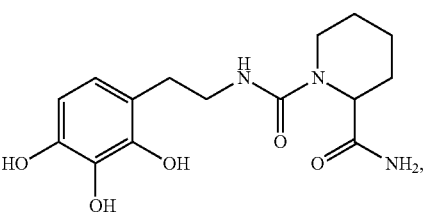 [SMILES: NC(=O)C1CCCCN1C(=O)NCCc1ccc(O)c(O)c1O]

-continued

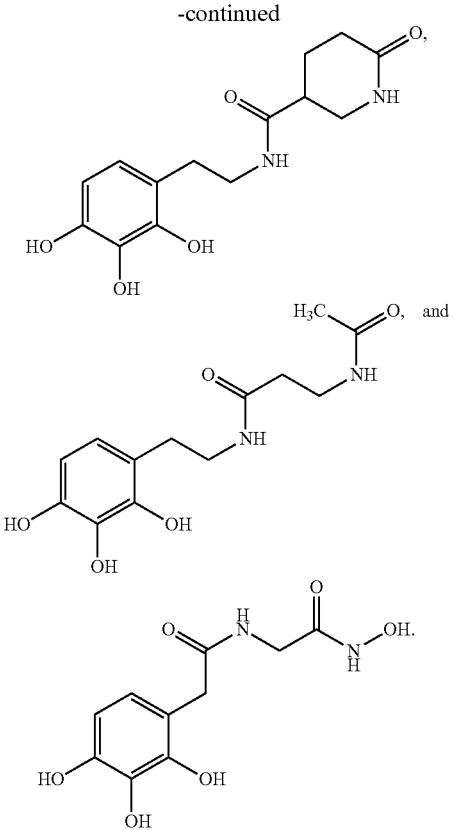

Various embodiments of the present invention provide a compound of Formula I, wherein the compound is selected from:

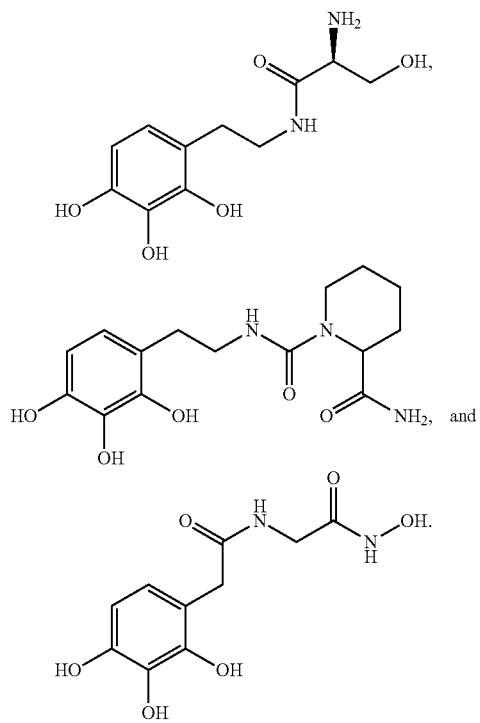

Various embodiments of the present invention provide a compound of Formula I, wherein the compound is selected from:

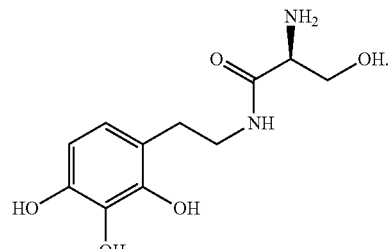

Various embodiments of the present invention provide a compound of Formula I, wherein the compound is selected from:

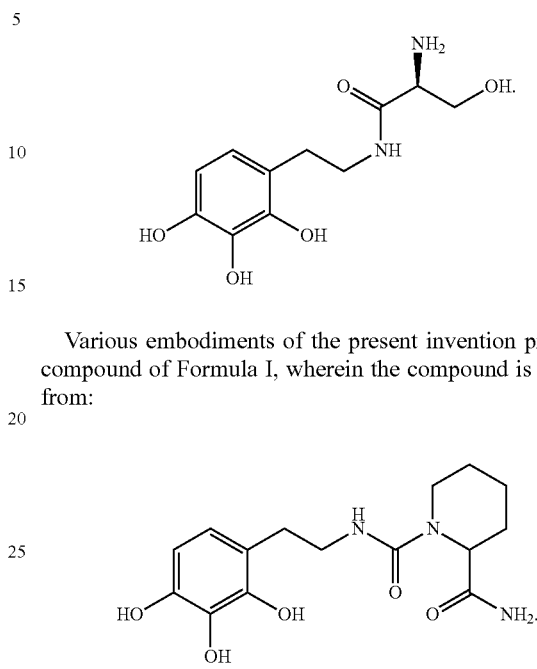

Various embodiments of the present invention provide a compound of Formula I, wherein the compound is selected from:

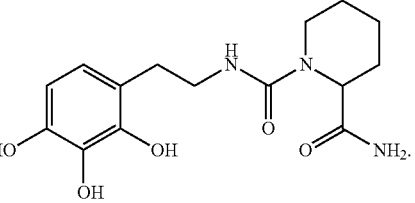

Various embodiments of the present invention provide a compound of Formula I, wherein the compound is selected from:

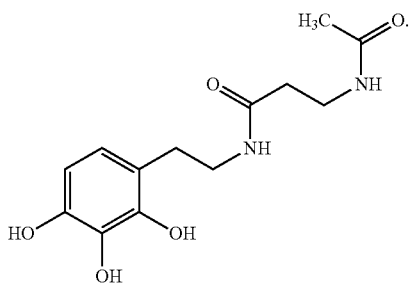 [SMILES: CC(=O)NCCC(=O)NCCc1ccc(O)c(O)c1O]

Various embodiments of the present invention provide a compound of Formula I, wherein the compound is selected from:

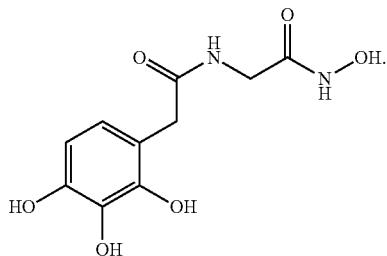 [SMILES: O=C(CNC(=O)Cc1ccc(O)c(O)c1O)NO]

Various embodiments of the present invention provide a compound of Formula I, wherein the compound is selected from:

COMPOUND CSRM617

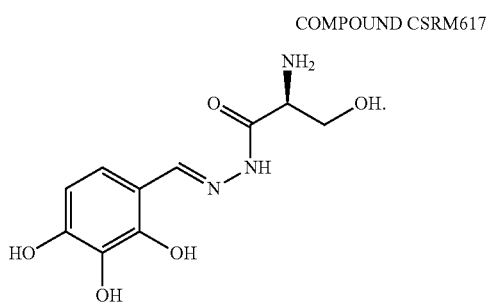 [SMILES: N[C@@H](CO)C(=O)N/N=C/c1ccc(O)c(O)c1O]

Various embodiments of the present invention provide a compound of Formula I, provided the compound is not:

COMPOUND CSRM617

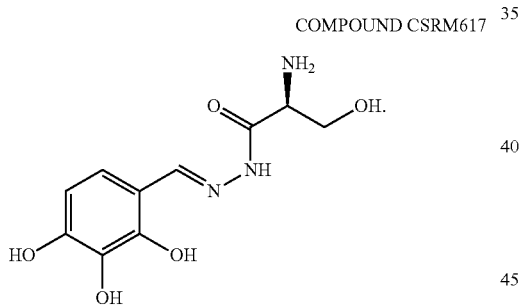

Various embodiments of the present invention provide a compound of Formula I, wherein the compound is selected from:

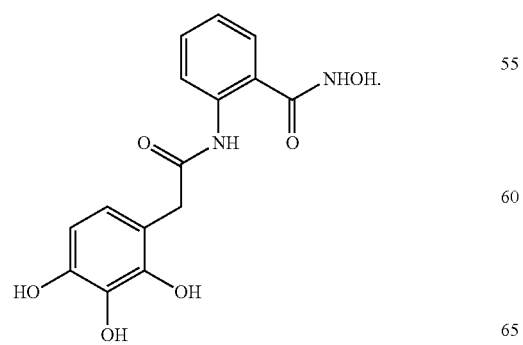

Various embodiments of the present invention provide a compound of Formula II, wherein the compound is selected from:

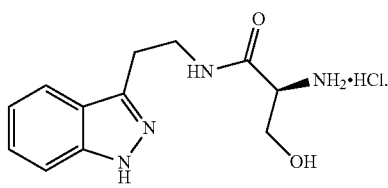

Various embodiments of the present invention provide a compound of Formula III, wherein the compound is selected from:

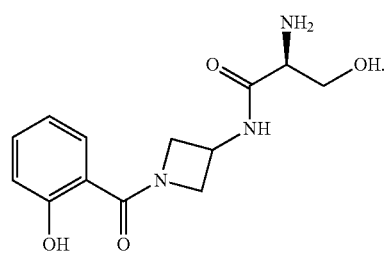 [SMILES: N[C@@H](CO)C(=O)NC1CN(C(=O)c2ccccc2O)C1]

Various embodiments of the present invention provide a compound of Formula IV, wherein the compound is selected from:

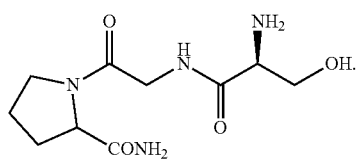 [SMILES: NC(=O)C1CCCN1C(=O)CNC(=O)[C@@H](N)CO]

Various embodiments of the present invention provide a compound of Formula V, wherein the compound is selected from:

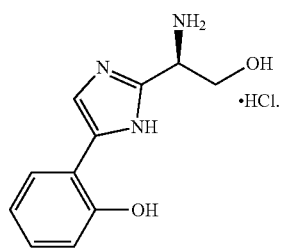

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., $(C_6-C_{10})aryl(C_0-C_3)alkyl$ includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Non-limiting examples of substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

As used herein, the term "alkenyl" refers to unsaturated straight-chain, branched-chain or cyclic hydrocarbon radicals having at least one carbon-carbon double bond. $C_x$ alkenyl and $C_x-C_y$ alkenyl are typically used where X and Y indicate the number of carbon atoms in the chain. For example, $C_2-C_6$ alkenyl includes alkenyls that have a chain of between 2 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x-C_y$ alkynyl are typically used where X and Y indicate the number of carbon atoms in the chain. For example, $C_2-C_6$ alkynyl includes alkynls that have a chain of between 2 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkenyl, and alkynyl" radicals. Prefixes $C_x$ and $C_x-C_y$ are typically used where X and Y indicate the number of carbon atoms in the chain. For example, $C_1-C_6$ alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =$CR_aR_b$. Non-limiting examples of $R_a$ and $R_b$ are each independently hydrogen, alkyl, substituted alkyl, alkenyl, or substituted alkenyl. $C_x$ alkylidene and $C_x-C_y$ alkylidene are typically used where X and Y indicate the number of carbon atoms in the chain. For example, $C_2-C_6$ alkylidene includes methylidene (=$CH_2$), ethylidene (=$CHCH_3$), isopropylidene (=$C(CH_3)_2$), propylidene (=$CHCH_2CH_3$), allylidene (=CH—CH=$CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted $(C_1-C_3)$alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x-C_y$ aryl are typically used where X and Y indicate the number of carbon atoms in the ring system. For example, $C_6-C_{12}$ aryl includes aryls that have 6 to 12 carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzi soxazolyl, benzi sothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a sub stituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_X$ heteroaryl and $C_x$-$C_y$ heteroaryl are typically used where X and Y indicate the number of carbon atoms in the ring system. For example, $C_4$-$C_9$ heteroaryl includes heteroaryls that have 4 to 9 carbon atoms in the ring system. Heteroaryls include, but are not limited to, those derived from benzo[b] furan, benzo[b] thiophene, benzimidazole, imidazo[4,5-c] pyridine, quinazoline, thieno[2,3-c]pyridine, thieno[3,2-b] pyridine, thieno[2,3-b]pyridine, indolizine, imidazo[1,2a] pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a] pyrimidine, imidazo[1,5-c]pyrimidine, pyrrolo[2,3-b] pyridine, pyrrolo[2,3 cj pyridine, pyrrolo[3,2-c]pyridine, pyrrolo[3,2-b]pyridine, pyrrolo[2,3-d]pyrimidine, pyrrolo [3,2-d]pyrimidine, pyrrolo [2,3-b]pyrazine, pyrazolo[1,5-a] pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, IH-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cycyl are typically used where X and Y indicate the number of carbon atoms in the ring system. For example, $C_3$-$C_8$ cyclyl includes cyclyls that have 3 to 8 carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3,—CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heterocyclyl and $C_x$-$C_y$ heterocyclyl are typically used where X and Y indicate the number of carbon atoms in the ring system. For example, $C_4$-$C_9$ heterocyclyl includes heterocyclyls that have 4-9 carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$-pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$-pyridinyl, and the like.

The term "alkylamino" means —NH(alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino"—NH-(alkyl)-(cycloalkyl), such as —NHCH$_2$-cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH3) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

Various embodiments of the present invention provide prodrugs, isomers, dimers, enantiomers, and derivatives of a compound selected from Formula I-Formula V.

Various embodiments of the present invention provide prodrugs, isomers, dimers, enantiomers, and derivatives of a compound selected from Formula I-Formula V, provided that the compound is not

COMPOUND CSRM617

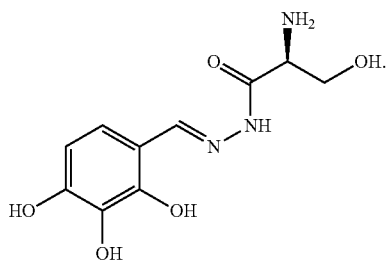

Various embodiments of the present invention provide prodrugs, isomers, dimers, enantiomers, and derivatives of a compound selected from:

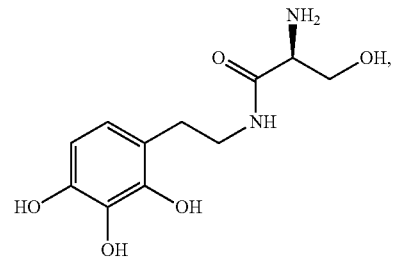

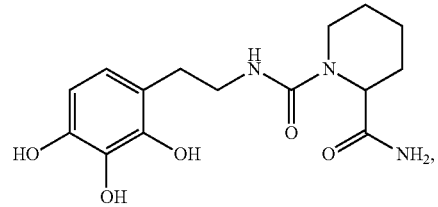

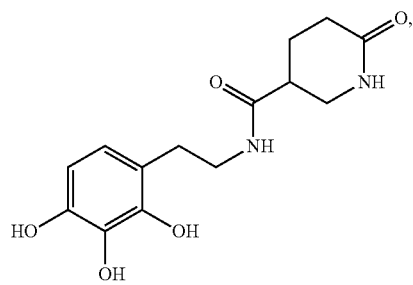

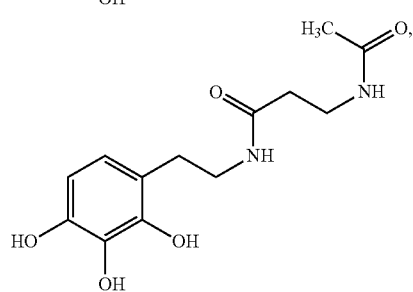

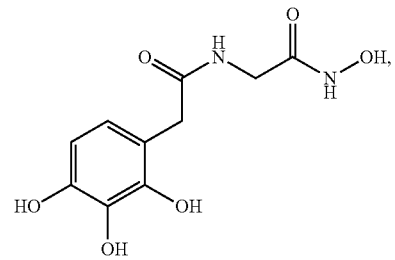

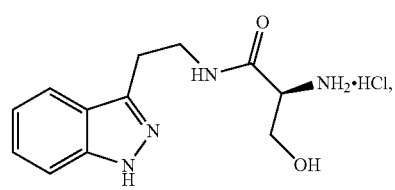

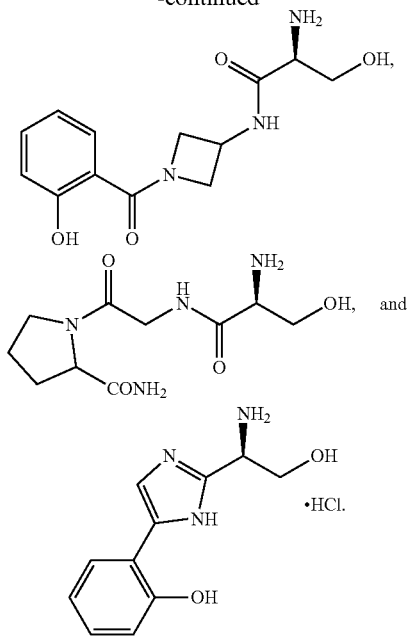
Various embodiments of the present invention provide prodrugs, isomers, dimers, enantiomers, and derivatives of a compound selected from:
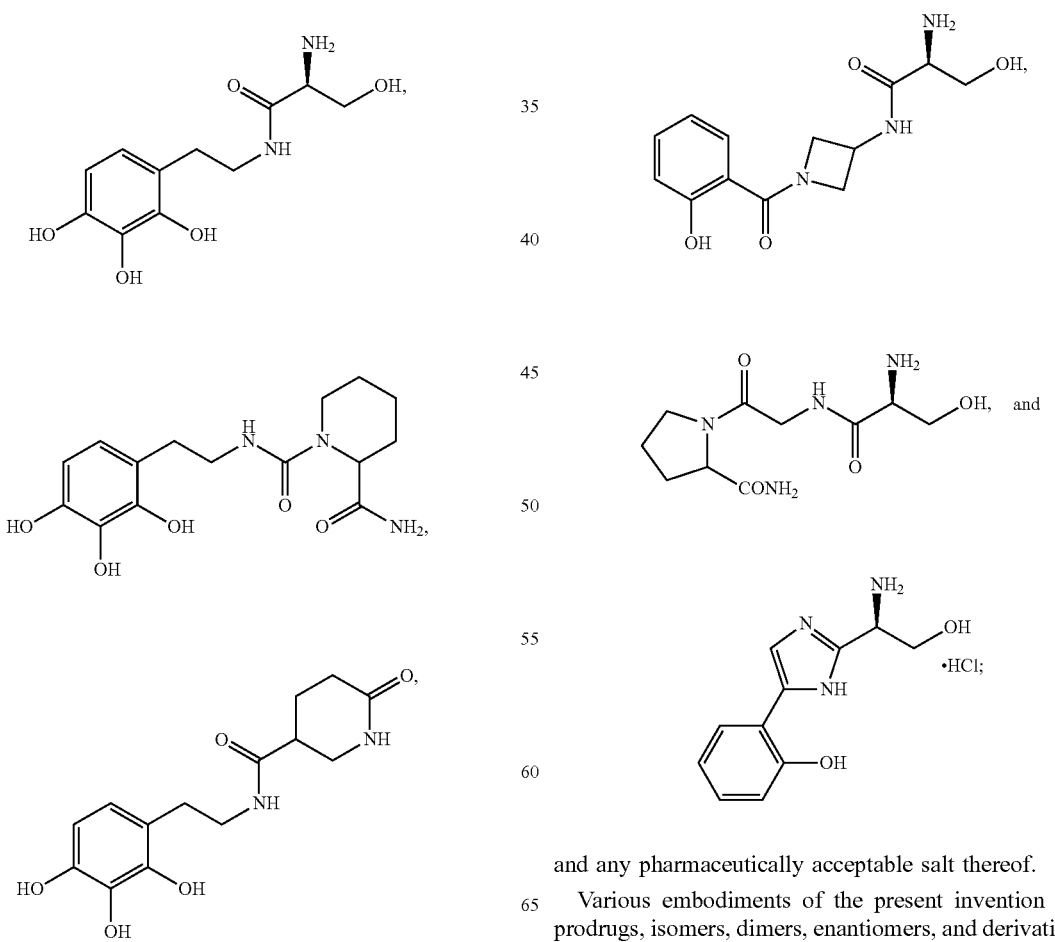
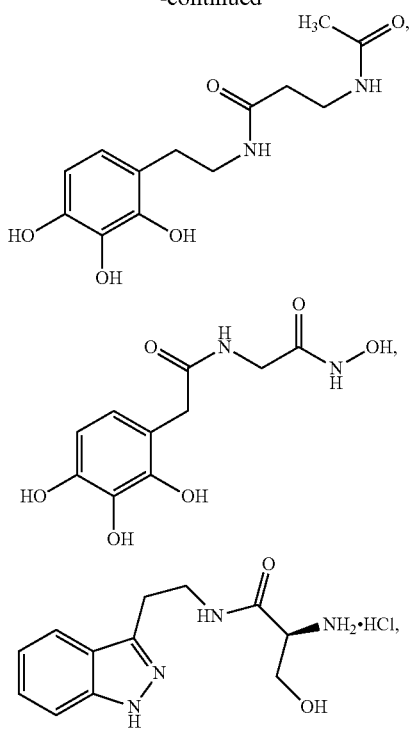
and any pharmaceutically acceptable salt thereof.
Various embodiments of the present invention provide prodrugs, isomers, dimers, enantiomers, and derivatives of a compound selected from:

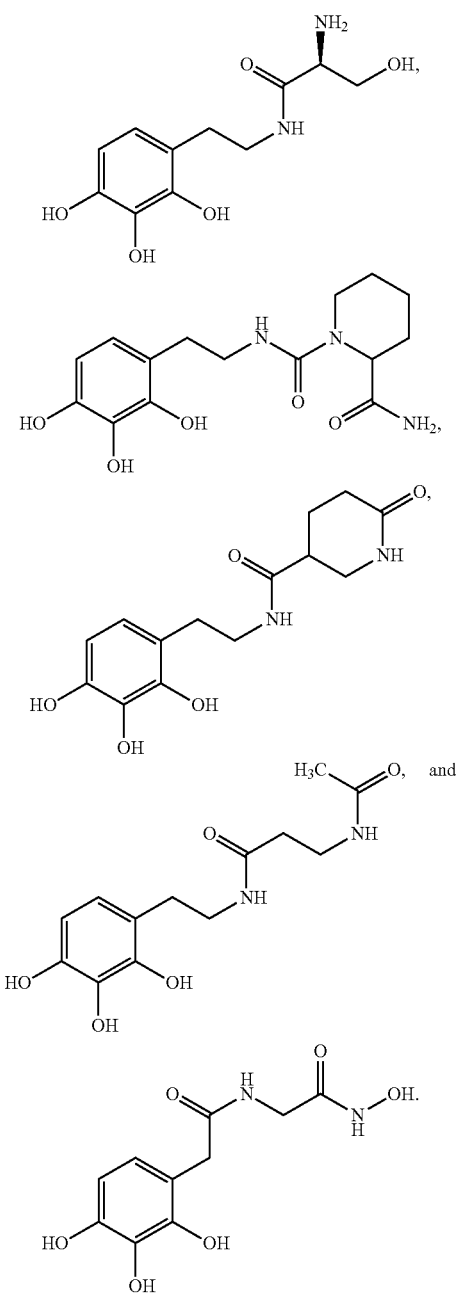 [SMILES: N[C@@H](CO)C(=O)NCCc1ccc(O)c(O)c1O ; NC(=O)C1CCCCN1C(=O)NCCc1ccc(O)c(O)c1O ; O=C1CCC(C(=O)NCCc2ccc(O)c(O)c2O)CN1 ; CC(=O)NCCC(=O)NCCc1ccc(O)c(O)c1O ; "and" ; O=C(CNC(=O)Cc1ccc(O)c(O)c1O)NO]
Various embodiments of the present invention provide prodrugs, isomers, dimers, enantiomers, and derivatives of a compound selected from:
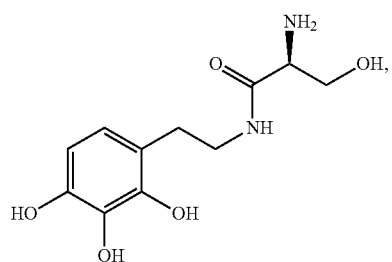 [SMILES: N[C@@H](CO)C(=O)NCCc1ccc(O)c(O)c1O]
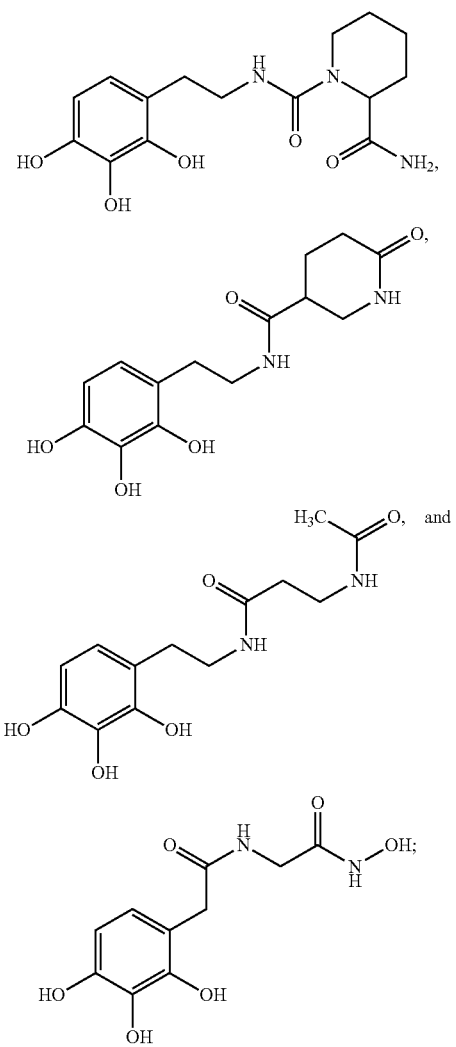
and any pharmaceutically acceptable salt thereof.
Various embodiments of the present invention provide prodrugs, isomers, dimers, enantiomers, and derivatives of a compound selected from:
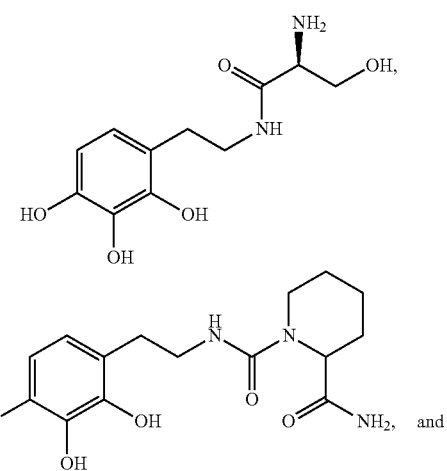

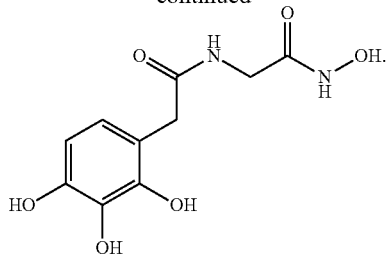

Various embodiments of the present invention provide prodrugs, isomers, dimers, enantiomers, and derivatives of a compound selected from:

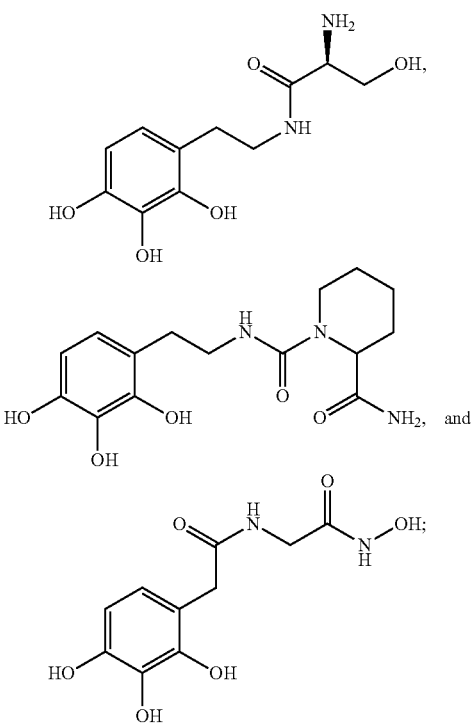

and any pharmaceutically acceptable salt thereof.

Various embodiments of the present invention provide prodrugs, isomers, dimers, enantiomers, and derivatives of a compound selected from:

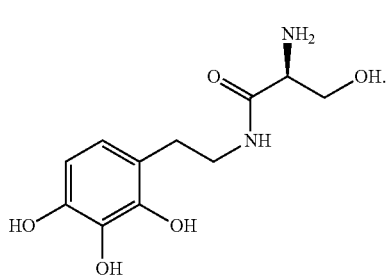 [SMILES: N[C@@H](CO)C(=O)NCCc1ccc(O)c(O)c1O]

Various embodiments of the present invention provide prodrugs, isomers, dimers, enantiomers, and derivatives of a compound selected from:

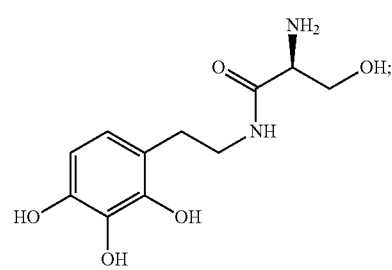

and any pharmaceutically acceptable salt thereof.

Various embodiments of the present invention provide prodrugs, isomers, dimers, enantiomers, and derivatives of a compound selected from:

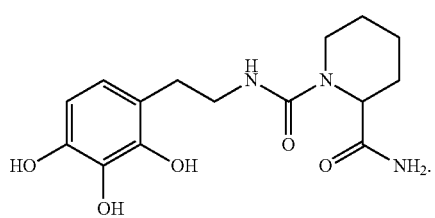 [SMILES: NC(=O)C1CCCCN1C(=O)NCCc1ccc(O)c(O)c1O]

Various embodiments of the present invention provide prodrugs, isomers, dimers, enantiomers, and derivatives of a compound selected from:

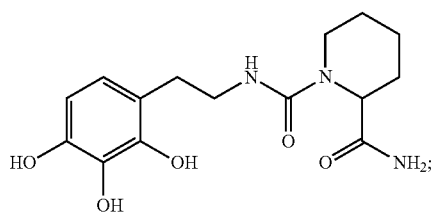 [SMILES: NC(=O)C1CCCCN1C(=O)NCCc1ccc(O)c(O)c1O]

and any pharmaceutically acceptable salt thereof.

Various embodiments of the present invention provide prodrugs, isomers, dimers, enantiomers, and derivatives of a compound selected from:

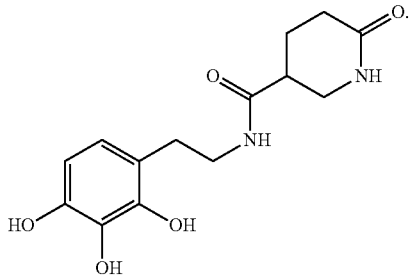 [SMILES: O=C1CCC(C(=O)NCCc2ccc(O)c(O)c2O)CN1]

Various embodiments of the present invention provide prodrugs, isomers, dimers, enantiomers, and derivatives of a compound selected from:

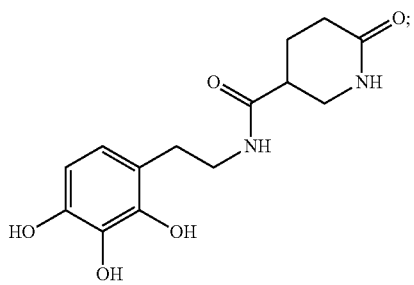 [SMILES: O=C1CCC(C(=O)NCCc2ccc(O)c(O)c2O)CN1]

and any pharmaceutically acceptable salt thereof.

Various embodiments of the present invention provide prodrugs, isomers, dimers, enantiomers, and derivatives of a compound selected from:

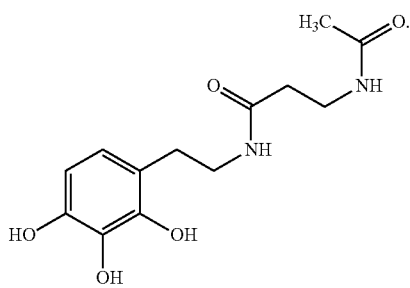 [SMILES: CC(=O)NCCC(=O)NCCc1ccc(O)c(O)c1O]

Various embodiments of the present invention provide prodrugs, isomers, dimers, enantiomers, and derivatives of a compound selected from:

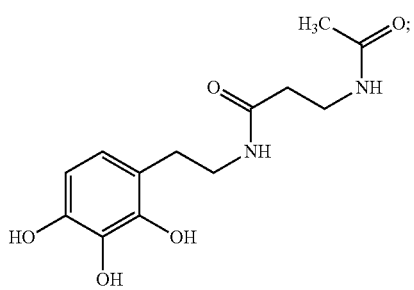 [SMILES: CC(=O)NCCC(=O)NCCc1ccc(O)c(O)c1O]

and any pharmaceutically acceptable salt thereof.

Various embodiments of the present invention provide prodrugs, isomers, dimers, enantiomers, and derivatives of a compound selected from:

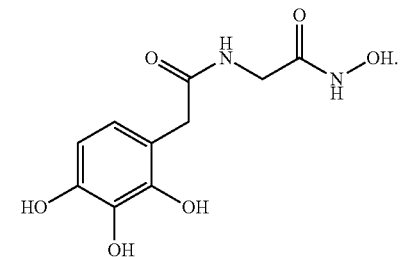

Various embodiments of the present invention provide prodrugs, isomers, dimers, enantiomers, and derivatives of a compound selected from:

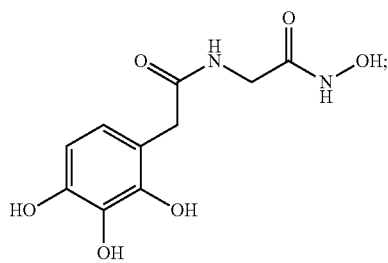 [SMILES: O=C(CNC(=O)Cc1ccc(O)c(O)c1O)NO]

and any pharmaceutically acceptable salt thereof.

Various embodiments of the present invention provide prodrugs, isomers, dimers, enantiomers, and derivatives of a compound selected from:

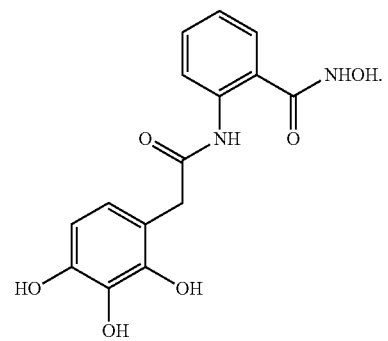

Various embodiments of the present invention provide prodrugs, isomers, dimers, enantiomers, and derivatives of a compound selected from:

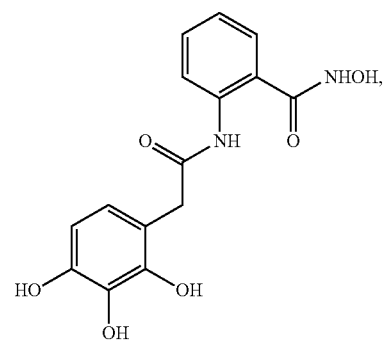

or any pharmaceutically acceptable salt thereof.

Various embodiments of the present invention provide prodrugs, isomers, dimers, enantiomers, and derivatives of a compound selected from:

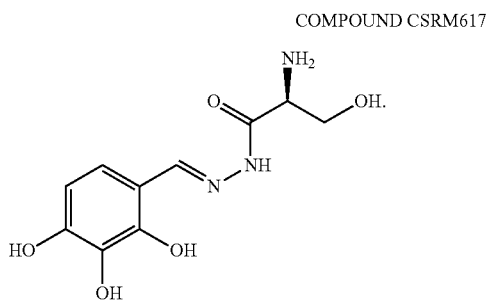 [SMILES: N[C@@H](CO)C(=O)N/N=C/c1ccc(O)c(O)c1O]
Various embodiments of the present invention provide prodrugs, isomers, dimers, enantiomers, and derivatives of a compound selected from:
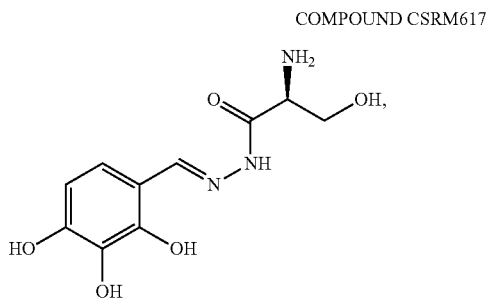 [SMILES: N[C@@H](CO)C(=O)N/N=C/c1ccc(O)c(O)c1O]
or any pharmaceutically acceptable salt thereof.
In various embodiments the present invention provides the following compounds as shown in Table 1.
TABLE 1
| Compound ID | Compound |
|---|---|
| CSRM617 | |
| 122 | |
| 123 | |
| 848 | |
| 844 | |
| 843 | |
| 121 | |
| 846 | |

TABLE 1-continued

| Compound ID | Compound |
|---|---|
| 847 | 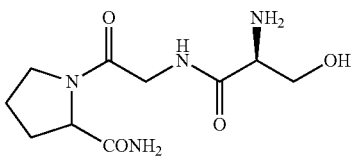 [SMILES: NC(=O)C1CCCN1C(=O)CNC(=O)[C@@H](N)CO] |
| 845 | 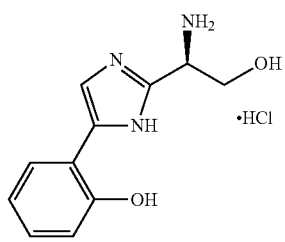 [SMILES: N[C@@H](CO)c1ncc(-c2ccccc2O)[nH]1 ; Cl] |

Various embodiments of the present invention provide a compound having the structure:

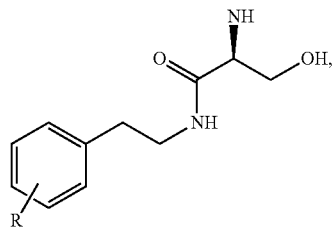

or a prodrug, isomer, dimer, enantiomer, derivative, or pharmaceutically acceptable salt thereof, wherein:
R is independently one or more of hydrogen or optionally substituted sub stituent.

Various embodiments of the present invention provide a compound having the structure:

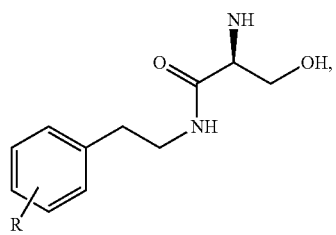

wherein:
R is independently one or more of hydrogen or optionally substituted sub stituent.

Various embodiments of the present invention provide a compound having the structure:

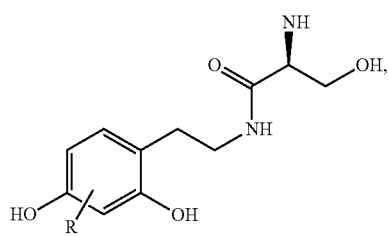

or a prodrug, isomer, dimer, enantiomer, derivative, or pharmaceutically acceptable salt thereof, wherein:
R is independently one or more of hydrogen or optionally substituted sub stituent.

Various embodiments of the present invention provide a compound having the structure:

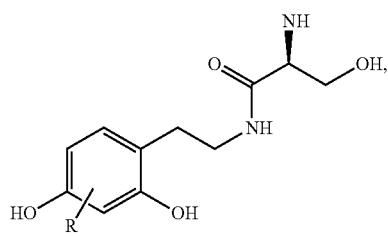

wherein:
R is independently one or more of hydrogen or optionally substituted substituent.

Various embodiments of the present invention provide a compound having the structure:

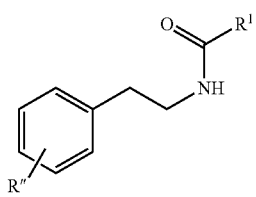

or a prodrug, isomer, dimer, enantiomer, derivative, or pharmaceutically acceptable salt thereof wherein:
R" is independently one or more of hydrogen or optionally substituted substituent; and
$R^1$ is hydrogen or optionally substituted substituent.

Various embodiments of the present invention provide a compound having the structure:

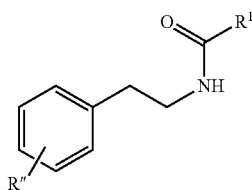

wherein:
R" is independently one or more of hydrogen or optionally substituted substituent; and
$R^1$ is hydrogen or optionally substituted substituent.

Various embodiments of the present invention provide a compound having the structure:

73

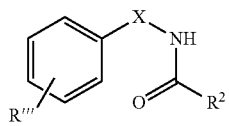

or a prodrug, isomer, dimer, enantiomer, derivative, or pharmaceutically acceptable salt thereof, wherein:
R''' is independently one or more of hydrogen or optionally substituted substituent;
$R^2$ is hydrogen or optionally substituted substituent; and
X is NHC(O), C(O)NH, OC(O), C(O)O, C(O), or CH=N.

Various embodiments of the present invention provide a compound having the structure:

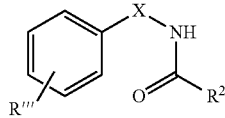

wherein:
R''' is independently one or more of hydrogen or optionally substituted substituent;
$R^2$ is hydrogen or optionally substituted substituent; and
X is NHC(O), C(O)NH, OC(O), C(O)O, C(O), or CH=N.

Various embodiments of the present invention provide a compound having the structure:

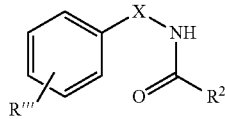

or a prodrug, isomer, dimer, enantiomer, derivative, or pharmaceutically acceptable salt thereof, wherein:
R''' is independently one or more of hydrogen or optionally substituted substituent;
$R^2$ is hydrogen or optionally substituted substituent; and
X is NHC(O), C(O)NH, OC(O), C(O)O, C(O), or CH=N, provided that the compound is not

COMPOUND CSRM617

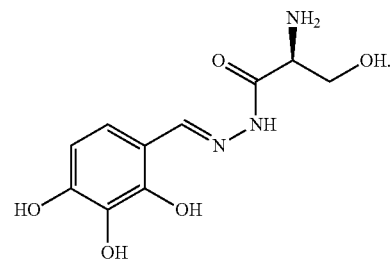

Various embodiments of the present invention provide a compound having the structure:

74

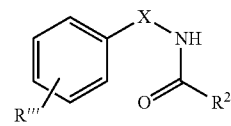

wherein:
R''' is independently one or more of hydrogen or optionally substituted substituent;
$R^2$ is hydrogen or optionally substituted substituent; and
X is NHC(O), C(O)NH, OC(O), C(O)O, C(O), or CH=N, provided that the compound is not

COMPOUND CSRM617

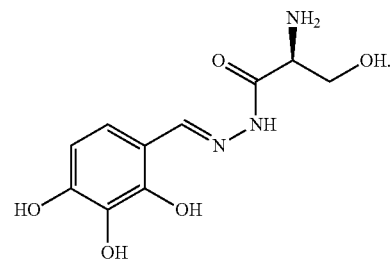

Various embodiments of the present invention provide a compound having the structure:

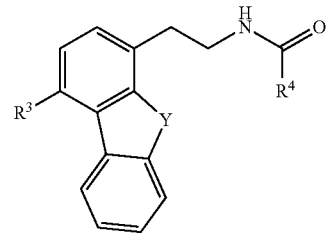

or a prodrug, isomer, dimer, enantiomer, derivative, or pharmaceutically acceptable salt thereof, wherein:
$R^3$ is hydrogen or optionally substituted substituent;
$R^4$ is hydrogen or optionally substituted substituent; and
X is O or S.

Various embodiments of the present invention provide a compound having the structure:

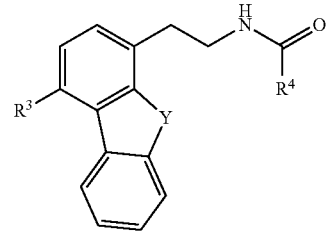

wherein:
$R^3$ is hydrogen or optionally substituted substituent;
$R^4$ is hydrogen or optionally substituted substituent; and
X is O or S.

Various embodiments of the present invention provide a compound having the structure:

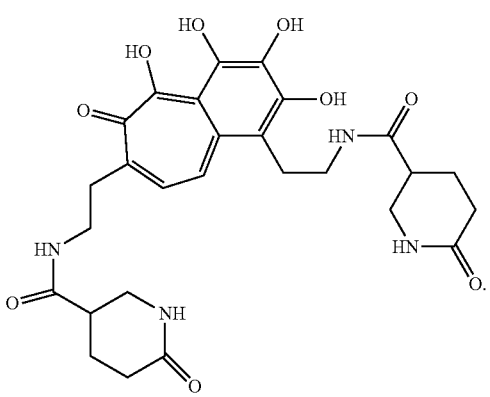 [SMILES: O=C1CCC(C(=O)NCCc2ccc3c(CCNC(=O)C4CCC(=O)NC4)c(O)c(O)c(O)c3c(O)c2=O)CN1]

Various embodiments of the present invention provide a compound having the structure:

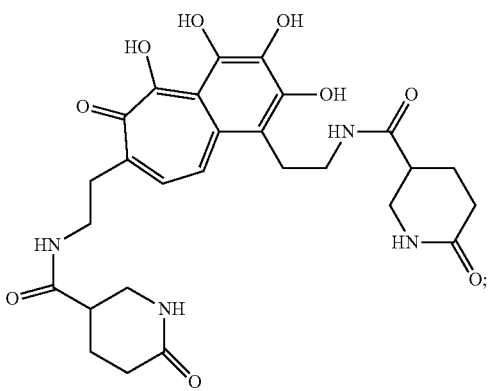 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof.

In various embodiments, compounds of the present invention as disclosed herein may be synthesized using any synthetic method available to one of skill in the art. Non-limiting examples of synthetic methods used to prepare various embodiments of compounds of the present invention are disclosed in the Examples section herein.

Therapeutic Methods

In some embodiments, provided herein are methods for treating, inhibiting, reducing the severity of, delaying progression (slowing metastasis) of and/or preventing metastases of cancers that overexpress ONECUT2 in a subject in need thereof. The methods comprise administering a therapeutically effective amount of an agent that inhibits the expression or function of ONECUT2 to a subject in need thereof, so as to treat, inhibit, reduce the severity of, slow progression of and/or prevent metastases of cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of cancer in the subject.

In some embodiments, provided herein are methods for treating, inhibiting, reducing the severity of, delaying progression (slowing metastasis) of and/or preventing metastases of prostate cancer in a subject in need thereof. In one embodiment, the subject with prostate cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of prostate cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of prostate cancer in the subject.

In some embodiments, provided herein are methods for treating, inhibiting, reducing the severity of, delaying progression (slowing metastasis) of and/or preventing metastases of castration resistant prostate cancer (CRPC) in a subject in need thereof. In one embodiment, the subject with CRPC overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of CRPC in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of CRPC in the subject.

In some embodiments, provided herein are methods for treating, inhibiting, reducing the severity of, delaying progression and/or improving the survival of breast cancer in a subject in need thereof. In one embodiment, the subject with breast cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of breast cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of breast cancer in the subject.

In some embodiments, provided herein are methods for treating, inhibiting, reducing the severity of, delaying progression and/or improving survival of gastric cancer in a subject in need thereof. In one embodiment, the subject with gastric cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of gastric cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of gastric cancer in the subject.

In some embodiments, provided herein are methods for treating, inhibiting, reducing the severity of, delaying progression and/or improving survival of colon cancer in a subject in need thereof. In one embodiment, the subject with colon cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of colon cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of colon cancer in the subject.

In some embodiments, provided herein are methods for treating, inhibiting, reducing the severity of, delaying progression and/or improving survival of renal cancer in a subject in need thereof. In one embodiment, the subject with renal cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of renal cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of renal cancer in the subject.

In some embodiments, provided herein are methods for treating, inhibiting, reducing the severity of, delaying progression and/or improving survival of brain cancer in a subject in need thereof. In one embodiment, the subject with brain cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of brain cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of brain cancer in the subject.

In some embodiments, provided herein are methods for treating, inhibiting, reducing the severity of, delaying progression and/or improving survival of medulloblastoma in a subject in need thereof. In one embodiment, the subject with medulloblastoma overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of medulloblastoma in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of medulloblastoma in the subject.

In some embodiments, provided herein are methods for treating, inhibiting, reducing the severity of, delaying progression and/or improving survival of lung cancer in a subject in need thereof. In one embodiment, the subject with lung cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of lung cancer in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of lung cancer in the subject.

In some embodiments, provided herein are methods for treating, inhibiting, reducing the severity of, delaying progression and/or improving survival of non-small cell lung cancer (NSCLC) in a subject in need thereof. In one embodiment, the subject with non-small cell lung cancer overexpresses ONECUT2. The methods comprise administering a therapeutically effective amount of an agent that inhibits the expression or function of ONECUT2 to a subject in need thereof, so as to treat, inhibit, reduce the severity of, slow progression of and/or prevent metastases of NSCLC in the subject. In some embodiments, the methods comprise providing an agent that inhibits the expression or function of ONECUT2 and administering a therapeutically effective amount of the agent to the subject so as to treat, inhibit, reduce the severity of, slow progression of and/or prevent metastases of NSCLC in the subject.

In some embodiments, the agent that inhibits the expression or function of ONECUT2 for use with the therapeutic methods described herein is a direct inhibitor of ONECUT2. In some embodiments, the agent that inhibits the expression or function of ONECUT2 for use with the therapeutic methods described herein is an indirect inhibitor of ONECUT2, wherein the indirect inhibitor inhibits the binding partner of ONECUT2 thereby inhibiting ONECUT2. In one embodiment, ONECUT2 is inhibited by inhibiting KDM5B.

In exemplary embodiments, the agent that inhibits (directly or indirectly) the expression or function of ONECUT2 for use with the therapeutic methods described herein is any one or more of small molecule, a peptide, an antibody or a fragment thereof, a nucleic acid molecule, a protein-drug conjugate, or a combination thereof. In some embodiments, the antibody is selected from the group consisting of monoclonal antibody or fragment thereof, a polyclonal antibody or a fragment thereof, chimeric antibodies, humanized antibodies, human antibodies, and a single chain antibody.

In various embodiments of the present invention the agent for inhibiting the expression or activity or function of ONECUT2 or modulating the activity of ONECUT2 for use in the therapeutic methods described herein is a compound CSRM617:

COMPOUND CSRM617

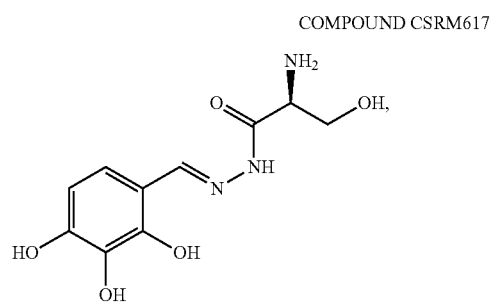 [SMILES: N[C@@H](CO)C(=O)N/N=C/c1ccc(O)c(O)c1O]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is compound CSRM617 or a pharmaceutically acceptable salt thereof:

COMPOUND CSRM617

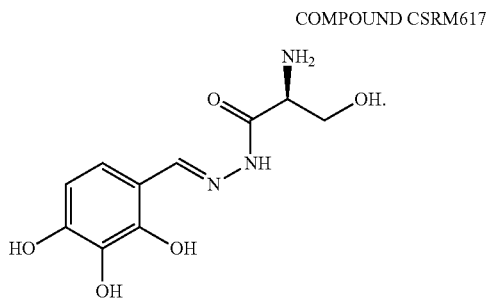 [SMILES: N[C@@H](CO)C(=O)N/N=C/c1ccc(O)c(O)c1O]

In various embodiments of the present invention the agent for inhibiting the expression or activity or function of ONECUT2 or modulating the activity of ONECUT2 for use in the therapeutic methods described herein is compound CSRM617:

COMPOUND CSRM617

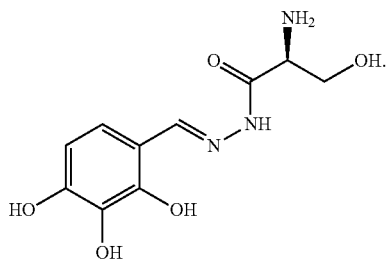

In various embodiments of the present invention the agent for inhibiting the expression or activity or function of ONECUT2 or modulating the activity of ONECUT2 for use in the therapeutic methods described herein is a compound of Formula I:

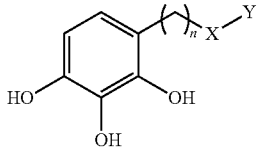
(FORMULA I)

or a prodrug, isomer, dimer, enantiomer, derivative, or pharmaceutically acceptable salt thereof, wherein:

n is 0, 1, 2, 3, 4 or 5;

X is NHC(O), C(O)NH, OC(O), C(O)O, C(O), or CH=N; and

Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula I:

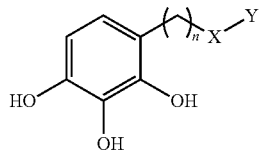
(FORMULA I)

wherein:

n is 0, 1, 2, 3, 4 or 5;

X is NHC(O), C(O)NH, OC(O), C(O)O, C(O), or CH=N;

Y is alkyl, heteroalkyl, cyclyl, heterocyclyl, aryl, or heteroaryl, each of which can be optionally substituted; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula I:

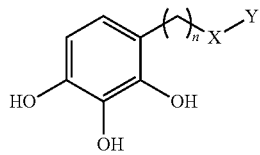
(FORMULA I)

wherein:

n is 0, 1, 2, 3, 4 or 5;

X is NHC(O), C(O)NH, OC(O), C(O)O, C(O), or CH=N;

Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula I:

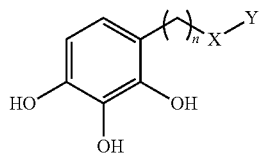
(FORMULA I)

or a prodrug, isomer, dimer, enantiomer, derivative, or pharmaceutically acceptable salt thereof, wherein:

n is 0, 1, 2, 3, 4 or 5;

X is NHC(O), C(O)NH, OC(O), C(O)O, C(O), or CH=N; and

Y is alkyl, heteroalkyl, cyclyl, heterocyclyl, aryl, or heteroaryl, each of which can be optionally substituted, provided that the compound is not

COMPOUND CSRM617

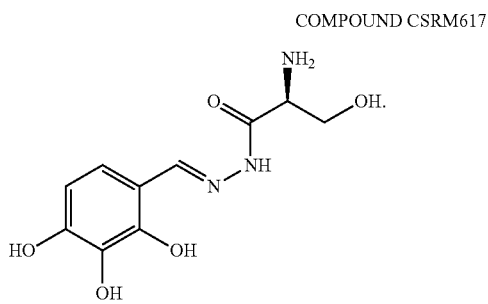 [SMILES: N[C@@H](CO)C(=O)N/N=C/c1ccc(O)c(O)c1O]

In various embodiments of the present invention the agent for inhibiting the expression or activity or function of ONECUT2 or modulating the activity of ONECUT2 for use in the therapeutic methods described herein is a compound of Formula I:

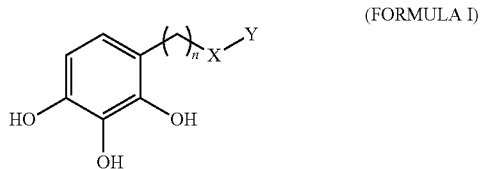
(FORMULA I)

wherein:
n is 0, 1, 2, 3, 4 or 5;
X is NHC(O), C(O)NH, OC(O), C(O)O, C(O), or CH=N;
Y is alkyl, heteroalkyl, cyclyl, heterocyclyl, aryl, or heteroaryl, each of which can be optionally substituted; and any pharmaceutically acceptable salt thereof, provided that the compound is not

COMPOUND CSRM617

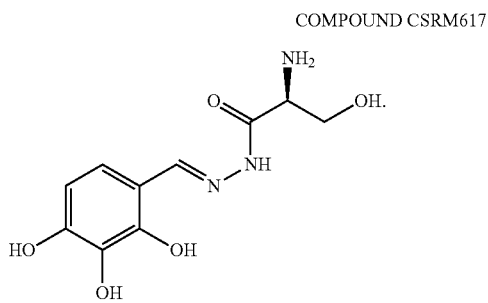 [SMILES: N[C@@H](CO)C(=O)N/N=C/c1ccc(O)c(O)c1O]

In various embodiments of the present invention the agent for inhibiting the expression or activity or function of ONECUT2 or modulating the activity of ONECUT2 for use in the therapeutic methods described herein is a compound of Formula I:

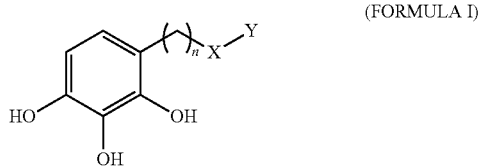
(FORMULA I)

wherein:
n is 0, 1, 2, 3, 4 or 5;
X is NHC(O), C(O)NH, OC(O), C(O)O, C(O), or CH=N;
Y is alkyl, heteroalkyl, cyclyl, heterocyclyl, aryl, or heteroaryl, each of which can be optionally substituted, provided that the compound is not

COMPOUND CSRM617

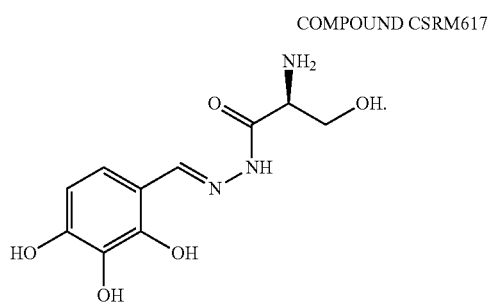 [SMILES: N[C@@H](CO)C(=O)N/N=C/c1ccc(O)c(O)c1O]

In various embodiments of the present invention the agent for inhibiting the expression or activity or function of ONECUT2 or modulating the activity of ONECUT2 for use in the therapeutic methods described herein is a compound of Formula II:

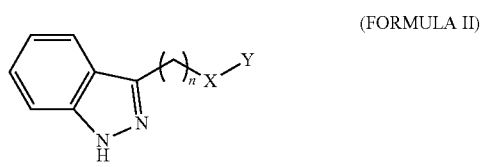
(FORMULA II)

or a prodrug, isomer, dimer, enantiomer, derivative, or pharmaceutically acceptable salt thereof, wherein:
n is 0, 1, 2, 3, 4 or 5;
X is NHC(O), C(O)NH, OC(O), C(O)O, or C(O); and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula II:

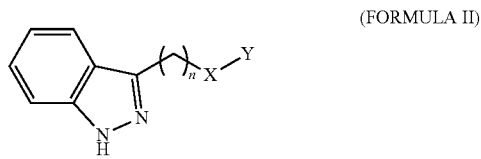
(FORMULA II)

wherein:
n is 0, 1, 2, 3, 4 or 5;
X is NHC(O), C(O)NH, OC(O), C(O)O, or C(O);
Y is alkyl, heteroalkyl, cyclyl, heterocyclyl, aryl, or heteroaryl, each of which can be optionally substituted; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula II:

(FORMULA II)

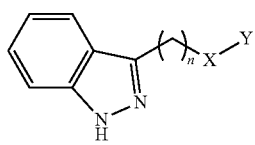

wherein:
n is 0, 1, 2, 3, 4 or 5;
X is NHC(O), C(O)NH, OC(O), C(O)O, or C(O); and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula III:

(FORMULA III)

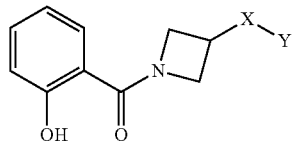

or a prodrug, isomer, dimer, enantiomer, derivative, or pharmaceutically acceptable salt thereof, wherein:
X is NH, or O; and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula III:

(FORMULA III)

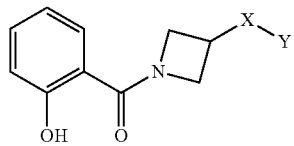

wherein:
X is NH, or O;
Y is alkyl, heteroalkyl, cyclyl, heterocyclyl, aryl, or heteroaryl, each of which can be optionally substituted; and
any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula III:

(FORMULA III)

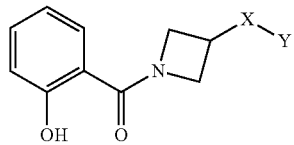

wherein:
X is NH, or O; and
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula IV:

(FORMULA IV)

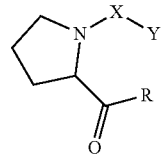

or a prodrug, isomer, dimer, enantiomer, derivative, or pharmaceutically acceptable salt thereof, wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5; and
R is H, CH$_3$, alkyl, NH$_2$, or OR', where R' is H, CH$_3$, or alkyl.

In various embodiments of the present invention the agent for inhibiting the expression or activity or function of ONECUT2 or modulating the activity of ONECUT2 for use in the therapeutic methods described herein is a compound of Formula IV:

(FORMULA IV)

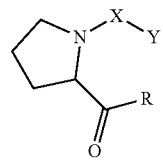

wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5;
R is H, CH$_3$, alkyl, NH$_2$, or OR', where R' is H, CH$_3$, or alkyl; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula IV:

(FORMULA IV)

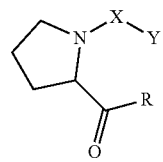

wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5;
R is H, CH$_3$, alkyl, NH$_2$, or OR', where R' is H, CH$_3$, or alkyl.

In various embodiments of the present invention the agent for inhibiting the expression or activity or function of ONECUT2 or modulating the activity of ONECUT2 for use in the therapeutic methods described herein is a compound of Formula V:

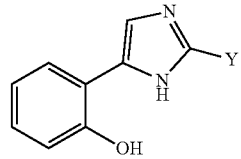

(FORMULA V)

or a prodrug, isomer, dimer, enantiomer, derivative, or pharmaceutically acceptable salt thereof, wherein:
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound of Formula V:

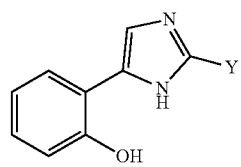

(FORMULA V)

wherein:
Y is alkyl, heteroalkyl, cyclyl, heterocyclyl, aryl, or heteroaryl, each of which can be optionally substituted; and any pharmaceutically acceptable salt thereof.

In various embodiments of the present invention the agent for inhibiting the expression or activity or function of ONECUT2 or modulating the activity of ONECUT2 for use in the therapeutic methods described herein is a compound of Formula V:

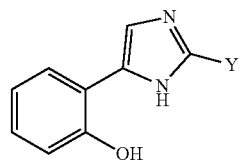

(FORMULA V)

wherein:
Y is alkyl, heteroalkyl, cyclyl, heterocyclyl, aryl, or heteroaryl, each of which can be optionally substituted.

In various embodiments of the present invention the agent for inhibiting the expression or activity or function of ONECUT2 or modulating the activity of ONECUT2 for use in the therapeutic methods described herein is a compound selected from:

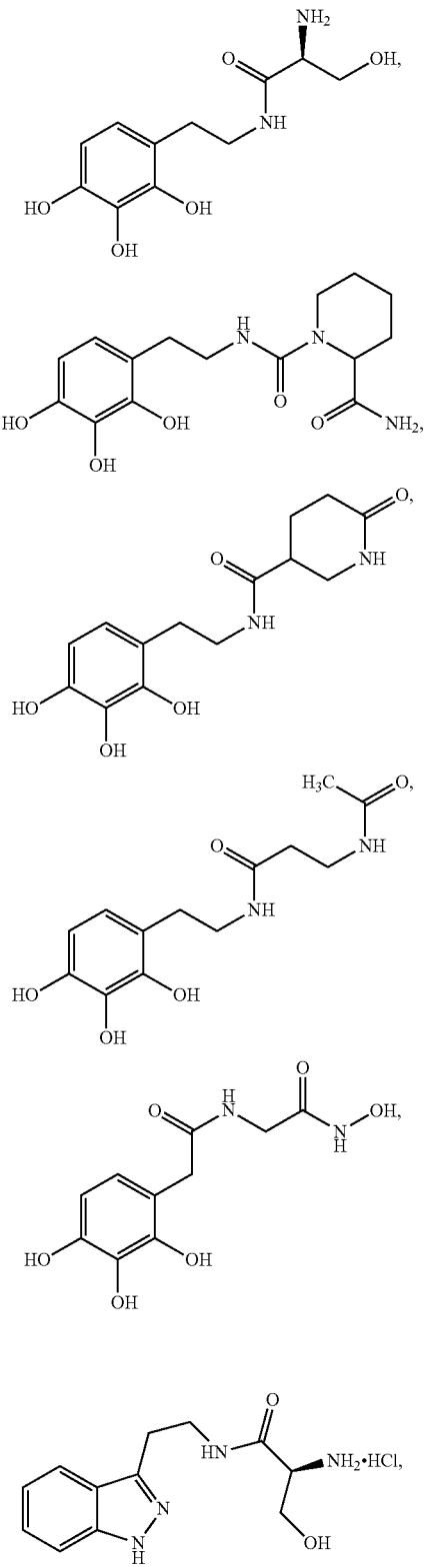

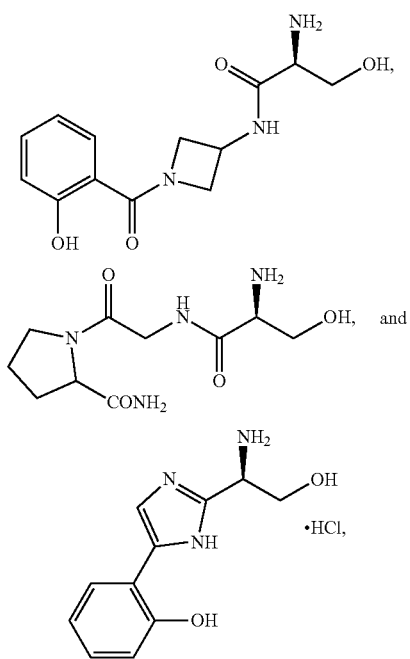

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

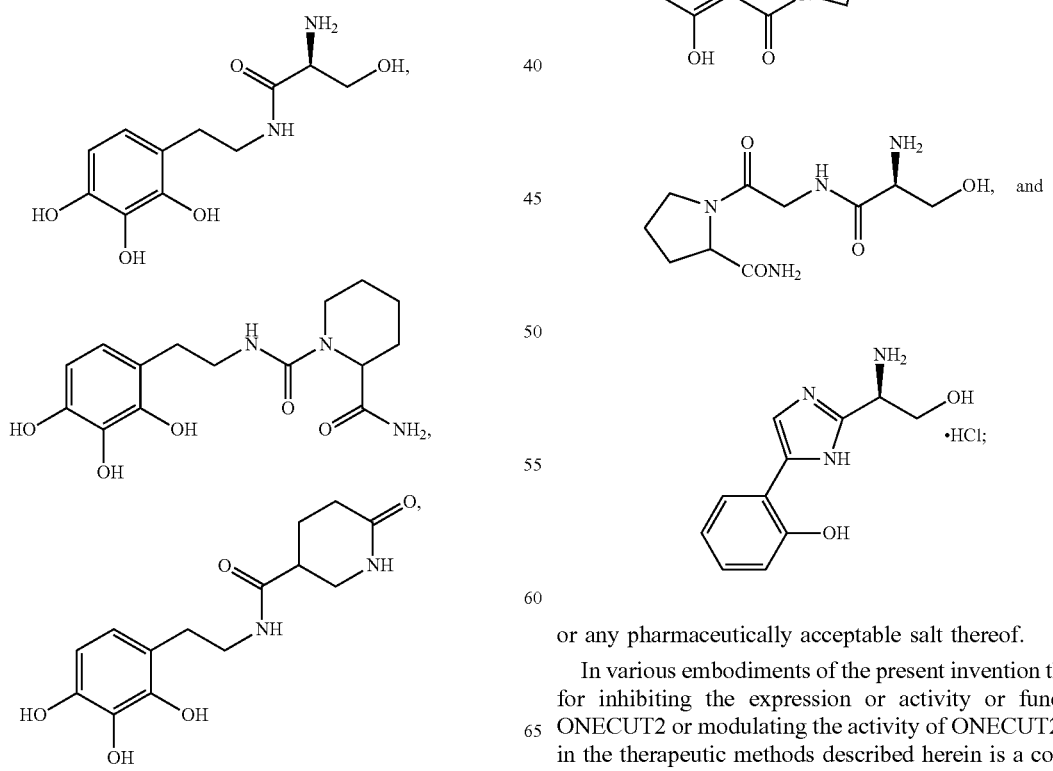

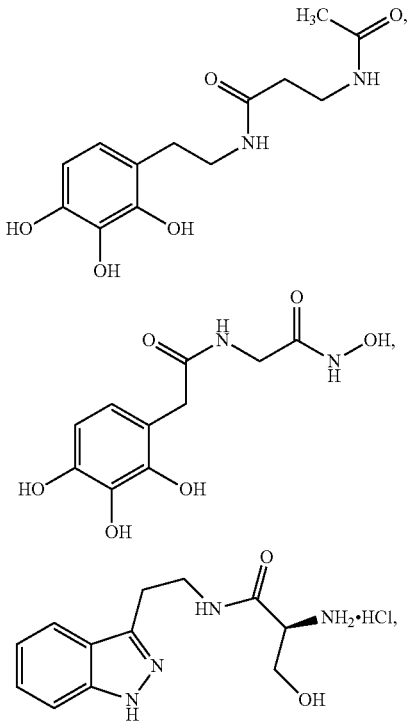

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

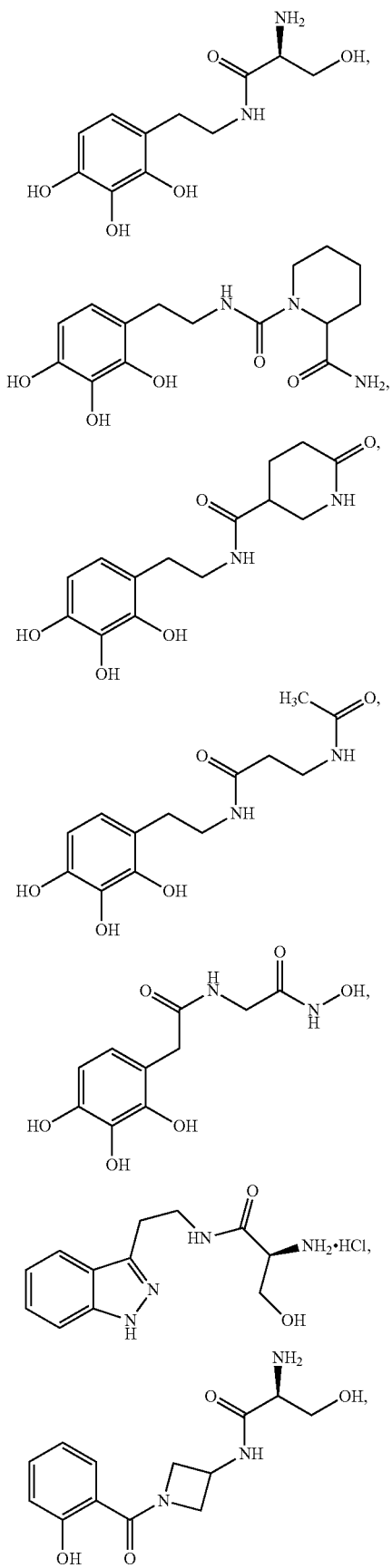
-continued
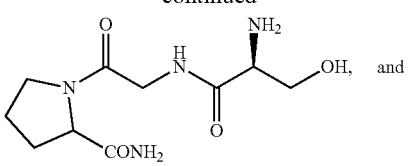
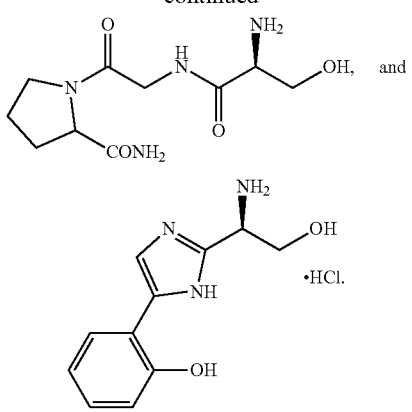
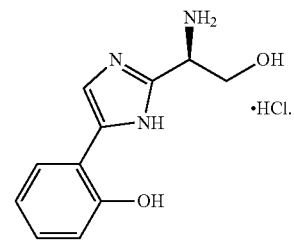
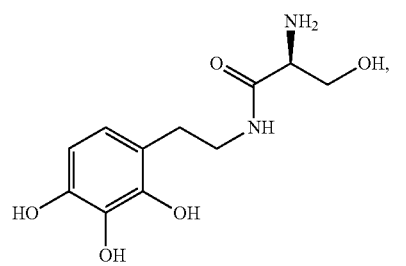 [SMILES: N[C@@H](CO)C(=O)NCCc1ccc(O)c(O)c1O]
In various embodiments of the present invention the agent for inhibiting the expression or activity or function of ONECUT2 or modulating the activity of ONECUT2 for use in the therapeutic methods described herein is a compound selected from:
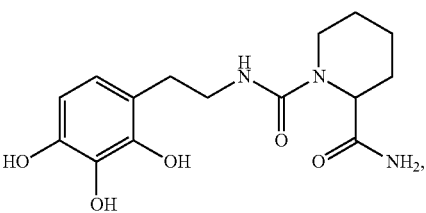
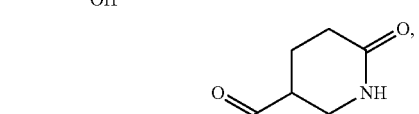
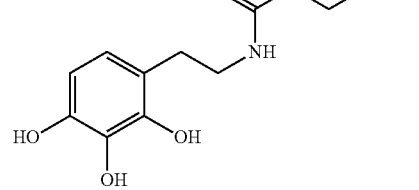
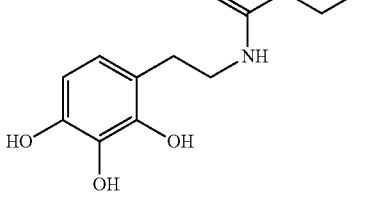

-continued

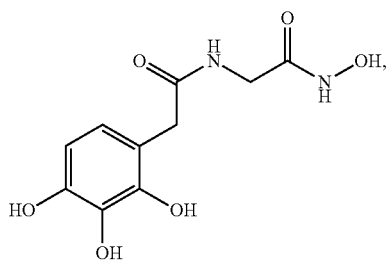

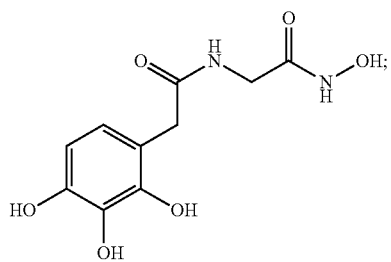

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

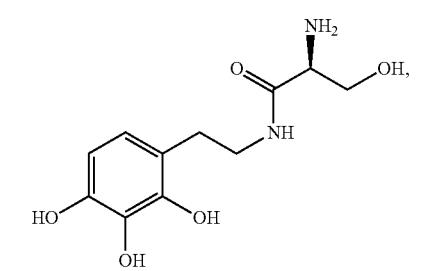 [SMILES: N[C@@H](CO)C(=O)NCCc1ccc(O)c(O)c1O]

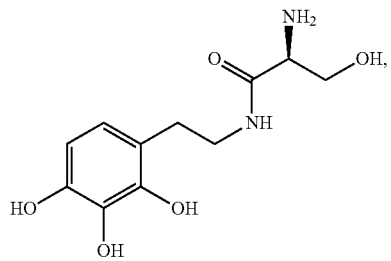 [SMILES: N[C@@H](CO)C(=O)NCCc1ccc(O)c(O)c1O]

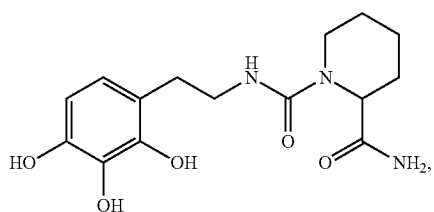

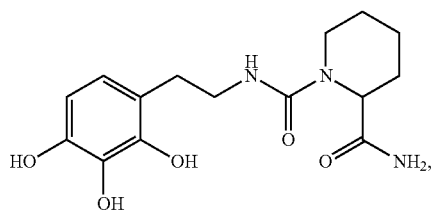 [SMILES: NC(=O)C1CCCCN1C(=O)NCCc1ccc(O)c(O)c1O]

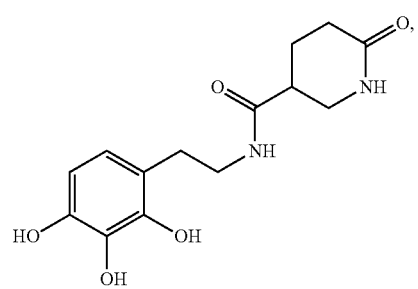

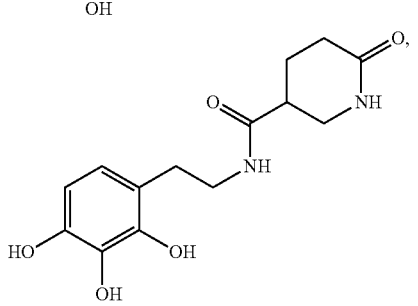

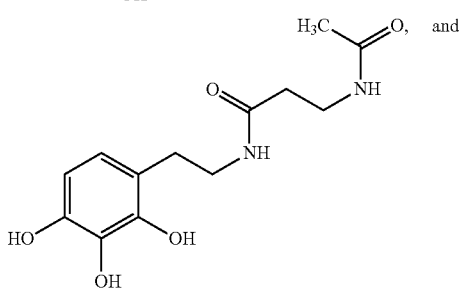

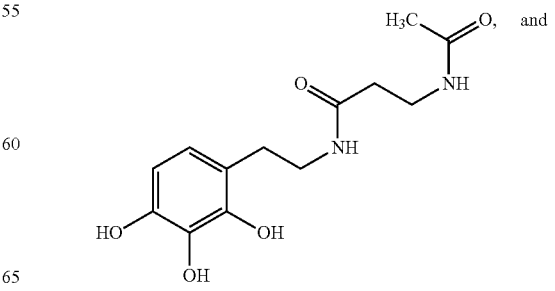

-continued

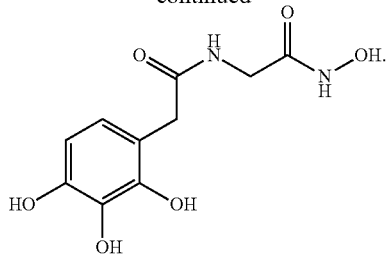

In various embodiments of the present invention the agent for inhibiting the expression or activity or function of ONECUT2 or modulating the activity of ONECUT2 for use in the therapeutic methods described herein is a compound selected from:

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

-continued

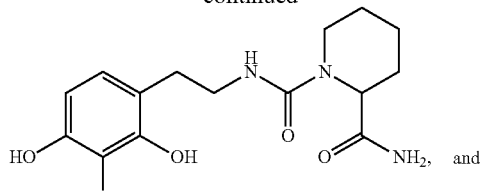

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

In various embodiments of the present invention the agent for inhibiting the expression or activity or function of ONECUT2 or modulating the activity of ONECUT2 for use in the therapeutic methods described herein is a compound selected from:

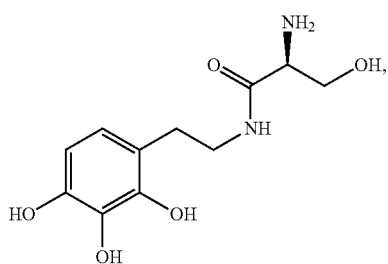

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

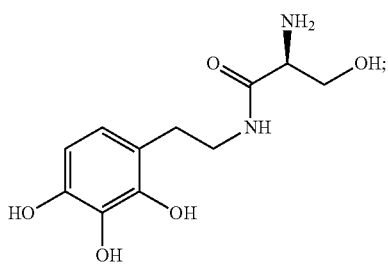

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

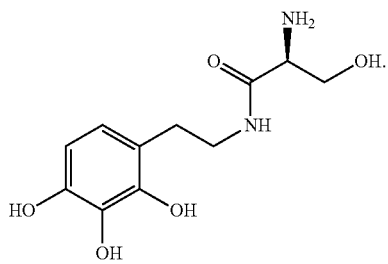

In various embodiments of the present invention the agent for inhibiting the expression or activity or function of ONECUT2 or modulating the activity of ONECUT2 for use in the therapeutic methods described herein is a compound selected from:

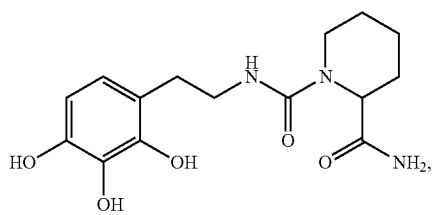

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

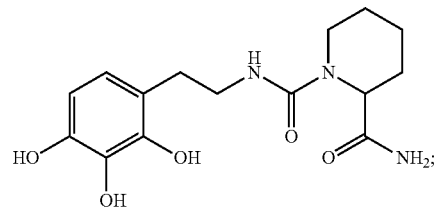 [SMILES: NC(=O)C1CCCCN1C(=O)NCCc1ccc(O)c(O)c1O]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

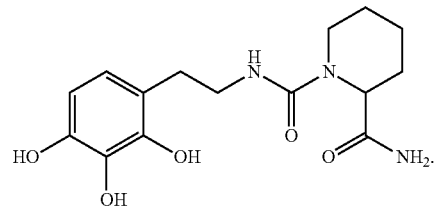 [SMILES: NC(=O)C1CCCCN1C(=O)NCCc1ccc(O)c(O)c1O]

In various embodiments of the present invention the agent for inhibiting the expression or activity or function of ONECUT2 or modulating the activity of ONECUT2 for use in the therapeutic methods described herein is a compound selected from:

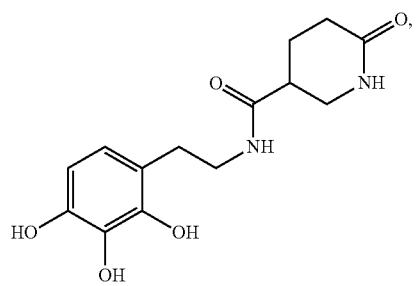

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

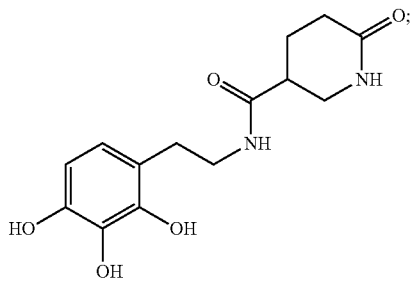 [SMILES: O=C1CCC(C(=O)NCCc2ccc(O)c(O)c2O)CN1]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

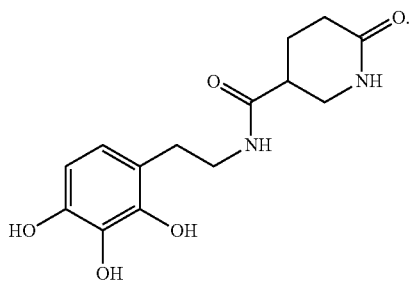 [SMILES: O=C1CCC(C(=O)NCCc2ccc(O)c(O)c2O)CN1]

In various embodiments of the present invention the agent for inhibiting the expression or activity or function of ONECUT2 or modulating the activity of ONECUT2 for use in the therapeutic methods described herein is a compound selected from:

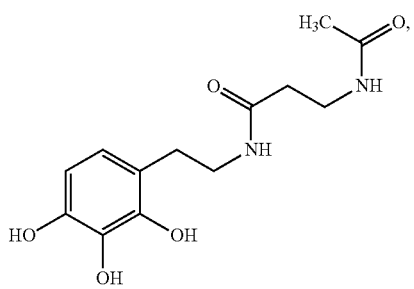 [SMILES: CC(=O)NCCC(=O)NCCc1ccc(O)c(O)c1O]

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

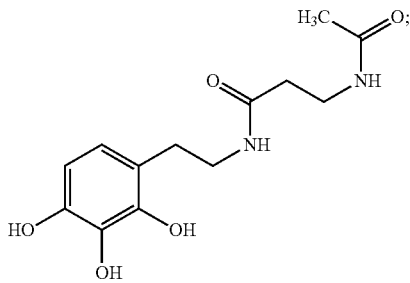 [SMILES: CC(=O)NCCC(=O)NCCc1ccc(O)c(O)c1O]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

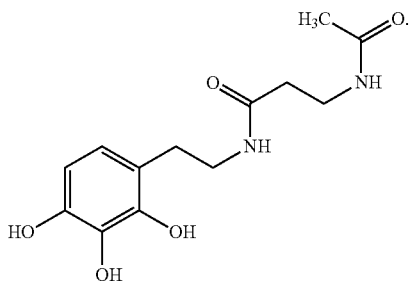 [SMILES: CC(=O)NCCC(=O)NCCc1ccc(O)c(O)c1O]

In various embodiments of the present invention the agent for inhibiting the expression or activity or function of ONECUT2 or modulating the activity of ONECUT2 for use in the therapeutic methods described herein is a compound selected from:

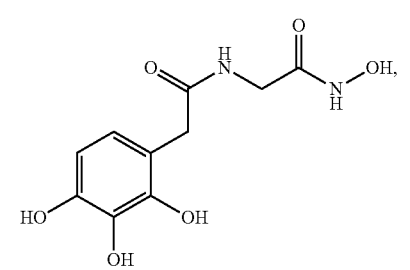

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

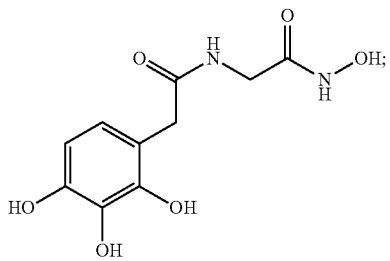 [SMILES: O=C(CNC(=O)Cc1ccc(O)c(O)c1O)NO]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

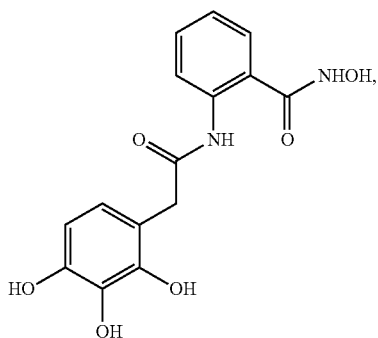

In various embodiments of the present invention the agent for inhibiting the expression or activity or function of ONECUT2 or modulating the activity of ONECUT2 for use in the therapeutic methods described herein is a compound selected from:

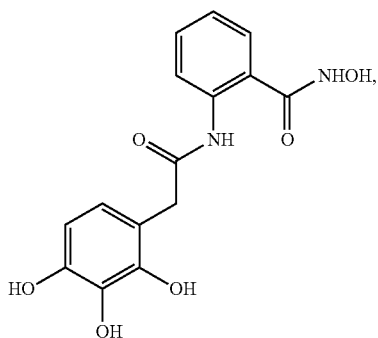

or a prodrug, isomer, dimer, enantiomer, derivative, or pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

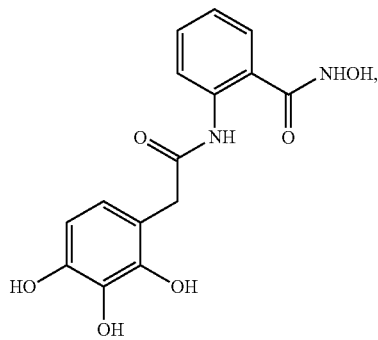

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound selected from:

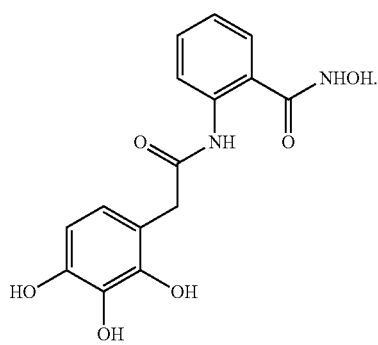

In various embodiments of the present invention the agent for inhibiting the expression or activity or function of ONECUT2 or modulating the activity of ONECUT2 for use in the therapeutic methods described herein is a compound having the structure:

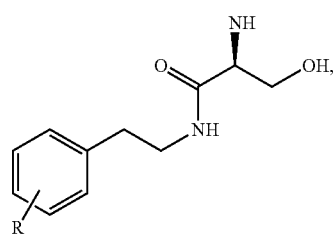

or a prodrug, isomer, dimer, enantiomer, derivative, or pharmaceutically acceptable salt thereof, wherein:

R is independently one or more of hydrogen or optionally substituted sub stituent.

In various embodiments of the present invention the agent for inhibiting the expression or activity or function of ONECUT2 or modulating the activity of ONECUT2 for use in the therapeutic methods described herein is a compound having the structure:

101

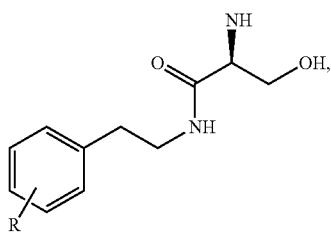

wherein:

R is independently one or more of hydrogen or optionally substituted sub stituent.

In various embodiments of the present invention the agent for inhibiting the expression or activity or function of ONECUT2 or modulating the activity of ONECUT2 for use in the therapeutic methods described herein is a compound having the structure:

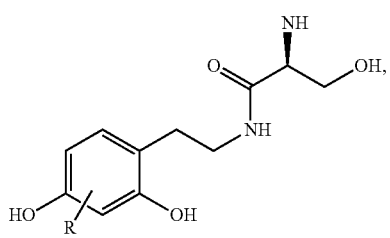

or a prodrug, isomer, dimer, enantiomer, derivative, or pharmaceutically acceptable salt thereof, wherein:

R is independently one or more of hydrogen or optionally substituted sub stituent.

In various embodiments of the present invention the agent for inhibiting the expression or activity or function of ONECUT2 or modulating the activity of ONECUT2 for use in the therapeutic methods described herein is a compound having the structure:

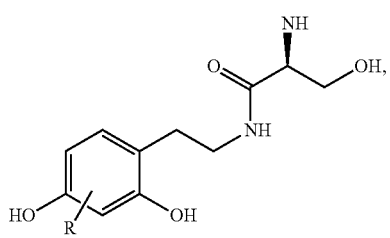

wherein:

R is independently one or more of hydrogen or optionally substituted sub stituent.

In various embodiments of the present invention the agent for inhibiting the expression or activity or function of ONECUT2 or modulating the activity of ONECUT2 for use in the therapeutic methods described herein is a compound having the structure:

102

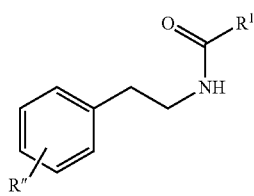

or a prodrug, isomer, dimer, enantiomer, derivative, or pharmaceutically acceptable salt thereof wherein:

R" is independently one or more of hydrogen or optionally substituted sub stituent; and $R^1$ is hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

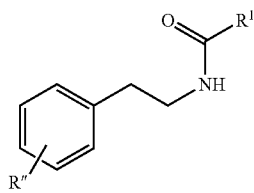

wherein:

R" is independently one or more of hydrogen or optionally substituted sub stituent; and $R^1$ is hydrogen or optionally substituted substituent.

In various embodiments of the present invention the agent for inhibiting the expression or activity or function of ONECUT2 or modulating the activity of ONECUT2 for use in the therapeutic methods described herein is a compound having the structure:

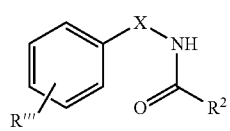

or a prodrug, isomer, dimer, enantiomer, derivative, or pharmaceutically acceptable salt thereof, wherein:

R''' is independently one or more of hydrogen or optionally substituted substituent;

$R^2$ is hydrogen or optionally substituted substituent; and

X is NHC(O), C(O)NH, OC(O), C(O)O, C(O), or CH=N.

In various embodiments of the present invention the agent for inhibiting the expression or activity or function of ONECUT2 or modulating the activity of ONECUT2 for use in the therapeutic methods described herein is a compound having the structure:

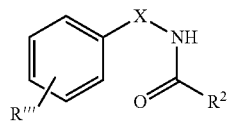

wherein:

R''' is independently one or more of hydrogen or optionally substituted substituent;

R² is hydrogen or optionally substituted substituent; and

X is NHC(O), C(O)NH, OC(O), C(O)O, C(O), or CH=N.

In various embodiments of the present invention the agent for inhibiting the expression or activity or function of ONECUT2 or modulating the activity of ONECUT2 for use in the therapeutic methods described herein is a compound having the structure:

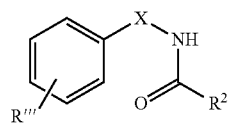

or a prodrug, isomer, dimer, enantiomer, derivative, or pharmaceutically acceptable salt thereof, wherein:

R''' is independently one or more of hydrogen or optionally substituted substituent;

R² is hydrogen or optionally substituted substituent; and

X is NHC(O), C(O)NH, OC(O), C(O)O, C(O), or CH=N, provided that the compound is not

COMPOUND CSRM617

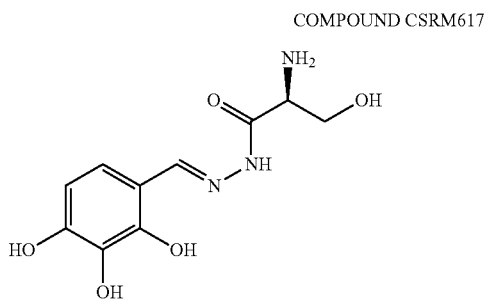 [SMILES: N[C@@H](CO)C(=O)N/N=C/c1ccc(O)c(O)c1O]

In various embodiments of the present invention the agent for inhibiting the expression or activity or function of ONECUT2 or modulating the activity of ONECUT2 for use in the therapeutic methods described herein is a compound having the structure:

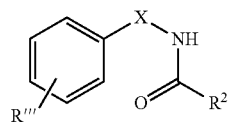

wherein:

R''' is independently one or more of hydrogen or optionally substituted substituent;

R² is hydrogen or optionally substituted substituent; and

X is NHC(O), C(O)NH, OC(O), C(O)O, C(O), or CH=N, provided that the compound is not

COMPOUND CSRM617

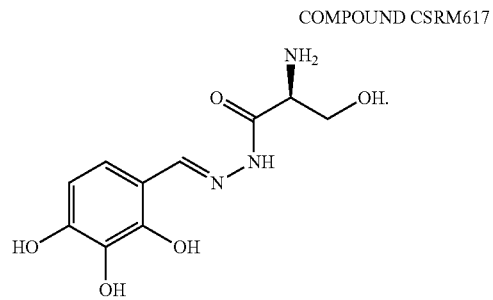 [SMILES: N[C@@H](CO)C(=O)N/N=C/c1ccc(O)c(O)c1O]

In various embodiments of the present invention the agent for inhibiting the expression or activity or function of ONECUT2 or modulating the activity of ONECUT2 is a compound having the structure:

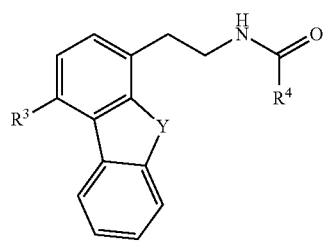

or a prodrug, isomer, dimer, enantiomer, derivative, or pharmaceutically acceptable salt thereof, wherein:

R³ is hydrogen or optionally substituted substituent;

R⁴ is hydrogen or optionally substituted substituent; and

X is O or S.

In various embodiments of the present invention the agent for inhibiting the expression or activity or function of ONECUT2 or modulating the activity of ONECUT2 for use in the therapeutic methods described herein is a compound having the structure:

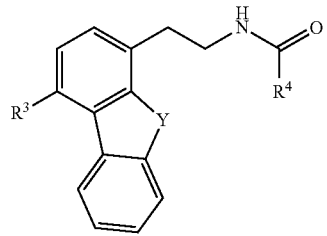

wherein:

R³ is hydrogen or optionally substituted substituent;

R⁴ is hydrogen or optionally substituted substituent; and

X is O or S.

In various embodiments of the present invention the agent for inhibiting the expression or activity or function of ONECUT2 or modulating the activity of ONECUT2 for use in the therapeutic methods described herein is a compound having the structure:

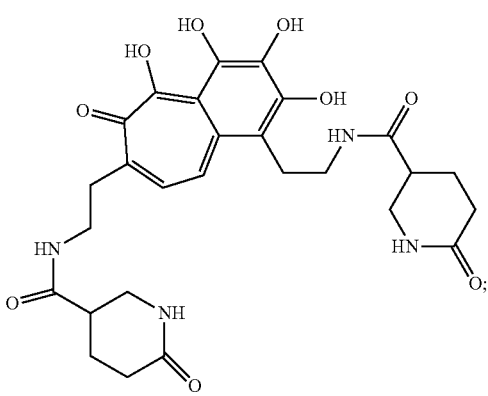 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof.

In various embodiments of the present invention the agent for inhibiting the expression or activity or function of ONECUT2 or modulating the activity of ONECUT2 for use in the therapeutic methods described herein is a compound having the structure:

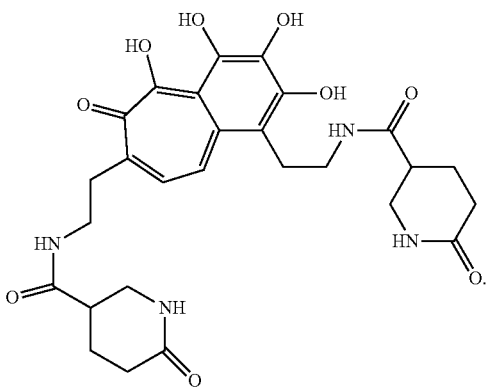 [SMILES: O=C1CCC(C(=O)NCCc2ccc3c(CCNC(=O)C4CCC(=O)NC4)c(O)c(O)c(O)c3c(O)c2=O)CN1]

In various embodiments of the present invention, one or more agents and/or compounds for inhibiting the expression or activity or function of ONECUT2 or modulating the activity of ONECUT2 may be used in combination. In various embodiments of the present invention, agents and/or compounds for inhibiting the expression or activity or function of ONECUT2 or modulating the activity of ONE-CUT2 may be used in combination.

In some embodiments, the subject is undergoing androgen-deprivation therapy sequentially or simultaneously with administration of the agent described herein. In some embodiments, the agent that reduces or inhibits the expression or function of ONECUT2 protein is administered 1-3 times per day or 1-7 times per week. In some embodiments, the agent that reduces or inhibits the expression or function of ONECUT2 protein is administered for 1-5 days, 1-5 weeks, 1-5 months, or 1-5 years.

In some embodiments, the agent that inhibits the expression or activity or function of ONECUT2 or modulates the activity of ONECUT2 is administered 1-3 times per day or 1-7 times per week. In some embodiments, the agent that inhibits the expression or activity or function of ONECUT2 or modulates the activity of ONECUT2 is administered for 1-5 days, 1-5 weeks, 1-5 months, or 1-5 years.

In some embodiments, the therapeutically effective amount of the agent that inhibits the expression or activity or function of ONECUT2 or modulates the activity of ONECUT2 is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

Also provided herein is a method for assessing the efficacy of the therapeutic methods described herein which methods include administering an agent that inhibits expression or activity of ONECUT2. In some embodiments, the methods for assessing efficacy include detecting the level of cancer specific markers in the subject that has undergone therapy with an agent that inhibits expression or activity of ONECUT2, wherein a decrease in the level of cancer specific marker relative to the reference value indicates that the therapy with an agent that inhibits expression or activity of ONECUT2 is efficacious. In one embodiment, the reference value is the mean or median amount of the cancer specific marker in the subject prior to starting treatment with the agent described herein. For example, the method for assessing efficacy may include measuring the levels of prostate-specific antigen (PSA) in the subject in need thereof during and/or after treatment with the agent and determining that the agent is effective if the PSA levels are reduced relative to the reference value or determining that the agent is not effective if the PSA levels are not reduced relative to the reference value. In one embodiment, the reference value is the mean or median amount of PSA in the subject prior to starting treatment with the agent described herein.

The agent reduces or inhibits the expression or function of ONECUT2 protein by a statistically significant amount. However, for avoidance of doubt, "reduced", "reduction" or "decrease" or "inhibit" in reference to expression of function of ONECUT2 protein means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level. In some embodiments, the reference level can be the level in absence of the agent.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the peptide. Measured or measurable parameters include clinically detectable markers of disease, for example, elevated or depressed levels of a biological marker, as well as parameters related to a clinically accepted scale of symptoms or markers for cancer (such as ONECUT2 overexpressing cancers). It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

In some embodiments, the method further comprises administration or treatment with one or more additional anti-cancer therapy to the subject in need thereof. In some embodiments, the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

In some embodiments, the agent and the additional anti-cancer therapy are administered sequentially or simultaneously In some embodiments, the method further comprises administration or treatment with one or more anti-cancer therapeutic agents. In some such embodiments, the anti-cancer therapeutic agent is a chemotherapeutic agent, a growth inhibitor agent, an anti-angiogenesis agent, a cytotoxic agent, an anti-hormonal agent, a prodrug, or a cytokine.

In some embodiments, the method comprises co-administering the Compound CSRM617 and an anti-cancer therapeutic agent to the subject.

In some embodiments, the method comprises co-administering a compound selected from Formula I-Formula V; and an anti-cancer therapeutic agent to the subject.

In some embodiments, the method comprises co-administering a compound selected from Formula I-Formula V; and an anti-cancer therapeutic agent to the subject, provided that the compound is not

COMPOUND CSRM617

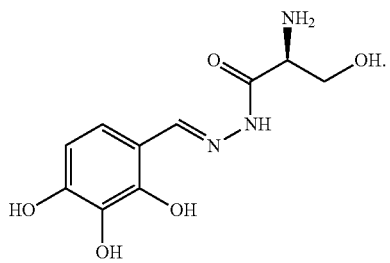

In some embodiments, the method comprises co-administering a compound selected from:

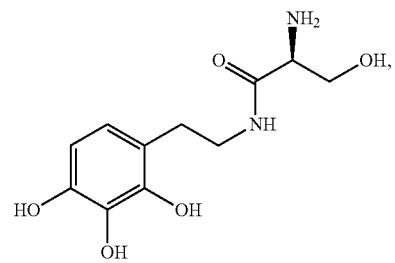 [SMILES: N[C@@H](CO)C(=O)NCCc1ccc(O)c(O)c1O]

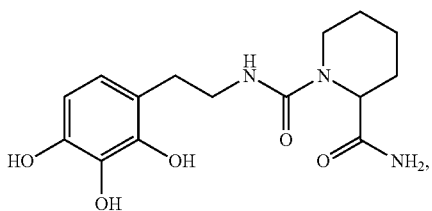

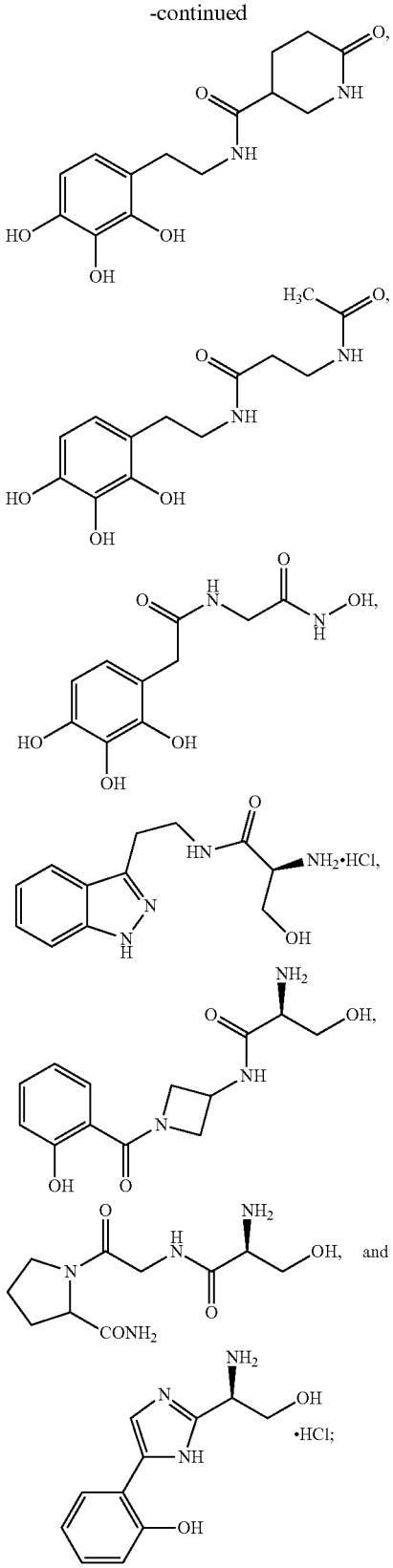

and an anti-cancer therapeutic agent to the subject.

In some embodiments, the method comprises co-administering a compound selected from:

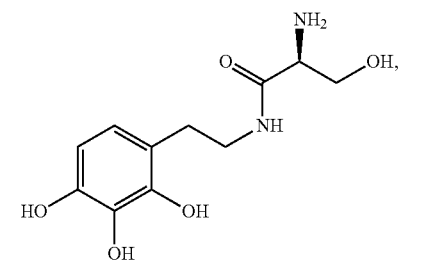
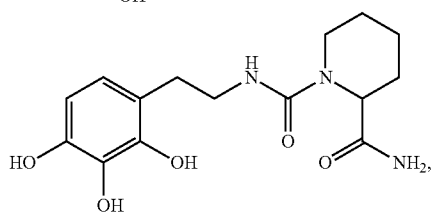
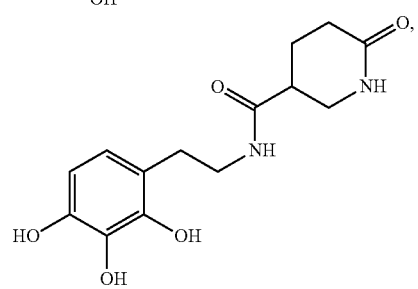
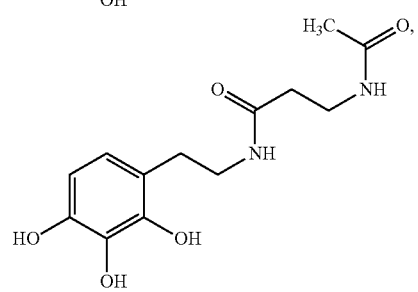
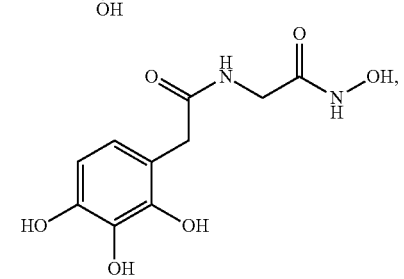
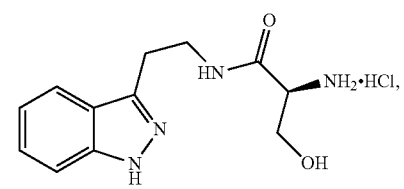
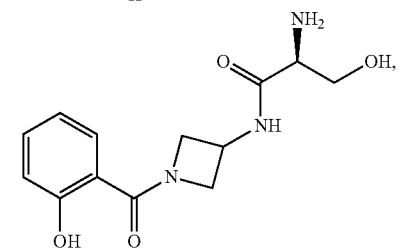
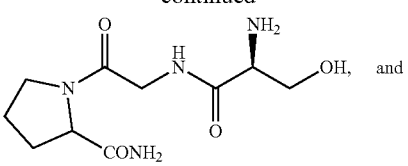 and
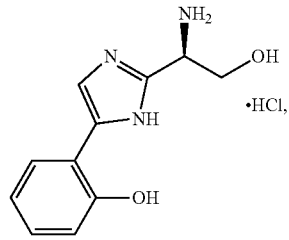
or any pharmaceutically acceptable salt thereof; and an anti-cancer therapeutic agent to the subject.
In some embodiments, the method comprises co-administering a compound selected from:
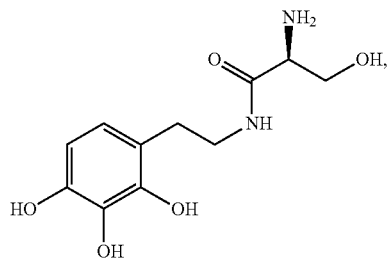 [SMILES: N[C@@H](CO)C(=O)NCCc1ccc(O)c(O)c1O]
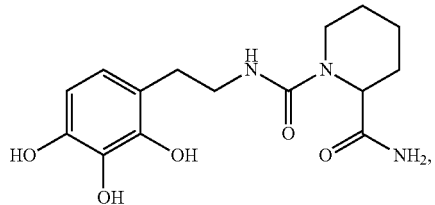
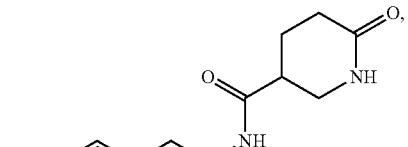
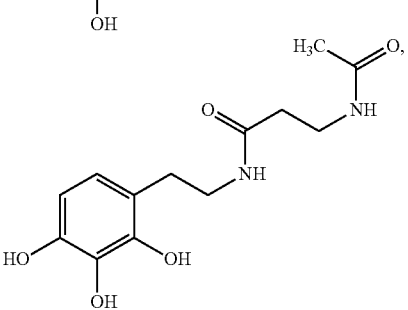

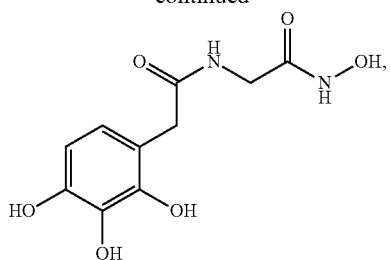

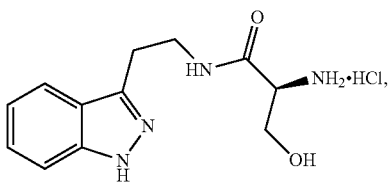

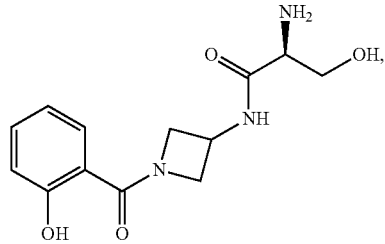

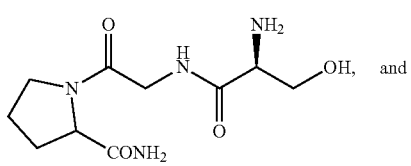

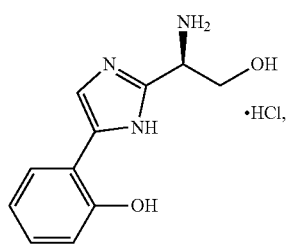

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

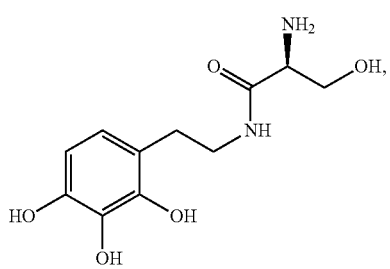 [SMILES: N[C@@H](CO)C(=O)NCCc1ccc(O)c(O)c1O]

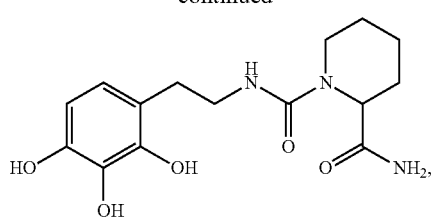

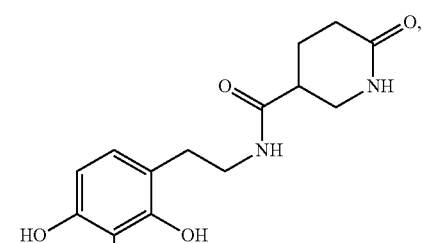

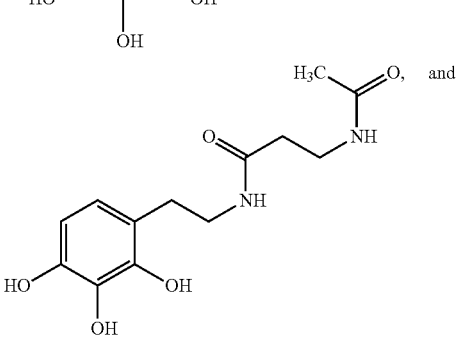

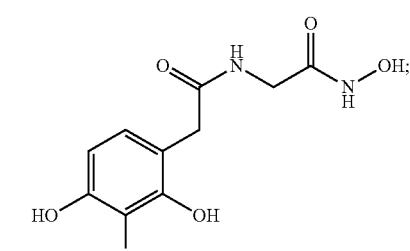

and an anti-cancer therapeutic agent to the subject.

In some embodiments, the method comprises co-administering a compound selected from:

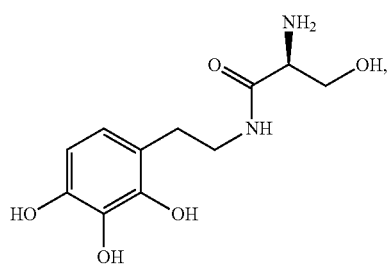

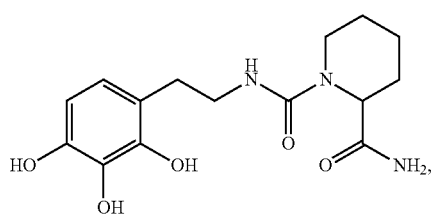 [SMILES: NC(=O)C1CCCCN1C(=O)NCCc1ccc(O)c(O)c1O]

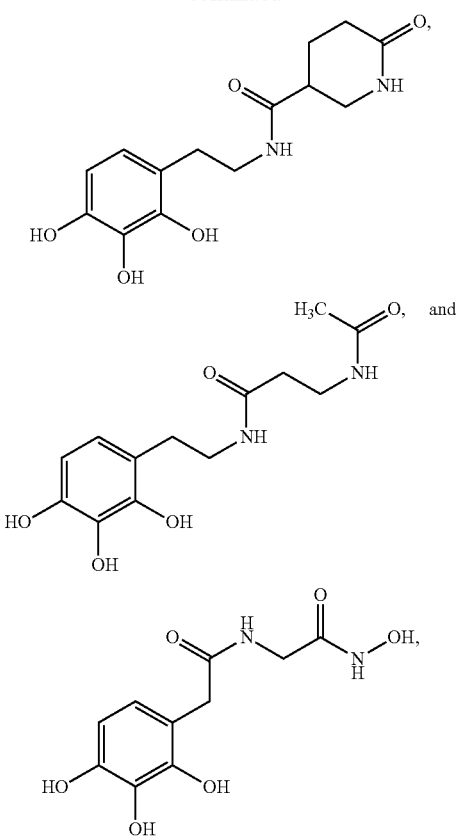

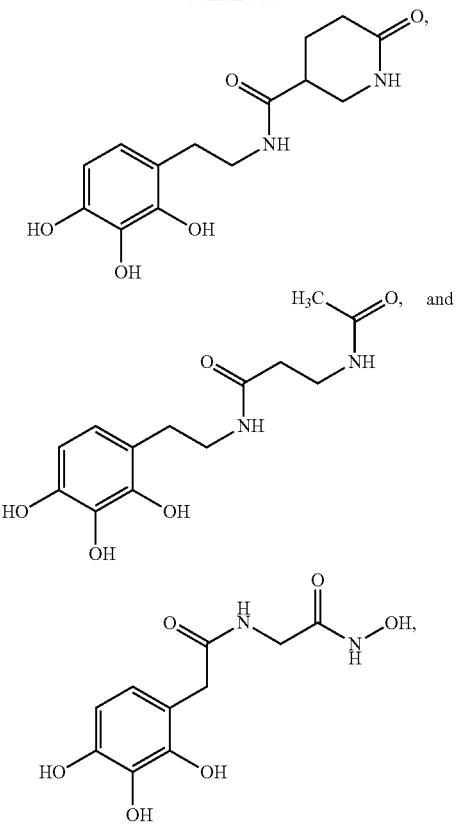

or any pharmaceutically acceptable salt thereof; and an anti-cancer therapeutic agent to the subject.

In some embodiments, the method comprises co-administering a compound selected from:

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

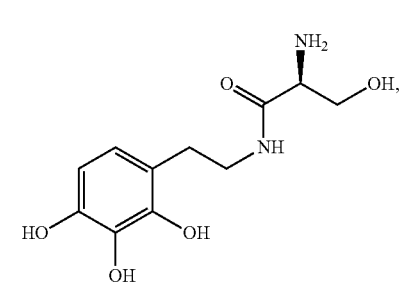

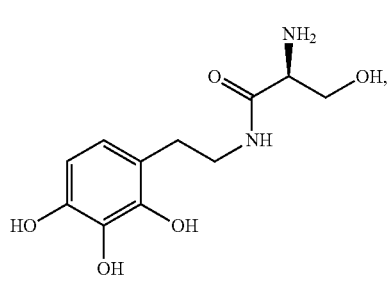

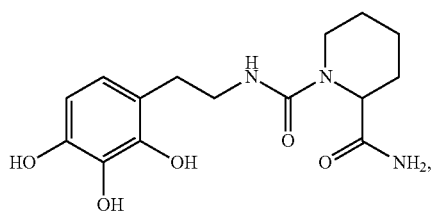

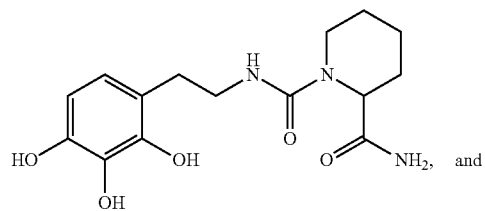

-continued

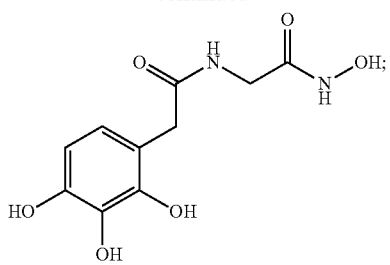

and an anti-cancer therapeutic agent to the subject.

In some embodiments, the method comprises co-administering a compound selected from:

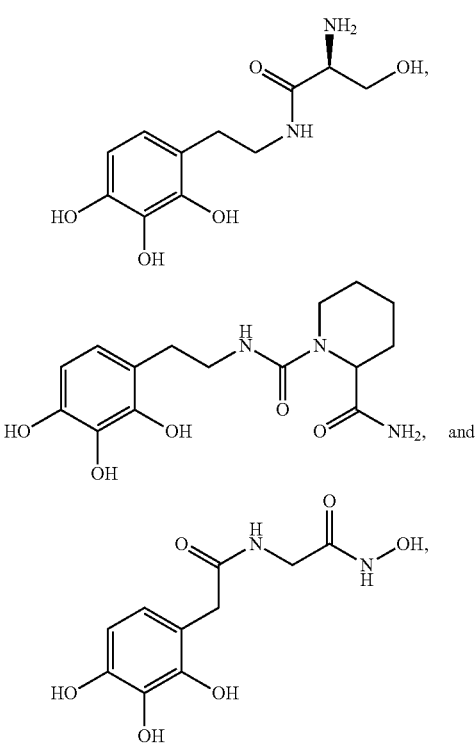

or any pharmaceutically acceptable salt thereof; and an anti-cancer therapeutic agent to the subject.

In some embodiments, the method comprises co-administering a compound selected from:

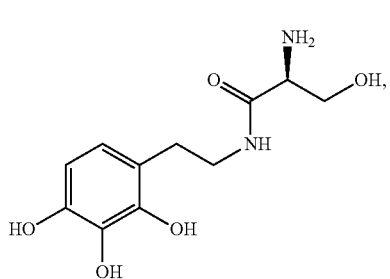

-continued

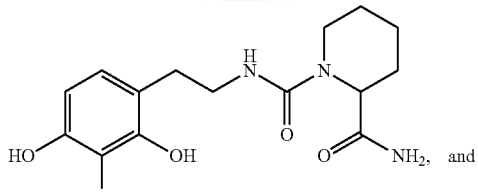

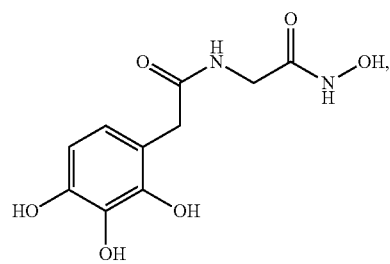

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

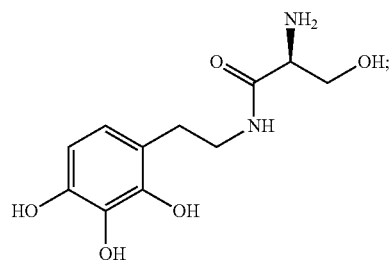

and an anti-cancer therapeutic agent to the subject.

In some embodiments, the method comprises co-administering a compound selected from:

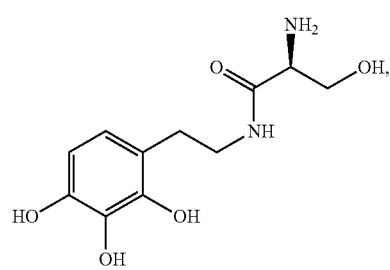

or any pharmaceutically acceptable salt thereof; and an anti-cancer therapeutic agent to the subject.

In some embodiments, the method comprises co-administering a compound selected from:

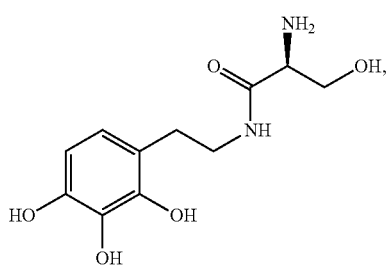

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

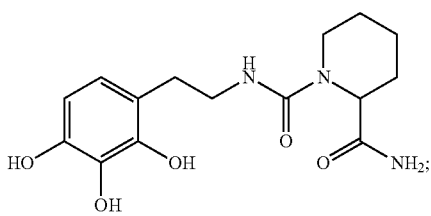

and an anti-cancer therapeutic agent to the subject.

In some embodiments, the method comprises co-administering a compound selected from:

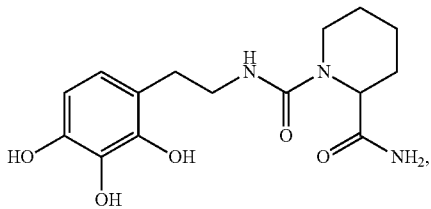

or any pharmaceutically acceptable salt thereof; and an anti-cancer therapeutic agent to the subject.

In some embodiments, the method comprises co-administering a compound selected from:

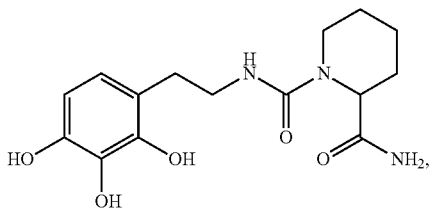

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

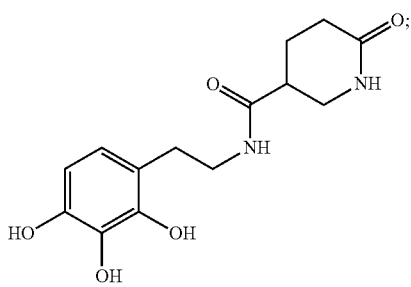

and an anti-cancer therapeutic agent to the subject.

In some embodiments, the method comprises co-administering a compound selected from:

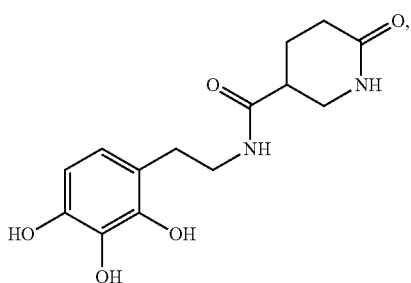

or any pharmaceutically acceptable salt thereof; and an anti-cancer therapeutic agent to the subject.

In some embodiments, the method comprises co-administering a compound selected from:

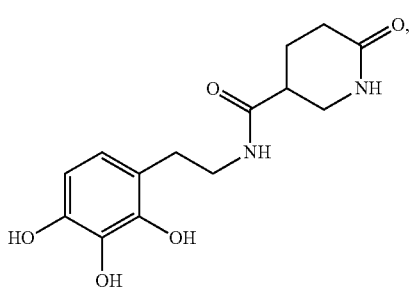 [SMILES: O=C1CCC(C(=O)NCCc2ccc(O)c(O)c2O)CN1]

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

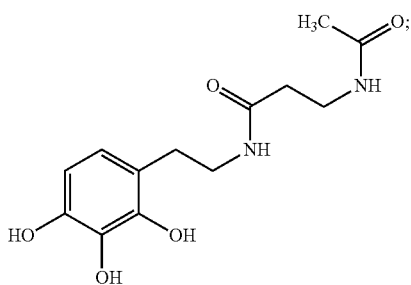

and an anti-cancer therapeutic agent to the subject.

In some embodiments, the method comprises co-administering a compound selected from:

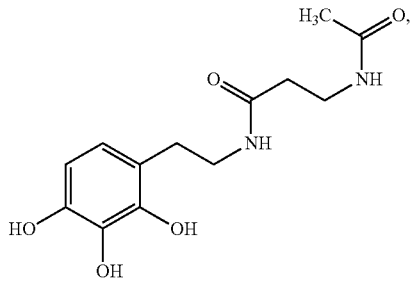 [SMILES: CC(=O)NCCC(=O)NCCc1ccc(O)c(O)c1O]

or any pharmaceutically acceptable salt thereof; and an anti-cancer therapeutic agent to the subject.

In some embodiments, the method comprises co-administering a compound selected from:

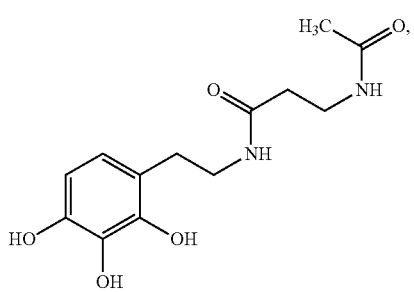 [SMILES: CC(=O)NCCC(=O)NCCc1ccc(O)c(O)c1O]

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

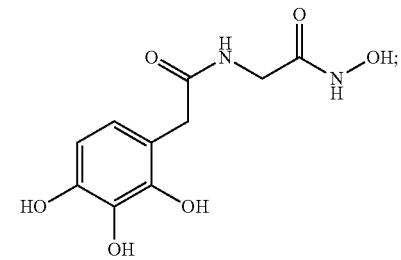 [SMILES: O=C(CNC(=O)Cc1ccc(O)c(O)c1O)NO]

and an anti-cancer therapeutic agent to the subject.

In some embodiments, the method comprises co-administering a compound selected from:

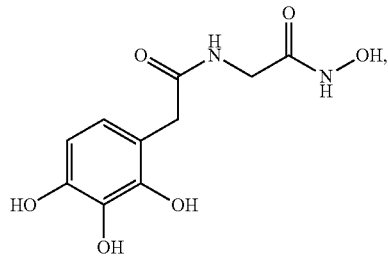

or any pharmaceutically acceptable salt thereof; and an anti-cancer therapeutic agent to the subject.

In some embodiments, the method comprises co-administering a compound selected from:

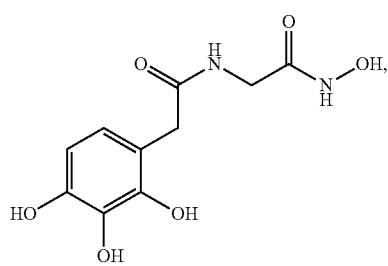

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

COMPOUND CSRM617

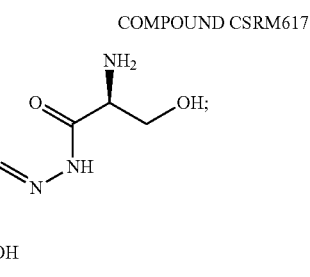

and an anti-cancer therapeutic agent to the subject.

In some embodiments, the method comprises co-administering a compound selected from:

COMPOUND CSRM617

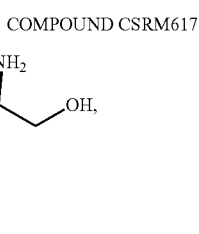

or any pharmaceutically acceptable salt thereof; and an anti-cancer therapeutic agent to the subject.

In some embodiments, the method comprises co-administering a compound selected from:

COMPOUND CSRM617

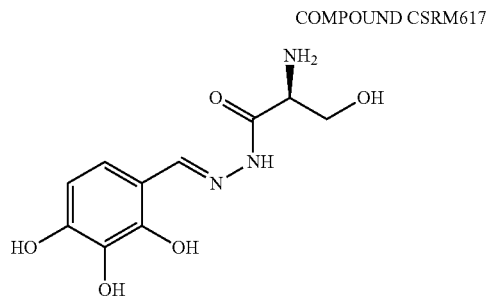 [SMILES: N[C@@H](CO)C(=O)N/N=C/c1ccc(O)c(O)c1O]

or a prodrug, an isomer, a dimer, an enantiomer, a derivative, or a pharmaceutically acceptable salt thereof; and an anti-cancer therapeutic agent to the subject.

In some embodiments, the method comprises co-administering a compound selected from:

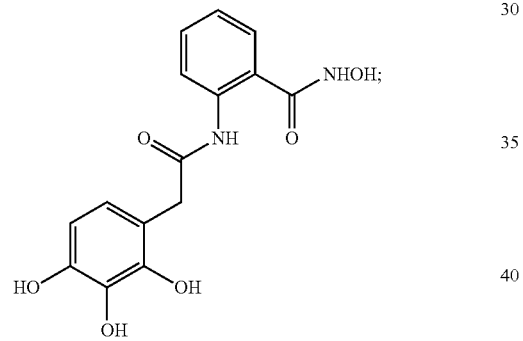

and an anti-cancer therapeutic agent to the subject.

In some embodiments, the method comprises co-administering a compound selected from:

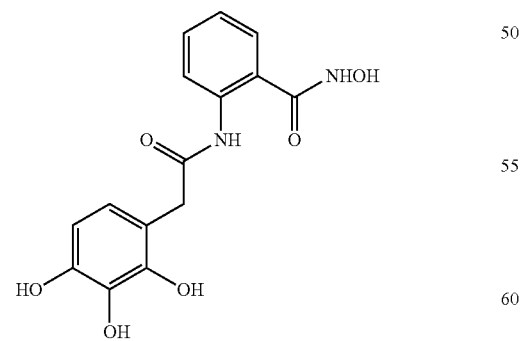

or any pharmaceutically acceptable salt thereof; and an anti-cancer therapeutic agent to the subject.

In some embodiments, the method comprises co-administering a compound selected from:

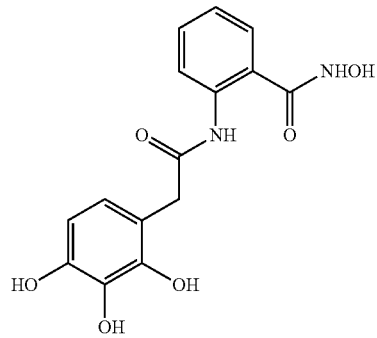

or a prodrug, an isomer, a dimer, an enantiomer, a derivative, or a pharmaceutically acceptable salt thereof; and an anti-cancer therapeutic agent to the subject.

In some embodiments, the method comprises co-administering a compound having the structure:

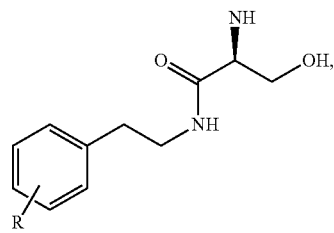

or a prodrug, isomer, dimer, enantiomer, derivative, or pharmaceutically acceptable salt thereof, wherein:

R is independently one or more of hydrogen or optionally substituted sub stituent; and and an anti-cancer therapeutic agent to the subject.

In some embodiments, the method comprises co-administering a compound having the structure:

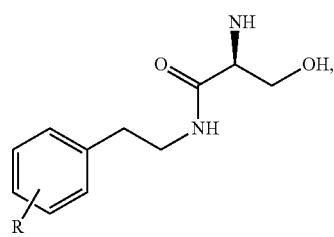

wherein:
R is independently one or more of hydrogen or optionally substituted sub stituent; and an anti-cancer therapeutic agent to the subject.

In some embodiments, the method comprises co-administering a compound having the structure:

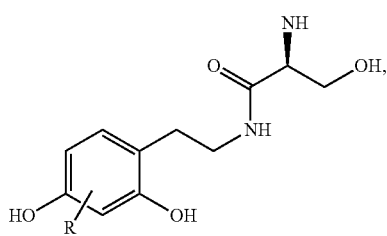

or a prodrug, isomer, dimer, enantiomer, derivative, or pharmaceutically acceptable salt thereof, wherein:
R is independently one or more of hydrogen or optionally substituted sub stituent; and an anti-cancer therapeutic agent to the subject.

In some embodiments, the method comprises co-administering a compound having the structure:

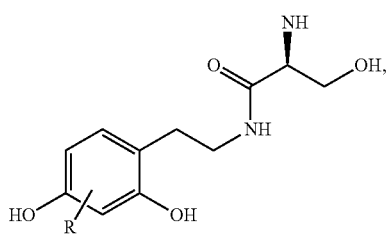

wherein:
R is independently one or more of hydrogen or optionally substituted sub stituent; and an anti-cancer therapeutic agent to the subject.

In some embodiments, the method comprises co-administering a compound having the structure:

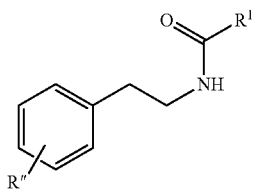

or a prodrug, isomer, dimer, enantiomer, derivative, or pharmaceutically acceptable salt thereof wherein:
R" is independently one or more of hydrogen or optionally substituted sub stituent; and
$R^1$ is hydrogen or optionally substituted substituent; and an anti-cancer therapeutic agent to the subject.

In some embodiments, the method comprises co-administering a compound having the structure:

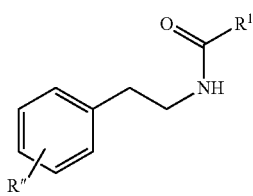

wherein:
R" is independently one or more of hydrogen or optionally substituted substituent; and $R^1$ is hydrogen or optionally substituted substituent; and an anti-cancer therapeutic agent to the subject.

In some embodiments, the method comprises co-administering a compound having the structure:

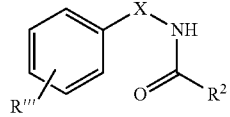

or prodrug, isomer, dimer, enantiomer, derivative, or pharmaceutically acceptable salt thereof, wherein:
R'" is independently one or more of hydrogen or optionally substituted substituent;
$R^2$ is hydrogen or optionally substituted substituent; and
X is NHC(O), C(O)NH, OC(O), C(O)O, C(O), or CH=N; and an anti-cancer therapeutic agent to the subject.

In some embodiments, the method comprises co-administering a compound having the structure:

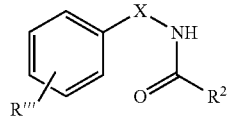

wherein:
R'" is independently one or more of hydrogen or optionally substituted substituent;
$R^2$ is hydrogen or optionally substituted substituent; and
X is NHC(O), C(O)NH, OC(O), C(O)O, C(O), or CH=N; and an anti-cancer therapeutic agent to the subject.

In some embodiments, the method comprises co-administering a compound having the structure:

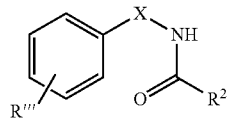

or prodrug, isomer, dimer, enantiomer, derivative, or pharmaceutically acceptable salt thereof, wherein:
R'" is independently one or more of hydrogen or optionally substituted substituent;
$R^2$ is hydrogen or optionally substituted substituent; and
X is NHC(O), C(O)NH, OC(O), C(O)O, C(O), or CH=N; and an anti-cancer therapeutic agent to the subject, provided that the compound is not

COMPOUND CSRM617

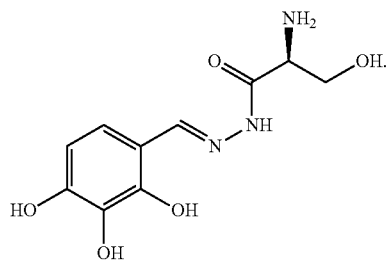

In some embodiments, the method comprises co-administering a compound having the structure:

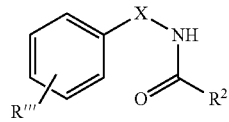

wherein:

R''' is independently one or more of hydrogen or optionally substituted substituent;

R² is hydrogen or optionally substituted substituent; and

X is NHC(O), C(O)NH, OC(O), C(O)O, C(O), or CH=N; and an anti-cancer therapeutic agent to the subject, provided that the compound is not

COMPOUND CSRM617

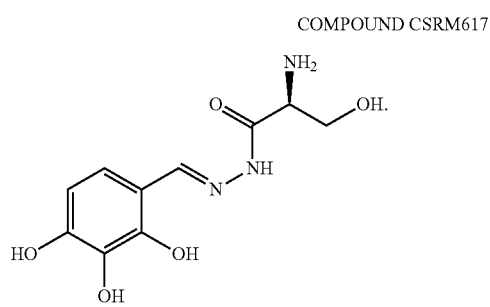 [SMILES: N[C@@H](CO)C(=O)N/N=C/c1ccc(O)c(O)c1O]

In some embodiments, the method comprises co-administering a compound having the structure:

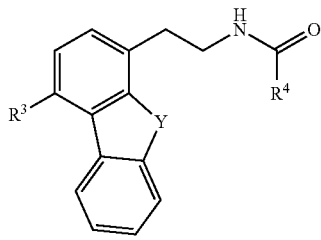

or a prodrug, an isomer, a dimer, an enantiomer, a derivative, or a pharmaceutically acceptable salt thereof, wherein:

R³ is hydrogen or optionally substituted substituent;

R⁴ is hydrogen or optionally substituted substituent; and

X is O or S; and an anti-cancer therapeutic agent to the subject.

In some embodiments, the method comprises co-administering a compound selected from:

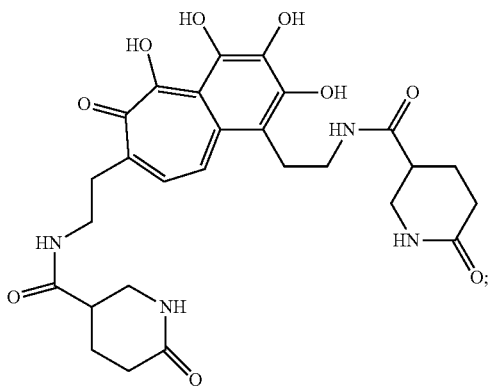 [SMILES: O=C1CCC(C(=O)NCCc2ccc3c(CCNC(=O)C4CCC(=O)NC4)c(O)c(O)c(O)c3c(O)c2=O)CN1]

and an anti-cancer therapeutic agent to the subject.

In some embodiments, the method comprises co-administering a compound selected from:

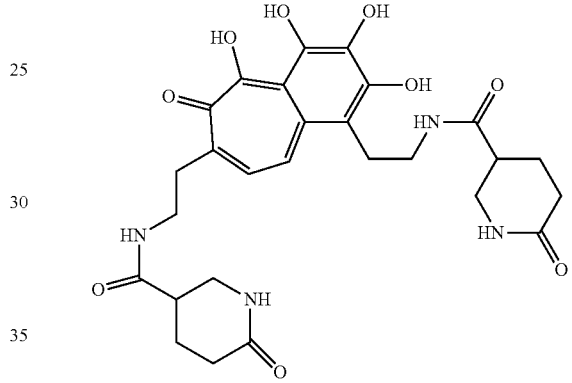

or any pharmaceutically acceptable salt thereof; and an anti-cancer therapeutic agent to the subject.

As used herein, the term "anti-cancer agent" or "anti-cancer therapeutic agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is incorporated herein by reference in its entirety.

The methods of the invention are especially useful in combination with anti-cancer treatments that involve administering a second drug that acts in a different phase of the cell cycle.

Methods for Identifying Inhibitors of ONECUT2

Also provided herein is a method for identifying inhibitors of ONECUT2. The method includes contacting the ONECUT2 in a ONECUT2 positive cell with a molecule of interest; and determining whether the contact results in decreased expression of ONECUT2, a decrease in expression indicating that the molecule of interest is an inhibitor of ONECUT2. In some embodiments, the method includes determining whether the contact results in decreased expression of genes controlled by ONECUT2 (for example, PEG10), wherein a decrease in expression of gene controlled by ONECUT2 indicates that the molecule of interest is an inhibitor of ONECUT2. In exemplary embodiments, the inhibitors is any one or more of small molecule, a peptide, an antibody or a fragment thereof, intrabody, aptamer, antisense construct, RNA interference agent, siRNA, shRNA, ribozyme, antibody-drug conjugate, or combination thereof. In some embodiments, the antibody is selected from the group consisting of monoclonal antibody or fragment thereof, a polyclonal antibody or a fragment thereof, chimeric antibodies, humanized antibodies, human antibodies, and a single chain antibody. In some embodiments, the screening methods for identifying inhibitors of ONECUT2 comprise separately contacting each of a plurality of samples to be tested. In some embodiments, the plurality of samples comprises more than about $10^4$ samples. In some embodiments, the plurality of samples comprises more than about $5 \times 10^4$ samples.

Various embodiments of the present invention provide a screening method for identifying inhibitors of ONECUT2 comprising: (i) contacting the ONECUT2 in a ONECUT2 positive cell with a molecule of interest; and (ii) determining whether the contact results in decreased expression of ONECUT2, a decrease in expression indicating that the molecule of interest is an inhibitor of ONECUT2; and separately contacting each of a plurality of samples to be tested. In some embodiments, the inhibitor is any one or more of small molecule, a peptide, an antibody or a fragment thereof, intrabody, aptamer, antisense construct, RNA interference agent, siRNA, shRNA, ribozyme, antibody-drug conjugate, or combination thereof. In some embodiments, the plurality of samples comprises more than about $10^4$ samples. In some embodiments, the plurality of samples comprises more than about $5 \times 10^4$ samples.

In exemplary embodiments, a candidate compound (molecule of interest) is a small molecule comprising Formula I:

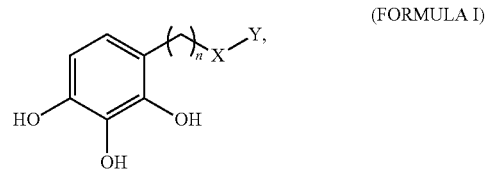

(FORMULA I)

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted.

In exemplary embodiments, a candidate compound (molecule of interest) is a small molecule comprising Formula I:

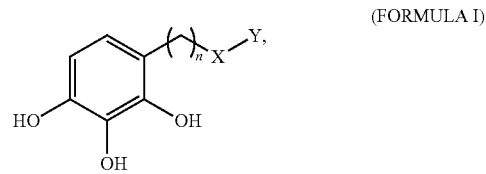

(FORMULA I)

wherein: n is 0, 1, 2, 3, 4 or 5; X is NHC(O), C(O)NH, OC(O), C(O)O, C(O), or CH=N; and Y is alkyl, heteroalkyl, cyclyl, heterocyclyl, aryl, or heteroaryl, each of which can be optionally substituted, provided that the compound is not Compound CSRM617 or a compound of Formula I as provided in Table 1.

In exemplary embodiments, a candidate compound (molecule of interest) is a small molecule comprising Formula II:

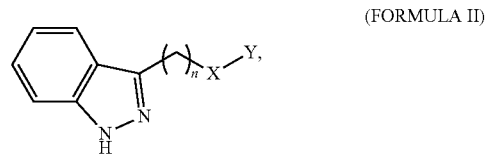

(FORMULA II)

wherein: n is 0, 1, 2, 3, 4 or 5; X is NHC(O), C(O)NH, OC(O), C(O)O, or C(O); and Y is alkyl, heteroalkyl, cyclyl, heterocyclyl, aryl, or heteroaryl, each of which can be optionally substituted.

In exemplary embodiments, a candidate compound (molecule of interest) is a small molecule comprising Formula III:

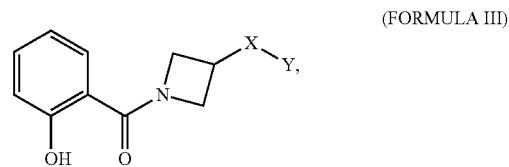

(FORMULA III)

wherein: X is NH, or O; and Y is alkyl, heteroalkyl, cyclyl, heterocyclyl, aryl, or heteroaryl, each of which can be optionally substituted.

In exemplary embodiments, a candidate compound (molecule of interest) is a small molecule comprising Formula IV:

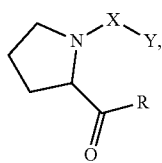

(FORMULA IV)

wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl.

In exemplary embodiments, a candidate compound (molecule of interest) is a small molecule comprising Formula V:

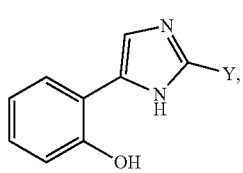

(FORMULA V)

wherein: Y is alkyl, heteroalkyl, cyclyl, heterocyclyl, aryl, or heteroaryl, each of which can be optionally substituted.

In exemplary embodiments, a candidate compound (molecule of interest) is a small molecule comprising the structure:

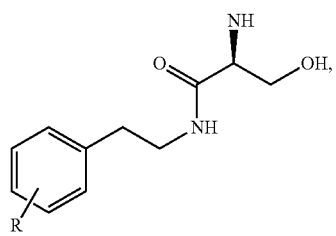

wherein:
R is independently one or more of hydrogen or optionally substituted substituent.

In exemplary embodiments, a candidate compound (molecule of interest) is a small molecule comprising the structure:

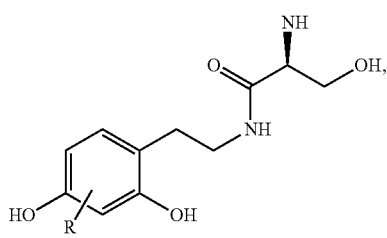

wherein:
R is independently one or more of hydrogen or optionally substituted substituent.

In exemplary embodiments, a candidate compound (molecule of interest) is a small molecule comprising the structure:

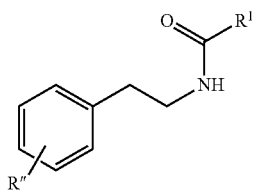

wherein:
R" is independently one or more of hydrogen or optionally substituted substituent; and
R$^1$ is hydrogen or optionally substituted substituent.

In exemplary embodiments, a candidate compound (molecule of interest) is a small molecule comprising the structure:

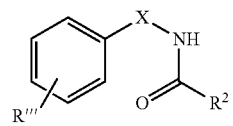

wherein:
R'" is independently one or more of hydrogen or optionally substituted substituent;
R$^2$ is hydrogen or optionally substituted substituent; and
X is NHC(O), C(O)NH, OC(O), C(O)O, C(O), or CH=N.

In exemplary embodiments, a candidate compound (molecule of interest) is a small molecule comprising the structure:

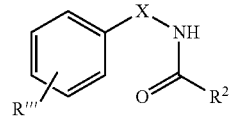

wherein:
R'" is independently one or more of hydrogen or optionally substituted substituent;
R$^2$ is hydrogen or optionally substituted substituent; and
X is NHC(O), C(O)NH, OC(O), C(O)O, C(O), or CH=N, provided that the compound is not

COMPOUND CSRM617

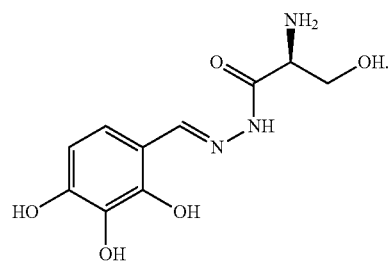

In exemplary embodiments, a candidate compound (molecule of interest) is a small molecule comprising the structure:

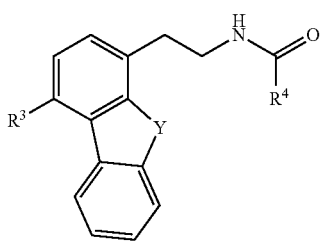

wherein:
$R^3$ is hydrogen or optionally substituted substituent;
$R^4$ is hydrogen or optionally substituted substituent; and
X is O or S.

Various embodiments of the present invention provide a screening method for identifying inhibitors of ONECUT2 comprising: (i) contacting the ONECUT2 in a ONECUT2 positive cell with a molecule of interest; and (ii) determining whether the contact results in decreased expression of ONECUT2, a decrease in expression indicating that the molecule of interest is an inhibitor of ONECUT2; and separately contacting each of a plurality of samples to be tested. In some embodiments, the inhibitor is any one or more of small molecule, a peptide, an antibody or a fragment thereof, intrabody, aptamer, antisense construct, RNA interference agent, siRNA, shRNA, ribozyme, antibody-drug conjugate, or combination thereof. In some embodiments, the plurality of samples comprises more than about $10^4$ samples. In some embodiments, the plurality of samples comprises more than about $5 \times 10^4$ samples.

Assays of the Invention

Various embodiments of the present invention provide an assay for determining the prognosis of cancer in a subject in need thereof comprising: obtaining a sample from the subject having or suspected of having cancer; assaying the sample to determine the expression level of ONECUT2; and determining that the subject has poor prognosis if the expression of ONECUT2 is increased relative to a reference value. In some embodiments, the sample is blood, plasma, urine, tissue or combinations thereof. In some embodiments, the sample is obtained before, during or after treatment for cancer. In some embodiments, the subject is human. In some embodiments, the reference value is the mean or median level of ONECUT2 expression in a population of subjects that do not have cancer. In some embodiments, the reference value is the mean or median level of ONECUT2 expression in a population of subjects that have cancer and have been treated for cancer. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have ONECUT2 overexpressing cancer and have undergone or are undergoing treatment for the ONECUT2 overexpressing cancer. In some embodiments, the expression of ONECUT2 is increased 2-fold, 3-fold, 4-fold, 5-fold, 10-fold, 20-fold, 50-fold, or 100-fold relative to a reference value.

Provided herein is an assay for determining the likelihood of CRPC in a subject in need thereof. The assay includes obtaining a sample from the subject; assaying the sample to determine the expression level of ONECUT2; and determining that the subject has increased likelihood of CRPC if the expression of ONECUT2 is increased relative to a reference value, or determining that the subject has decreased likelihood of CRPC if the expression of ONECUT2 is decreased relative to the reference value. In one embodiment, the subject has prostate cancer.

Also provided herein is an assay for selecting a subject for therapy targeting ONECUT2. The assay includes obtaining a sample from the subject; assaying the sample to determine the expression level of ONECUT2; and selecting the subject for therapy that inhibits ONECUT2 if the expression of ONECUT2 is increased relative to a reference value. In one embodiment, the subject has prostate cancer. In various embodiments of the assays provided herein, the sample is blood, plasma, urine, tissue or combinations thereof. In some embodiments, the sample is obtained before, during or after treatment for CRPC. In one embodiment, the subject is human. In exemplary embodiments, the reference value is (i) the mean or median level of ONECUT2 expression in a population of subjects that do not have cancer; (ii) the mean or median level of ONECUT2 expression in a population of subjects that have cancer but do not overexpress ONECUT2; (iii) the mean or median level of ONECUT2 expression in a population of subjects that have prostate cancer but do not have CRPC; (iv) the mean or median level of ONECUT2 expression in the subject being tested, wherein the sample is obtained from the subject at an earlier time period; (v) mean or median level of ONECUT2 expression in a population of subjects that have CRPC and have undergone or are undergoing treatment for CRPC; or (vi) combinations thereof.

Various embodiments of the present invention provide an assay for determining the likelihood of CRPC in a subject in need thereof comprising: obtaining a sample from the subject; assaying the sample to determine the expression level of ONECUT2; and determining that the subject has increased likelihood of CRPC if the expression of ONECUT2 is increased relative to a reference value. In some embodiments, the sample is blood, plasma, urine, tissue or combinations thereof. In some embodiments, the sample is obtained before, during or after treatment for CRPC. In some embodiments, the subject is human. In some embodiments, the reference value is the mean or median level of ONECUT2 expression in a population of subjects that do not have prostate cancer. In some embodiments, the reference value is the mean or median level of ONECUT2 expression in a population of subjects that have prostate cancer but do not have CRPC. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have CRPC and have undergone or are undergoing treatment for CRPC.

Various embodiments of the present invention provide an assay for selecting a subject for therapy targeting ONECUT2 comprising: obtaining a sample from the subject; assaying the sample to determine the expression level of ONECUT2; and selecting the subject for therapy that inhibits ONECUT2 if the expression of ONECUT2 is increased relative to a reference value. In some embodiments, the sample is blood, plasma, urine, tissue or combinations thereof. In some embodiments, the sample is obtained before, during or after treatment for CRPC. In some embodiments, the sample is obtained before, during or after treatment for cancer. In some embodiments, the subject is human. In some embodiments, the reference value is the mean or median level of ONECUT2 expression in a population of subjects that do not have prostate cancer. In some embodiments, the reference value is the mean or median level of ONECUT2 expression in a population of subjects that have prostate cancer but do not have CRPC. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have CRPC and have undergone or are undergoing treatment for CRPC. In some embodiments, the cancer is castration resistant prostate cancer (CRPC), breast cancer, lung cancer, colon cancer, renal cancer, gastric cancer, brain cancer or medulloblastoma. In some embodiments, the reference value is the mean or median level of ONECUT2 expression in a population of subjects that do not have cancer. In some embodiments, the reference value is the mean or median level of ONECUT2 expression in a population of subjects that have cancer and have been treated for cancer. In some embodiments, the reference value is the mean or median level of ONECUT2 expression in the subject, wherein the sample is obtained from the subject at an earlier time period. In some embodiments, the reference value is the mean or median level of ONECUT2 expression in a population of subjects that have ONECUT2 overexpressing cancer and have undergone or are undergoing treatment for the ONECUT2 overexpressing cancer.

Pharmaceutical Compositions of the Invention

Various embodiments of the present invention provide a pharmaceutical composition comprising a compound selected from Formula I-Formula V; and any pharmaceutically acceptable excipient or carrier.

Various embodiments of the present invention provide a pharmaceutical composition comprising a compound selected from Formula I-Formula V; and any pharmaceutically acceptable excipient or carrier, provided that the compound is not

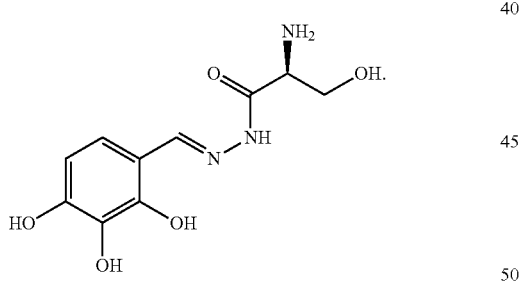

COMPOUND CSRM617

Various embodiments of the present invention provide a pharmaceutical composition comprising a compound selected from:

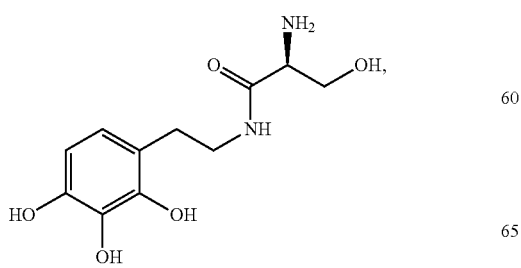

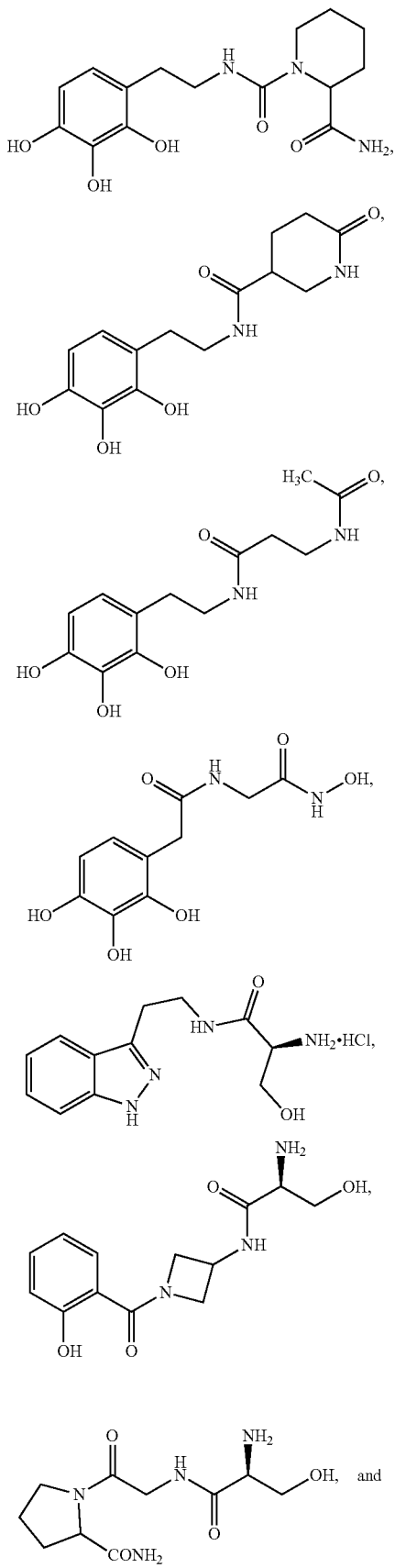

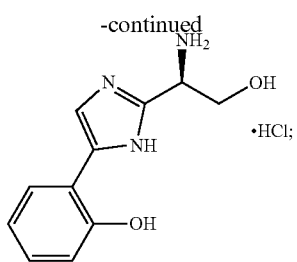

and a pharmaceutically acceptable excipient or carrier.

Various embodiments of the present invention provide a pharmaceutical composition comprising a compound selected from:

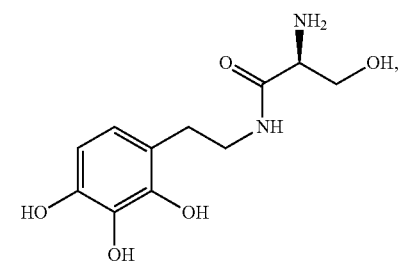 [SMILES: N[C@@H](CO)C(=O)NCCc1ccc(O)c(O)c1O]

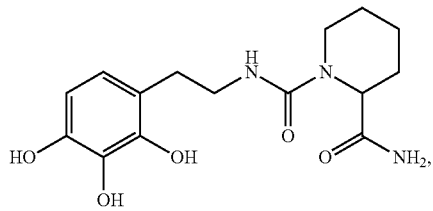

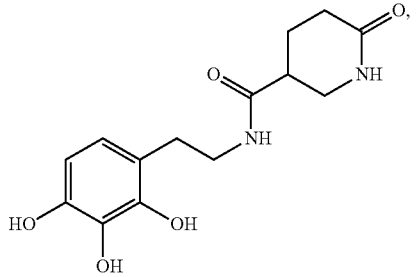

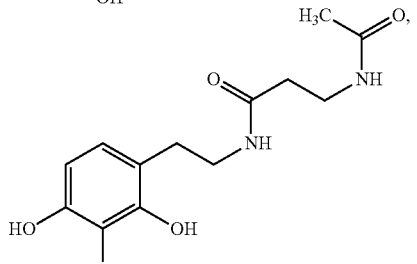

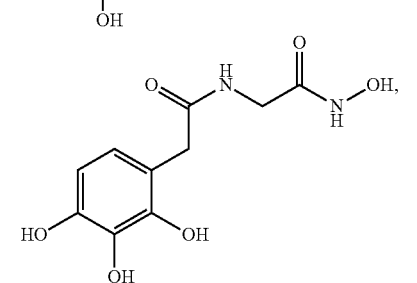

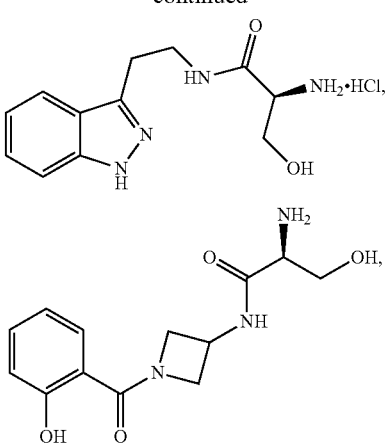

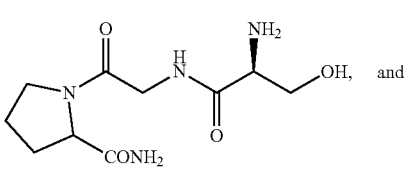

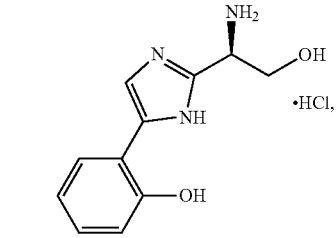

or any pharmaceutically acceptable salt thereof; and a pharmaceutically acceptable excipient or carrier.

Various embodiments of the present invention provide a pharmaceutical composition comprising a compound selected from:

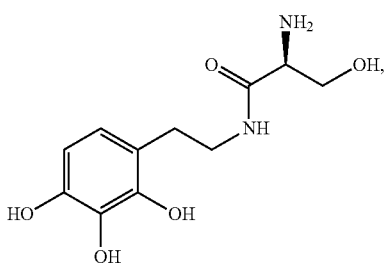

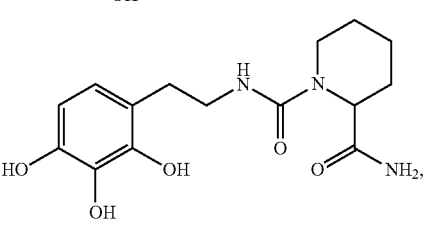

-continued

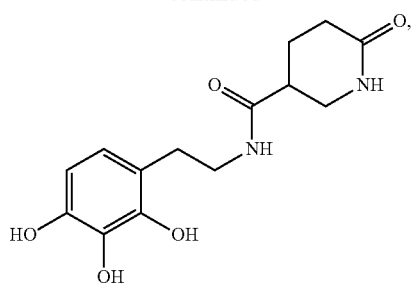

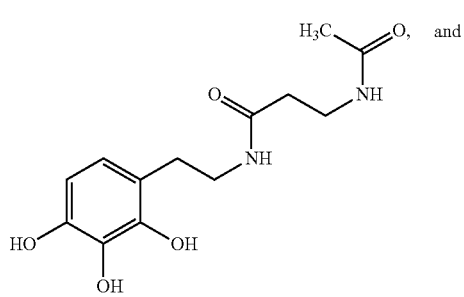

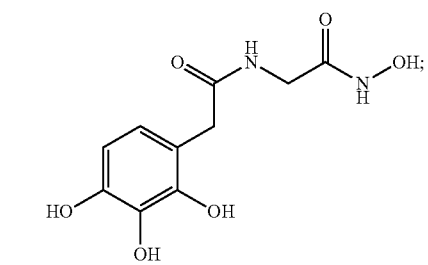

and a pharmaceutically acceptable excipient or carrier.

Various embodiments of the present invention provide a pharmaceutical composition comprising a compound selected from:

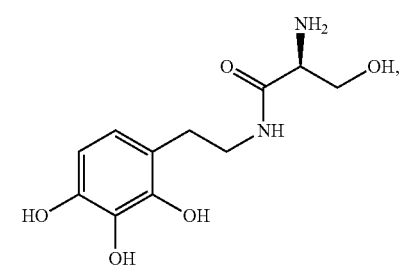 [SMILES: N[C@@H](CO)C(=O)NCCc1ccc(O)c(O)c1O]

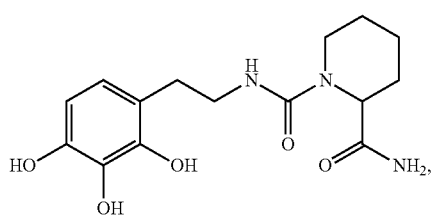

-continued

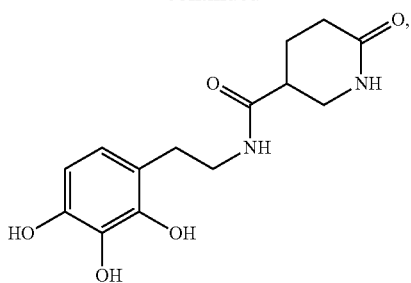

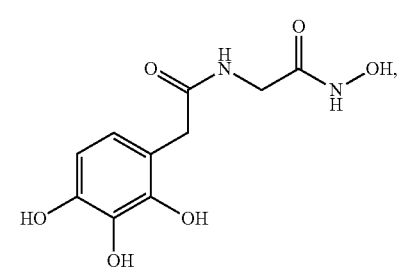

or any pharmaceutically acceptable salt thereof; and a pharmaceutically acceptable excipient or carrier.

Various embodiments of the present invention provide a pharmaceutical composition comprising a compound selected from:

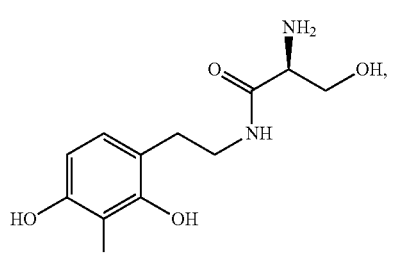

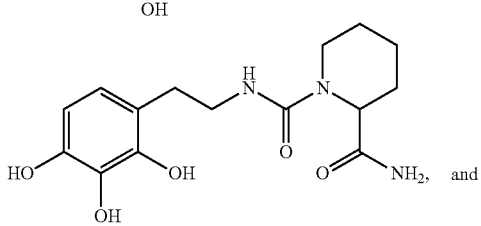

-continued

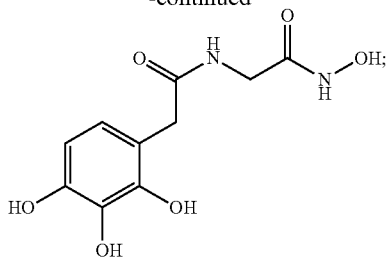

and a pharmaceutically acceptable excipient or carrier.

Various embodiments of the present invention provide a pharmaceutical composition comprising a compound selected from:

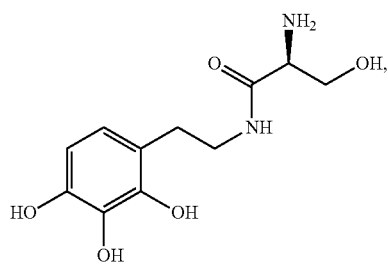

or any pharmaceutically acceptable salt thereof; and a pharmaceutically acceptable excipient or carrier.

Various embodiments of the present invention provide a pharmaceutical composition comprising a compound selected from:

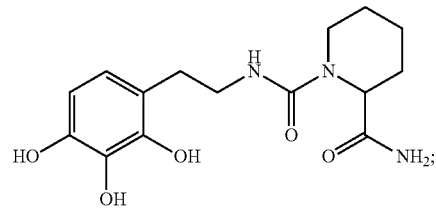 [SMILES: NC(=O)C1CCCCN1C(=O)NCCc1ccc(O)c(O)c1O]

and a pharmaceutically acceptable excipient or carrier.

Various embodiments of the present invention provide a pharmaceutical composition comprising a compound selected from:

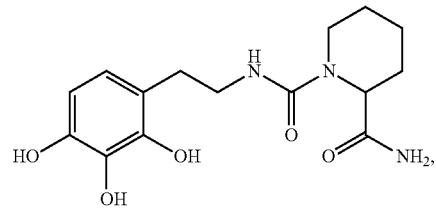 [SMILES: NC(=O)C1CCCCN1C(=O)NCCc1ccc(O)c(O)c1O]

or any pharmaceutically acceptable salt thereof; and a pharmaceutically acceptable excipient or carrier.

Various embodiments of the present invention provide a pharmaceutical composition comprising a compound selected from:

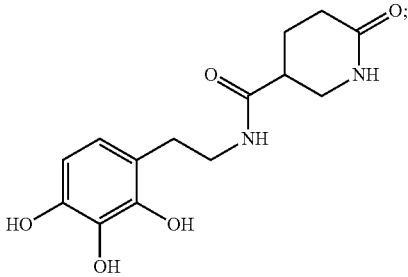

and a pharmaceutically acceptable excipient or carrier.

Various embodiments of the present invention provide a pharmaceutical composition comprising a compound selected from:

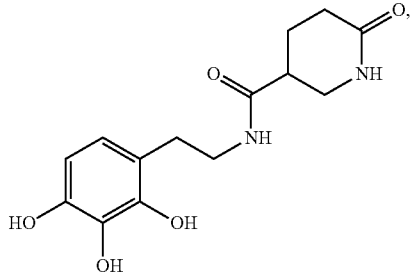 [SMILES: O=C1CCC(C(=O)NCCc2ccc(O)c(O)c2O)CN1]

or any pharmaceutically acceptable salt thereof; and a pharmaceutically acceptable excipient or carrier.

Various embodiments of the present invention provide a pharmaceutical composition comprising a compound selected from:

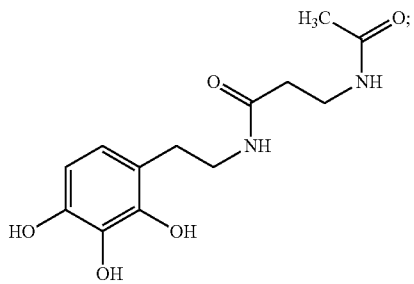 [SMILES: CC(=O)NCCC(=O)NCCc1ccc(O)c(O)c1O]

and a pharmaceutically acceptable excipient or carrier.

Various embodiments of the present invention provide a pharmaceutical composition comprising a compound selected from:

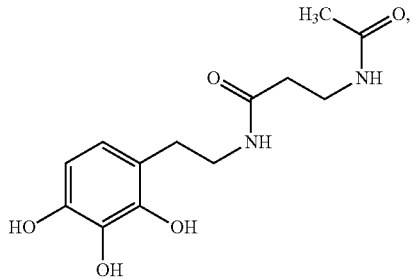 [SMILES: CC(=O)NCCC(=O)NCCc1ccc(O)c(O)c1O]

or any pharmaceutically acceptable salt thereof; and a pharmaceutically acceptable excipient or carrier.

Various embodiments of the present invention provide a pharmaceutical composition comprising a compound selected from:

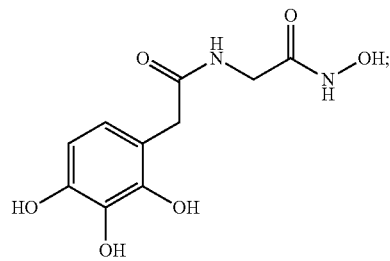 [SMILES: O=C(CNC(=O)Cc1ccc(O)c(O)c1O)NO]

and a pharmaceutically acceptable excipient or carrier.

Various embodiments of the present invention provide a pharmaceutical composition comprising a compound selected from:

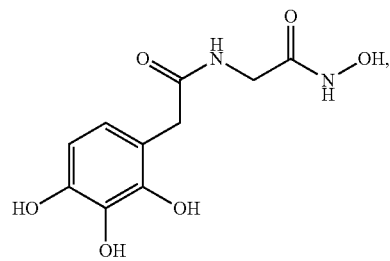

or any pharmaceutically acceptable salt thereof; and a pharmaceutically acceptable excipient or carrier.

Various embodiments of the present invention provide a pharmaceutical composition comprising Compound CSRM617 and a pharmaceutically acceptable excipient or carrier, wherein the Compound CSRM617 has the structure:

COMPOUND CSRM617

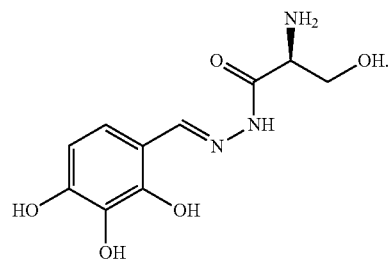

Various embodiments of the present invention provide a pharmaceutical composition comprising Compound CSRM617 and a pharmaceutically acceptable excipient or carrier, wherein the Compound CSRM617 has the structure:

COMPOUND CSRM617

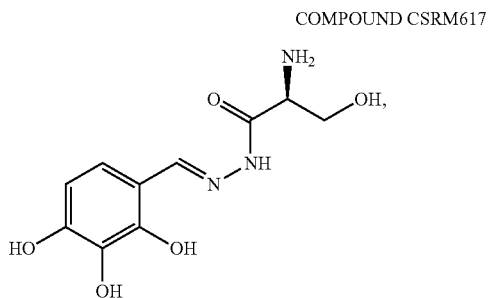 [SMILES: N[C@@H](CO)C(=O)N/N=C/c1ccc(O)c(O)c1O]

or any pharmaceutically acceptable salt thereof.

Various embodiments of the present invention provide a pharmaceutical composition comprising a compound selected from:

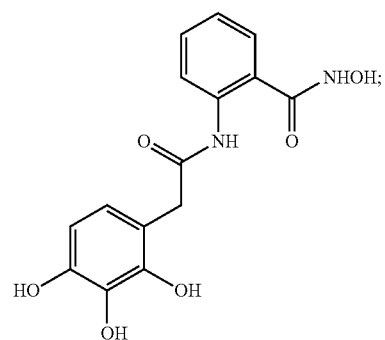

and a pharmaceutically acceptable excipient or carrier.

Various embodiments of the present invention provide a pharmaceutical composition comprising a compound selected from:

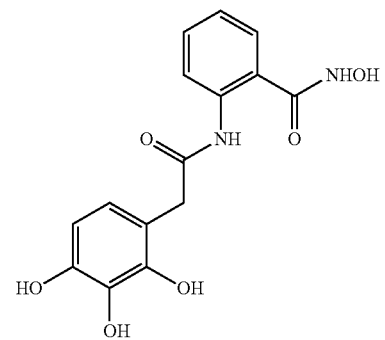

or any pharmaceutically acceptable salt thereof; and a pharmaceutically acceptable excipient or carrier.

Various embodiments of the present invention provide a pharmaceutical composition comprising a compound of structure:

COMPOUND CSRM617

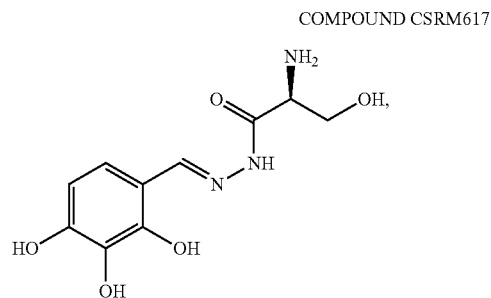 [SMILES: N[C@@H](CO)C(=O)N/N=C/c1ccc(O)c(O)c1O]

and a pharmaceutically acceptable excipient or carrier.

Various embodiments of the present invention provide a pharmaceutical composition comprising a compound of Formula I:

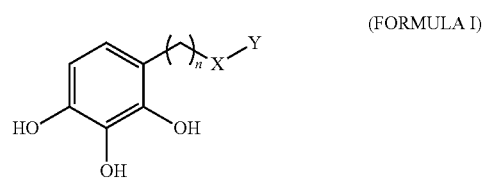

(FORMULA I)

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier.

Various embodiments of the present invention provide a pharmaceutical composition comprising a compound of Formula I:

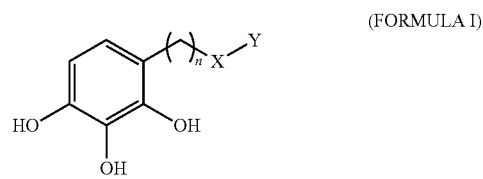

(FORMULA I)

wherein: n is 0, 1, 2, 3, 4 or 5; X is NHC(O), C(O)NH, OC(O), C(O)O, C(O), or CH=N; Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier, provided that the compound is not

COMPOUND CSRM617

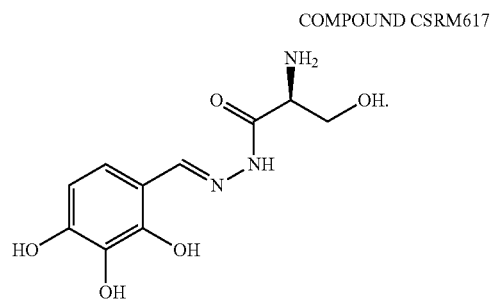

Various embodiments of the present invention provide a pharmaceutical composition comprising a compound of Formula II:

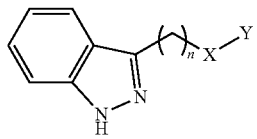

(FORMULA II)

wherein: n is 0, 1, 2, 3, 4 or 5; X is NHC(O), C(O)NH, OC(O), C(O)O, or C(O); Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier.

Various embodiments of the present invention provide a pharmaceutical composition comprising a compound of Formula III:

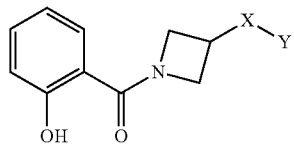

(FORMULA III)

wherein: X is NH, or O; Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier Various embodiments of the present invention provide a pharmaceutical composition comprising a compound of Formula IV:

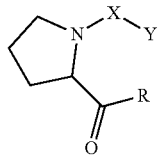

(FORMULA IV)

wherein: X is C(O), C(O)(CH$_2$)$_m$O, or C(O)(CH$_2$)$_m$NH; Y is alkyl, heteroalkyl, cyclyl, heterocyclyl, aryl, or heteroaryl, each of which can be optionally substituted; m is 0, 1, 2, 3, 4, or 5; R is H, CH$_3$, alkyl, NH$_2$, or OR', where R' is H, CH$_3$, or alkyl; and any pharmaceutically acceptable salt thereof; and a pharmaceutically acceptable excipient or carrier.

Various embodiments of the present invention provide a pharmaceutical composition comprising a compound of Formula V:

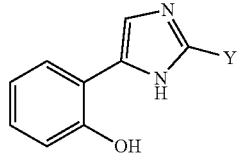

(FORMULA V)

wherein: Y is alkyl, heteroalkyl, cyclyl, heterocyclyl, aryl, or heteroaryl, each of which can be optionally substituted; and any pharmaceutically acceptable salt thereof; and a pharmaceutically acceptable excipient or carrier.

Various embodiments of the present invention provide a pharmaceutical composition comprising a compound having the structure:

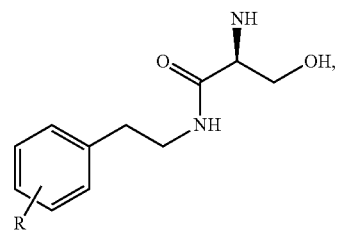

or a prodrug, an isomer, dimer, enantiomer, derivative, or pharmaceutically acceptable salt thereof, wherein:
R is independently one or more of hydrogen or optionally substituted sub stituent.

Various embodiments of the present invention provide a pharmaceutical composition comprising a compound having the structure:

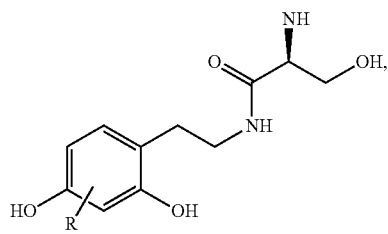

or a prodrug, isomer, dimer, enantiomer, derivative, or pharmaceutically acceptable salt thereof, wherein:
R is independently one or more of hydrogen or optionally substituted sub stituent.

Various embodiments of the present invention provide a pharmaceutical composition comprising a compound having the structure:

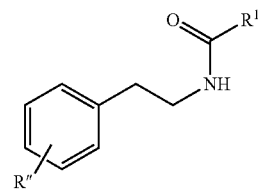

or a prodrug, isomer, dimer, enantiomer, derivative, or pharmaceutically acceptable salt thereof wherein:

R" is independently one or more of hydrogen or optionally substituted substituent; and R¹ is hydrogen or optionally substituted substituent.

Various embodiments of the present invention provide a pharmaceutical composition comprising a compound having the structure:

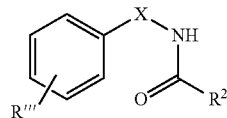

or a prodrug, isomer, dimer, enantiomer, derivative, or pharmaceutically acceptable salt thereof, wherein:
R''' is independently one or more of hydrogen or optionally substituted substituent;
R² is hydrogen or optionally substituted substituent; and
X is NHC(O), C(O)NH, OC(O), C(O)O, C(O), or CH=N.

Various embodiments of the present invention provide a pharmaceutical composition comprising a compound having the structure:

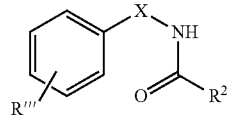

or a prodrug, isomer, dimer, enantiomer, derivative, or pharmaceutically acceptable salt thereof, wherein:
R''' is independently one or more of hydrogen or optionally substituted substituent;
R² is hydrogen or optionally substituted substituent; and
X is NHC(O), C(O)NH, OC(O), C(O)O, C(O), or CH=N, provided that the compound is not

COMPOUND CSRM617

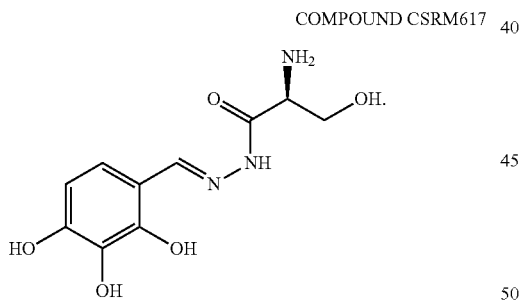

Various embodiments of the present invention provide a pharmaceutical composition comprising a compound having the structure:

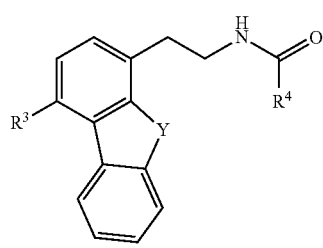

or prodrug, isomer, dimer, enantiomer, derivative, or pharmaceutically acceptable salt thereof, wherein:
R³ is hydrogen or optionally substituted substituent;
R⁴ is hydrogen or optionally substituted substituent; and
X is O or S.

Various embodiments of the present invention provide a pharmaceutical composition comprising a compound selected from:

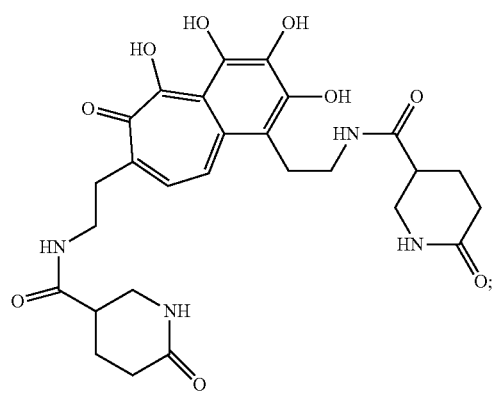 [SMILES: O=C1CCC(C(=O)NCCc2ccc3c(CCNC(=O)C4CCC(=O)NC4)c(O)c(O)c(O)c3c(O)c2=O)CN1]

and a pharmaceutically acceptable excipient or carrier.

Various embodiments of the present invention provide a pharmaceutical composition comprising a compound selected from:

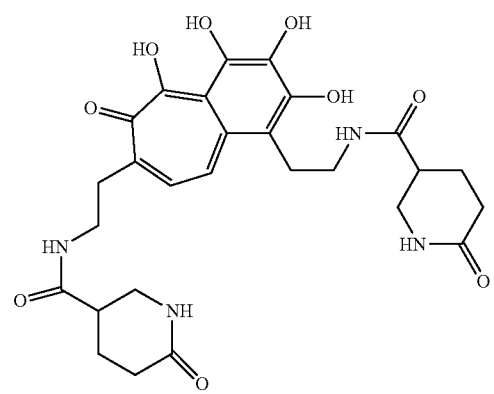 [SMILES: O=C1CCC(C(=O)NCCc2ccc3c(CCNC(=O)C4CCC(=O)NC4)c(O)c(O)c(O)c3c(O)c2=O)CN1]

or any pharmaceutically acceptable salt thereof; and a pharmaceutically acceptable excipient or carrier.

For administration to a subject, the agents for modulating activity of ONECUT2 protein can be provided in pharmaceutically acceptable compositions. These pharmaceutically acceptable compositions comprise an agent capable of modulating activity of ONECUT2 protein formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, contents of all of which are herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical compositions are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The phrase "therapeutically effective amount" as used herein means that amount of an agent, compound, material, or composition comprising the same which is effective for producing some desired therapeutic effect in at least a sub-population of cells in an animal at a reasonable benefit/risk ratio applicable to a medical treatment. Determination of a therapeutically effective amount is well within the capability of those skilled in the art. Generally, a therapeutically effective amount can vary with the subject's history, age, condition, well as the severity and type of the medical condition in the subject, and administration of The amount of the ONECUT2 modulating agent that can be combined with a carrier material to produce a single dosage form will generally be that amount of the agent that produces a therapeutic effect. Generally out of one hundred percent, this amount will range from about 0.01% to 99% of agent, preferably from about 5% to about 70%, most preferably from 10% to about 30%.

Toxicity and therapeutic efficacy can be determined by standard pharmaceutical procedures in cell cultures or experimental animals, e.g., for determining the $LD_{50}$ (the dose lethal to 50% of the population) and the $ED5_0$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The dosage can be determined by a physician and adjusted, as necessary, to suit observed effects of the treatment. Generally, the compositions are administered so that the agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that agent or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

"Contacting" as used here with reference to contacting a cell with an agent (e.g., a compound disclosed herein) refers to any method that is suitable for placing the agent on, in or adjacent to a target cell. For example, when the cells are in vitro, contact the cells with the agent can comprise adding the agent to culture medium containing the cells. For example, when the cells are in vivo, contacting the cells with the agent can comprise administering the agent to the subject.

As used herein, the term "administering" refers to the placement of an agent or a composition as disclosed herein into a subject by a method or route which results in at least partial localization of the agents or composition at a desired site such that a desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

"Route of administration" may refer to any administration pathway known in the art, including but not limited to oral, topical, aerosol, nasal, via inhalation, anal, intra-anal, perianal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres, nanoparticles comprised of proteineous or non-proteineous components or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments of the various aspects described herein, the compositions are administered by intravenous infusion or injection.

A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-mefhylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

The term "prodrug" as used herein refers to compounds that can be converted via some chemical or physiological process (e.g., enzymatic processes and metabolic hydrolysis) to compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* ll:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drug s", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal ab sorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which are herein incorporated by reference in its entirety.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the term "co-administer" refers to administration of two or more therapies or two or more therapeutic agents (e.g., Compound CSRM617 and additional anti-cancer therapy; a compound of Formula I-Formula V and additional anti-cancer therapy; or an agent or compound disclosed herein for inhibiting the expression or function of ONECUT2 or modulating the activity of ONECUT2, and an additional anti-cancer therapy) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. For example, when the Compound CSRM617 and the additional anti-cancer therapy are administered in different pharmaceutical compositions or at different times, routes of administration can be same or different. For example, when the compound of Formula I-Formula V and additional anti-cancer therapy are administered in different pharmaceutical compositions or at different times, routes of administration can be same or different. For example, when the agent or compound disclosed herein for inhibiting the expression or function of ONECUT2 or modulating the activity of ONECUT2, and an additional anti-cancer therapy are administered in different pharmaceutical compositions or at different times, routes of administration can be same or different.

KITS

In various embodiments, the present invention provides a kit for treating cancers that overexpress ONECUT2. The kit comprises components to treat cancers that overexpress ONECUT2 in the subject and instructions for use.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat cancers that overexpress ONECUT. Optionally, the kit also contains other useful components, such as, measuring tools, diluents, buffers, pharmaceutical compositions, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

In various embodiments, the present invention provides a kit for for treating cancers that overexpress ONECUT2 in a subject, the kit comprising an agent that inhibits expression or activity of ONECUT2. In some embodiments, the kit further comprises instructions for using the kit.

Some embodiments of the present invention can be defined as any of the following numbered paragraphs:

1. A method for treating cancers that overexpress ONECUT2 in a subject in need thereof, comprising providing an agent that inhibits expression or activity of ONECUT2 and administering a therapeutically effective amount of the agent so as to treat cancers that overexpress ONECUT2 in the subject.

2. The method of paragraph 1, wherein the cancer is castration resistant prostate cancer (CRPC), breast cancer, lung cancer, colon cancer, renal cancer, gastric cancer, brain cancer or medulloblastoma.

3. The method of paragraph 1, wherein the agent is Compound CSRM617 of structure:

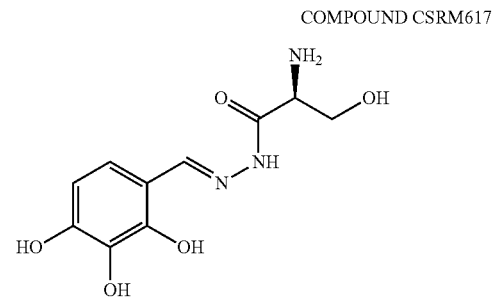 [SMILES: N[C@@H](CO)C(=O)N/N=C/c1ccc(O)c(O)c1O]

COMPOUND CSRM617 or a pharmacetucially acceptable salt thereof.

4. The method of paragraph 1, wherein the method further comprises administration or treatment with one or more additional anti-cancer therapy to the subject in need thereof.

5. The method of paragraph 4, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

6. The method of paragraph 1, wherein the therapeutically effective amount of the agent is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

7. The method of paragraph 1, wherein the subject is human.

8. The method of paragraph 1, wherein the agent is administered to the subject 1-3 times per day or 1-7 times per week.

9. The method of paragraph 1, wherein the agent is administrated to the subject for 1-5 days, 1-5 weeks, 1-5 months, or 1-5 years.

10. The method of paragraph 4, wherein the agent and the additional anti-cancer therapy are administered sequentially or simultaneously.

11. An assay for determining the likelihood of CRPC in a subject in need thereof comprising: obtaining a sample from the subject; assaying the sample to determine the expression level of ONECUT2; and determining that the subject has increased likelihood of CRPC if the expression of ONECUT2 is increased relative to a reference value, or determining that the subject has decreased likelihood of CRPC if the expression of ONECUT2 is decreased relative to the reference value.

12. An assay for selecting a subject for therapy targeting ONECUT2 comprising: obtaining a sample from the subject; assaying the sample to determine the expression level of ONECUT2; and selecting the subject for therapy that inhibits ONECUT2 if the expression of ONECUT2 is increased relative to a reference value.

13. The assay of paragraphs 11 or 12, wherein the sample is blood, plasma, urine, tissue or combinations thereof.

14. The assay of paragraph 11, wherein the sample is obtained before, during or after treatment for CRPC.

15. The assay of paragraphs 11 or 12, wherein the subject is human.

16. The assay of paragraph 11, wherein the reference value is the mean or median level of ONECUT2 expression in a population of subjects that do not have prostate cancer.

17. The assay of paragraph 11, wherein the reference value is the mean or median level of ONECUT2 expression in a population of subjects that have prostate cancer but do not have CRPC.

18. The assay of paragraphs 11 or 12, wherein the reference value is the mean or median level of ONECUT2 expression in the subject of claim 11 or 12, wherein the sample is obtained from the subject at an earlier time period.

19. The assay of paragraph 11, wherein the reference value is the mean or median level of ONECUT2 expression in a population of subjects that have CRPC but have not undergone or are not undergoing treatment for CRPC.

20. A method for identifying inhibitors of ONECUT2 comprising: (i) contacting the ONECUT2 in a ONECUT2 positive cell with a molecule of interest; and (ii) determining whether the contact results in decreased expression of ONECUT2 and/or decreased expression of gene expression controlled by ONECUT2, wherein a decrease in expression indicating that the molecule of interest is an inhibitor of ONECUT2.

21. The method of paragraph 20, wherein the inhibitors is any one or more of small molecule, a peptide, an antibody or a fragment thereof, intrabody, aptamer, antisense construct, RNA interference agent, siRNA, shRNA, ribozyme, antibody-drug conjugate, or combination thereof.

22. A screening method of paragraph 20 or 21, comprising separately contacting each of a plurality of samples to be tested.

23. The screening method of paragraph 22, wherein the plurality of samples comprises more than about $10^4$ samples.

24. The screening method of paragraph 22, wherein the plurality of samples comprises more than about $5 \times 10^4$ samples.

25. A compound of Formula I:

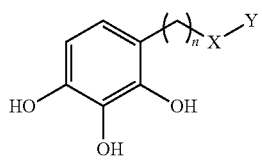

(FORMULA I)

wherein:
n is 0, 1, 2, 3, 4 or 5;
X is NHC(O), C(O)NH, OC(O), C(O)O, C(O), or CH=N;
Y is alkyl, heteroalkyl, cyclyl, heterocyclyl, aryl, or heteroaryl, each of which can be optionally substituted; and any pharmaceutically acceptable salt thereof, provided that the compound is not

COMPOUND CSRM617

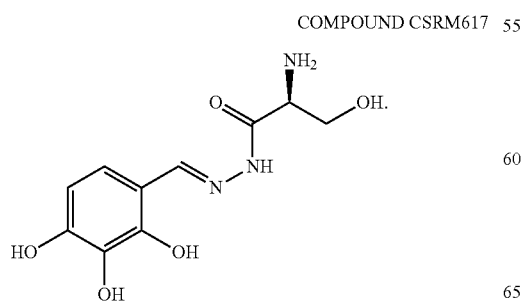

26. A compound of Formula II:

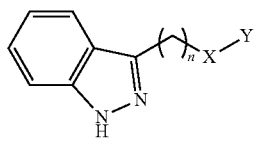

(FORMULA II)

wherein:
n is 0, 1, 2, 3, 4 or 5;
X is NHC(O), C(O)NH, OC(O), C(O)O, or C(O);
Y is alkyl, heteroalkyl, cyclyl, heterocyclyl, aryl, or heteroaryl, each of which can be optionally substituted; and any pharmaceutically acceptable salt thereof.

27. A compound of Formula III:

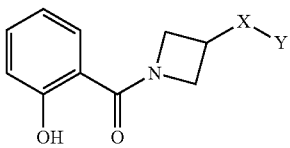

(FORMULA III)

wherein:
X is NH, or O;
Y is alkyl, heteroalkyl, cyclyl, heterocyclyl, aryl, or heteroaryl, each of which can be optionally substituted; and any pharmaceutically acceptable salt thereof.

28. A compound of Formula IV:

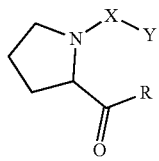

(FORMULA IV)

wherein:
X is C(O), C(O)(CH$_2$)$_m$O, or C(O)(CH$_2$)$_m$NH
Y is alkyl, heteroalkyl, cyclyl, heterocyclyl, aryl, or heteroaryl, each of which can be optionally substituted;
m is 0, 1, 2, 3, 4, or 5;
R is H, CH$_3$, alkyl, NH$_2$, or OR', where R' is H, CH$_3$, or alkyl; and any pharmaceutically acceptable salt thereof.

29. A compound of Formula V:

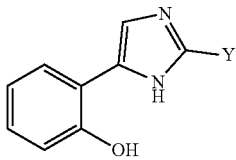

(FORMULA V)

wherein:
Y is alkyl, heteroalkyl, cyclyl, heterocyclyl, aryl, or heteroaryl, each of which can be optionally substituted; and any pharmaceutically acceptable salt thereof.

30. A compound selected from:

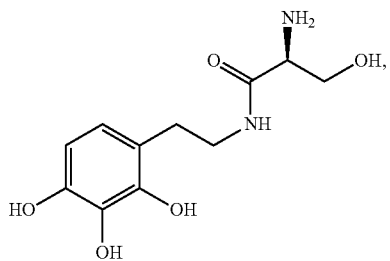

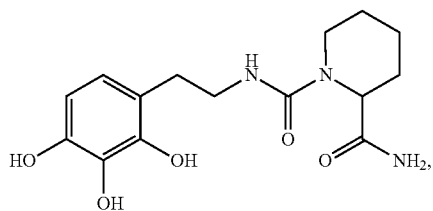

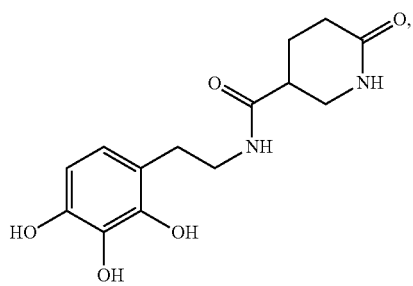

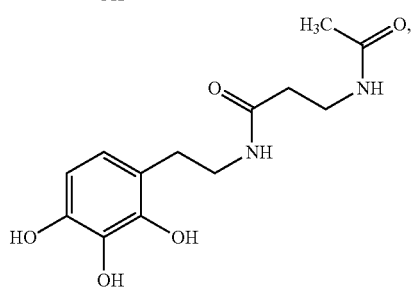

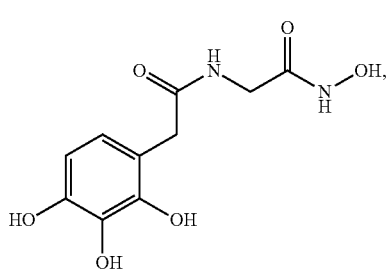

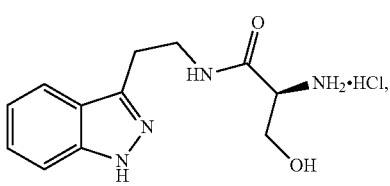

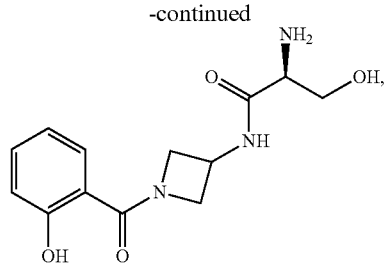

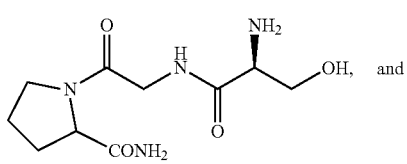

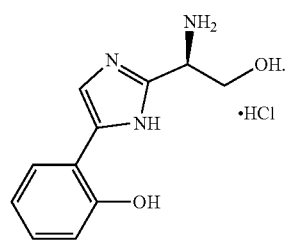

31. A method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from a compound of any one of paragraphs 25-30.

32. The method of paragraph 31, wherein the cancer is castration resistant prostate cancer (CRPC), breast cancer, lung cancer, colon cancer, renal cancer, gastric cancer, brain cancer or medulloblastoma.

33. The method of paragraph 31, wherein the method further comprises administration or treatment with one or more additional anti-cancer therapy to the subject in need thereof.

34. The method of paragraph 33, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

35. A method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is selected from:

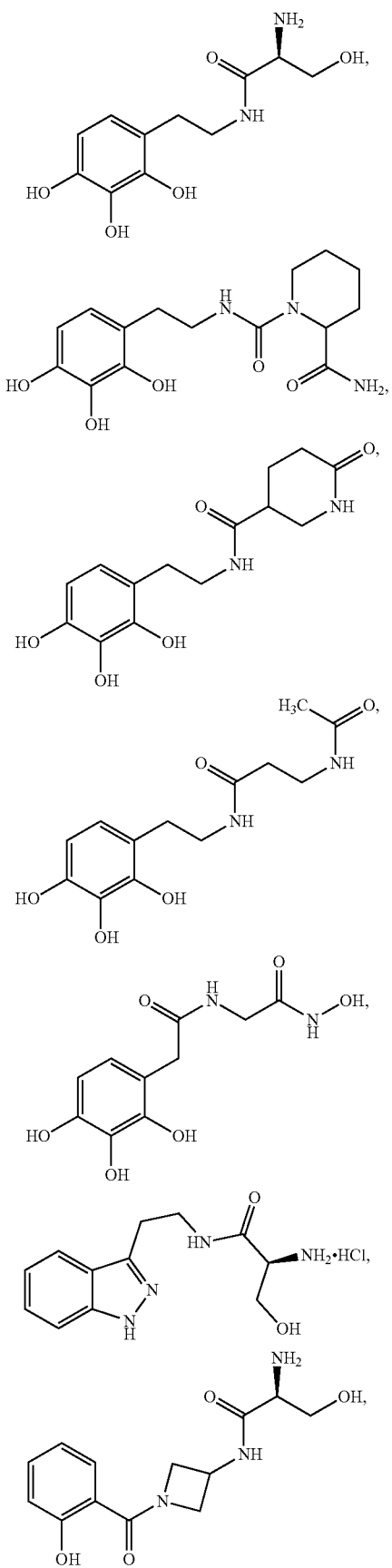

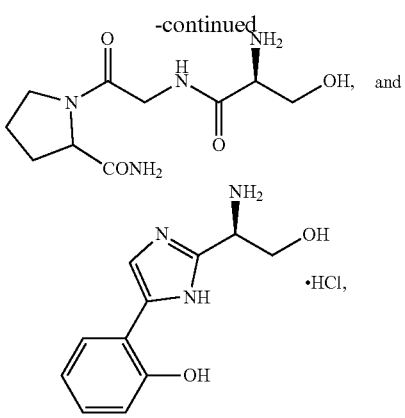

or a pharmaceutically acceptable salt thereof.

36. The method of paragraph 35, wherein the cancer is castration resistant prostate cancer (CRPC), breast cancer, lung cancer, colon cancer, renal cancer, gastric cancer, brain cancer or medulloblastoma 37. The method of paragraph 35, wherein the method further comprises administration or treatment with one or more additional anti-cancer therapy to the subject in need thereof.

38. The method of paragraph 37, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

39. A pharmaceutical composition comprising a compound of claim 3; and a pharmaceutically acceptable excipient or carrier.

40. A pharmaceutical composition comprising a compound selected from any one of paragraphs 25-30; and a pharmaceutically acceptable excipient or carrier.

41. A pharmaceutical composition comprising a compound selected from paragraph 30; and a pharmaceutically acceptable excipient or carrier.

42. The method of paragraph 20, wherein the small molecule is a compound selected from any one of paragraphs 25-29.

43. A method for treating, inhibiting and/or reducing the severity of cancers that overexpress ONECUT2 in a subject in need thereof, comprising providing an agent that inhibits expression or activity of ONECUT2 and administering a therapeutically effective amount of the agent so as to treat, inhibit and/or reduce the severity of cancers that overexpress ONECUT2 in the subject, wherein the agent is Compound CSRM617 of structure:

COMPOUND CSRM617

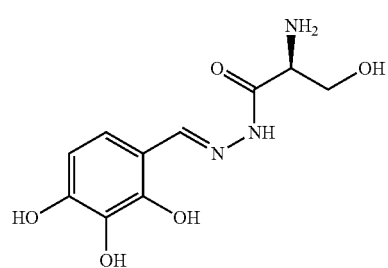

or a pharmacetucially acceptable salt thereof.

44. The method of paragraph 43, wherein the cancer is castration resistant prostate cancer (CRPC), breast cancer, lung cancer, colon cancer, renal cancer, gastric cancer, brain cancer or medulloblastoma
45. The method of paragraph 43, wherein the method further comprises administration or treatment with one or more additional anti-cancer therapy to the subject in need thereof.
46. The method of paragraph 45, wherein the additional therapy is selected from the group consisting of surgery, chemotherapy, radiation therapy, thermotherapy, immunotherapy, hormone therapy, laser therapy, biotherapy, anti-angiogenic therapy, photodynamic therapy, and any combinations thereof.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Unless otherwise noted, reagents and solvents were used as received from commercial suppliers. Nuclear magnetic resonance spectra were obtained on a Bruker AC 300, a Bruker AV 300 spectrometer, or on a Bruker AV 500 spectrometer. Spectra are given in ppm (δ) and coupling constants, J, are reported in Hertz. Tetramethylsilane was used as an internal standard for proton spectra. Flash chromatography often utilized the Isco Combiflash $R_f$ MPLC system. Mass spectra and LC/MS data reported using the Waters Aquity system as outlined in LC/MS Conditions "Method A" as the default.

HPLC Conditions:
Method A
Column: Luna C18(2) column (250×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 223 nm
Method A Gradient

| Time (min) | Flow (mL/min) | % A | % B |
|---|---|---|---|
| 0.0 | 1.0 | 95.0 | 5.0 |
| 20.0 | 1.0 | 5.0 | 95.0 |
| 27.0 | 1.0 | 5.0 | 95.0 |

Method B
Column: Luna C18(2) column (250×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 254 nm
Method B Gradient

| Time (min) | Flow (mL/min) | % A | % B |
|---|---|---|---|
| 0.0 | 1.0 | 95.0 | 5.0 |
| 20.0 | 1.0 | 5.0 | 95.0 |
| 27.0 | 1.0 | 5.0 | 95.0 |

Method C
Column: Luna C18(2) column (250×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 254 nm
Method C Gradient

| Time (min) | Flow (mL/min) | % A | % B |
|---|---|---|---|
| 0.0 | 1.0 | 95.0 | 5.0 |
| 20.0 | 1.0 | 50.0 | 50.0 |
| 27.0 | 1.0 | 50.0 | 50.0 |

Method D
Column: Luna C18(2) column (150×4.6 mm, Phenomenex)
Mobile Phase A: Water containing 0.1% v/v Trifluoroacetic Acid
Mobile Phase B: Acetonitrile containing 0.1% v/v Trifluoroacetic Acid
Detection: 254 nm
Method D Gradient

| Time (min) | Flow (mL/min) | % A | % B |
|---|---|---|---|
| 0.0 | 1.0 | 90.0 | 10.0 |
| 15.0 | 1.0 | 0.0 | 100.0 |
| 20.0 | 1.0 | 0.0 | 100.0 |

LC/MS Conditions:
Method A (Default)
Instrument: Waters Acquity, SQ Detector
Column: Acquity UPLC BEH C18 (2.1 mm×50 mm)
Mobile Phase A: Water containing 0.1% v/v Formic Acid
Mobile Phase B: Acetonitrile containing 0.1% v/v Formic Acid
UV Detection: 254 nm
MS Detection: ESI
Method A Gradient

| Time (min) | Flow (mL/min) | % A | % B |
|---|---|---|---|
| 0.0 | 0.5 | 98.0 | 2.0 |
| 2.25 | 0.5 | 5.0 | 95.0 |
| 3.0 | 0.5 | 5.0 | 95.0 |

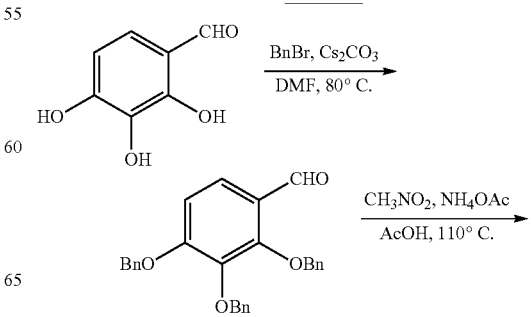

Scheme 1.

-continued

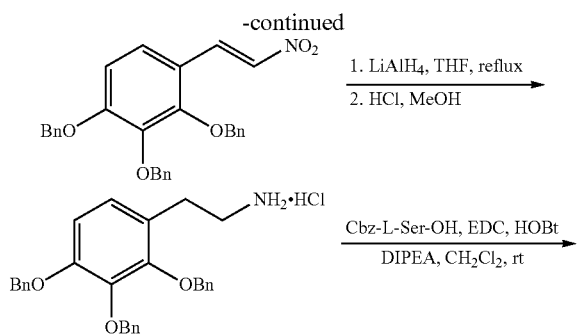

Preparation of 2,3,4-Tris(benzyloxy)benzaldehyde

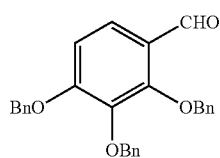

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 $[C_{28}H_{24}O_4+H]^+$.

Preparation of (E)-(((4-(2-Nitrovinyl)benzene-1,2,3-triyl)tris(oxy))tris(methylene)) tribenzene

A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 $[C_{29}H_{25}NO_5+H]^+$.

Preparation of 2-(2,3,4-Tris(benzyloxy)phenyl)ethanamine hydrochloride

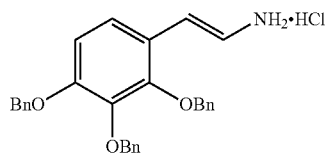

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid:

$^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 $[C_{29}H_{29}NO_3+H]^+$.

Preparation of (S)-Benzyl (3-hydroxy-1-oxo-1-((2,3,4-tris(benzyloxy)phenethyl) amino) propan-2-yl) carbamate

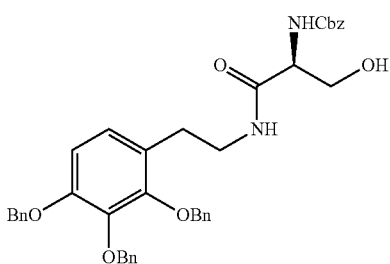 [SMILES: O=C(N[C@@H](CO)C(=O)NCCc1ccc(OCc2ccccc2)c(OCc2ccccc2)c1OCc1ccccc1)OCc1ccccc1]

A suspension of 2-(2,3,4-tris(benzyloxy)phenyl)ethanamine hydrochloride (246 mg, 0.517 mmol) and (S)-2-(((benzyloxy)carbonyl)amino)-3-hydroxypropanoic acid (150 mg, 0.627 mmol) in methylene chloride (10 mL) was treated with 1-ethyl-3-(3-dimethylaminopropyl)carbodiimide (119 mg, 0.621 mmol), hydroxybenzotriazole (87 mg, 0.64 mmol), and N,N-diisopropylethylamine (0.30 mL, 1.7 mmol). The mixture was stirred under a nitrogen atmosphere for 16 h. After this time, the reaction mixture was diluted with methylene chloride (25 mL); washed with water (25 mL), saturated sodium bicarbonate (25 mL), and brine (25 mL); dried over sodium sulfate; filtered; and concentrated under reduced pressure. The crude residue was purified by column chromatography (silica gel, 0-50% ethyl acetate/methylene chloride) to provide (S)-benzyl (3-hydroxy-1-oxo-1-((2,3,4-tris(benzyloxy)phenethyl)amino)propan-2-yl) carbamate (195 mg, 57%) as a white solid: $^1$H NMR (300 MHz, DMSO-$d_6$) δ 7.93 (t, J=5.0 Hz, 1H), 7.49-7.29 (m, 20H), 7.14 (d, J=8.4 Hz, 1H), 6.88 (s, 2H), 5.11 (s, 2H), 5.03-4.97 (m, 6H), 4.82 (t, J=5.6 Hz, 1H), 4.05-3.98 (m, 1H), 3.61-3.46 (m, 2H), 3.26-3.19 (m, 2H), 2.65 (t, J=6.8 Hz, 2H); ESI MS m/z 661 $[C_{40}H_{40}N_2O_7+H]$+.

Preparation of (S)-2-Amino-3-hydroxy-N-(2,3,4-trihydroxyphenethyl) propanamide

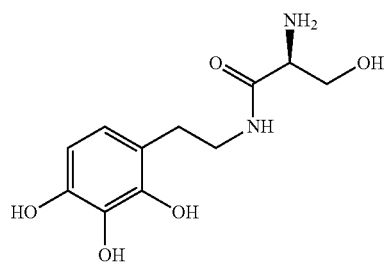 [SMILES: N[C@@H](CO)C(=O)NCCc1ccc(O)c(O)c1O]

A solution of (S)-benzyl (3-hydroxy-1-oxo-1-((2,3,4-tris(benzyloxy)phenethyl)amino)propan-2-yl)carbamate (195 mg, 0.295 mmol) in ethyl acetate (10 mL) and ethanol (10 mL) was bubbled with nitrogen gas for 10 min. The solution was treated with 10% palladium on carbon (28 mg) and bubbled with nitrogen gas for 5 min. The mixture was bubbled with hydrogen gas for 10 min and stirred under a hydrogen atmosphere (balloon) for 16 h. After this time, the reaction mixture was bubbled with nitrogen gas for 5 min and filtered over diatomaceous earth. The filtrate was concentrated under reduced pressure. The residue was dissolved in methanol and concentrated under reduced pressure (3×) and freeze dried from water to provide (S)-2-amino-3-hydroxy-N-(2,3,4-trihydroxyphenethyl)propanamide, (74 mg, 98%) as a fluffy, off-white solid: $^1$H NMR (300 MHz, DMSO-$d_6$) δ 8.79 (br s, 1H), 7.82 (t, J=5.7 Hz, 1H), 6.33 (d, J=8.1 Hz, 1H), 6.20 (d, J=8.1 Hz, 1H), 4.70 (br s, 1H), 3.49 (dd, J=10.5, 4.5 Hz, 1H), 3.38-3.32 (m, 1H, partially obscured by water peak), 3.22-3.14 (m, 3H), 2.55 (t, J=7.5 Hz, 2H, partially obscured by solvent peak), 4 exchangeable protons not observed; ESI MS m/z 257 $[C_{11}H_{16}N_2O_5+H]^+$; HPLC (Method A) 96.1% (AUC), $t_R$=5.92 min.

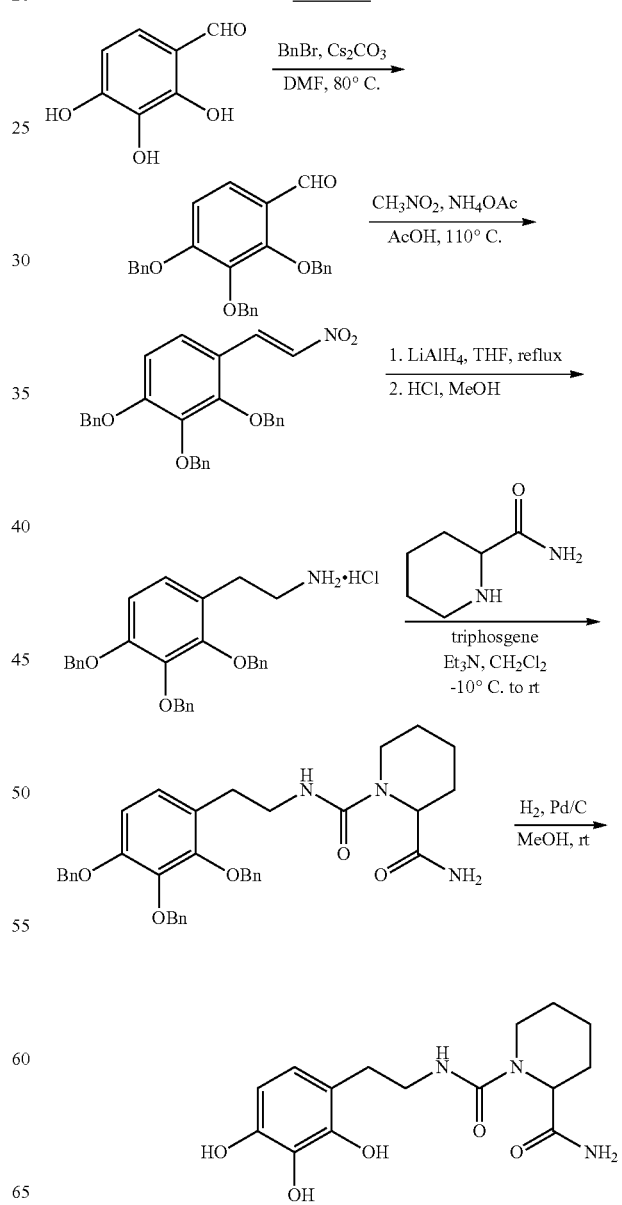

Scheme 2.

Preparation of 2,3,4-Tris(benzyloxy)benzaldehyde

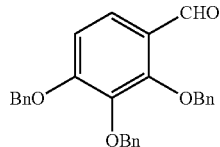 [SMILES: O=Cc1ccc(OCc2ccccc2)c(OCc2ccccc2)c1OCc1ccccc1]

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 $[C_{28}H_{24}O_4+H]^+$.

Preparation of (E)-(((4-(2-Nitrovinyl)benzene-1,2,3-triyl)tris(oxy))tris (methylene)) tribenzene

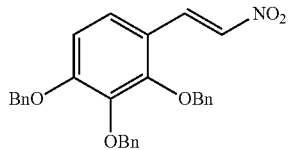 [SMILES: O=[N+]([O-])/C=C/c1ccc(OCc2ccccc2)c(OCc2ccccc2)c1OCc1ccccc1]

A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 $[C_{29}H_{25}NO_5+H]^+$.

Preparation of 2-(2,3,4-Tris(benzyloxy)phenyl)ethanamine hydrochloride

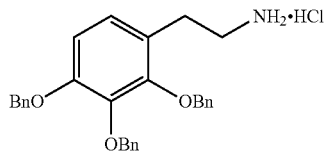

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid: $^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 $[C_{29}H_{29}NO_3+H]^+$.

Preparation of $N^1$-(2,3,4-Tris(benzyloxy)phenethyl)piperidine-1,2-dicarboxamide

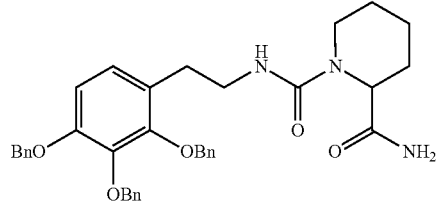 [SMILES: NC(=O)C1CCCCN1C(=O)NCCc1ccc(OCc2ccccc2)c(OCc2ccccc2)c1OCc1ccccc1]

A mixture of 2-(2,3,4-tris(benzyloxy)phenyl)ethanamine hydrochloride (250 mg, 0.525 mmol), piperidine-2-carboxamide (90 mg, 0.70 mmol) and triethylamine (0.50 mL, 3.6 mmol) in methylene chloride (8 mL) was cooled to −10° C. (ice/methanol bath) under a nitrogen atmosphere. Triphosgene (105 mg, 0.354 mmol) was added in one portion, and the mixture was stirred at −10° C. to room temperature over 2.5 h. After this time, the mixture was diluted with ethyl acetate and washed with 10% citric acid, water, and brine. The organic extract was dried over sodium sulfate, filtered, and concentrated. The residue was purified by column chromatography (silica gel, 0-100% ethyl acetate/heptane) to provide $N^1$-(2,3,4-tris(benzyloxy)phenethyl)piperidine-1,2-dicarboxamide (130 mg, 42%): ESI MS m/z 594 $[C_{36}H_{39}N_3O_5+H]^+$.

Preparation of N$^{1'}$-(2,3,4-Trihydroxyphenethyl)piperidine-1,2-dicarboxamide

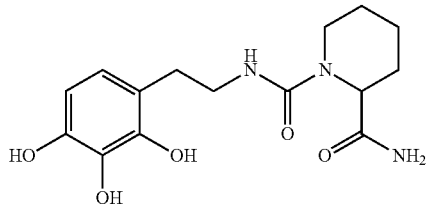 [SMILES: NC(=O)C1CCCCN1C(=O)NCCc1ccc(O)c(O)c1O]

A mixture of N$^1$-(2,3,4-tris(benzyloxy)phenethyl)piperidine-1,2-dicarboxamide (355 mg, 0.599 mmol) and palladium (10% on carbon, 200 mg) in methanol (20 mL) was stirred at room temperature under balloon pressure hydrogen for 3 h. After this time, the reaction mixture was purged with nitrogen and filtered over diatomaceous earth. The filtrate was concentrated under reduced pressure. The residue was purified by column chromatography (silica gel, 0-10% methanol/methylene chloride) and freeze dried from water to provide N$^1$-(2,3,4-trihydroxyphenethyl)piperidine-1,2-dicarboxamide, (99 mg, 51%) as a white solid: $^1$H NMR (300 MHz, DMSO-d$_6$) δ 8.76 (s, 1H), 8.32 (s, 1H), 8.13 (s, 1H), 7.09 (s, 1H), 6.95 (s, 1H), 6.48 (t, J=5.0 Hz, 1H), 6.32 (d, J=8.2 Hz, 1H), 6.19 (d, J=8.2 Hz, 1H), 4.63 (d, J=3.8 Hz, 1H), 3.69 (d, J=12.2 Hz, 1H), 3.17-3.02 (m, 2H), 3.02-2.90 (m, 1H), 2.56 (t, J=8.0 Hz, 2H), 2.06 (d, J=12.6 Hz, 1H), 1.59-1.20 (m, 5H); ESI MS m/z 324 [C$_{15}$H$_{21}$N$_3$O$_5$+H]$^+$; HPLC (Method B) 95.0% (AUC), t$_R$=8.95 min.

Scheme 3.

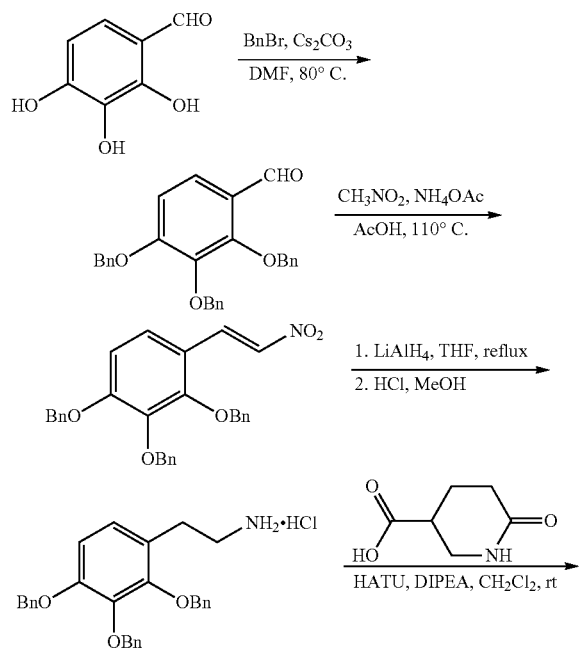

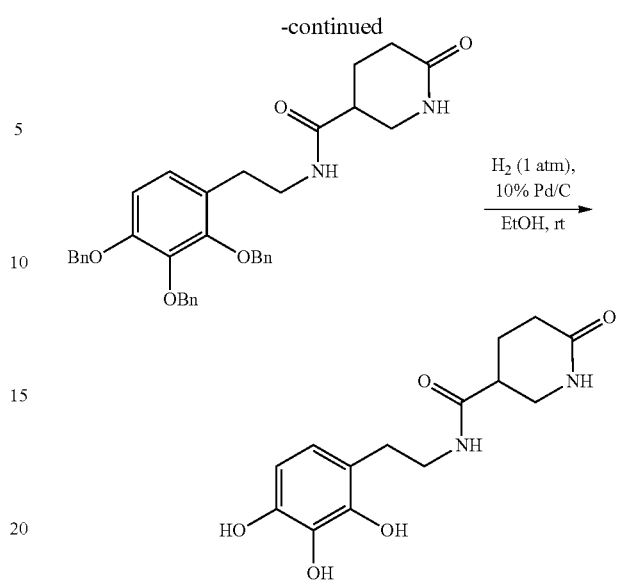

Preparation of 2,3,4-Tris(benzyloxy)benzaldehyde

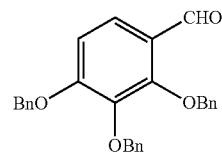

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 [C$_{28}$H$_{24}$O$_4$+H]$^+$.

Preparation of (E)-(((4-(2-Nitrovinyl)benzene-1,2,3-triyl)tris(oxy))tris (methylene)) tribenzene

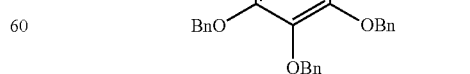

A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 [$C_{29}H_{25}NO_5$+H]$^+$.

Preparation of 2-(2,3,4-Tris(benzyloxy)phenyl)ethanamine hydrochloride

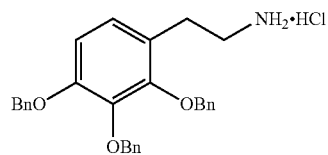

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid: $^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 [$C_{29}H_{29}NO_3$+H]$^+$.

Preparation of 6-Oxo-N-(2,3,4-tris(benzyloxy)phenethyl)piperidine-3-carboxamide

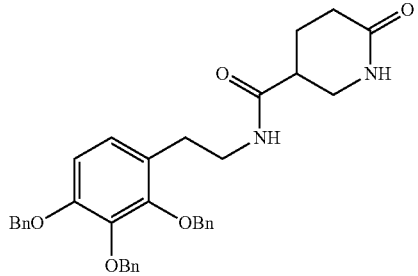 [SMILES: O=C1CCC(C(=O)NCCc2ccc(OCc3ccccc3)c(OCc3ccccc3)c2OCc2ccccc2)CN1]

A suspension of 2-(2,3,4-tris(benzyloxy)phenyl)ethanamine hydrochloride (461 mg, 0.968 mmol) and 6-oxopiperidine-3-carboxylic acid (166 mg, 1.16 mmol) in methylene chloride (10 mL) was treated with (1-[bis(dimethylamino)methylene]-1H-1,2,3-triazolo[4,5-b]pyridinium 3-oxide hexafluorophosphate) (442 mg, 1.16 mmol) and N,N-diisopropylethylamine (0.56 mL, 3.2 mmol). The mixture was stirred under a nitrogen atmosphere for 16 h. After this time, the reaction mixture was diluted with methylene chloride (25 mL); washed with 10% citric acid (25 mL), saturated sodium bicarbonate (25 mL), and brine (25 mL); dried over sodium sulfate; filtered; and concentrated under reduced pressure. The crude residue was purified by column chromatography (silica gel, 0-10% methanol/methylene chloride) to provide 6-oxo-N-(2,3,4-tris(benzyloxy)phenethyl)piperidine-3-carboxamide (430 mg, 79%) as a white solid: $^1$H NMR (300 MHz, DMSO-$d_6$) δ 7.98 (t, J=5.7 Hz, 1H), 7.50-7.29 (m, 16H), 6.91-6.86 (m, 2H), 5.13 (s, 2H), 5.00 (s, 2H), 4.99 (s, 2H), 3.24-3.14 (m, 4H), 2.65 (t, J=7.2 Hz, 2H), 2.49-2.43 (m, 1H, partially obscured by solvent peak), 2.16-2.09 (m, 2H), 1.84-1.70 (m, 2H); ESI MS m/z 565 [$C_{35}H_{36}N_2O_5$+H]$^+$.

Preparation of 6-Oxo-N-(2,3,4-trihydroxyphenethyl)piperidine-3-carboxamide

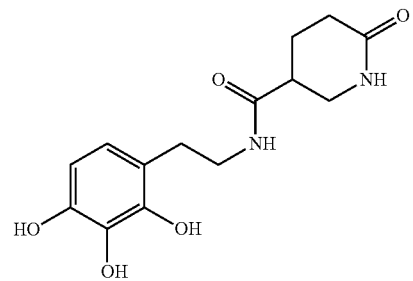 [SMILES: O=C1CCC(C(=O)NCCc2ccc(O)c(O)c2O)CN1]

A solution of 6-oxo-N-(2,3,4-tris(benzyloxy)phenethyl)piperidine-3-carboxamide (428 mg, 0.758 mmol) in ethanol (15 mL) was bubbled with nitrogen gas for 10 min. The solution was treated with 10% palladium on carbon (63 mg) and bubbled with nitrogen gas for 5 min. The mixture was bubbled with hydrogen gas for 10 min and stirred under a hydrogen atmosphere (balloon) for 16 h. After this time, the reaction mixture was bubbled with nitrogen gas for 5 min and filtered over diatomaceous earth. The filtrate was concentrated under reduced pressure. The residue was purified by column chromatography (silica gel, 1-10% methanol/methylene chloride) and freeze dried from acetonitrile/water to provide 6-oxo-N-(2,3,4-trihydroxyphenethyl)piperidine-3-carboxamide, (110 mg, 49%) as a fluffy white solid: $^1$H NMR (300 MHz, DMSO-$d_6$) δ 8.82 (s, 1H), 8.16 (s, 2H), 7.93 (t, J=5.4 Hz, 1H), 7.42 (br s, 1H), 6.30 (d, J=8.1 Hz, 1H), 6.19 (d, J=8.1 Hz, 1H), 3.18-3.13 (m, 4H), 2.56-2.45 (m, 3H, partially obscured by solvent peak), 2.22-2.05 (m, 2H), 1.88-1.68 (m, 2H); ESI MS m/z 295 [$C_{14}H_{18}N_2O_5$+H]$^-$; HPLC (Method B) 96.6% (AUC), $t_R$=7.50 min.

Scheme 4.

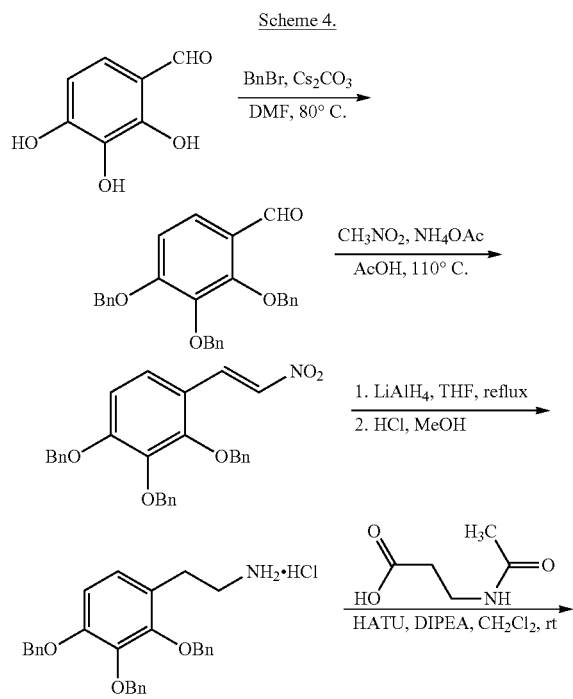

Preparation of 2,3,4-Tris(benzyloxy)benzaldehyde

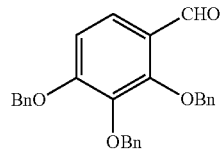

A solution of 2,3,4-trihydroxybenzaldehyde (3.00 g, 19.5 mmol) in N,N-dimethylformamide (100 mL) was treated with cesium carbonate (31.73 g, 97.39 mmol) and benzyl bromide (11.6 mL, 97.5 mmol) and heated at 80° C. under a nitrogen atmosphere for 16 h. After this time, the reaction mixture was cooled to room temperature and diluted with water (100 mL). The mixture was extracted with ethyl acetate (300 mL). The organic layer was washed with water (100 mL), 5% aqueous lithium chloride (100 mL), and brine (100 mL); dried over sodium sulfate; filtered; and concentrated under reduced pressure. The crude residue was purified by column chromatography (silica gel, 0-30% ethyl acetate/heptane) to provide 2,3,4-tris(benzyloxy)benzaldehyde (8.17 g, 99%) as a white solid: ESI MS m/z 425 [$C_{28}H_{24}O_4$+H]$^+$.

Preparation of (E)-(((4-(2-Nitrovinyl)benzene-1,2,3-triyl)tris(oxy))tris (methylene)) tribenzene

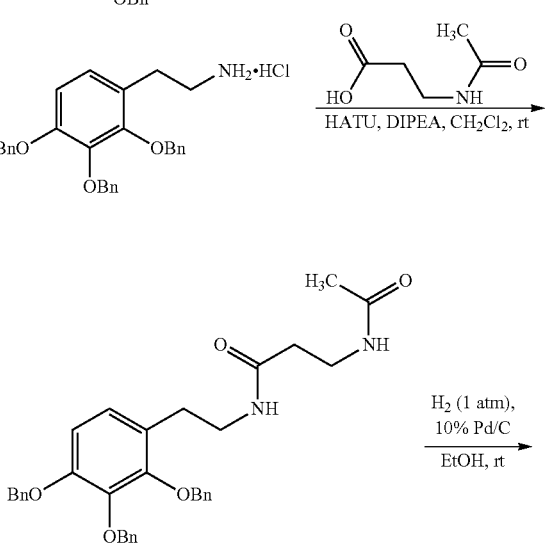

A solution of 2,3,4-tris(benzyloxy)benzaldehyde (1.52 g, 3.58 mmol) in acetic acid (15 mL) was treated with nitromethane (1.0 mL, 18 mmol) and ammonium acetate (149 mg, 1.93 mmol) and heated under a nitrogen atmosphere at 110° C. for 2.5 h. The mixture was treated with additional nitromethane (0.5 mL, 9 mmol) and heated at 110° C. for 16 h. After this time, the reaction mixture was concentrated under reduced pressure. The crude residue was purified by column chromatography (silica gel, 0-50% methylene chloride/heptane) to provide (E)-(((4-(2-nitrovinyl)benzene-1,2,3-triyl)tris(oxy))tris(methylene))tribenzene (1.21 g, 72%) as a yellow solid: $^1$H NMR (300 MHz, DMSO-$d_6$) δ 8.05-7.95 (m, 2H), 7.64 (d, J=9.0 Hz, 1H), 7.52-7.31 (m, 15H), 7.09 (d, J=9.0 Hz, 1H), 5.27 (s, 2H), 5.12 (s, 2H), 5.06 (s, 2H); ESI MS m/z 468 [$C_{29}H_{25}NO_5$+H]$^+$.

Preparation of 2-(2,3,4-Tris(benzyloxy)phenyl)ethanamine hydrochloride

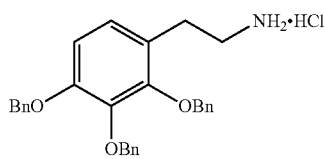

A solution of (E)-(((4-(2-nitrovinyl)benzene-1,2,3-triyl)tris(oxy))tris(methylene))tribenzene (1.74 g, 3.72 mmol) in tetrahydrofuran (40 mL) was cooled in an ice bath and treated dropwise with a 1.0 M solution of lithium aluminum hydride in tetrahydrofuran (11.2 mL, 11.2 mmol) under a nitrogen atmosphere. The ice bath was removed, and the mixture was stirred at ambient temperature for 40 minutes. The mixture was then heated at reflux for 30 min. After this time, the mixture was allowed to cool to ambient temperature and then cooled in an ice bath. The mixture was carefully treated with water (0.4 mL), 15% aqueous sodium hydroxide (0.4 mL), and water (1.2 mL). The mixture was diluted with tetrahydrofuran (10 mL) and stirred for 30 min. After this time, the solids were removed by filtration and washed with ethyl acetate (50 mL). The filtrate and rinsings were concentrated under reduced pressure to provide 2-(2,3,4-tris(benzyloxy)phenyl)ethanamine as a pale yellow oil. The oil was dissolved in methanol (15 mL) and treated with a ~1 M solution of hydrogen chloride in methanol (7 mL) under a nitrogen atmosphere. The mixture was concentrated under reduced pressure to provide a solid residue. The residue was triturated/sonicated with diethyl ether, isolated by filtration, washed with diethyl ether, and dried under vacuum to provide 2-(2,3,4-tris(benzyloxy)phenyl)ethanamine hydrochloride (990 mg, 56%) as a white solid: $^1$H NMR (300 MHz, DMSO-$d_6$) δ 7.82 (br s, 3H), 7.50-7.29 (m, 15H), 6.93 (s, 2H), 5.16 (s, 2H), 5.02 (s, 2H), 5.01 (s, 2H), 2.95-2.85 (m, 2H), 2.83-2.78 (m, 2H); ESI MS m/z 440 $[C_{29}H_{29}NO_3+H]^+$.

Preparation of 3-Acetamido-N-(2,3,4-tris(benzyloxy)phenethyl)propanamide

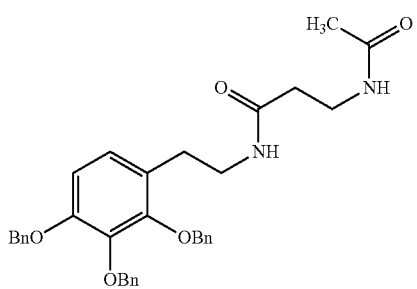 [SMILES: CC(=O)NCCC(=O)NCCc1ccc(OCc2ccccc2)c(OCc2ccccc2)c1OCc1ccccc1]

A suspension of 2-(2,3,4-tris(benzyloxy)phenyl)ethanamine hydrochloride (289 mg, 0.607 mmol) and 3-acetamidopropanoic acid (96 mg, 0.73 mmol) in methylene chloride (6 mL) was treated with (1-[bis(dimethyl amino)methylene]-1H-1,2,3-tri azolo [4,5-b]pyri dinium 3-oxide hexafluorophosphate) (278 mg, 0.731 mmol) and N,N-diisopropylethylamine (0.35 mL, 2.0 mmol). The mixture was stirred under a nitrogen atmosphere for 16 h. After this time, the reaction mixture was diluted with methylene chloride (25 mL); washed with 10% citric acid (25 mL), saturated sodium bicarbonate (25 mL), and brine (25 mL); dried over sodium sulfate; filtered; and concentrated under reduced pressure. The crude residue was purified by column chromatography (silica gel, 0-10% methanol/methylene chloride) to provide 3-acetamido-N-(2,3,4-tris(benzyloxy)phenethyl)propanamide (193 mg, 58%) as a white solid: $^1$H NMR (300 MHz, DMSO-$d_6$) δ 7.92 (t, J=5.7 Hz, 1H), 7.84 (t, J=5.7 Hz, 1H), 7.50-7.29 (m, 15H), 6.89 (s, 2H), 5.13 (s, 2H), 5.00 (s, 2H), 4.99 (s, 2H), 3.21-3.16 (m, 4H), 2.65 (t, J=7.5 Hz, 2H), 2.19 (t, J=7.1 Hz, 2H), 1.76 (s, 3H); ESI MS m/z 553 $[C_{34}H_{36}N_2O_5+H]^+$.

Preparation of 3-Acetamido-N-(2,3,4-trihydroxyphenethyl)propanamide

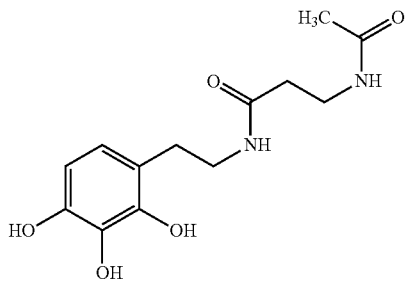 [SMILES: CC(=O)NCCC(=O)NCCc1ccc(O)c(O)c1O]

A solution of 3-acetamido-N-(2,3,4-tris(benzyloxy)phenethyl)propanamide (190 mg, 0.344 mmol) in ethyl acetate (4 mL) and ethanol (4 mL) was bubbled with nitrogen gas for 10 min. The solution was treated with 10% palladium on carbon (27 mg) and bubbled with nitrogen gas for 5 min. The mixture was bubbled with hydrogen gas for 10 min and stirred under a hydrogen atmosphere (balloon) for 16 h. After this time, the reaction mixture was bubbled with nitrogen gas for 5 min and filtered over diatomaceous earth. The filtrate was concentrated under reduced pressure. The residue was purified by column chromatography (silica gel, 1-10% methanol/methylene chloride) and freeze dried from water to provide 3-acetamido-N-(2,3,4-trihydroxyphenethyl)propanamide, (59 mg, 61%) as a fluffy white solid: $^1$H NMR (300 MHz, DMSO-$d_6$) δ 8.82 (s, 1H), 8.16 (s, 2H), 7.87-7.82 (m, 2H), 6.31 (d, J=8.1 Hz, 1H), 6.19 (d, J=8.1 Hz, 1H), 3.23-3.11 (m, 4H), 2.56-2.50 (m, 2H, partially obscured by solvent peak), 2.19 (t, J=6.9 Hz, 2H), 1.77 (s, 3H); ESI MS m/z 283 $[C_{13}H_{18}N_2O_5+H]^+$; HPLC (Method B) 96.6% (AUC), $t_R$=7.50 min.

Scheme 5.

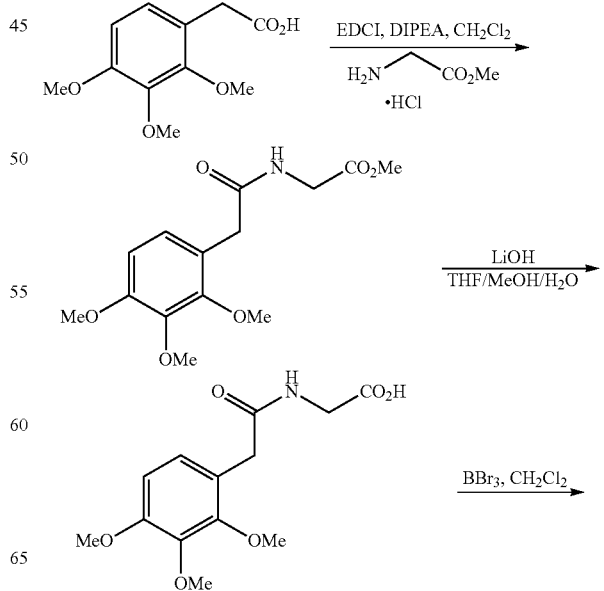

-continued

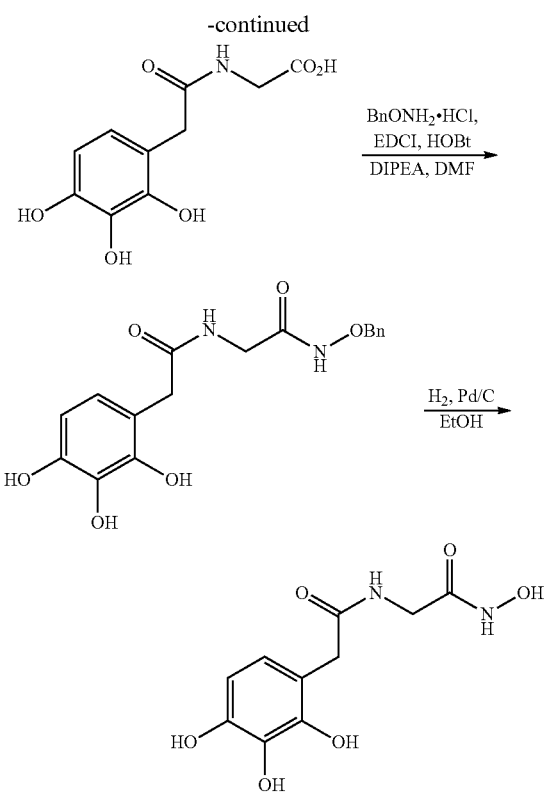

Preparation of Methyl 2-(2-(2,3,4-Trimethoxyphenyl)acetamido)acetate

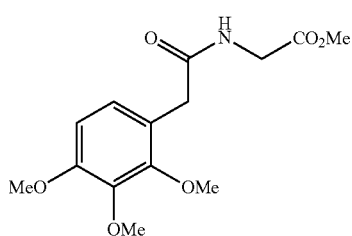 [SMILES: COC(=O)CNC(=O)Cc1ccc(OC)c(OC)c1OC]

A solution of 2-(2,3,4-trimethoxyphenyl)acetic acid (500 mg, 2.21 mmol), glycine hydrochloride (277 mg, 2.21 mmol) and diisopropylethylamine (686 mg, 5.30 mmol) in methylene chloride (25 mL) was cooled in an ice bath and treated with N-(3-dimethylaminopropyl)-N'-ethylcarbodiimide hydrochloride (636 mg, 3.32 mmol). The mixture was stirred at room temperature for 4 h. After this time, the reaction mixture was treated with water (40 mL) and extracted with ethyl acetate (2×40 mL). The combined organics were washed with 2 N hydrochloric acid (10 mL), saturated aqueous sodium bicarbonate (50 mL), and water (50 mL); dried over sodium sulfate; filtered; and concentrated under reduced pressure to provide methyl 2-(2-(2,3,4-trimethoxyphenyl)acetamido)acetate (392 mg, 59%) as a white solid: $^1$H NMR (300 MHz, CDCl$_3$) δ 6.94 (d, J=8.4 Hz, 1H), 6.65 (d, J=8.4 Hz, 1H), 6.32 (br s, 1H), 4.00 (d, J=5.1 Hz, 2H), 3.93 (s, 3H), 3.88 (s, 3H), 3.86 (s, 3H), 3.72 (s, 3H), 3.55 (s, 2H).

Preparation of 2-(2-(2,3,4-Trimethoxyphenyl)acetamido)acetic Acid

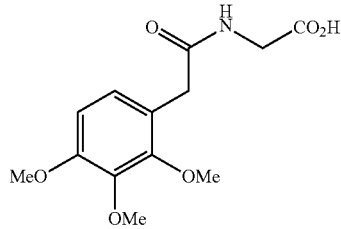 [SMILES: COc1ccc(CC(=O)NCC(=O)O)c(OC)c1OC]

Methyl 2-(2-(2,3,4-trimethoxyphenyl)acetamido)acetate (392 mg, 1.32 mmol), lithium hydroxide (126 mg, 5.27 mmol), tetrahydrofuran (5 mL), methanol (5 mL) and water (5 mL) were combined and stirred at room temperature for 2 h. After this time, the reaction mixture was concentrated under reduced pressure, and the residue was acidified to pH 2 with 2 N hydrochloric acid. The resulting suspension was extracted with ethyl acetate (2×20 mL). The combined organics were washed with brine (50 mL), dried over sodium sulfate, filtered, and concentrated under reduced pressure to provide 2-(2-(2,3,4-trimethoxyphenyl)acetamido)acetic acid (375 mg, 100%) as a white solid: $^1$H NMR (300 MHz, CDCl$_3$) δ 6.93 (d, J=8.4 Hz, 1H), 6.65 (d, J=8.4 Hz, 1H), 6.42 (br s, 1H), 4.03 (d, J=5.4 Hz, 2H), 3.93 (s, 3H), 3.88 (s, 3H), 3.86 (s, 3H), 3.56 (s, 2H), CO2H proton not observed.

Preparation of 2-(2-(2,3,4-Trihydroxyphenyl)acetamido)acetic Acid

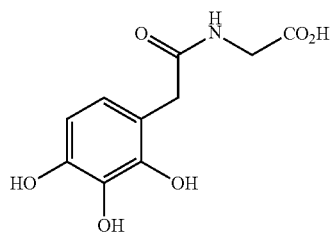 [SMILES: O=C(O)CNC(=O)Cc1ccc(O)c(O)c1O]

A solution of 2-(2-(2,3,4-trimethoxyphenyl)acetamido)acetic acid (375 mg, 1.32 mmol) in methylene chloride (40 mL) was cooled in an ice bath and treated dropwise with a 1.0 M solution of boron tribromide in methylene chloride (6.62 mL, 6.62 mmol). After addition was complete, the mixture was stirred at 0° C. for 4 min, and water (20 mL) was added slowly. The resulting suspension was extracted with ethyl acetate (2×20 mL). The combined organics were washed with brine (50 mL), dried over sodium sulfate, filtered, and concentrated under reduced pressure to provide 2-(2-(2,3,4-trihydroxyphenyl)acetamido)acetic acid (321 mg, 100%) as a white solid: $^1$H NMR (300 MHz, DMSO-d$_6$) δ 6.37 (d, J=8.4 Hz, 1H), 6.21 (d, J=8.4 Hz, 1H), 3.72 (m, 2H), 3.38 (m, 2H), 5 exchangeable protons not observed.

Preparation of N-(Benzyloxy)-2-(2-(2,3,4-trihydroxyphenyl)acetamido)acetamide

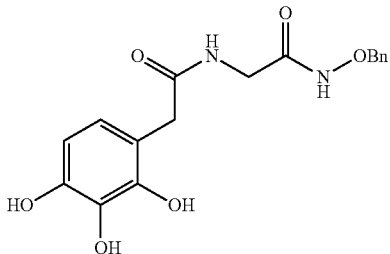 [SMILES: O=C(Cc1ccc(O)c(O)c1O)NCC(=O)NOCc1ccccc1]

A solution of 2-(2-(2,3,4-trihydroxyphenyl)acetamido)acetic acid (300 mg, 1.24 mmol), benzylhydroxylamine hydrochloride (397 mg, 2.49 mmol) and diisopropylethylamine (322 mg, 2.49 mmol) in N,N-dimethylformamide (10 mL) was treated with N-(3-dimethylaminopropyl)-N'-ethylcarbodiimide hydrochloride (477 mg, 2.49 mmol) and 1-hydroxybenzotriazole hydrate (336 mg, 2.49 mmol), and the mixture was stirred at room temperature for 16 h. After this time, the reaction mixture was treated with water (40 mL) and extracted with ethyl acetate (2×40 mL). The combined organics were dried over sodium sulfate, filtered, and concentrated under reduced pressure. The residue was purified by reversed phase column chromatography (50 g C18 column, 10-100% acetonitrile/water) to provide N-(benzyloxy)-2-(2-(2,3,4-trihydroxyphenyl)acetamido)acetamide (170 mg, 39%) as a white solid: $^1$H NMR (300 MHz, CD$_3$OD) δ 7.45-7.35 (m, 5H), 6.50 (d, J=8.1 Hz, 1H), 6.34 (d, J=8.1 Hz, 1H), 4.84 (s, 2H), 3.76 (s, 2H), 3.50 (s, 2H), 5 exchangeable protons not observed; ESI MS m/z 345 $[C_{17}H_{18}N_2O_6+H]^-$.

Preparation of N-Hydroxy-2-(2-(2,3,4-trihydroxyphenyl)acetamido)acetamide

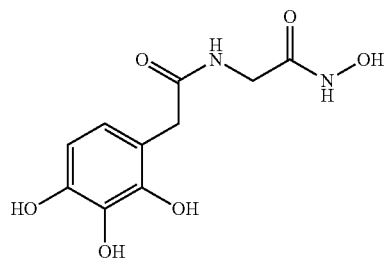 [SMILES: O=C(CNC(=O)Cc1ccc(O)c(O)c1O)NO]

A solution of N-(benzyloxy)-2-(2-(2,3,4-trihydroxyphenyl)acetamido)acetamide (170 mg, 0.491 mmol) in ethanol (5 mL) was sparged with nitrogen gas for 30 min. The solution was treated with 5% palladium on carbon (100 mg) and sparged with hydrogen gas for 5 min. The mixture was stirred under a hydrogen atmosphere for 2 h. After this time, the reaction mixture was sparged with nitrogen gas for 5 min and filtered through diatomaceous earth. The filtrate was concentrated under reduced pressure and the residue was purified by reversed phase column chromatography (50 g C18 column, 2-100% acetonitrile/water) to provide N-hydroxy-2-(2-(2,3,4-trihydroxyphenyl)acetamido)acetamide, (55 mg, 43%) as an off-white solid: $^1$H NMR (300 MHz, DMSO-d$_6$) δ 10.50 (br s, 1H), 9.02 (br s, 1H), 8.83 (br s, 1H), 8.78 (br s, 1H), 8.14 (m, 2H), 6.36 (d, J=8.4 Hz, 1H), 6.21 (d, J=8.4 Hz, 1H), 3.60 (d, J=5.7 Hz, 2H), 3.35 (s, 2H); ESI MS m/z 257 $[C_{10}H_{12}N_2O_6+H]^+$; HPLC (Method C) 96.5% (AUC), tR=5.18 min.

Scheme 6.

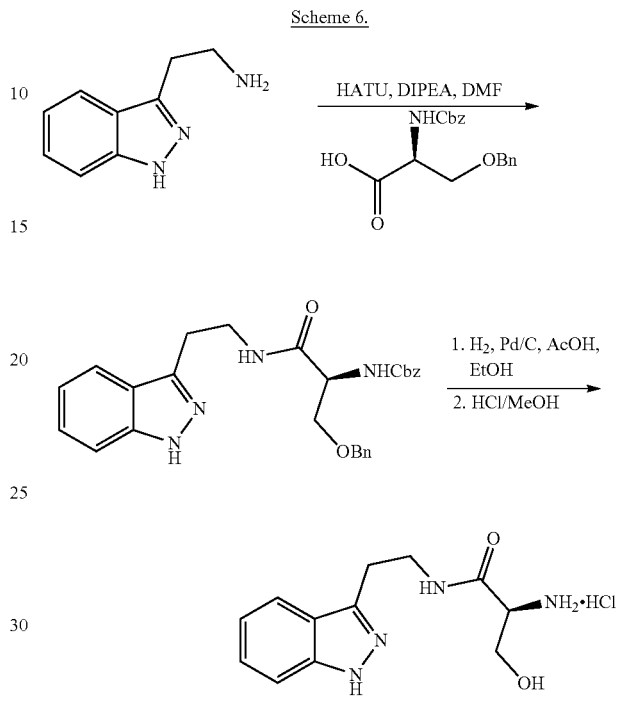

Preparation of (5)-Benzyl (1((2-(1H-indazol-3-yl)ethyl)amino)-3-(benzyloxy)-1-oxopropan-2-yl)carbamate

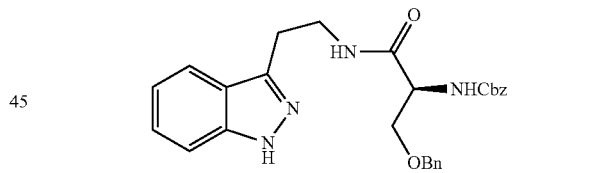

A solution of 2-(1H-indazol-3-yl)ethanamine (240 mg, 1.49 mmol), (S)-3-(benzyloxy)-2-(((benzyloxy)carbonyl)amino)propanoic acid (981 mg, 2.98 mmol) and diisopropylethylamine (578 mg, 4.47 mmol) in N,N-dimethylformamide (20 mL) was cooled to −10° C. and treated with 0-(7-azabbenzotriazol-1-yl)-N,N,N',N'-tetramethyluronium hexafluorophosphate (1.70 g, 4.47 mmol). The mixture was stirred at −10° C. for 1 h. After this time, the reaction mixture was treated with water (40 mL) and extracted with ethyl acetate (2×40 mL). The combined organics were washed with saturated aqueous sodium bicarbonate (40 mL), water (40 mL), and brine (40 mL); dried over sodium sulfate; filtered; and concentrated under reduced pressure. The residue was purified by column chromatography (40 g silica column, 0-100% ethyl acetate/heptane) to provide (5)-benzyl (1-((2-(1H-indazol-3-yl)ethyl)amino)-3-(benzyloxy)-1-oxopropan-2-yl)carbamate (535 mg, 75%) as a white solid: ESI MS m/z 473 $[C_{27}H_{28}N_4O_4+H]^+$.

Preparation of (S)—N-(2-(1H-Indazol-3-yl)ethyl)-2-amino-3-hydroxypropanamide hydrochloride

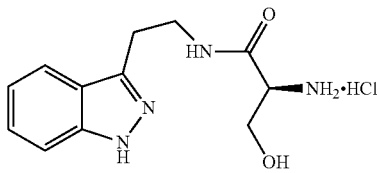

A solution of (S)-benzyl (1((2-(1H-indazol-3-yl)ethyl)amino)-3-(benzyloxy)-1-oxopropan-2-yl)carbamate (300 mg, 0.887 mmol) and acetic acid (1 mL) in ethanol (20 mL) was sparged with nitrogen gas for 30 min. The solution was treated with 5% palladium on carbon (100 mg) and sparged with hydrogen gas for 5 min. The mixture was stirred under a hydrogen atmosphere for 2 h. After this time, the reaction mixture was sparged with nitrogen gas for 5 min and filtered through diatomaceous earth. The filtrate was concentrated under reduced pressure and the residue was purified by reversed phase column chromatography (50 g C18 column, 2-100% acetonitrile/water). The resulting solid was treated with a 1.5 M solution of hydrogen chloride in methanol (2 mL) and concentrated under reduced pressure to provide (S)—N-(2-(1H-indazol-3-yl)ethyl)-2-amino-3-hydroxypropanamide hydrochloride, (71 mg, 28%) as an off-white solid: $^1$H NMR (300 MHz, DMSO-$d_6$) δ 12.78 (br s, 1H), 8.59 (t, J=5.7 Hz, 1H), 8.14 (br s, 3H), 7.74 (d, J=8.1 Hz, 1H), 7.48 (d, J=8.4 Hz, 1H), 7.33 (t, J=8.1 Hz, 1H), 7.09 (t, J=8.4 Hz, 1H), 3.75-3.44 (m, 5H), 3.08 (t, J=6.9 Hz, 2H), OH proton not observed; ESI MS m/z 249 [$C_{12}H_{16}N_4O_2$+H]$^+$; HPLC (Method B) 96.5% (AUC), $t_R$=5.18 min.

Scheme 7.

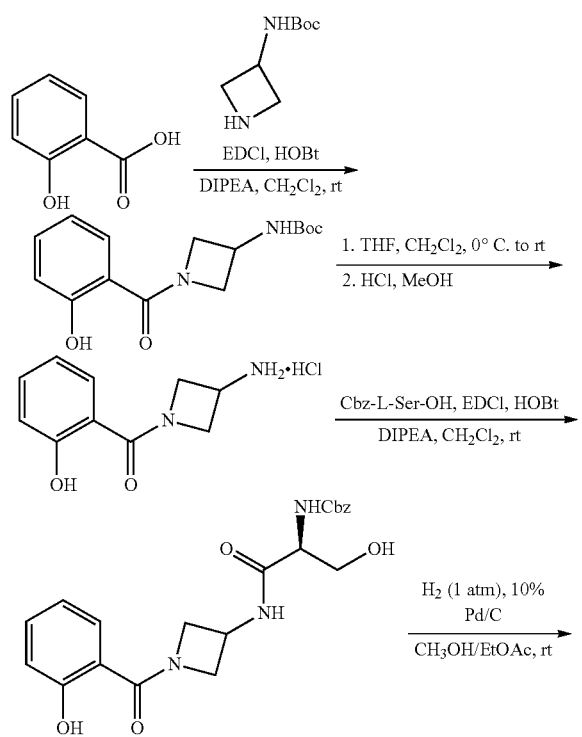

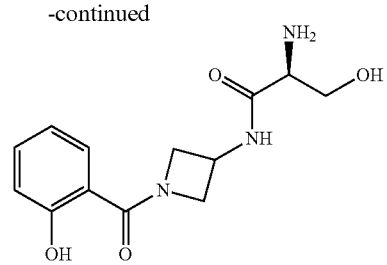

Preparation of tert-Butyl (1-(2-hydroxybenzoyl)azetidin-3-yl)carbamate

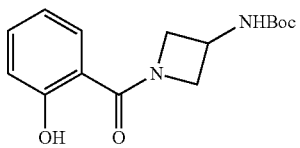 [SMILES: CC(C)(C)OC(=O)NC1CN(C(=O)c2ccccc2O)C1]

A solution of 2-hydroxybenzoic acid (640 mg, 4.63 mmol) in methylene chloride (20 mL) was treated with 1-ethyl-3-(3-dimethylaminopropyl)carbodiimide (1.4 mL, 8.1 mmol), hydroxybenzotriazole (938 mg, 6.95 mmol), and (tert-butyl azetidin-3-ylcarbamate (997 mg, 5.79 mmol) and stirred under a nitrogen atmosphere for 16 h. After this time, the reaction mixture was diluted with ethyl acetate (125 mL), washed with saturated sodium bicarbonate (50 mL) and brine (25 mL), dried over sodium sulfate, decanted, and concentrated under reduced pressure. The crude residue was purified by column chromatography (silica gel, 5-30% ethyl acetate/hexane s) to provide tert-butyl (1-(2-hydroxybenzoyl)azetidin-3-yl)carbamate (800 mg, 59%) as a white solid: $^1$H NMR (300 MHz, DMSO-$d_6$) δ 11.76 (s, 1H), 7.62 (d, J=6.3 Hz, 1H), 7.40-7.34 (m, 2H), 6.91-6.83 (m, 2H), 4.58 (br s, 1H), 4.33-4.21 (m, 3H), 3.92 (br s, 1H), 1.39 (s, 9H); ESI MS m/z 293 [$C_{15}H_{20}N_2O_4$+H]$^+$.

Preparation of (3-Aminoazetidin-1-yl)(2-hydroxyphenyl)methanone hydrochloride

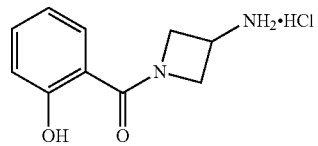

A solution of tert-butyl (1-(2-hydroxybenzoyl)azetidin-3-yl) carbamate (800 mg, 2.73 mmol) in methylene chloride (30 mL) was cooled in an ice bath and treated with trifluoroacetic acid (15 mL). The ice bath was removed, and the mixture was stirred at ambient temperature under a nitrogen atmosphere for 1 h. The mixture was concentrated under reduced pressure. The residue was treated with a ~1.2 M solution of hydrogen chloride in methanol (25 mL) and concentrated under reduced pressure. The hydrogen chloride treatment was repeated a second time to provide (3-aminoazetidin-1-yl)(2-hydroxyphenyl)methanone hydrochloride (679 mg, quantitative) as an off-white sticky solid: ESI MS m/z 193 $[C_{10}H_{12}N_2O_2+H]^+$.

Preparation of (S)-Benzyl (3-hydroxy-1-((1-(2-hydroxybenzoyl)azetidin-3-yl)amino)-1-oxopropan-2-yl)carbamate

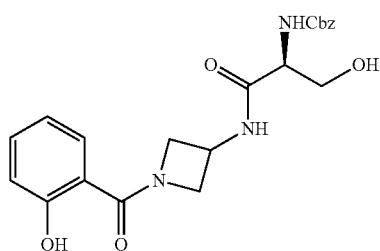 [SMILES: O=C(N[C@@H](CO)C(=O)NC1CN(C(=O)c2ccccc2O)C1)OCc1ccccc1]

A solution of (3-aminoazetidin-1-yl)(2-hydroxyphenyl) methanone hydrochloride (315 mg, 1.38 mmol) in methylene chloride (15 mL) was cooled in an ice bath and treated with N,N-diisopropylethylamine (0.36 mL, 2.1 mmol), 1-ethyl-3-(3-dimethylaminopropyl)carbodiimide (0.30 mL, 1.7 mmol), hydroxybenzotriazole (232 mg, 1.72 mmol), and (S)-2-(((benzyloxy)carbonyl)amino)-3-hydroxypropanoic acid (413 mg, 1.72 mmol). The ice bath was removed, and the mixture was stirred under a nitrogen atmosphere for 16 h. After this time, the reaction mixture was diluted with methylene chloride (30 mL), washed with saturated sodium bicarbonate (20 mL) and brine (20 mL), dried over sodium sulfate, decanted, and concentrated under reduced pressure. The crude residue was purified by column chromatography (silica gel, 0-75% ethyl acetate/methylene chloride) to provide (S)-benzyl (3-hydroxy-1-((1-(2-hydroxybenzoyl)azetidin-3-yl)amino)-1-oxopropan-2-yl)carbamate (200 mg, 35%) as a white solid: $^1$H NMR (500 MHz, DMSO-$d_6$) δ 11.74 (s, 1H), 8.63 (d, J=6.5 Hz, 1H), 7.40-7.30 (m, 6H), 7.17 (d, J=8.0 Hz, 1H), 6.92-6.85 (m, 2H), 5.07-5.00 (m, 2H), 4.86 (t, J=5.5 Hz, 1H), 4.63-4.53 (m, 2H), 4.33-4.23 (m, 2H), 4.04-3.98 (m, 2H), 3.61-3.54 (s, 2H), 1 exchangeable proton not observed; ESI MS m/z 414 $[C_{21}H_{23}N_3O_6+H]^+$.

Preparation of (S)-2-Amino-3-hydroxy-N-(1-(2-hydroxybenzoyl)azetidin-3-yl)propanamide

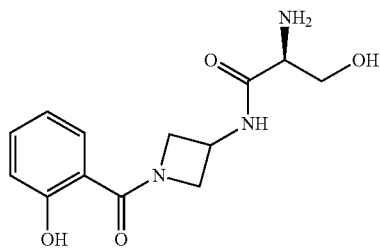 [SMILES: N[C@@H](CO)C(=O)NC1CN(C(=O)c2ccccc2O)C1]

A solution of (S)-benzyl (3-hydroxy-1-((1-(2-hydroxybenzoyl)azetidin-3-yl)amino)-1-oxopropan-2-yl)carbamate (183 mg, 0.443 mmol) in methanol (20 mL) and ethyl acetate (20 mL) was flushed with nitrogen gas and treated with 10% palladium on carbon (50 mg). The reaction vessel was flushed with hydrogen gas, and the reaction mixture was stirred under a hydrogen atmosphere (balloon) for 16 h. After this time, the reaction mixture was filtered over diatomaceous earth. The filtrate was concentrated under reduced pressure. The residue was purified by column chromatography (silica gel, 0-100% [90:9:1 methylene chloride/methanol/ammonium hydroxide]/methylene chloride) and freeze dried from acetonitrile/water to provide (S)-2-amino-3-hydroxy-N-(1-(2-hydroxybenzoyl)azetidin-3-yl) propanamide, (96 mg, 78%) as a fluffy white solid: $^1$H NMR (500 MHz, DMSO-$d_6$) δ 11.79 (br s, 1H), 8.53 (s, 1H), 7.41-7.35 (m, 2H), 6.91-6.84 (m, 2H), 4.71-4.55 (m, 3H), 4.28 (br s, 2H), 4.00 (br s, 1H), 3.47-3.40 (m, 2H), 3.19 (t, J=5.0 Hz, 1H), 1.75 (br s, 2H); ESI MS m/z 280 $[C_{13}H_{17}N_3O_4+H]^+$; HPLC (Method D) >99% (AUC), $t_R$=6.08 min.

Scheme 8.

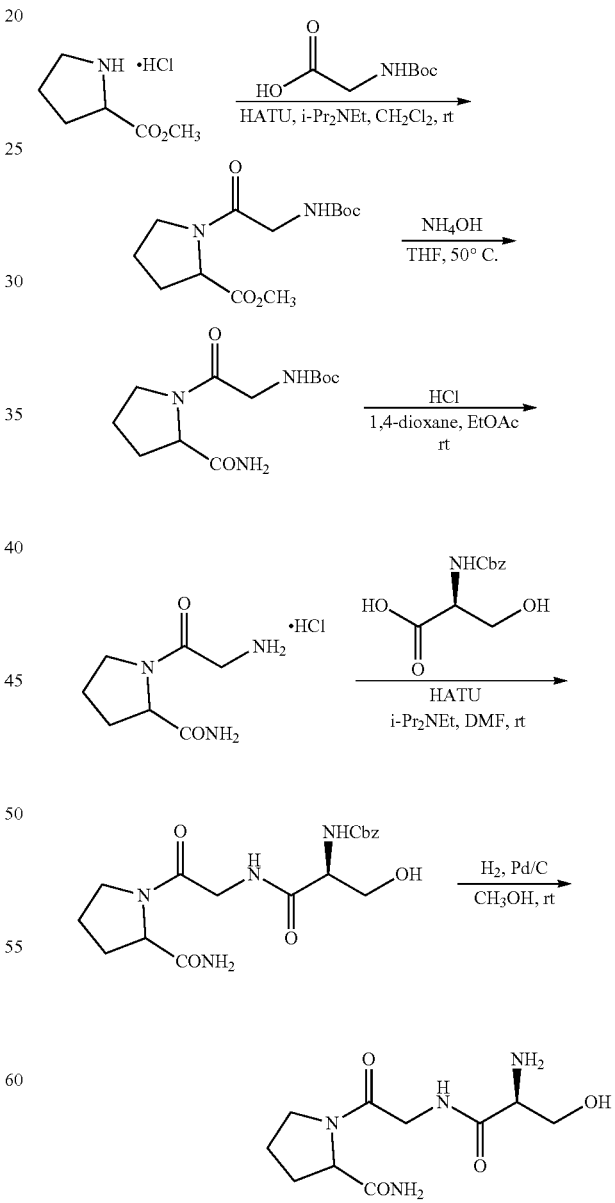

Preparation of Methyl 1-(2-((tert-butoxycarbonyl)amino)acetyl)pyrrolidine-2-carboxylate

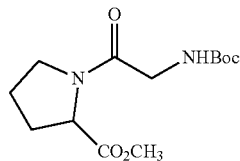 [SMILES: COC(=O)C1CCCN1C(=O)CNC(=O)OC(C)(C)C]

A mixture of N-Boc-glycine (2.30 g, 13.1 mmol) and methyl pyrrolidine-2-carboxylate hydrochloride (2.00 g, 12.1 mmol) in methylene chloride (25 mL) at room temperature was treated with N,N-diisopropylethylamine (4.25 mL, 24.4 mmol) followed by (1-[bis(dimethylamino)methyl ene]-1H-1,2,3-triazolo[4,5-b]pyridinium 3-oxide hexafluorophosphate) (5.00 g, 13.1 mmol). The mixture was stirred at room temperature for 18 h. After this time, the reaction mixture was diluted with methylene chloride and sequentially washed with water, saturated ammonium chloride, saturated sodium bicarbonate, water, and brine. The organic extract was dried over sodium sulfate, filtered, and concentrated to obtain crude methyl 1-(2-((tert-butoxycarbonyl)amino)acetyl)pyrrolidine-2-carboxylate (3.9 g), which was used in the next step without purification: ESI MS m/z 287 $[C_{13}H_{22}N_2O_5+H]^+$.

Preparation of tert-Butyl (2-(2-carbamoylpyrrolidin-1-yl)-2-oxoethyl)carbamate

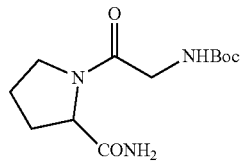

Crude methyl 1-(2-((tert-butoxycarbonyl)amino)acetyl)pyrrolidine-2-carb oxyl ate (3.9 g) was dissolved in tetrahydrofuran (5 mL) and treated with ammonium hydroxide (28-30%, 100 mL). The mixture was stirred in a sealed reactor at 50° C. for 18 h. After this time, the reaction mixture was concentrated to dryness to provide tert-butyl (2-(2-carbamoylpyrrolidin-1-yl)-2-oxoethyl)carbamate (3.6 g), which was used in the next step without purification: ESI MS m/z 272 $[C_{12}H_{21}N_3O_4+H]^+$.

Preparation of 1-(2-Aminoacetyl)pyrrolidine-2-carboxamide hydrochloride

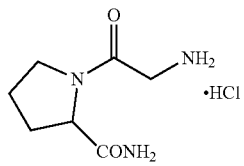 [SMILES: NCC(=O)N1CCCC1C(N)=O ; Cl]

A solution of crude tert-butyl (2-(2-carbamoylpyrrolidin-1-yl)-2-oxoethyl)carbamate (3.6 g) in ethyl acetate (12 mL) was treated with a 4 M solution of hydrogen chloride in 1,4-dioxane (10 mL) and stirred at room temperature for 1.5 h. After this time, heptane (10 mL) was added to obtain a precipitate that was collected by filtration to provide 1-(2-aminoacetyl)pyrrolidine-2-carboxamide hydrochloride (2.5 g): ESI MS m/z 172 $[C_7H_{13}N_3O_2+H]^+$.

Preparation of Benzyl ((2S)-1-((2-(2-carbamoylpyrrolidin-1-yl)-2-oxoethyl)amino)-3-hydroxy-1-oxopropan-2-yl)carbamate

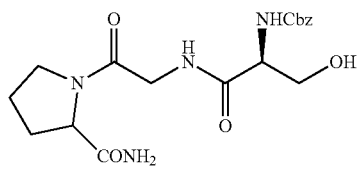 [SMILES: NC(=O)C1CCCN1C(=O)CNC(=O)[C@H](CO)NC(=O)OCc1ccccc1]

A mixture of crude 1-(2-aminoacetyl)pyrrolidine-2-carboxamide hydrochloride (2.5 g) and N-Cbz-L-serine (1.5 g, 6.2 mmol) in N,N-dimethylformamide (18 mL) at room temperature was treated with N,N-diisopropylethylamine (2.5 mL, 14 mmol) followed by (1-[bis(dimethylamino)methyl ene]-1H-1,2,3-triazolo[4,5-b]pyridinium 3-oxide hexafluorophosphate) (5.00 g, 13.1 mmol). The mixture was stirred at room temperature for 18 h. After this time, the reaction mixture was diluted with ethyl acetate and washed with 0.5 N hydrochloric acid. The aqueous layer was extracted three more times with ethyl acetate, and the organic extracts were combined, dried over sodium sulfate, and concentrated. The residue was purified by reversed phase column chromatography (50 g C18 column, 3-60% acetonitrile/water) to provide benzyl ((2S)-1-((2-(2-carbamoylpyrrolidin-1-yl)-2-oxoethyl)amino)-3-hydroxy-1-oxopropan-2-yl)carbamate (80 mg, 6% over four steps): ESI MS m/z 393 $[C_{18}H_{24}N_4O_6+H]^+$.

Preparation of 1-(2-((S)-2-Amino-3-hydroxypropanamido)acetyl)pyrrolidine-2-carboxamide

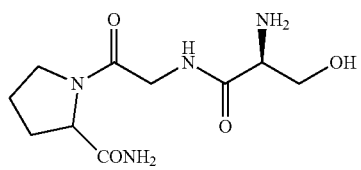

A mixture of benzyl ((2S)-1-((2-(2-carbamoylpyrrolidin-1-yl)-2-oxoethyl)amino)-3-hydroxy-1-oxopropan-2-yl)carbamate (135 mg, 0.344 mmol) and palladium (10% on carbon, 80 mg) in methanol (12 mL) was stirred under balloon pressure hydrogen for 2 h. After this time, the reaction mixture was purged with nitrogen, and the catalyst was removed by filtration. The filtrate was concentrated, and the residue was dissolved in water and freeze dried to provide 1-(2-((S)-2-amino-3-hydroxypropanamido)acetyl)pyrrolidine-2-carboxamide, (82 mg, 92%) as a white solid as a mixture of diastereomers: $^1$H NMR (300 MHz, DMSO-d6) δ 8.10 (s, 1H), 7.59 (s, 0.3H), 7.28 (s, 0.7H), 7.21 (s, 0.3H), 6.95 (s, 0.7H), 4.77 (broad s, 1H), 4.32 (dd, J=8.4, 2.4 Hz, 0.3H), 4.23-4.16 (m, 0.7H), 3.99-3.83 (m, 1.7 H)3.61-3.37 (m, 4.3H), 3.27-3.13 (m, 1H), 2.25-1.66 (m, 6H); ESI MS m/z 259 $[C_{10}H_{18}N_4O_4+H]^+$.

Scheme 9.

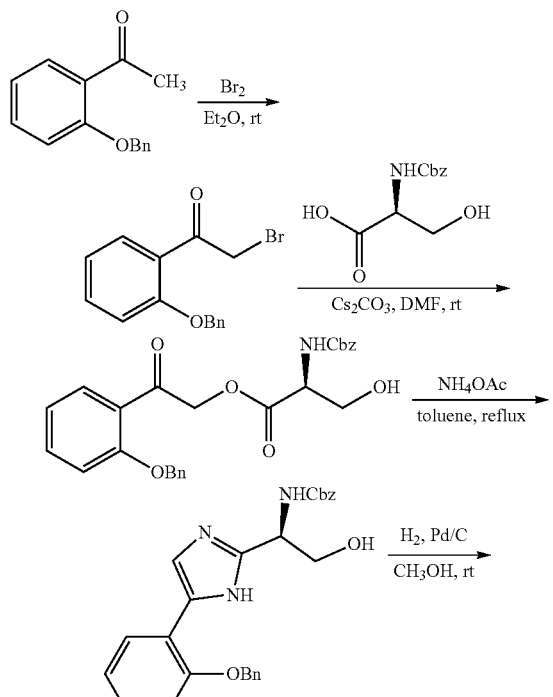

Preparation of
1-(2-(Benzyloxy)phenyl)-2-bromoethanone

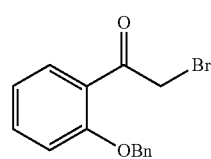 [SMILES: O=C(CBr)c1ccccc1OCc1ccccc1]

Bromine (0.7 mL, 13.7 mmol) was added dropwise to a solution of 1-(2-(benzyloxy)phenyl)ethanone (3.00 g, 13.3 mmol) in diethyl ether (100 mL), and the mixture was stirred at room temperature for 2 h. After this time, the mixture was washed with saturated sodium bicarbonate, water, and brine. The organic extract was dried over sodium sulfate, filtered and concentrated to dryness to provide 1-(2-(benzyloxy) phenyl)-2-bromoethanone (3.80 g, 94%): ESI MS m/z 305 $[C_{15}H_{13}BrO_2+H]^+$.

Preparation of (S)-2-(2-(Benzyloxy)phenyl)-2-oxo-ethyl 2-(((benzyloxy)carbonyl) amino)-3-hydroxy-propanoate A mixture of 1-(2-(benzyloxy)phenyl)-2-bromoethanone (1.80 g, 5.90 mmol), (S)-2-(((benzyloxy)carbonyl)amino)-3-hydroxypropanoic acid (1.60 g, 6.69 mmol), and cesium carbonate (1.40 g, 4.30 mmol) in N,N-dimethylformamide (15 mL) was stirred at room temperature for 2 h. After this time, the mixture was diluted with ethyl acetate and washed with 1 N hydrochloric acid, water, 5% lithium chloride, and brine. The organic extract was dried over sodium sulfate, filtered, and concentrated. The residue was purified by column chromatography (80 g silica, 0-100% ethyl acetate/ heptane) to provide (S)-2-(2-(benzyloxy)phenyl)-2-oxoethyl 2-(((benzyloxy)carbonyl)amino)-3-hydroxypropanoate (2.04 g, 75%): ESI MS m/z 464 $[C_{26}H_{25}NO_7+H]^+$.

Preparation of (R)-Benzyl (1-(5-(2-(benzyloxy)phe-nyl)-1H-imidazol-2-yl)-2-hydroxyethyl)carbamate A mixture of (S)-2-(2-(benzyloxy)phenyl)-2-oxoethyl 2-(((benzyloxy)carbonyl)amino)-3-hydroxypropanoate (1.95 g, 4.21 mmol) and ammonium acetate (2.20 g, 28.6 mmol) in toluene (100 mL) was stirred at reflux in a flask equipped with a Dean-Stark trap for 10 h. After this time, the mixture was cooled to room temperature, diluted with ethyl acetate, and washed with water and brine. The organic extract was dried over sodium sulfate, filtered, and concentrated. The residue was purified by column chromatography (120 g silica, 0-8% methanol/dichloromethane) to provide (R)-benzyl (1-(5-(2-(benzyloxy)phenyl)-1H-imidazol-2-yl)-2-hydroxyethyl)carbamate (0.89 g, 48%): ESI MS m/z 444 $[C_{26}H_{25}N_3O_4+H]^+$.

Preparation of (R)-2-(2-(1-Amino-2-hydroxyethyl)-1H-imidazol-5-yl)phenol hydrochloride

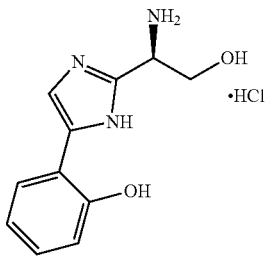 [SMILES: N[C@@H](CO)c1ncc(-c2ccccc2O)[nH]1 ; Cl]

A mixture of (R)-benzyl (1-(5-(2-(benzyloxy)phenyl)-1H-imidazol-2-yl)-2-hydroxyethyl)carbamate (440 mg, 0.99 mmol) and palladium (10% on carbon, 120 mg) in methanol (16 mL) was stirred under balloon pressure hydrogen for 5 h. After this time, the reaction mixture was purged with nitrogen, the catalyst was removed by filtration, and the filtrate was concentrated to dryness to obtain the product as a free base (200 mg, 92%). A portion of the material (105 mg) was dissolved in methanol (2 mL) and treated with a 1.25 M solution of hydrogen chloride in methanol (1 mL). The solution was concentrated to dryness, and the residue was dissolved in water and freeze dried to provide (R)-2-(2-(1-amino-2-hydroxyethyl)-1H-imidazol-5-yl)phenol hydrochloride, as an off-white solid: $^1$H NMR (300 MHz, DMSO-d6) δ 9.09 (broad s, 3H), 7.97 (s, 1H), 7.84 (dd, J=7.8, 1.2 Hz, 1H), 7.23 (t, J=7.2 Hz, 1H), 7.05 (d, J=8.0 Hz, 1H), 6.93 (t, J=7.5 Hz, 1H), 4.87-4.72 (m, 1H), 4.07-3.94 (m, 2H), 3 exchangeable protons not observed; ESI MS m/z 220 $[C_{11}H_{13}N_3O_2+H]^+$; HPLC (Method B) >99% (AUC), $t_R$=8.01 min.

Example 2

Figure 10A:
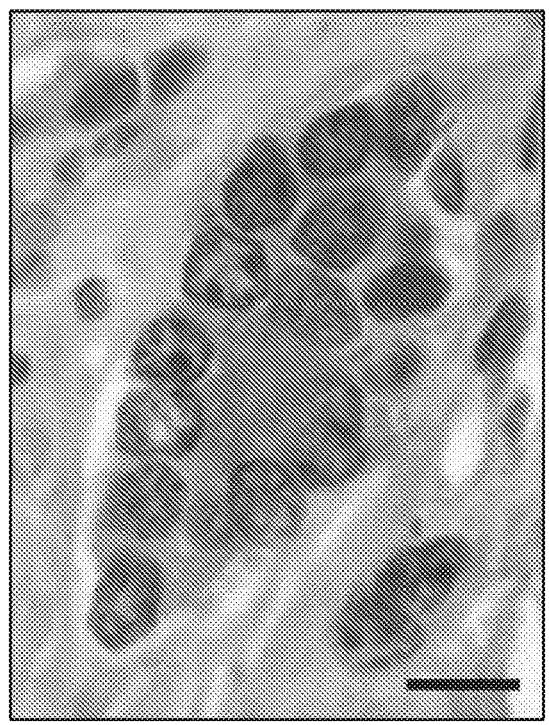
FIG. 10A-FIG. 10E depict in accordance with various embodiments of the invention, OC2 can functionally oppose the androgen receptor. Multiplex IHC and digital image analysis identifies an inverse relationship between nuclear OC2 and nuclear AR in aggressive human PC (Gleason grade 4 cores) (FIG. 10A) Representative IHC image of OC2 (red) and AR (brown) staining of high grade PC. (scale bar 20 μm).
Figure 10B:
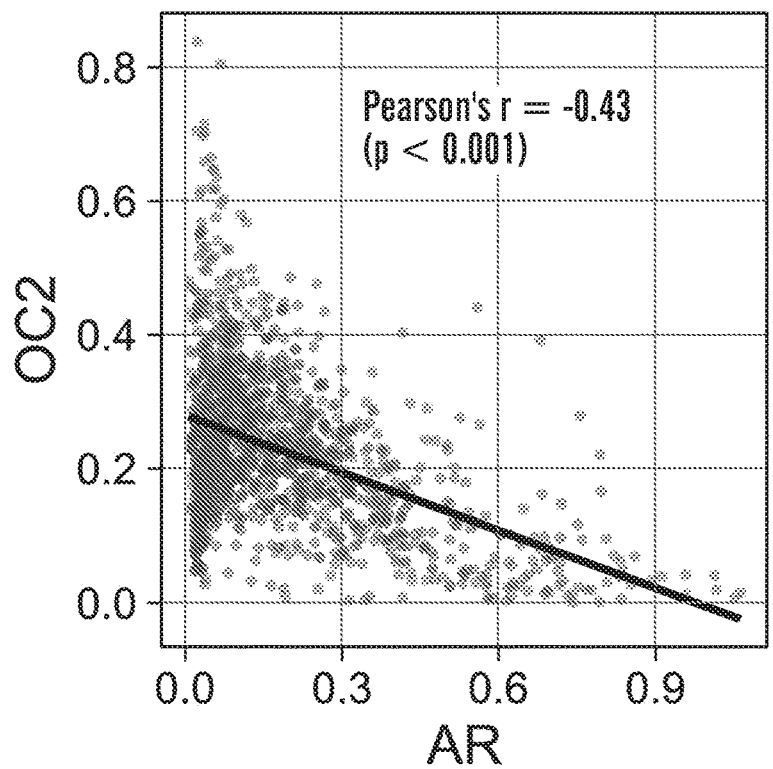
Figure 10C:
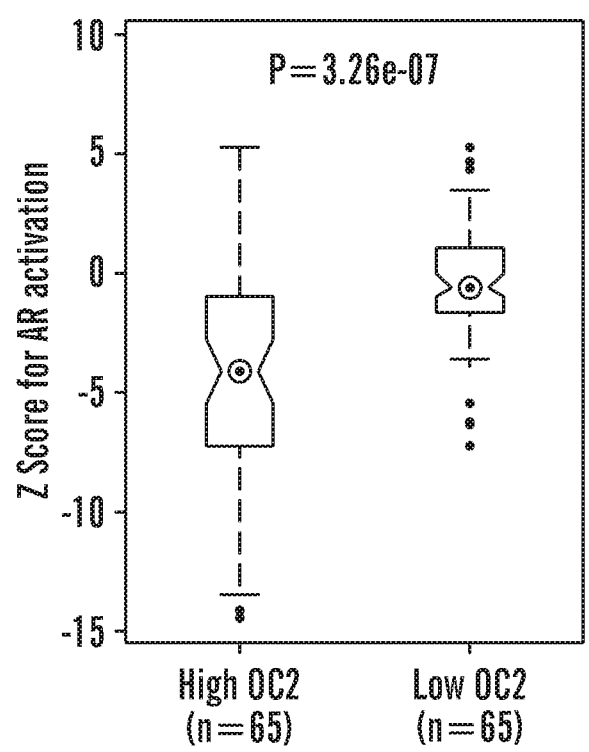
Figure 10D:
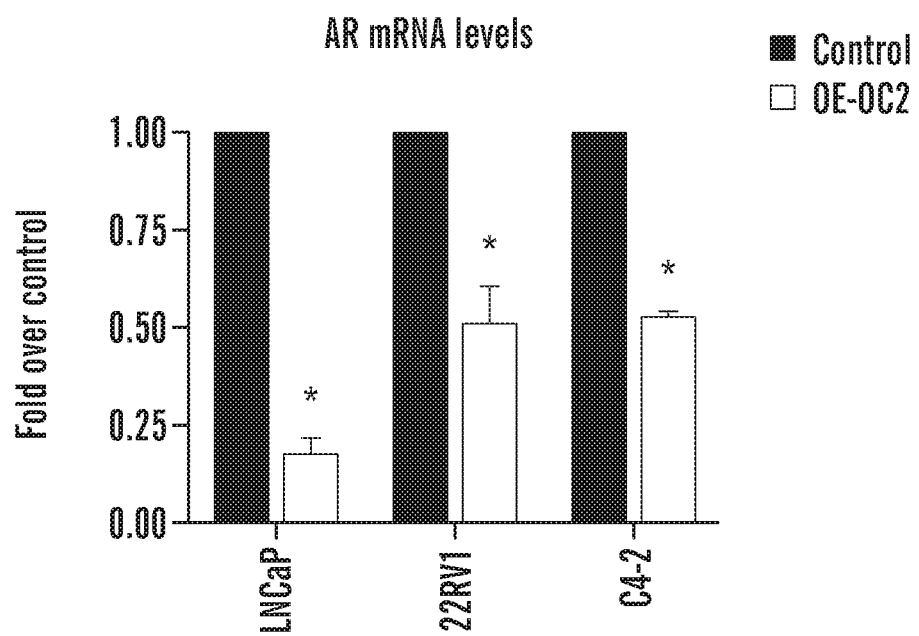
Figure 10E:
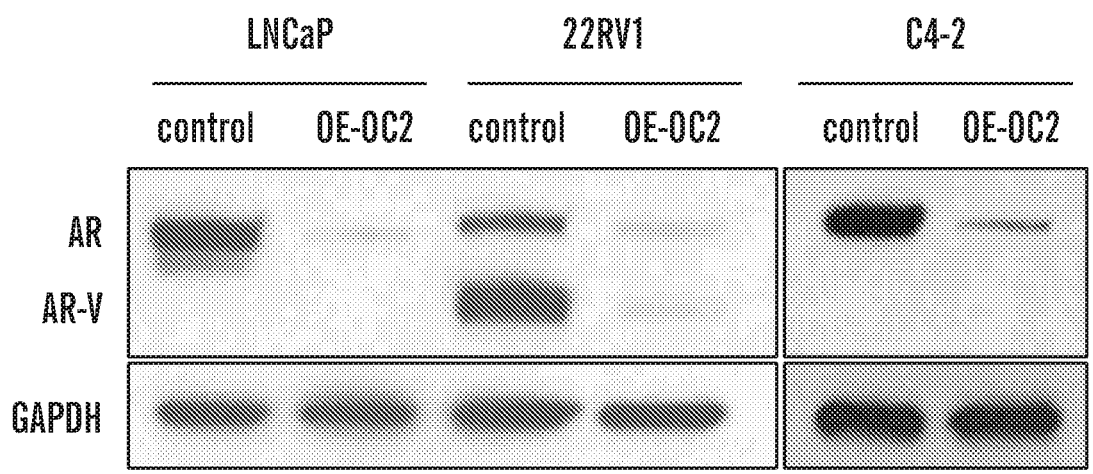
Figure 19A:
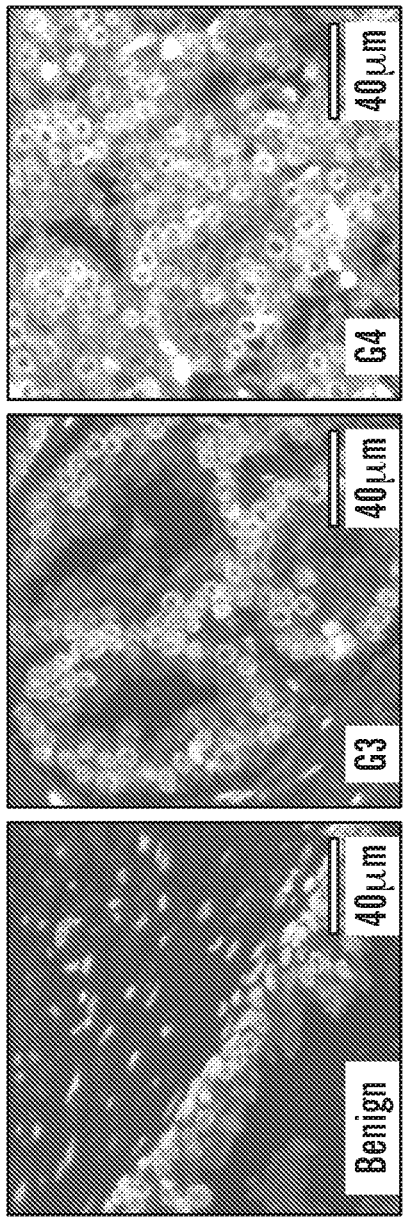
FIG. 19A and FIG. 19B depict in accordance with various embodiments of the invention.
Figure 19A:
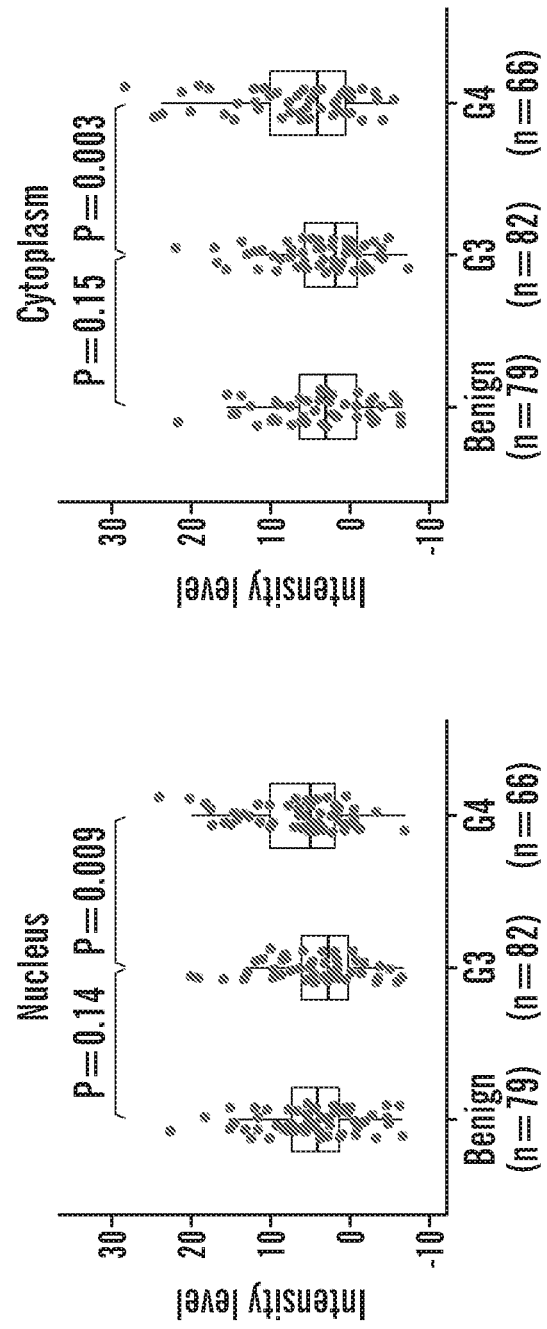
Figure 19B:
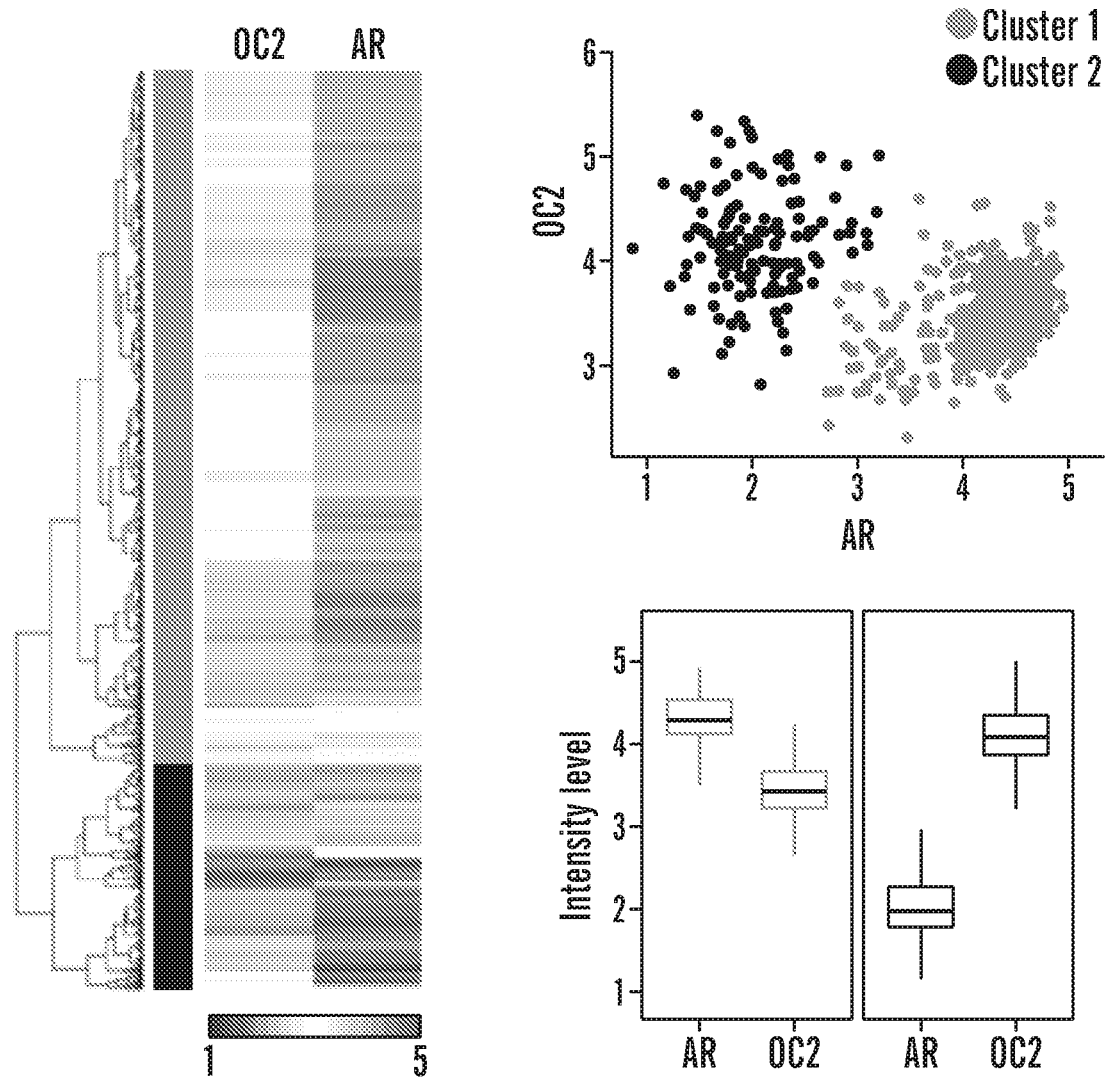
Figure 20A:
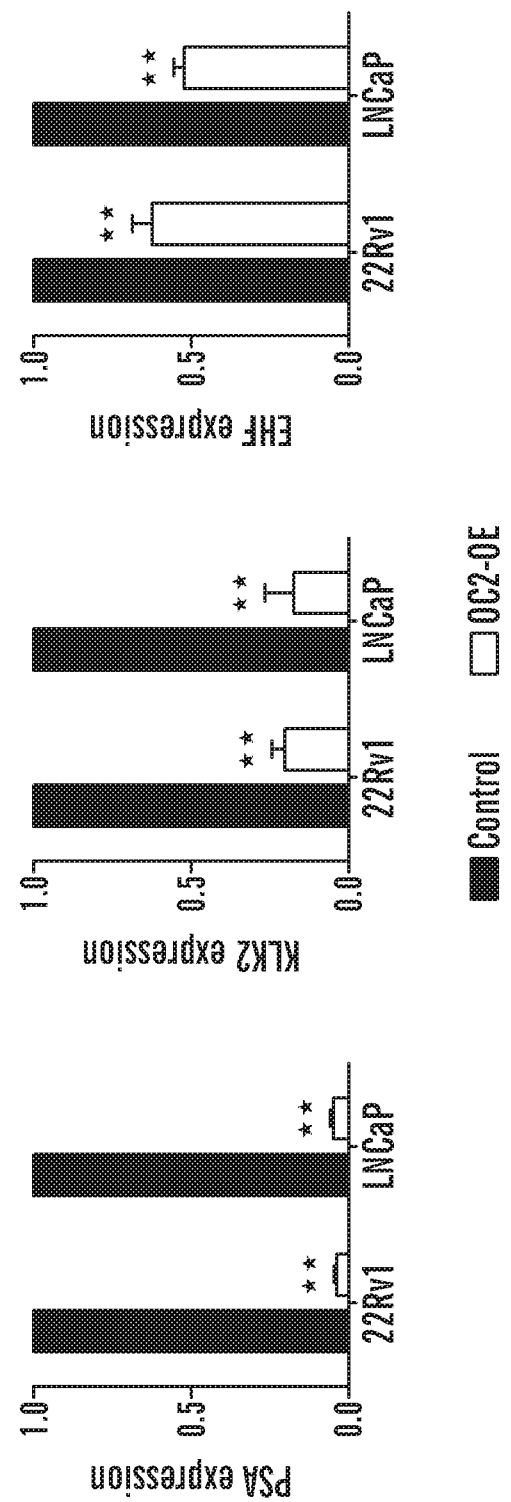
FIG. 20A-FIG. 20B depict in accordance with various embodiments of the invention.

OC2 is a master regulator of the AR network and is highly active in mCRPC. OC2 is expressed at relatively high levels in prostate, small cell lung cancer, neuroblastoma, medulloblastoma, and liver cell lines, according to the CCLE database (www.broadinstitute.org/ccle). Immunostaining of a PC tissue microarray containing benign prostate tissue and low and high grade cancers, and measurement of staining intensity and subcellular localization by digital imaging, showed that nuclear and cytoplasmic OC2 levels were increased in Gleason grade 4 vs 3 cancer (FIG. 19A). Anti-AR and anti-OC2 antibodies were multiplexed for immunostaining in 35 cases of high grade PC and nuclear localization of both proteins quantified (n=1,373 cells). Nuclear OC2 and AR were significantly inversely correlated (FIG. 19B). These findings suggested the possibility that OC2 suppresses AR activity. Consistent with this, mCRPCs with high OC2 expression exhibit low AR activation in comparison to tumors with low OC2 expression (FIG. 10C). Enforced OC2 expression in LNCaP, 22Rv1 and C4-2 cells dramatically downregulated AR expression as well as AR-regulated genes, such as KLK3/PSA (FIG. 20A).

We enforced OC2 expression in LNCaP and 22Rv1 cells, and silenced OC2 in 22Rv1 cells, and gene expression profiling was performed using the Affymetrix U133 Plus2 array platform. From these data, two sets of differentially expressed genes were identified with FDR <0.05 and fold change >2. The OC2-induced gene set consists of 82 genes that were significantly up-regulated by OC2 and down-regulated by OC2 silencing. The OC2-repressed gene set includes 55 genes significantly down-regulated by OC2 and up-regulated by OC2 silencing. OC2-induced genes were enriched for cell motion and neuron differentiation processes, while the OC2-repressed genes were enriched for regulation of AR activity. Use of this signature to quantify OC2 activity across the PC disease course indicates that activity is high in mCRPC.

Figure 20B:
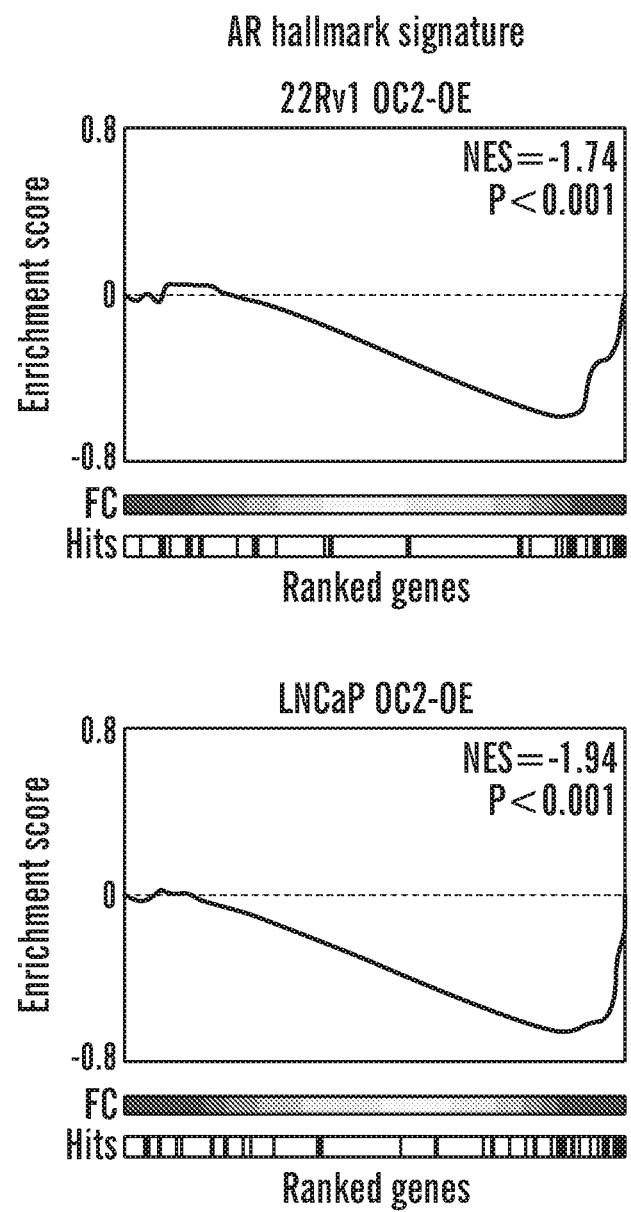
Figure 21A:
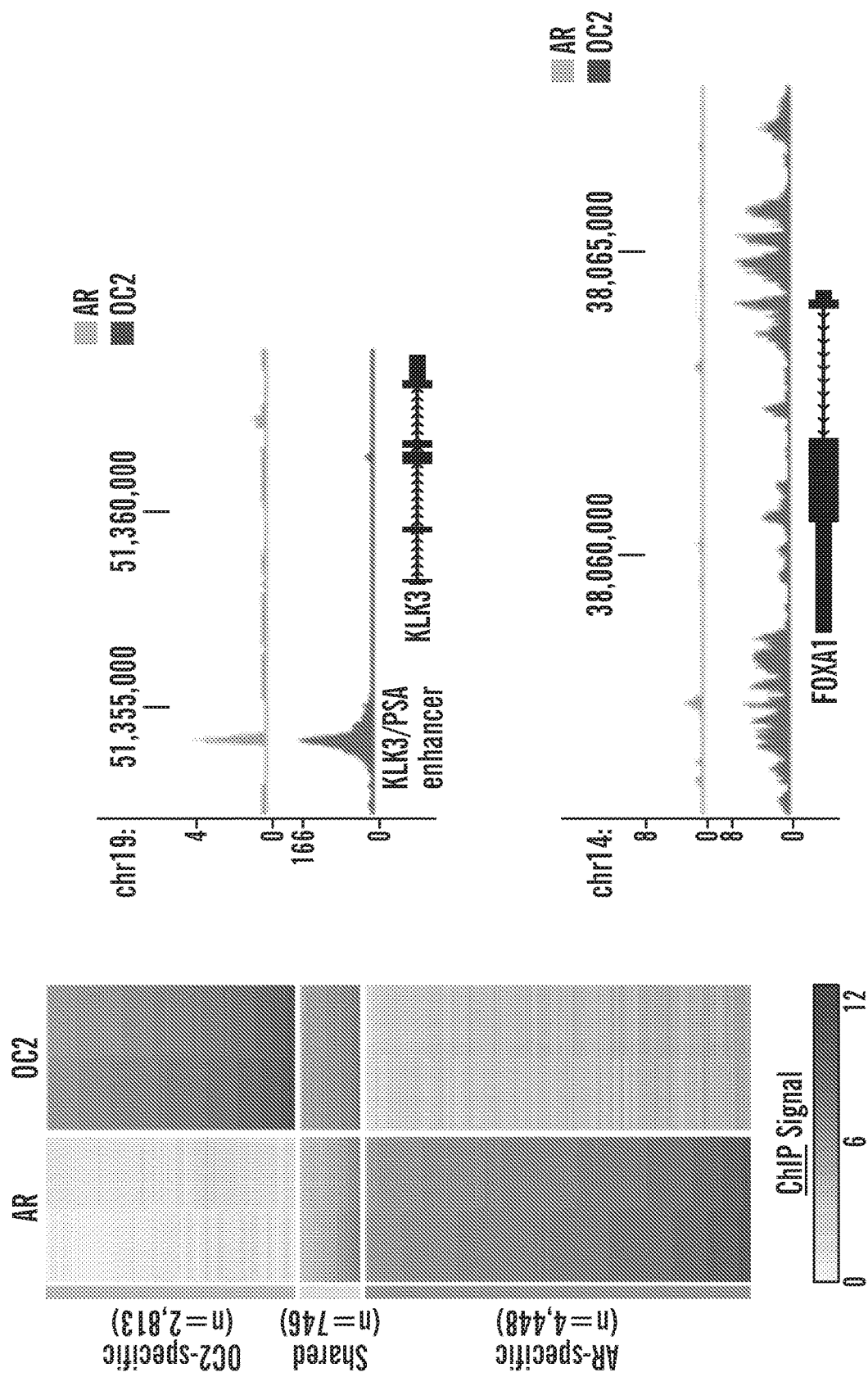
FIG. 21A-FIG. 21C depict in accordance with various embodiments of the invention.

ChIP-sequencing showed that endogenous OC2 bound to >3,500 chromatin sites in 22Rv1 cells, using high stringency criteria for peak calls. Integrating OC2 DNA binding sites with the OC2-regulated transcriptome in LNCaP and 22Rv1 revealed that 22% of OC2-regulated genes (1,558 out of 7,095) possess OC2 binding sites in either promoter or nearby enhancer regions. Of these, 392 genes were positively, and 526 genes negatively regulated by OC2 in 22Rv1 cells. We identified 746 regions (~20% of OC2 peaks) that were significantly bound by both OC2 and AR, however the majority of the OC2 peaks did not overlap with AR-binding regions, suggesting that OC2 can function independently of the AR (FIG. 21A). To address the functional relationship between OC2 and AR at shared promoter sites, we employed a gene set described as a hallmark AR gene signature (Liberzon A, Birger C, Thorvaldsottir H, Ghandi M, Mesirov J P, Tamayo P: The molecular signatures databse (MSigDB) hallmark gene set collection. Cell Syst 2016, 1(6):417-425). There was a highly significant enrichment of OC2 binding in the promoters of these hallmark AR-regulated genes (43/101, P=1.4×10-6). This gene set was significantly repressed (P<0.001) by OC2 overexpression in both 22Rv1 and LNCaP (FIG. 20B). These and other data not shown indicate that OC2 and AR act in functional opposition at promoter and enhancer sites throughout the genome.

Figures 11A, 11B:
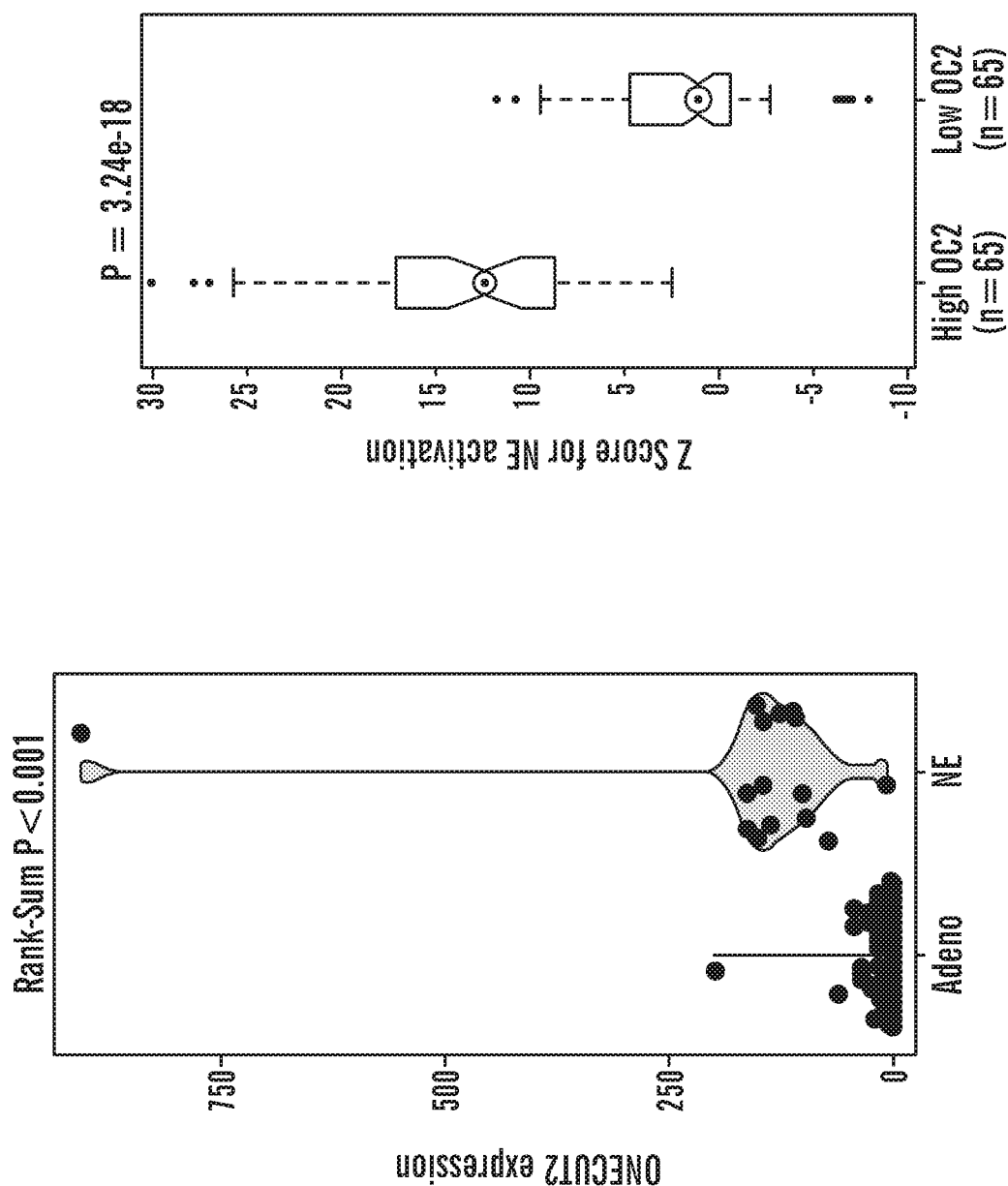
FIG. 11A and FIG. 11B depict in accordance with various embodiments of the invention, OC2 association with neuroendocrine prostate cancer.
Figure 12C:
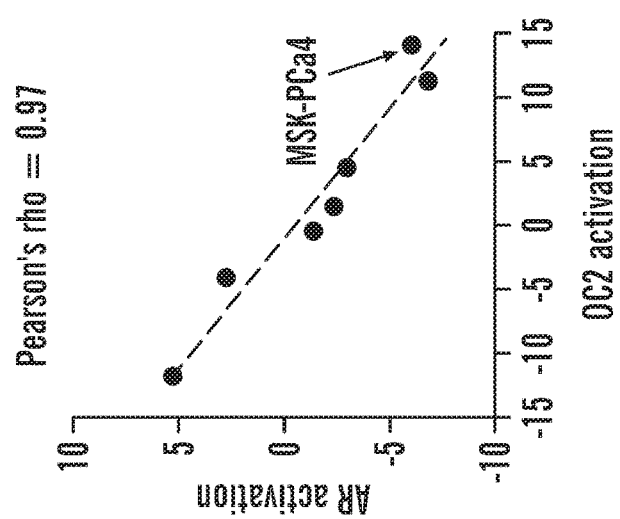
FIG. 12A-FIG. 12C depict in accordance with various embodiments of the invention, inverse association of OC2 and androgen receptor expression and activation in Memorial Sloan-Kettering human prostate cancer organoids. MSK-PCa4 is treatment-induced neuroendocrine cancer. In the MSK-PCa4 neuroendocrine cell line, OC2 expression and activity is relatively high compared to the other organoid cell lines and inversely correlated to the transcription factor REST (FIG. 12A). Loss of repression by REST has been implicated in transition to NEPC. In this cell line, OC2 activation is positively correlated with AR repression (FIG. 12B) and negatively correlated with AR activation (FIG. 12C). In a neuroendocrine cell lines derived from human prostate organoids, OC2 expression and activity is relatively high and these organoids may be sensitive to CSRM617.
Figure 12B:
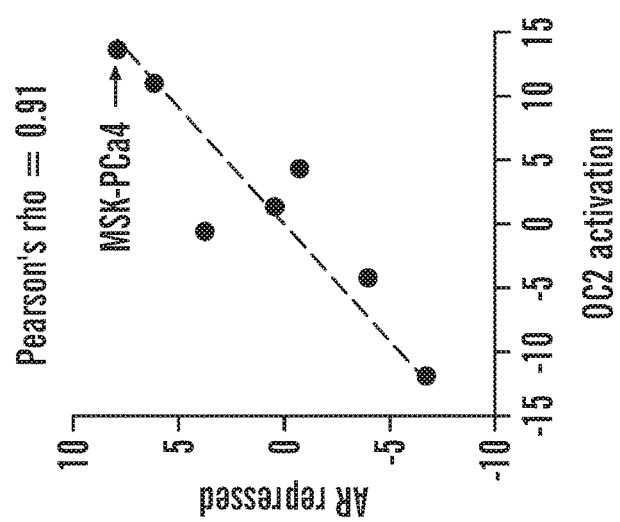
Figure 12A:
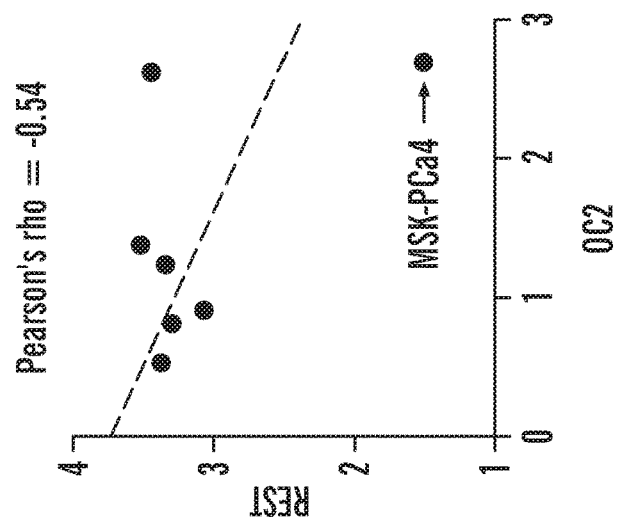
Figure 13:
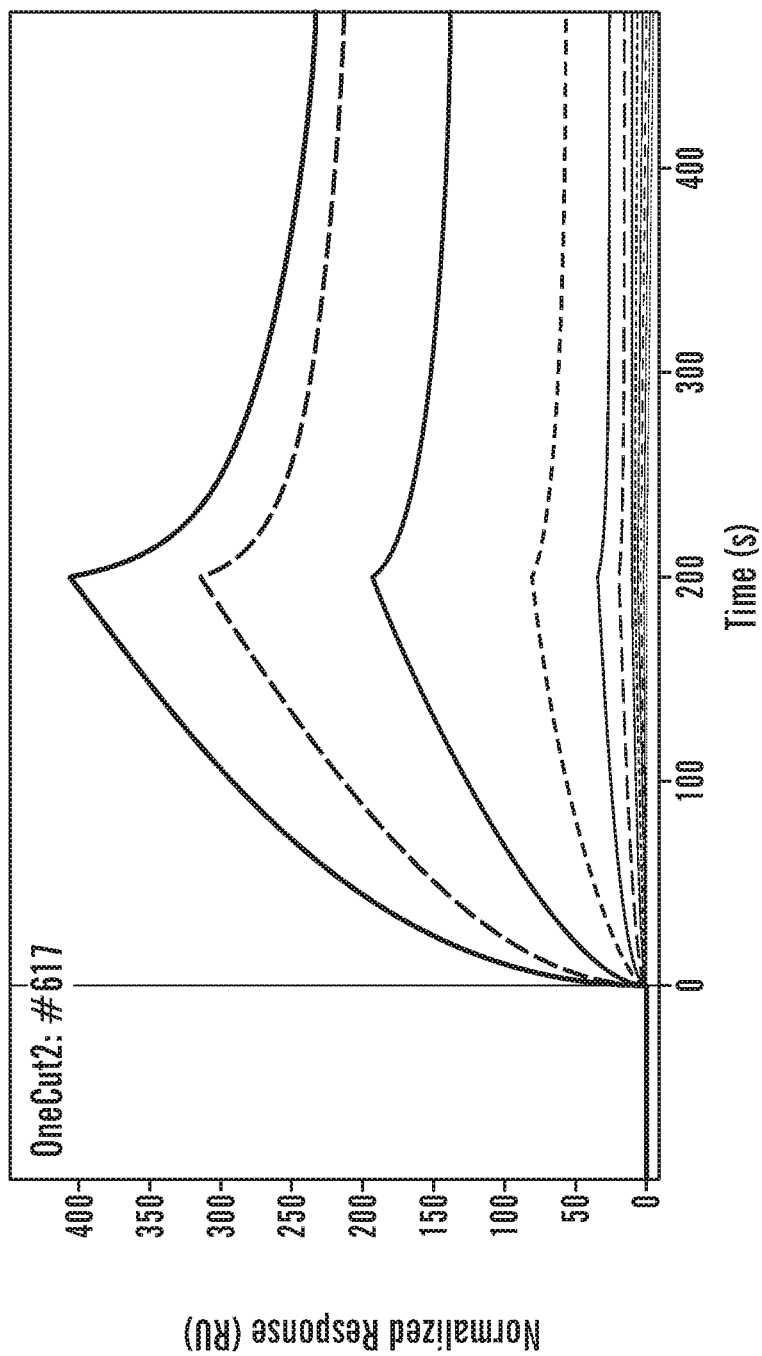
FIG. 13 depicts in accordance with various embodiments of the invention, Compound CSRM617 binds to ONECUT2 in a dose-dependent manner. To measure binding features of CSRM617, the OC2-HOX domain was recombinantly produced. Purified OC2-HOX binding domain was next immobilized on a HisCap sensor chip and CSRM617 was analyzed at serial doubling concentrations maximized at 100 μM. As measured by surface plasmon resonance (SPR), CSRM617 binds to the OC2 protein in a dose-dependent manner (Kd=7.43 μM).
Figure 21B:
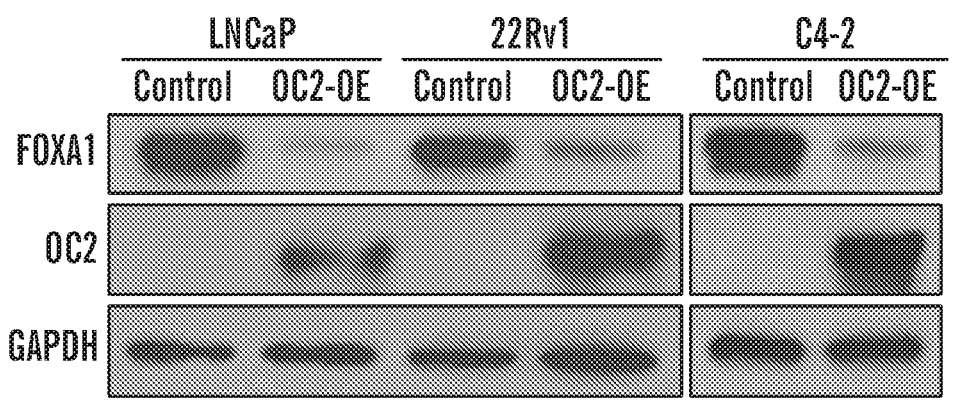
Figure 21C:
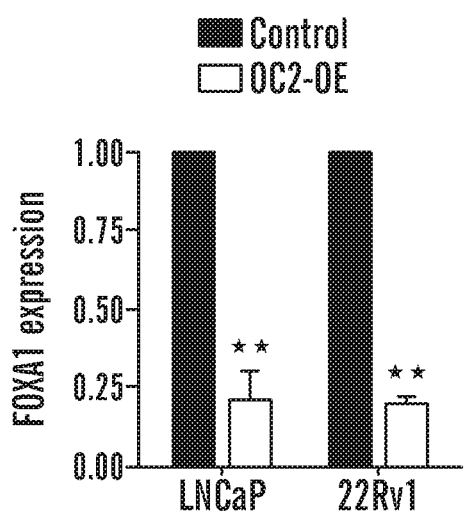
Figure 22A:
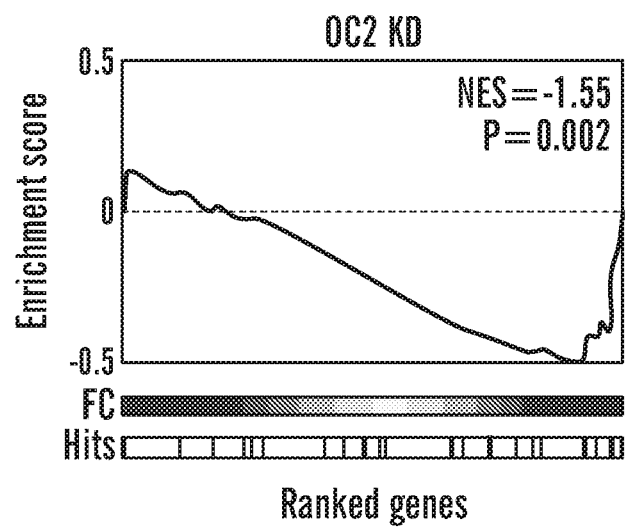
FIG. 22A-FIG. 22C depict in accordance with various embodiments of the invention.
Figure 22B:
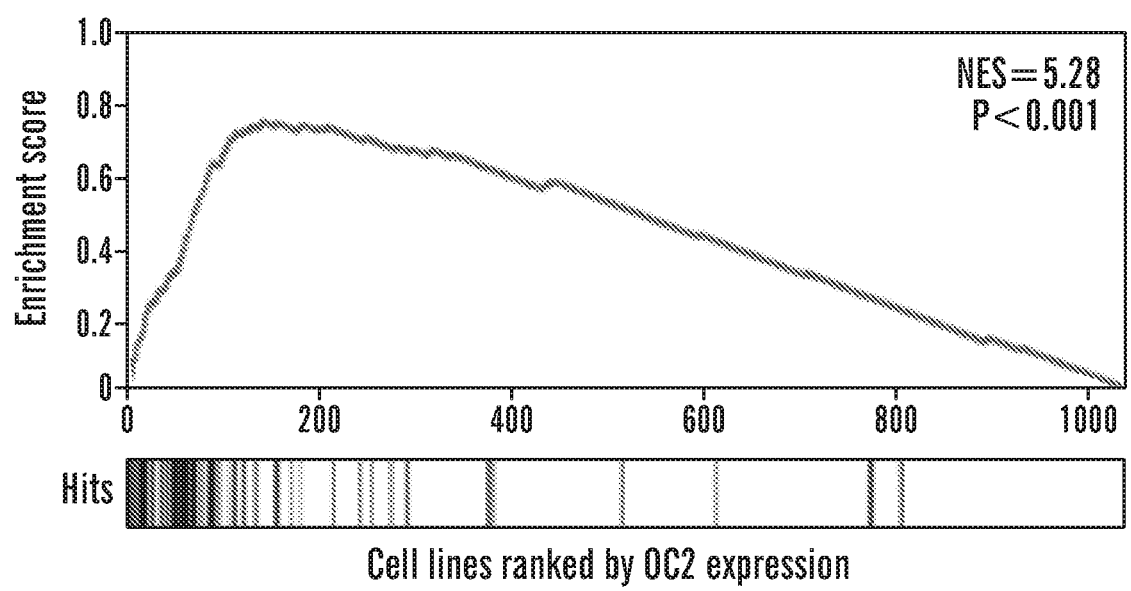
Figure 22C:
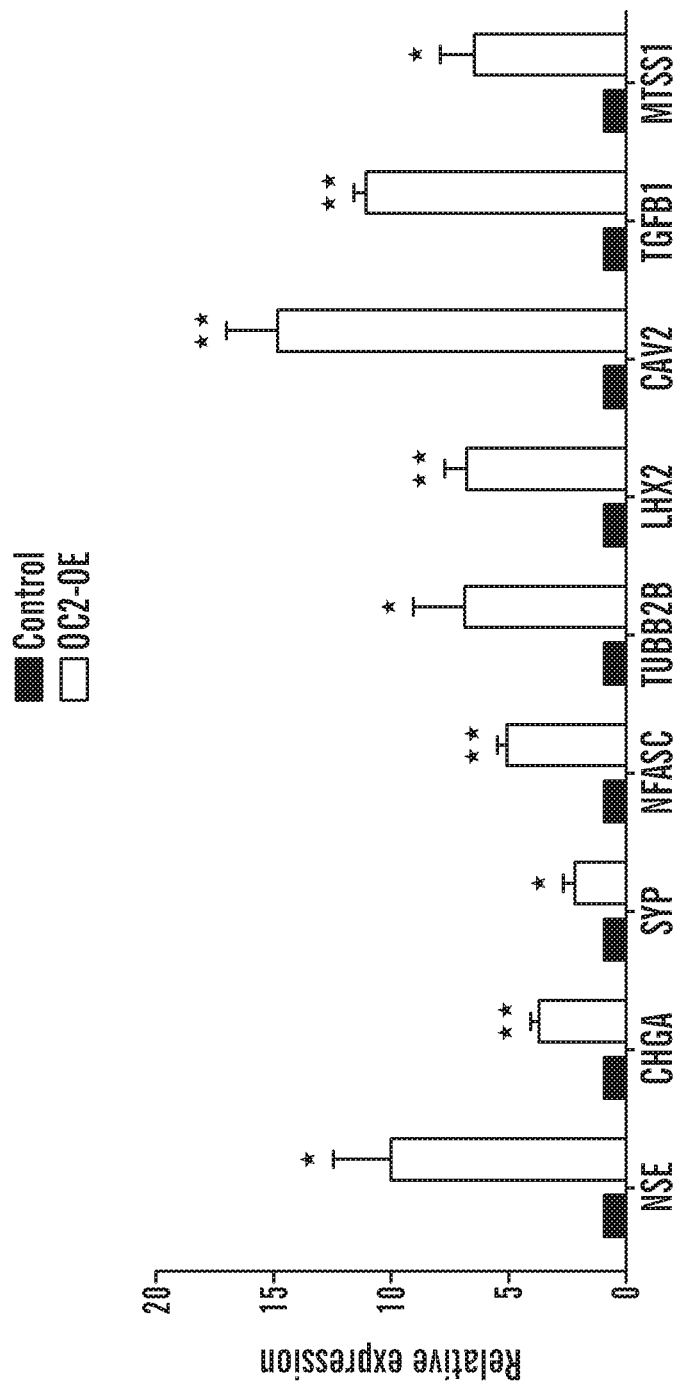
Figure 23:
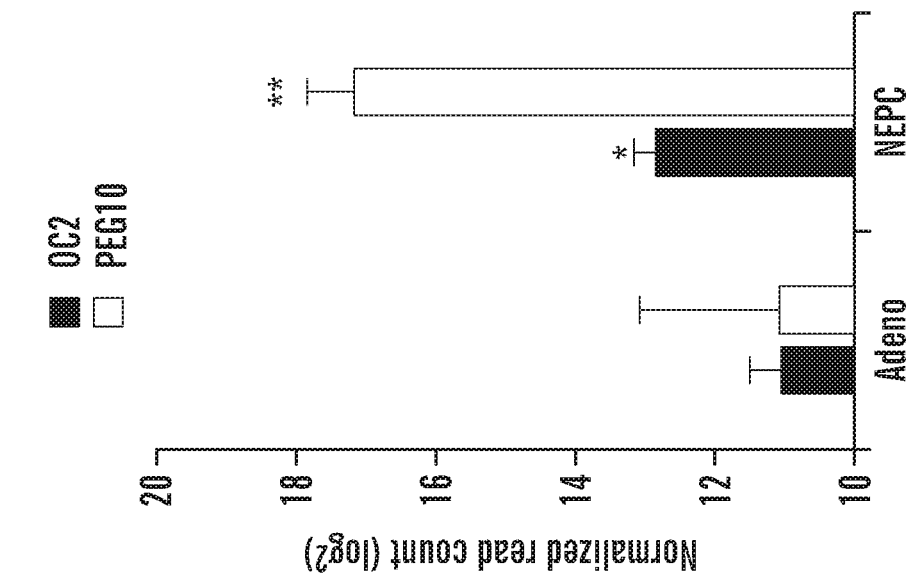
FIG. 23 depicts in accordance with various embodiments of the invention, ChIP-qPCR showing binding of endogenous REST to the OC2 promoter in LNCaP cells. O2 and PEG10 mRNA expression during NE transdifferentiation in the LTL331 transdifferentiation model.
Figure 23:
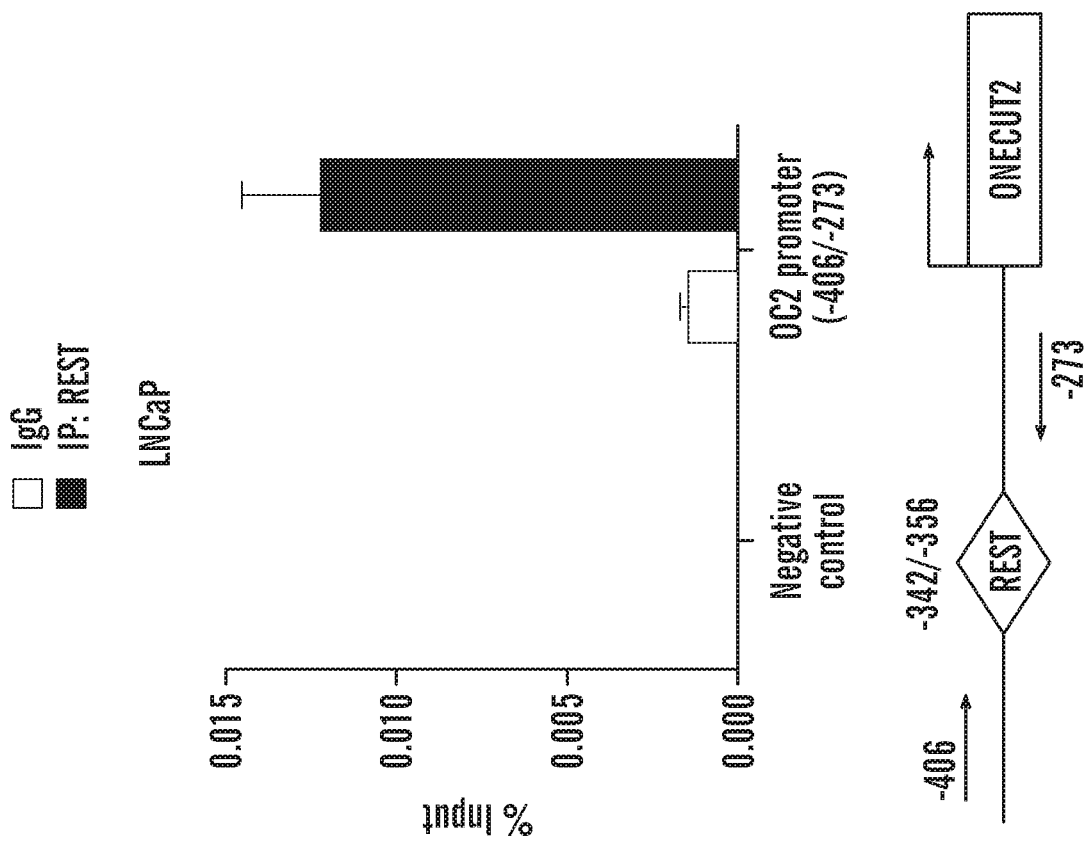

OC2 is a master regulator of neuroendocrine transdifferentiation in CRPC. The single enriched motif in the OC2-AR co-bound regions was a FOX-like motif (E-value=4.9×10-108). Endogenous OC2 bound the FOXA1 promoter, and at multiple sites within and adjacent to the FOXA1 gene (FIG. 21). Enforced OC2 repressed FOXA1 expression in LNCaP, 22Rv1 and C4-2 cells (FIG. 21). FOXA1 is well known as an AR pioneer factor and co-activator (Yang Y A, Yu J: Current perspectives on FOXA1 regulation of androgen receptor signaling and prostate cancer. Genes Dis 2015, 2(2):144-151), however a 2017 report has identified FOXA1 as an inhibitor of NEPC differentiation (Kim J, Jin H, Zhao J C, Yang Y A, Li Y, Yang X, Dong X, Yu J: FOXA1 inhibits prostate cancer neuroendocrine differentiation. Oncogene 2017, Mar 20. doi: 10.1038/onc.2017.50 [Epub ahead of print]). The direct repressive effect of OC2 on the FOXA1 gene suggests that OC2 may be a driver of NE differentiation. Consistent with this, OC2 is significantly up-regulated in well-defined NEPC compared to CRPC from two studies (Beltran H, Prandi D, Mosquera J M, Benelli M, Puca L, Cyrta J, Marotz C, Giannopoulou E, Chakravarthi B V, Varambally S et al: Divergent clonal evolution of castration-resistant neuroendocrine prostate cancer. Nat Med 2016, 22(3):298-305; Robinson D, Van Allen E M, Wu Y M, Schultz N, Lonigro R J, Mosquera J M, Montgomery B, Taplin M E, Pritchard C C, Attard G et al: Integrative clinical genomics of advanced prostate cancer. Cell 2015, 161(5):1215-1228) (FIG. 11A). In CRPC tumors from the DISC cohort, NE differentiation as evaluated from a published NE signature is significantly higher in tumors with high OC2 expression compared to those with low expression (FIG. 11B). Enrichment analysis revealed that OC2 depletion in 22Rv1 cells resulted in attenuation of gene expression marking NE differentiation (FIG. 22A). Cell lines in the CCLE (n=1,064) with high OC2 expression are enriched in NE differentiation gene expression (FIG. 22B). Consistent with these results, enforced OC2 resulted in the upregulation of genes associated with NE and neuronal differentiation (FIG. 22C). Relief from repression by the repressor element (RE)-1 silencing transcription factor REST has been implicated in transdifferentiation to NEPC (Lapuk A V, Wu C, Wyatt A W, McPherson A, McConeghy B J, Brahmbhatt S, Mo F, Zoubeidi A, Anderson S, Bell RH et al: From sequence to molecular pathology, and a mechanism driving the neuroendocrine phenotype in prostate cancer. *J Pathol* 2012, 227:286-297; Zhang X, Coleman I M, Brown L G, True L D, Kollath L, Lucas J M, Lam H M, Dumpit R, Corey E, Chery L et al: SRRM4 Expression and the loss of REST activity may promote the emergence of the neuroendocrine phenotype in castration-resistant prostate cancer. *Clin Cancer Res* 2015, 21(20):4698-4708). The OC2 promoter contains a highly-conserved REST binding site, suggesting that REST is a direct repressor of OC2 expression. Depletion of REST resulted in up-regulation of OC2 mRNA in C4-2 and LNCaP, consistent with a report of upregulation of OC2 mRNA following ablation of REST ablation in a model of pancreatic endocrine differentiation (Martin D, Kim Y H, Sever D, Mao C A, Haefliger J A, Grapin-Botton A: REST represses a subset of the pancreatic endocrine differentiation program. *Dev Biol* 2015, 405:316-327). ChIP-qPCR demonstrated direct binding of REST at the OC2 promoter, confirming the regulatory relationship (FIG. 23). Consistent with these data, REST and OC2 expression are inversely correlated in the mCRPC component of the DISC cohort (n=260; Spearman's rho=−0.21). This inverse correlation was also seen in the NEPC cohort from Beltran et al. (Beltran H, Prandi D, Mosquera J M, Benelli M, Puca L, Cyrta J, Marotz C, Giannopoulou E, Chakravarthi B V, Varambally S et al: Divergent clonal evolution of castration-resistant neuroendocrine prostate cancer. *Nat Med* 2016, 22(3):298-305) (Pearson's rho=−0.44, P<0.01).

The placental gene PEG10 was recently identified as a driver of transdifferentiation to NEPC from adenocarcinoma (Akamatsu S, Wyatt A W, Lin D, Lysakowski S, Zhang F, Kim S, Tse C, Want K, Mo F, Haegert A et al: The placental gene PEG10 promotes progression of neuroendocrine prostate cancer. *Cell Rep* 2015, 12:922-936). OC2 binds to the PEG10 promoter (FIG. 16B), indicating that OC2 is likely a direct regulator of PEG10 transcription. Consistent with this, enforced OC2 increased levels of PEG10 mRNA in C4-2 and LNCaP cells by 14- and 4-fold, respectively (FIG. 16B).

As described above, multiple lines of evidence support the conclusion that OC2 is a master regulator of NE transdifferentiation in CRPC: 1) OC2 represses AR throughout the genome, OC2 expression and inferred activity are inversely correlated with AR activity in human PC datasets, and inhibition of AR activity has been demonstrated to promote the appearance of NEPC (Akamatsu S, Wyatt A W, Lin D, Lysakowski S, Zhang F, Kim S, Tse C, Want K, Mo F, Haegert A et al: The placental gene PEG10 promotes progression of neuroendocrine prostate cancer. *Cell Rep* 2015, 12:922-936; Li Y, Donmez N, Sahinalp C, Xie N, Wang Y, Xue H, Mo F, Beltran H, Gleave M, Wang Y, Collins C, and Dong X: SRRM4 drives neuroendocrine transdifferentiation of prostate adenocarcinoma under androgen receptor pathway inhibition. *Eur Urol* 2017, 71:68-78); 2) OC2 activates a program of NE/neuronal gene expression; 3) the OC2 gene is regulated directly by REST; and 4) OC2 is a direct activator of the NEPC driver PEG10. ChIP-seq data also show that OC2 binds to the promoters of other neural transcription factors implicated in the appearance of NEPC from adenocarcinoma, including BRN2, ASCL1, HES6, SRRM4, and TTF1.

Example 3

Expression of ONECUT2 in relation to clinical outcome in the Cleveland Clinic Foundation cohort was evaluated (FIG. 1). The cohort was stratified according to tertiles of OC2 expression. Kaplan-Meier curves with the upper (High; n=60) and lower (Low; n=60) tertiles and Log-Rank test demonstrate patients with high OC2 expression exhibit significantly lower rates of BCR-free survival and Met-free survival compared to patients with low OC2 expression. HR=hazard ratio; BCR=biochemical recurrence; Met=metastasis. As shown in FIG. 1, high OC2 expression is an indicator of likelihood of progression to lethal disease in prostate cancer.

Figure 2A:
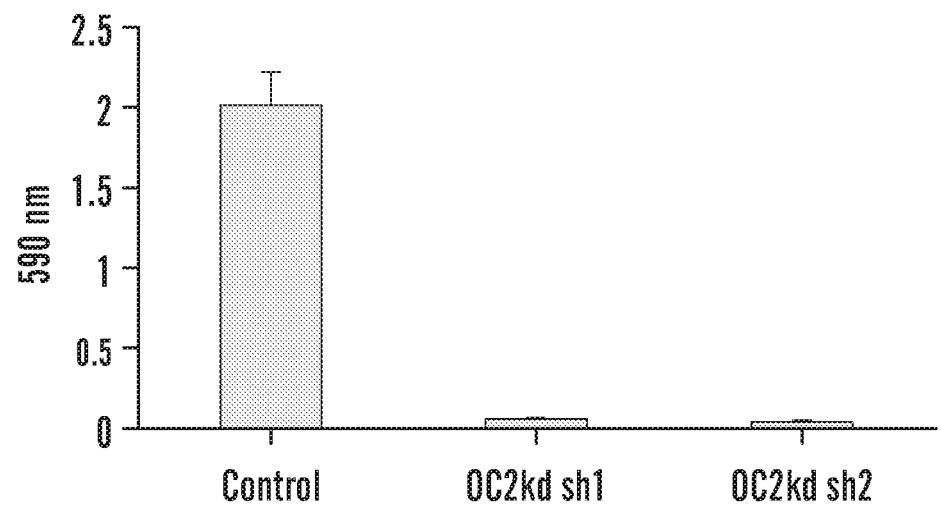
FIG. 2A and FIG. 2B depict in accordance with various embodiments of the invention, that aggressive human prostate cancer cells can become addicted to OC2 for growth and survival.
Figure 2A:
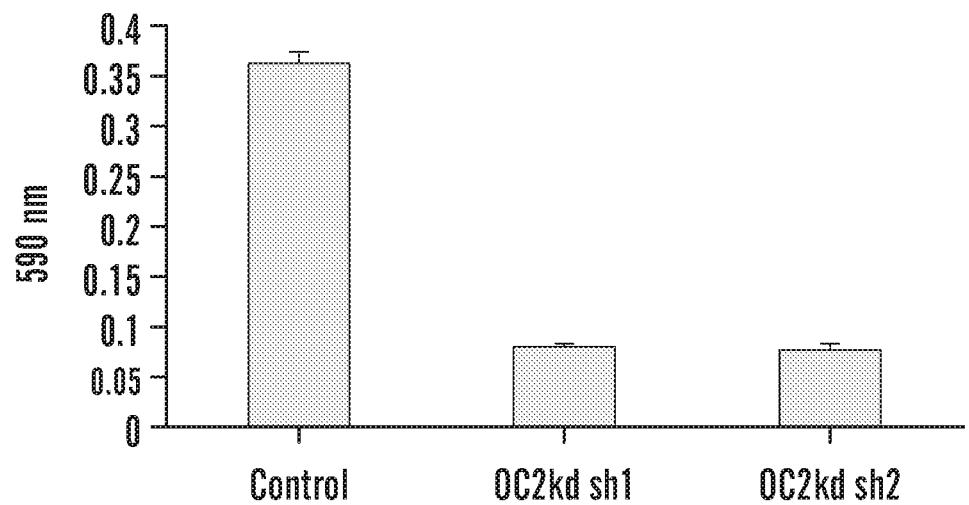
Figure 2B:
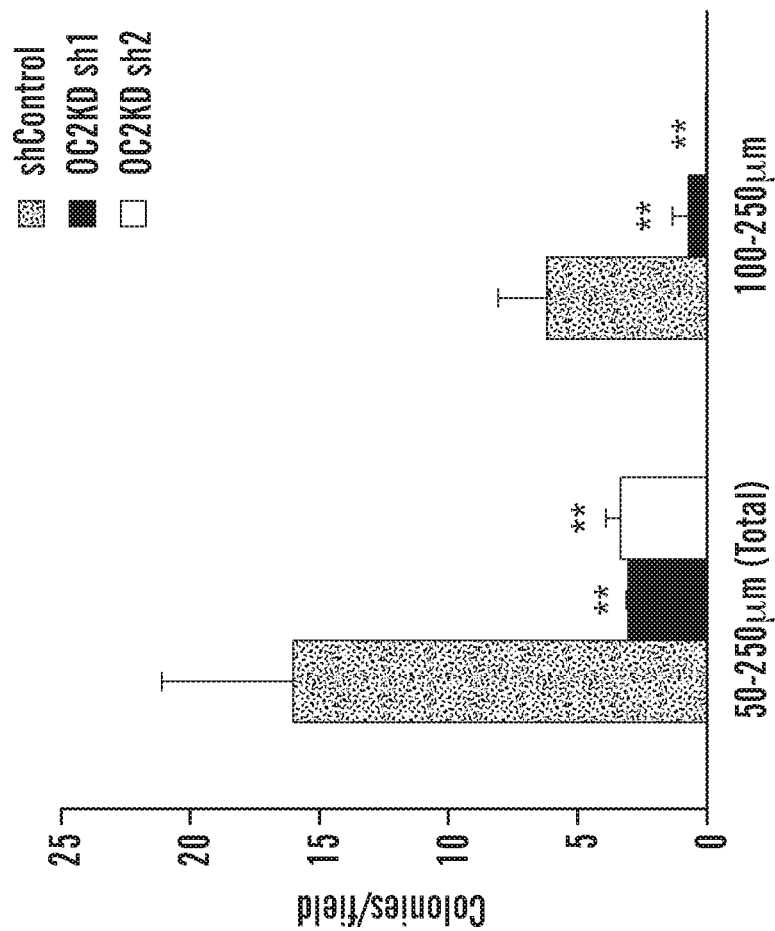
Figure 2B:
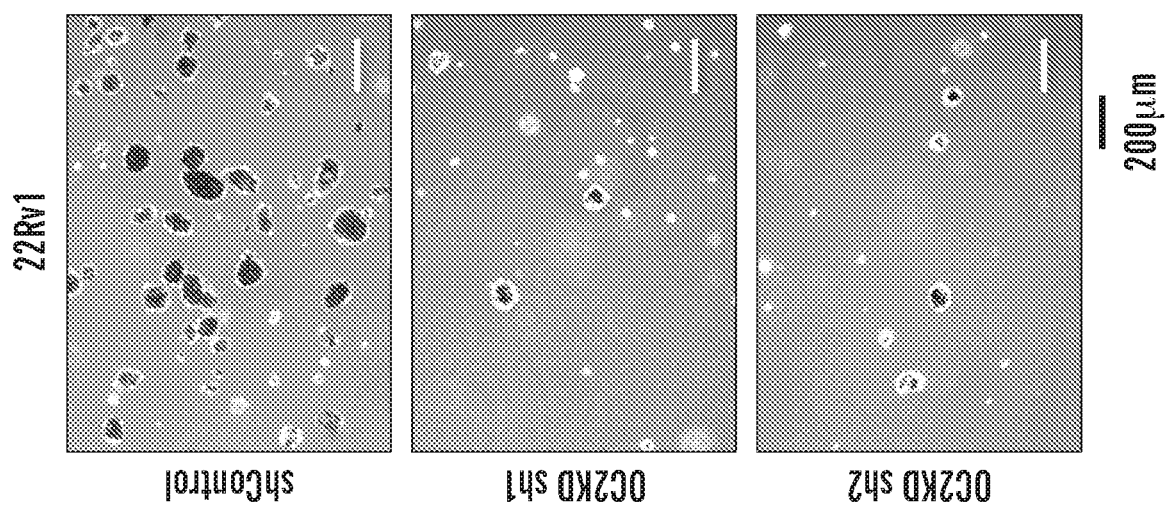

Knockdown of ONECUT2 by RNA silencing in human prostate cancer cell lines results in cell death and growth inhibition under 2D and 3D culture conditions (FIG. 2A and FIG. 2B). As shown in FIG. 2A and FIG. 2B, aggressive human prostate cancer cells can become addicted to OC2 for growth and survival.

Figure 3:
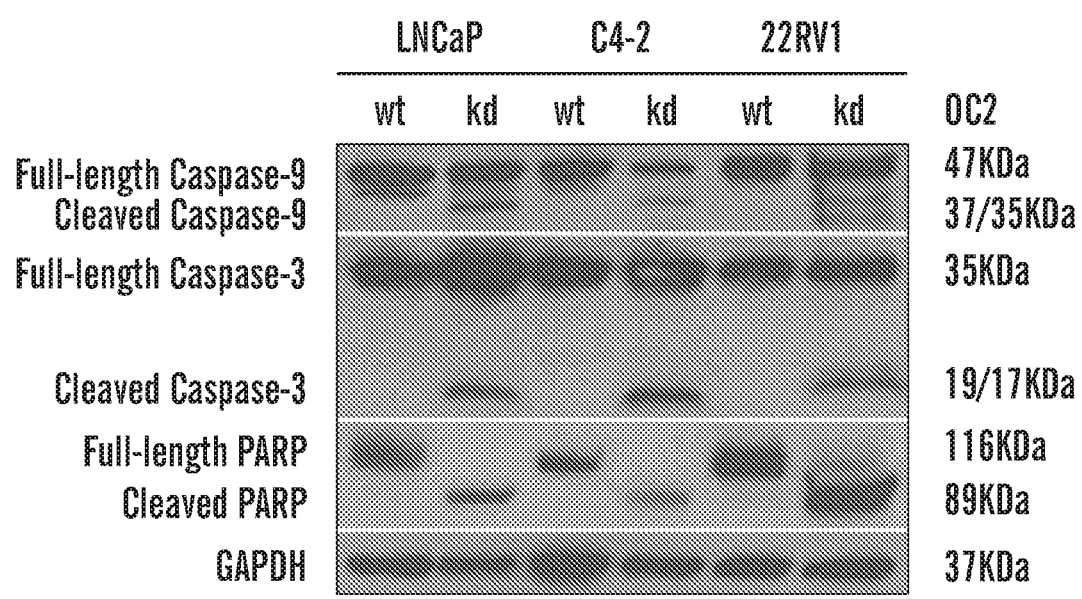
FIG. 3 depicts in accordance with various embodiments of the invention, that specific silencing of OC2 results in programmed cell death of aggressive prostate cancer cells.

Induction of apoptosis as determined by appearance of cleaved Caspase-9, Caspase-3 and PARP in LNCaP, C4-2 and 22RV1 prostate cancer cells by ONECUT2 (OC2) silencing was assessed (FIG. 3). GAPDH served as a loading control. As shown in FIG. 3, specific silencing of OC2 results in programmed cell death of aggressive prostate cancer cells.

Figure 4:
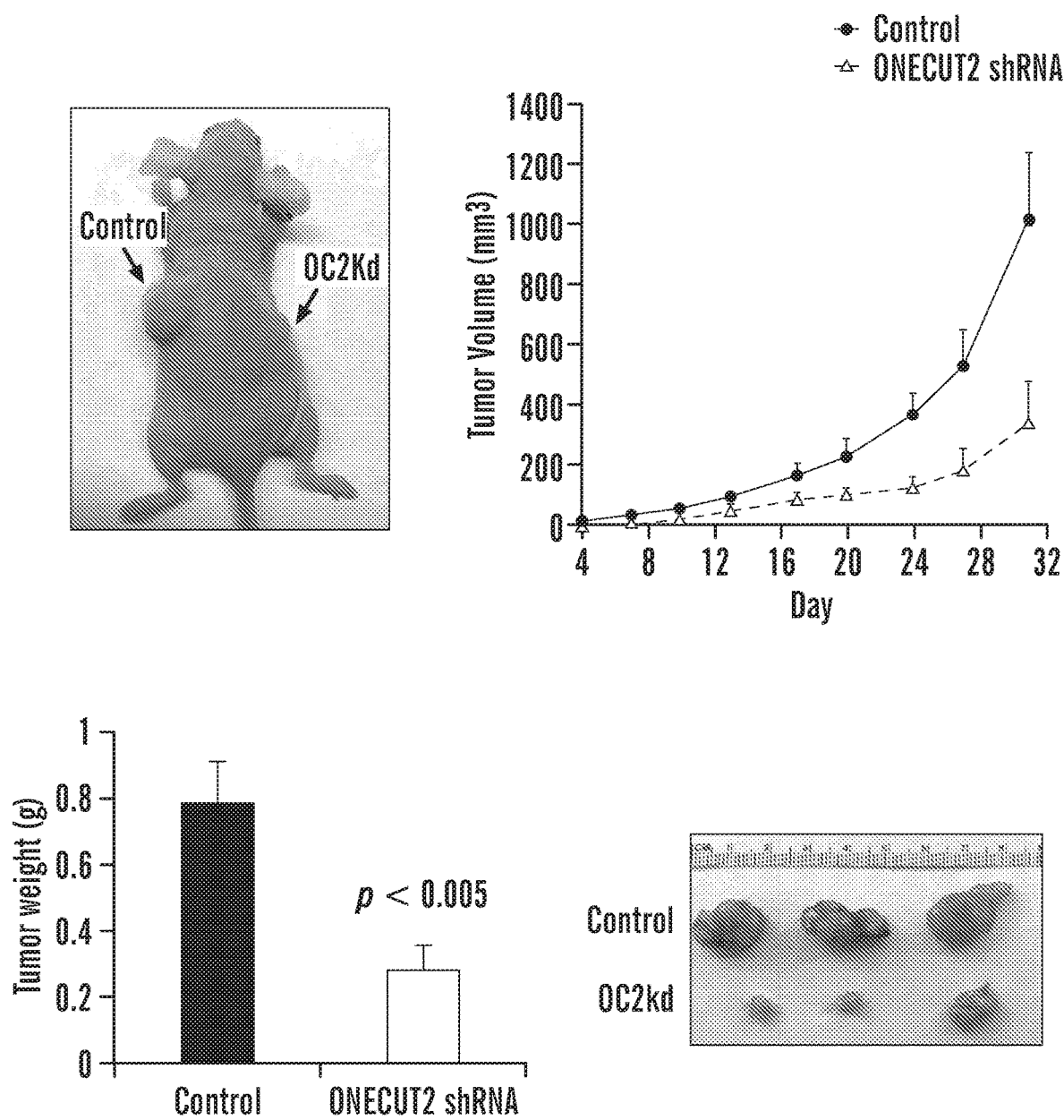
FIG. 4 depicts in accordance with various embodiments of the invention, that silencing of OC2 inhibits in vivo growth of aggressive human prostate cancer cells.

Growth inhibition of subcutaneous tumors derived from stably 22RV1-ONECUT2-knockdown 22RV1s. 22RV1 cells were subcutaneously injected in the flanks of male athymic mice (FIG. 4). The left panel of FIG. 4 shows the representative image of mice injected with 22RV1-Control and 22RV1-OC2 knockdown cells for 4 weeks. As shown in the middle panel of FIG. 4, the tumor volume was monitored for 4 weeks after injection. Each point represents the mean±SEM of the measured tumor volume (N=10/group). p<0.05, compared with the control group. The right panel of FIG. 4 shows the weight of the subcutaneous 22RV1 tumors. p<0.05, compared with the control group. Tumors were resected 4 weeks after initial cell injection. Representative tumor size from the experiment. As shown in FIG. 4, silencing of OC2 inhibits in vivo growth of aggressive human prostate cancer cells.

Figure 5:
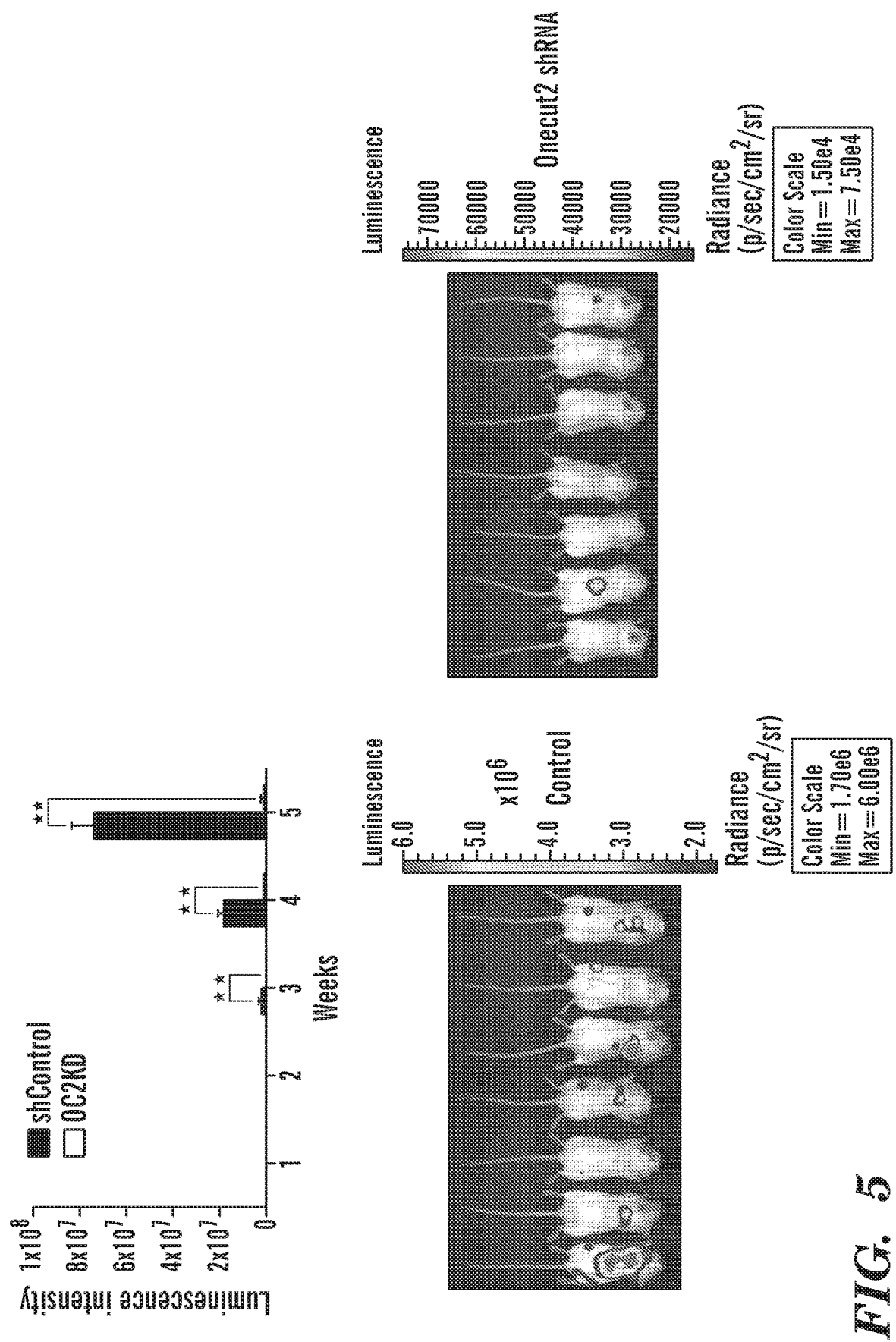
FIG. 5 depicts in accordance with various embodiments of the invention, that silencing of OC2 inhibits in vivo metastasis of aggressive human prostate cancer cells.

Knockdown of ONECUT2 by RNA silencing inhibits metastasis in vivo (FIG. 5). This is an ongoing experiment where we have performed intracardiac injections of luciferase-labeled control and OC2-knockdown 22RV1 cells in SCID/Beige mice to establish a rapid metastatic model and monitor tumor development of distant metastasis by weekly bioluminescence imaging. Compared to mice injected with control cells, which are developing prevalent metastasis through the body, mice harboring OC2-knockdown cells show fewer gross metastatic sites as well as smaller metastatic tumors. In the right, representative images of mice bearing metastatic 22RV1 shControl or OC2-knockdown tumors 4 weeks after intracardiac injection. As shown in FIG. 5, silencing of OC2 inhibits in vivo metastasis of aggressive human prostate cancer cells.

Figure 6A:
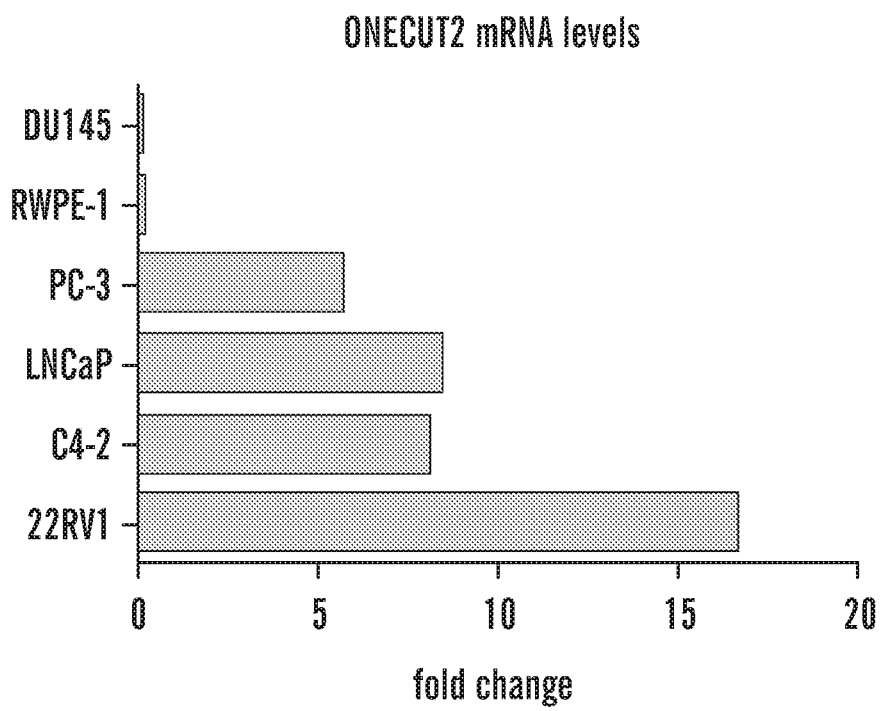
FIG. 6A and FIG. 6B depicts in accordance with various embodiments of the invention, that the sensitivity to Compound CSRM617 seen in human prostate cancer cell lines is inversely correlated to ONECUT2 expression levels.
Figure 6B:
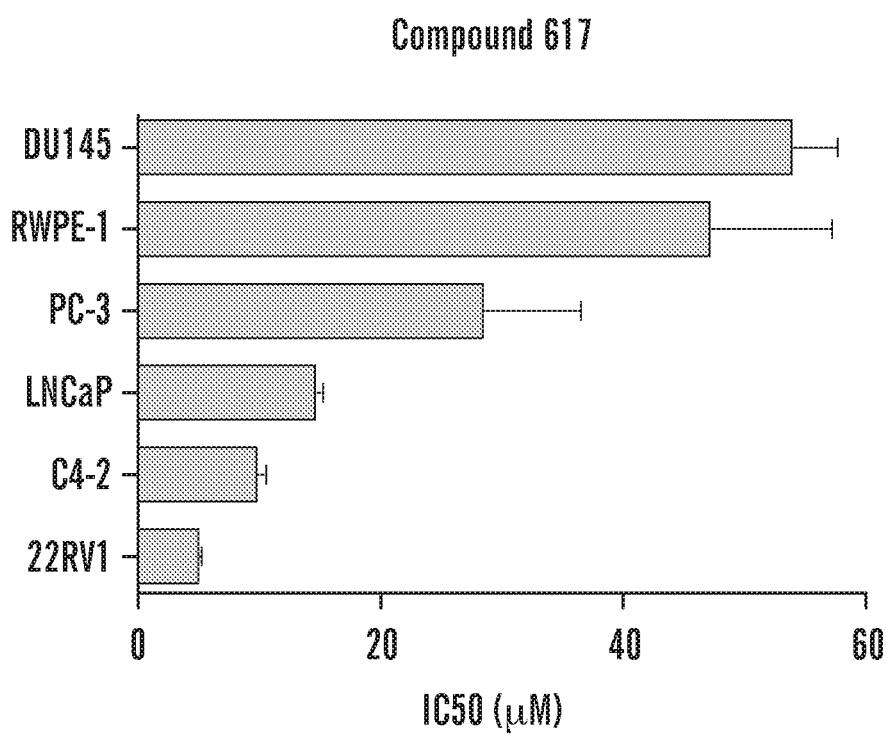

FIG. 6A shows relative Onecut2 mRNA levels in different prostate cell lines determined by RT-qPCR. ACTB and GAPDH expression levels were used for normalization. FIG. 6B shows the half-maximum inhibitory concentration (IC50) for Compound CSRM617 in each prostate cell line. Cells were seeded in 96-well plates at 500 cells per well in a total volume of 100 ul media containing 10% FBS. Serially diluted compound CSRM617 was added to the cells 24 h later. After 48 h incubation, cell viability was assessed by Cell-Titer GLO (Promega). The values were normalized and IC50 was calculated using GraphPad Prism software. As shown in FIG. 6, the sensitivity to Compound CSRM617 seen in human prostate cancer cell lines is inversely correlated to ONECUT2 expression levels. The castration resistant prostate cancer cell lines 22RV1 and C4-2 show the highest sensitivity to Compound CSRM617. RWPE-1 is a benign prostate cell line.

Figure 7:
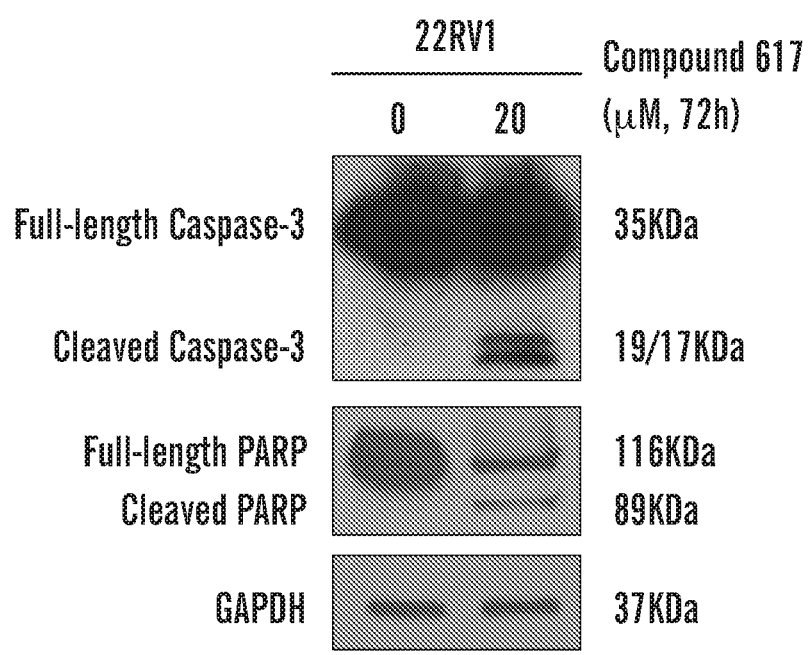
FIG. 7 depicts in accordance with various embodiments of the invention, that Compound CSRM617 induces apoptosis of the castration resistant prostate cancer cell line 22RV1.
Figure 8A:
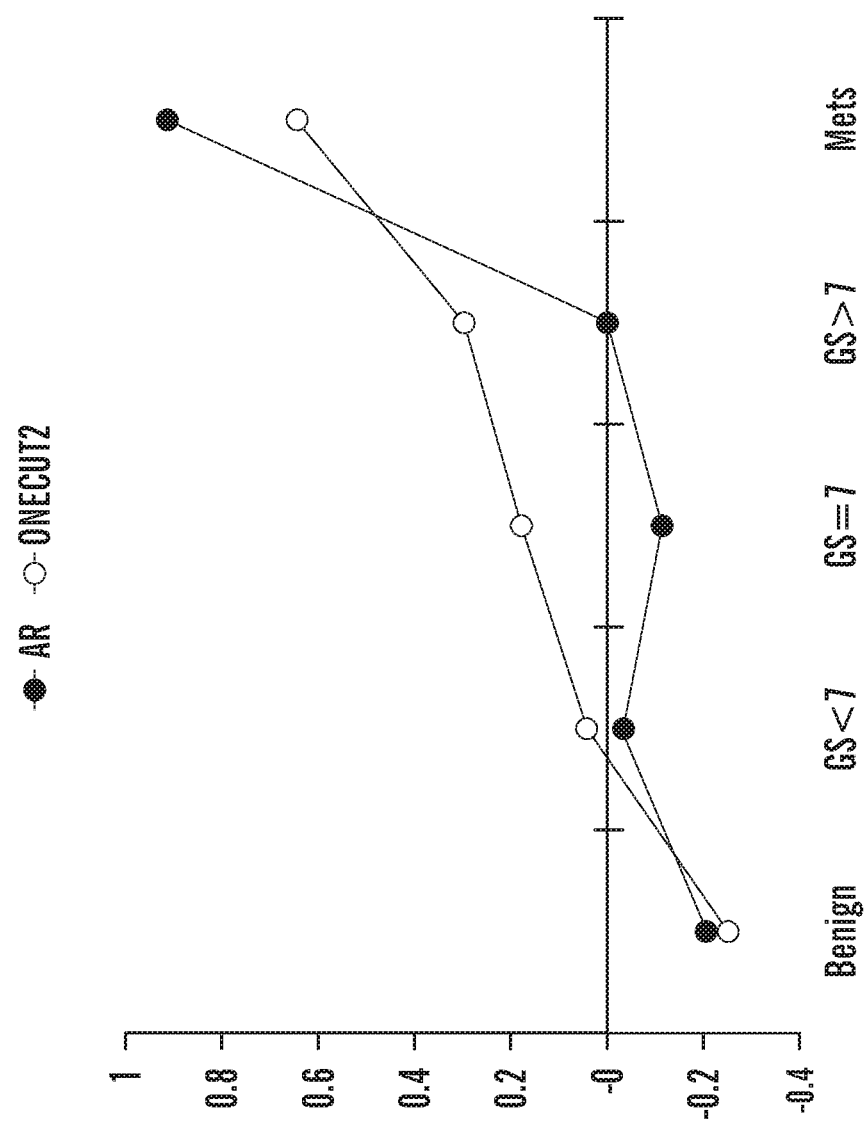
FIG. 8A-FIG. 8E depict in accordance with various embodiments of the invention, ONECUT2 (OC2) is highly active in aggressive prostate cancer and is most active in tumors with a repressed AR signature. Data from 2,115 cases of PC transcriptomes, including 260 cases of mCRPC, showing expression levels (FIG. 8A) and inferred activity (FIG. 8B) of OC2 and AR expression levels across disease categories. Inferred activity of OC2 in PCS subtypes. Relative levels of OC2-inducible genes (FIG. 8C), OC2-repressed genes (FIG. 8D) and the combination (FIG. 8E) in PC subtypes, calculated using microarray data from OC2 overexpression and knockdown in LNCaP and 22Rv1 cells. Red=PCS1; Green=PCS2; Blue=PCS3. OC2 is highly expressed and highly active in mCRPC. OC2-induced and OC2-repressed activity is highest in subtype PCS3, characterized by low AR activation.
Figure 8B:
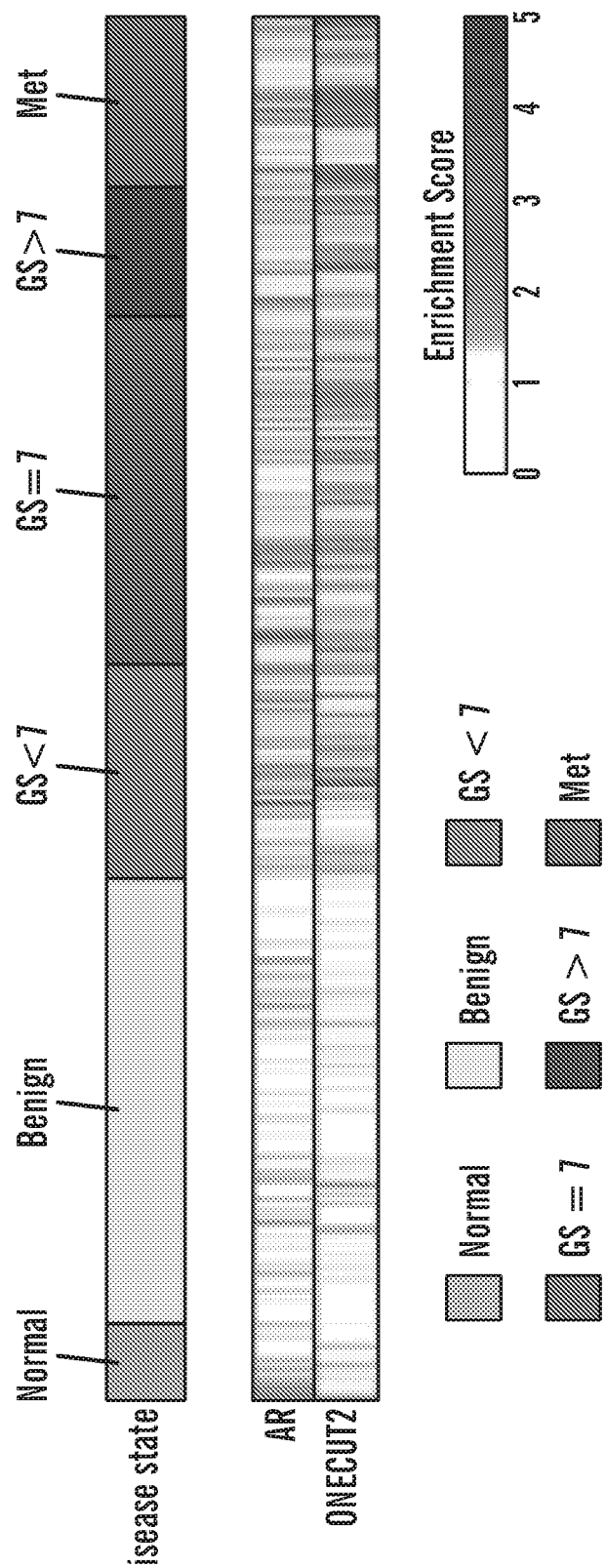
Figure 8E:
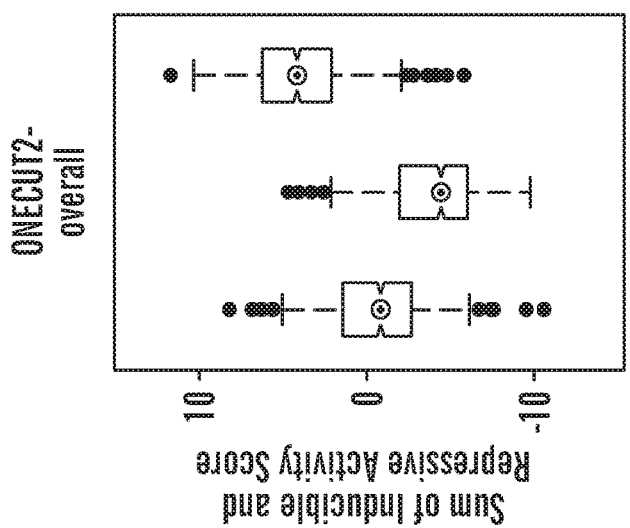
Figure 8D:
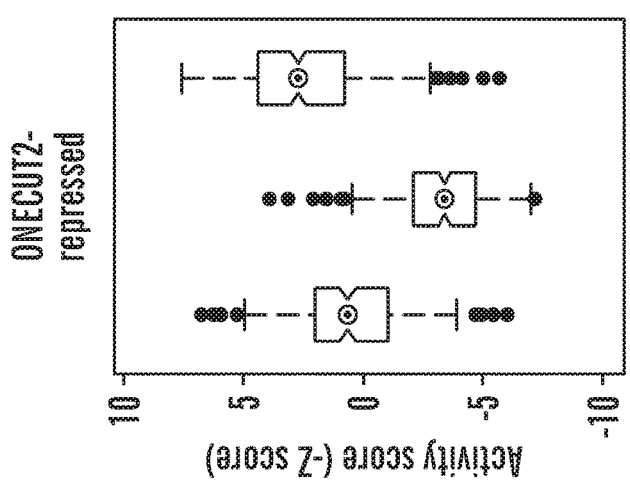
Figure 8C:
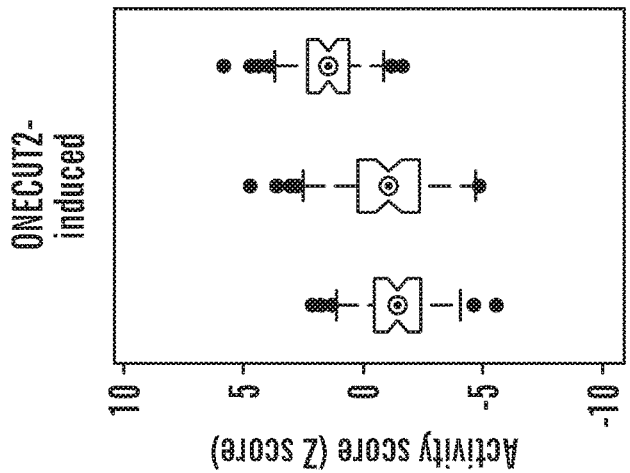
Figure 9A:
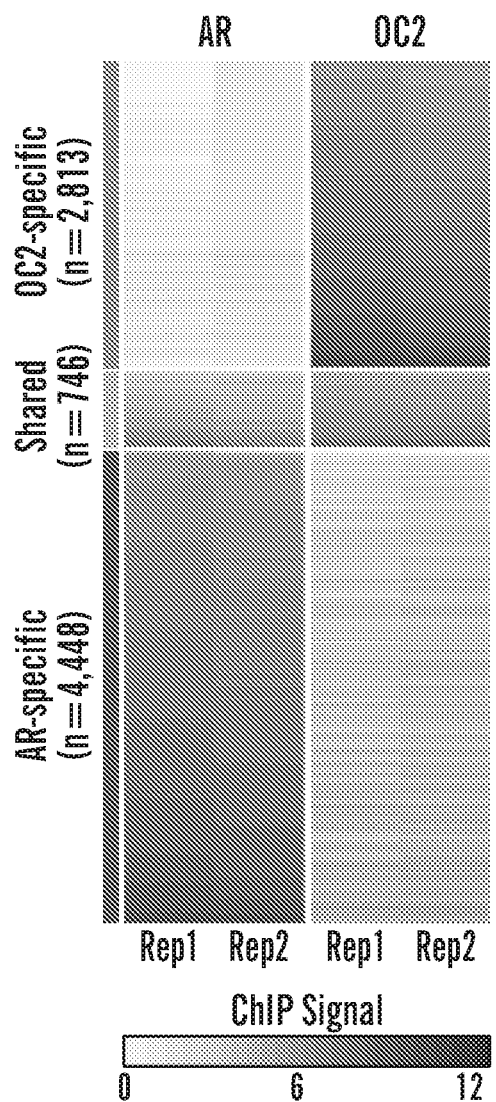
FIG. 9A-FIG. 9D depict in accordance with various embodiments of the invention, OC2 binding at chromatin sites in 22Rv1 CRPC cells. To determine whether OC2 and AR share common regulatory targets, we compared OC2 and AR chromatin immunoprecipitation—massively parallel DNA sequencing (ChIP-seq) data. We identified 746 regions significantly bound by both OC2 and AR (FIG. 9A). The consensus motifs with highest enrichment of solo OC2 binding sites were the ZBTB33-like (Kaiso) and the ONECUT-like motif (FIG. 9B). The consensus motifs with highest enrichment of solo AR binding sites were the AR and the FOXA1 motifs (FIG. 9C). The single enriched motif in the OC2-AR shared regions was a FOX-like motif (FIG. 9D). OC2 can function independently of the AR.
Figure 9B:
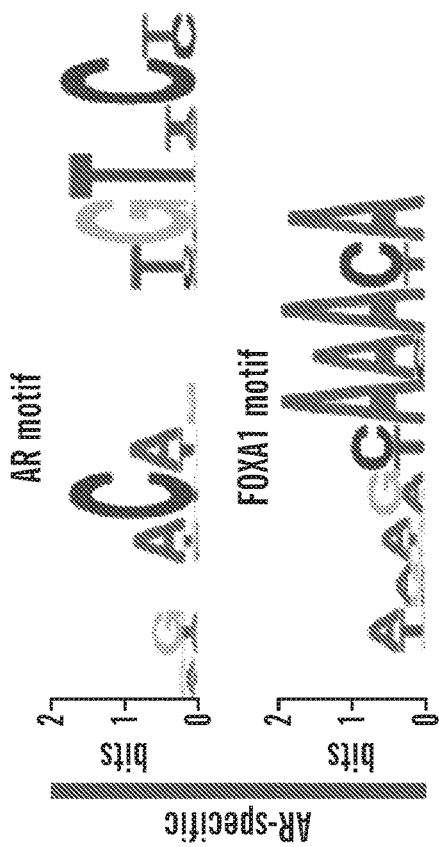
Figure 9C:
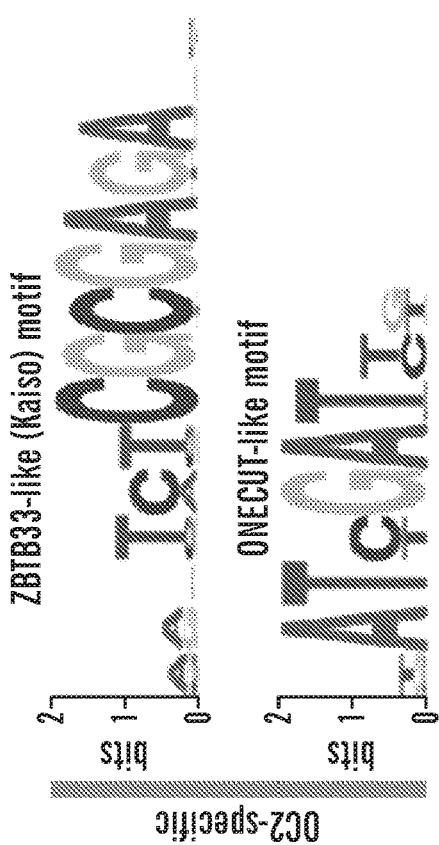
Figure 9D:
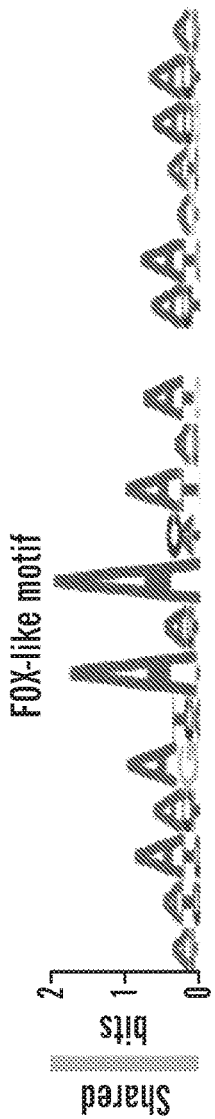

FIG. 7 shows induction of apoptosis in 22RV1 prostate cancer cells by Compound CSRM617 as determined by appearance of cleaved Caspase-3 and PARP. GAPDH served as a loading control. As shown in FIG. 7, Compound CSRM617 induces apoptosis of the castration resistant prostate cancer cell line 22RV1.

Figure 24A:
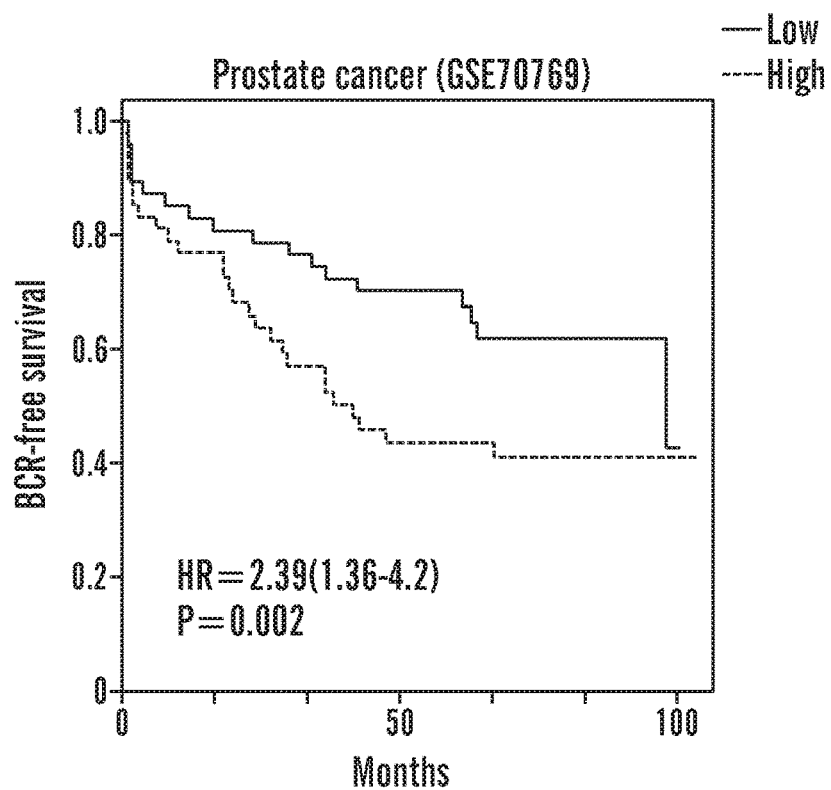
FIG. 24A and FIG. 24B depict in accordance with various embodiments of the invention.
Figure 24A:
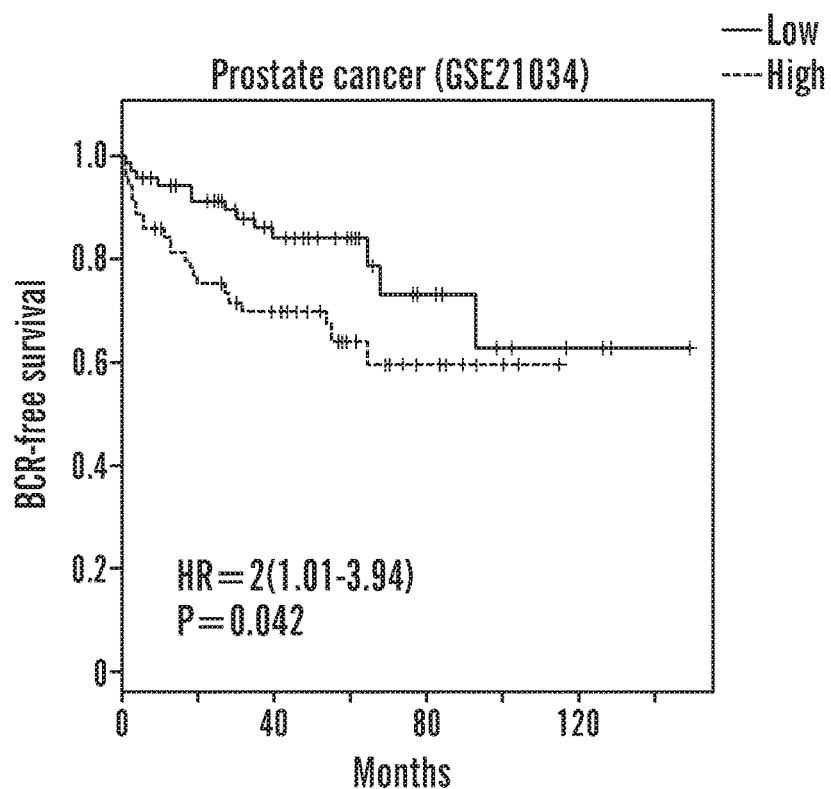
Figure 24B:
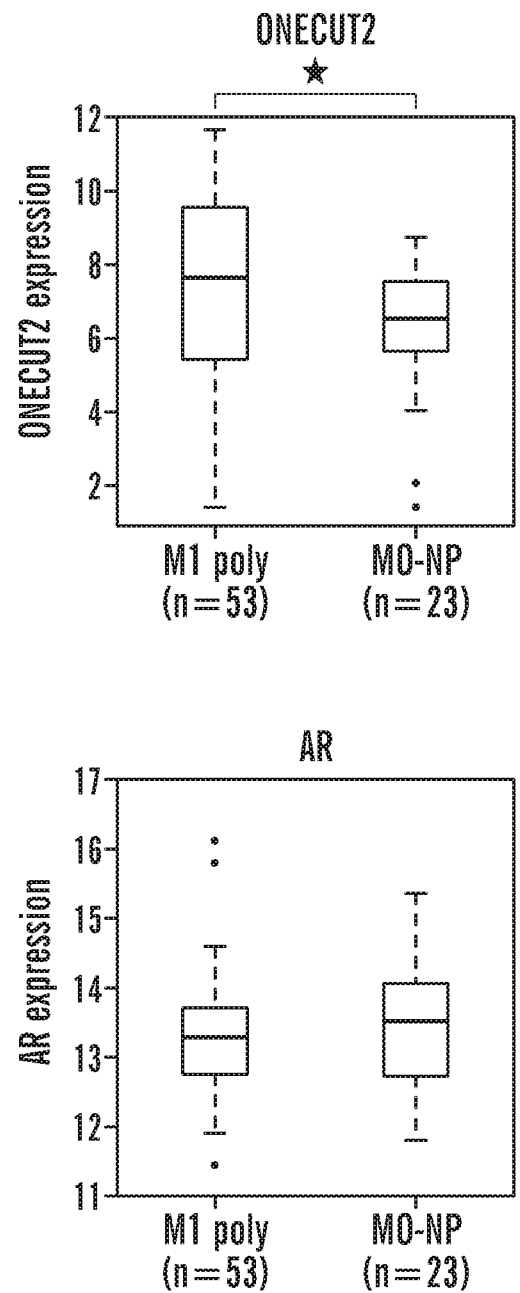

OC2 drives CRPC metastasis and can be targeted with a small molecule that is active in vivo. Several lines of evidence suggest that OC2 is a clinically relevant drug target for mCRPC. OC2 silencing in the hormone-independent lines C4-2 and 22Rv1 cells suppressed growth in vitro, and OC2 silencing in 22Rv1 cells suppressed subcutaneous tumor growth and metastasis in vivo (FIG. 5). Data from clinical PC cohorts indicate that high expression of OC2 is associated with risk of disease progression (FIG. 24A). Additionally, in a novel cohort of diagnostic needle biopsies collected from men with untreated PC at various stages of progression, OC2 mRNA expression was significantly elevated in high-grade cancer foci (GS>8) from men who either presented with (n=62) or developed (n=14) diffuse metastases during long-term follow-up, in comparison to men without metastasis who remained metastasis-free (n=23) (FIG. 24B). The findings in this cohort, suggest that tumors where OC2 is active may be present and identifiable in primary tumors of high-risk patients prior to therapy.

Figure 14A:
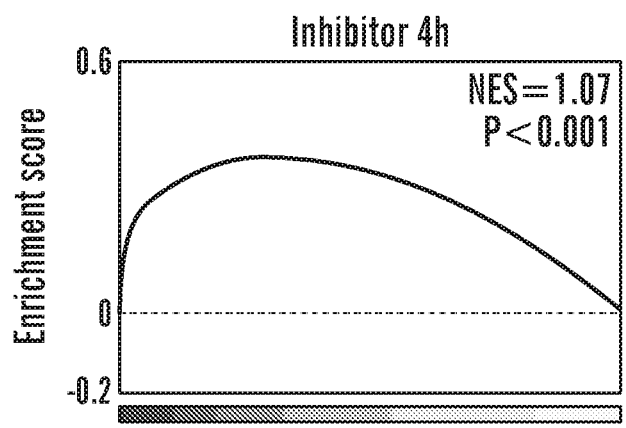
FIG. 14A-FIG. 14E depict in accordance with various embodiments of the invention, Compound CSRM617 perturbs OC2-regulated genes and suppresses 22Rv1 tumor growth in mice. To evaluate the specificity of CSRM617 for genes regulated by OC2, we generated gene expression microarray data from 22Rv1 cells treated with the compound at a concentration of 10 μM for 4, 6 and 16 h. For this analysis, the OC2 target gene set was defined by OC2 binding to the gene promoters as demonstrated by ChIP-seq. GSEA showed significant perturbation of OC2 target genes at 4 hours, 6 hours, and 16 hours. Compound CSRM617 alters OC2 target genes and reduces tumor growth of CRPC cells in vivo.
Figure 14B:
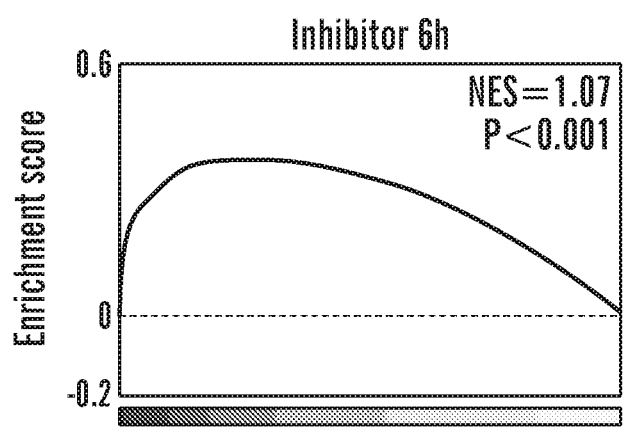
Figure 14C:
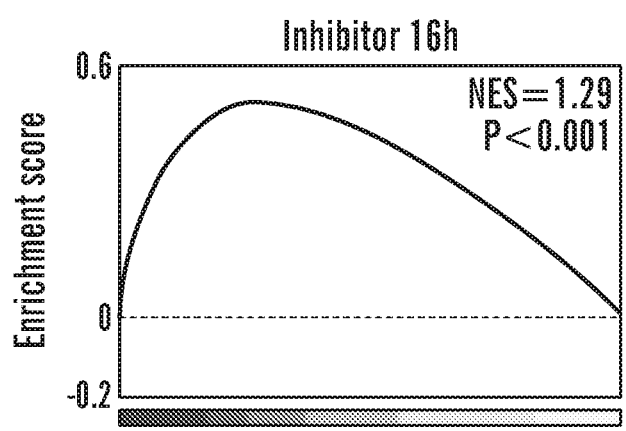
Figure 25A:
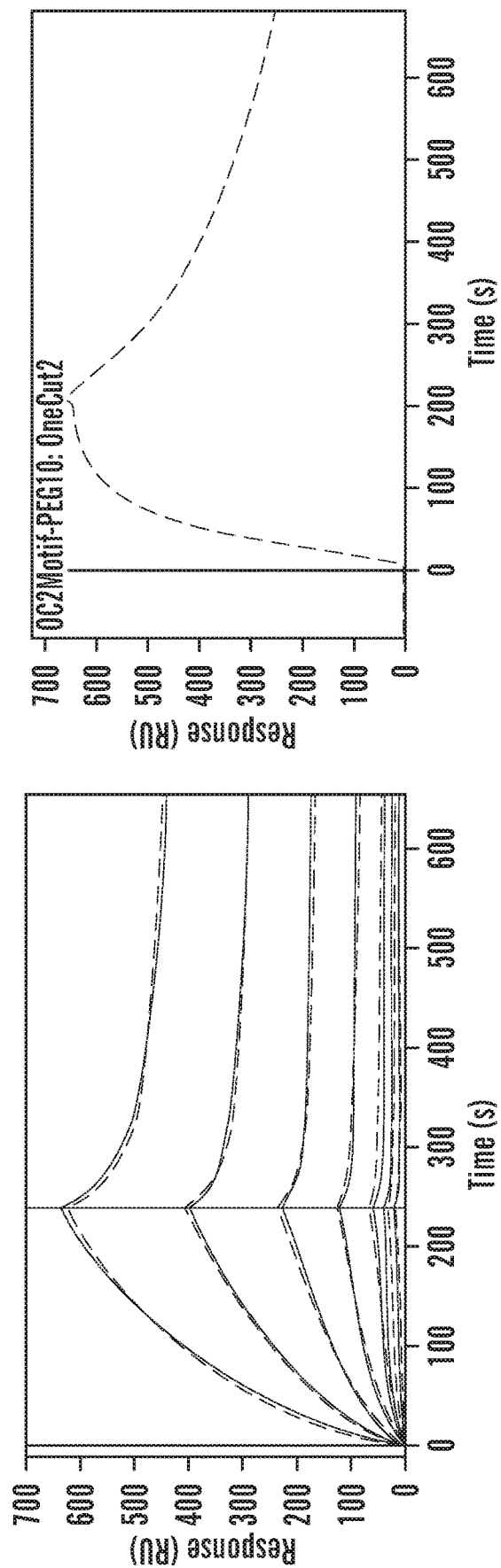
FIG. 25A-FIG. 25C depict in accordance with various embodiments of the invention.

To assess whether OC2 might be inhibited with a small molecule, we developed a structural model of OC2 binding to DNA using homology modeling, and conducted a virtual screen of a chemical library consisting of 5×105 compounds. 15 compounds were selected for biological activity testing using in vitro assays. One compound, compound CSRM617, was deemed to be biologically active and was selected for further study. Compound CSRM617 inhibited cell growth and induced apoptosis in PC cell lines that express medium to high levels of OC2 (FIG. 6B). OC2 mRNA expression levels correlated with the IC50, indicating that cell lines with low OC2 expression were less responsive to the treatment. To evaluate the selectivity of Compound CSRM617 for genes regulated by OC2, we generated gene expression microarray data from 22Rv1 cells treated with Compound CSRM617 for 4, 6 and 16 h. For this analysis, the OC2 target gene set was defined by OC2 binding to gene promoters as demonstrated by ChIP-seq. Gene set enrichment showed significant perturbation of OC2 target genes at all 3 time points (FIG. 14A-FIG. 14C). As described above, we identified PEG10 as a gene directly regulated by OC2 binding to the PEG10 promoter. Consistent with this, PEG10 mRNA expression was downregulated in a time-dependent manner in response to Compound CSRM617 (FIG. 16C). We used surface plasmon resonance (SPR) to show that Compound CSRM617 bound directly to purified recombinant OC2 HOX domain in a dose-dependent manner (Kd=7.43 µM) (FIG. 25A). The OC2 HOX fragment bound with high affinity (Kd=1 nM) to a DNA probe corresponding to the experimentally determined OC2 binding motif in the PEG10 promoter (FIG. 25A, right panel).

Figure 14D:
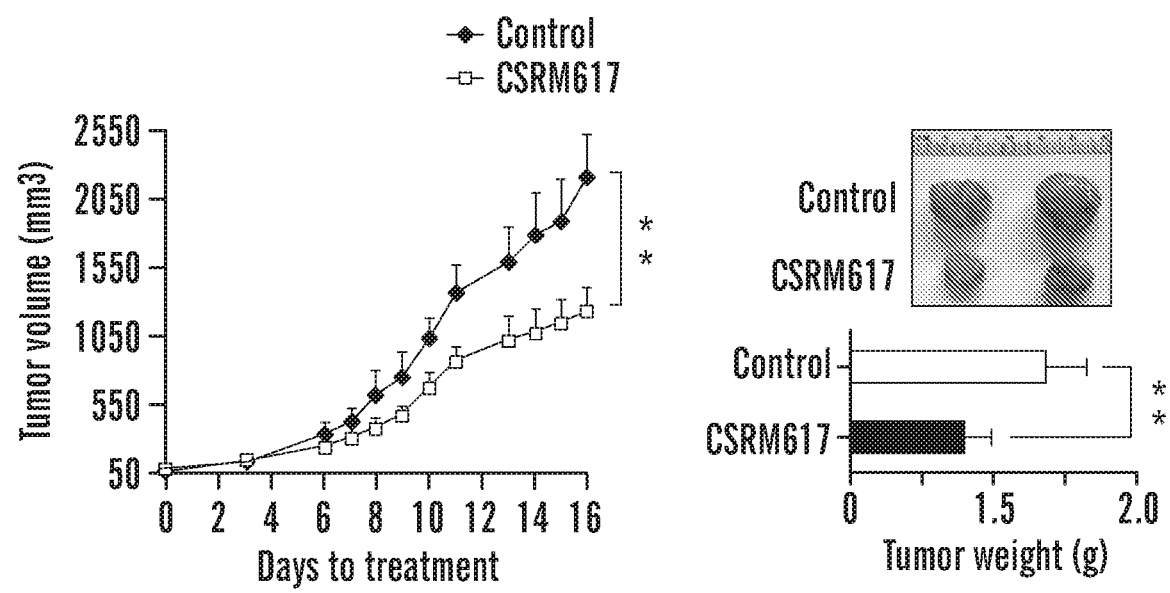
Figure 14E:
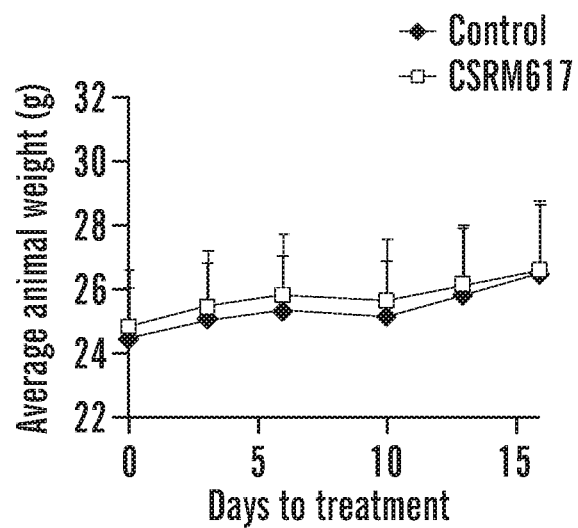
Figure 15:
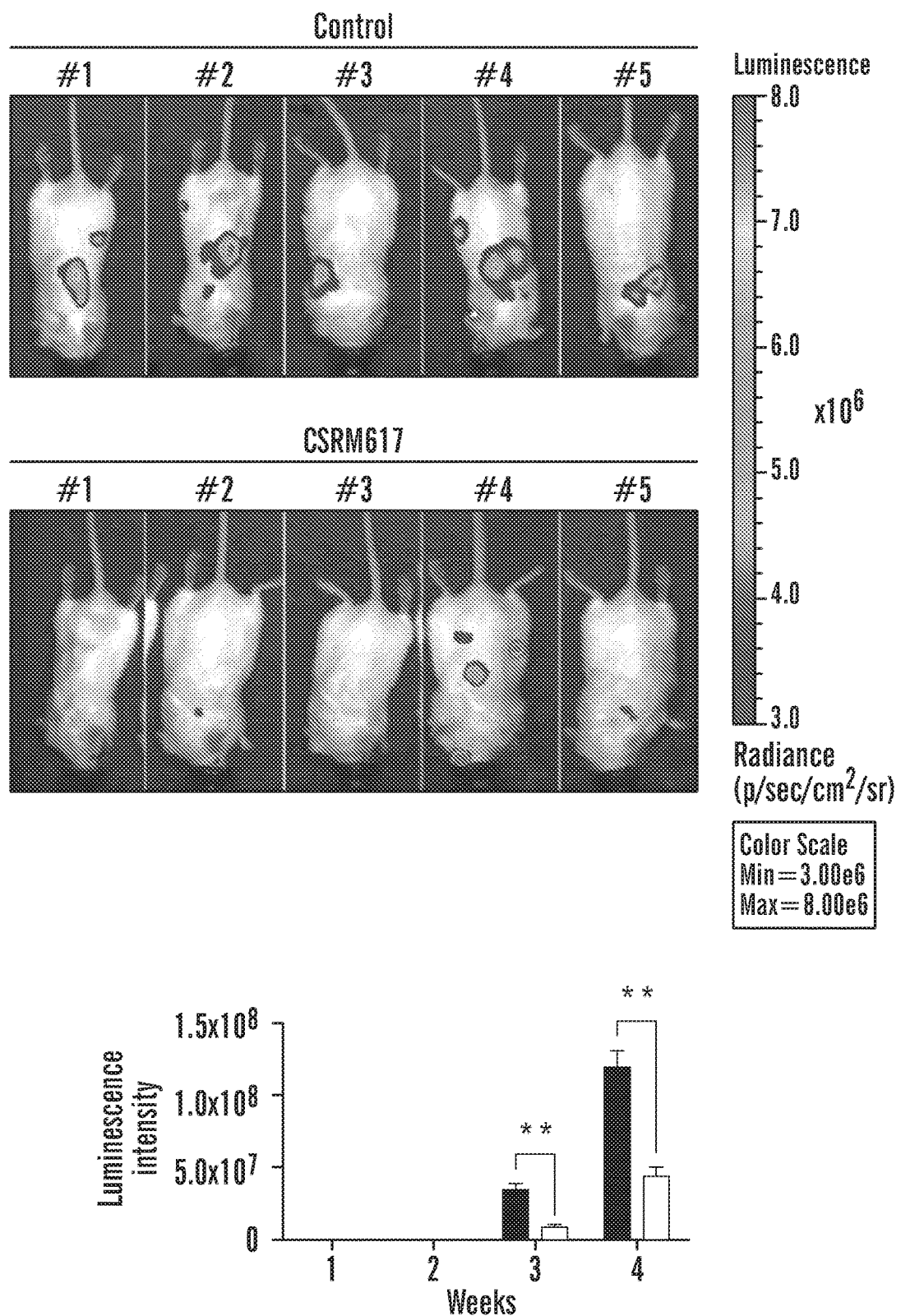
FIG. 15 depicts in accordance with various embodiments of the invention, Compound CSRM617 inhibits metastasis. 22Rv1-luciferase labeled cells were injected intracardially and mice were randomized (n=7 per group) to receive vehicle or 50 mg/kg$^{-1}$ CSRM617, daily. BLI images of mice bearing metastatic tumors 4 w after the injection (left) and graphical representation of normalized BLI signals (right). Mean±SD (n=7 per group) is shown; **P<0.01. Compound CSRM617 reduces significantly the onset and growth of diffuse metastases in vivo.
Figure 17A:
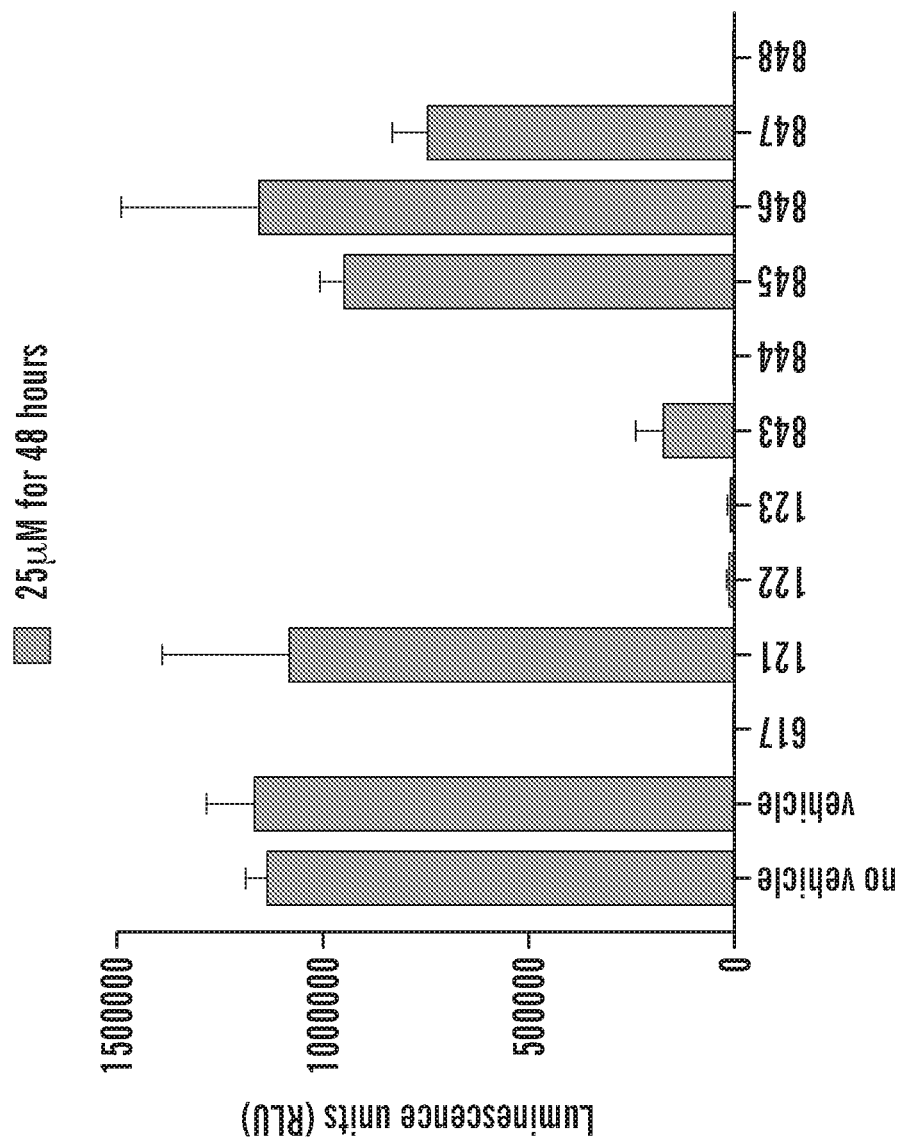
FIG. 17A and FIG. 17B depict in accordance with various embodiments of the invention, Compound CSRM617 derivatives with similar potency and improved solubility.
Figure 17B:
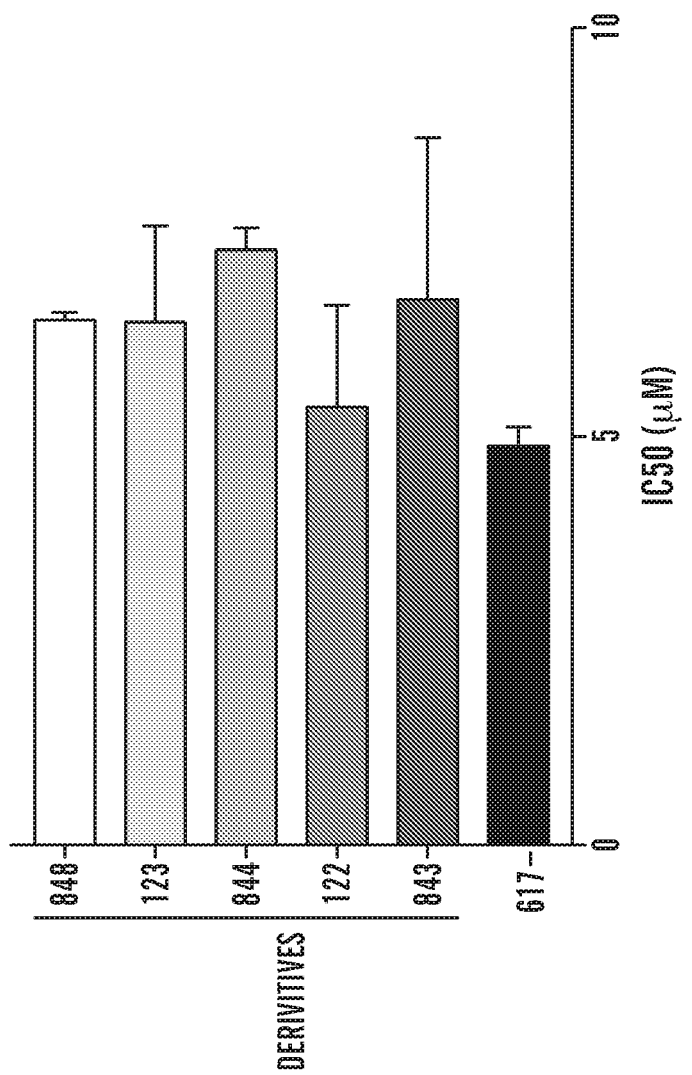
Figure 18A:
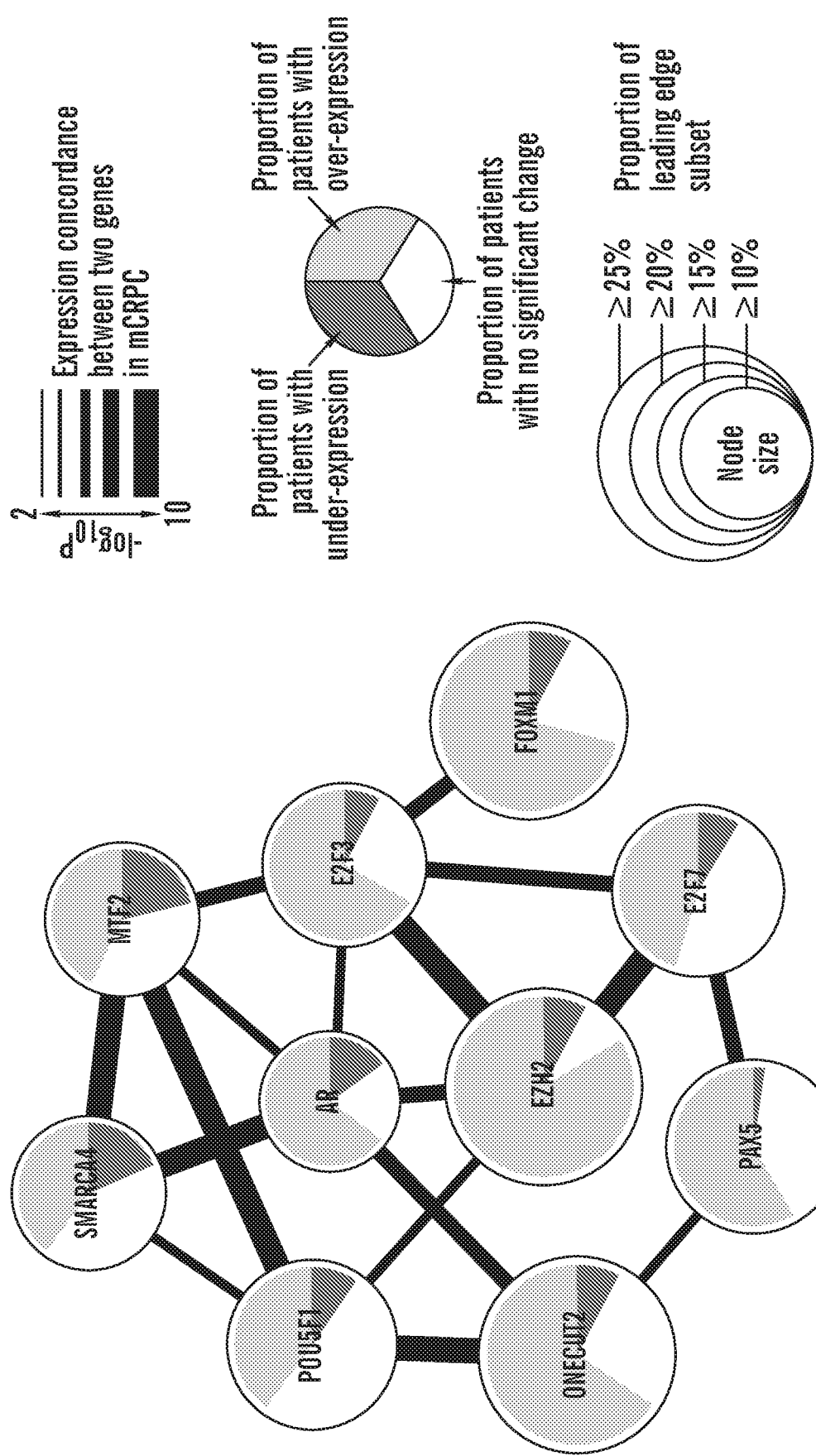
FIG. 18A-FIG. 18C depict in accordance with various embodiments of the invention.
Figure 18B:
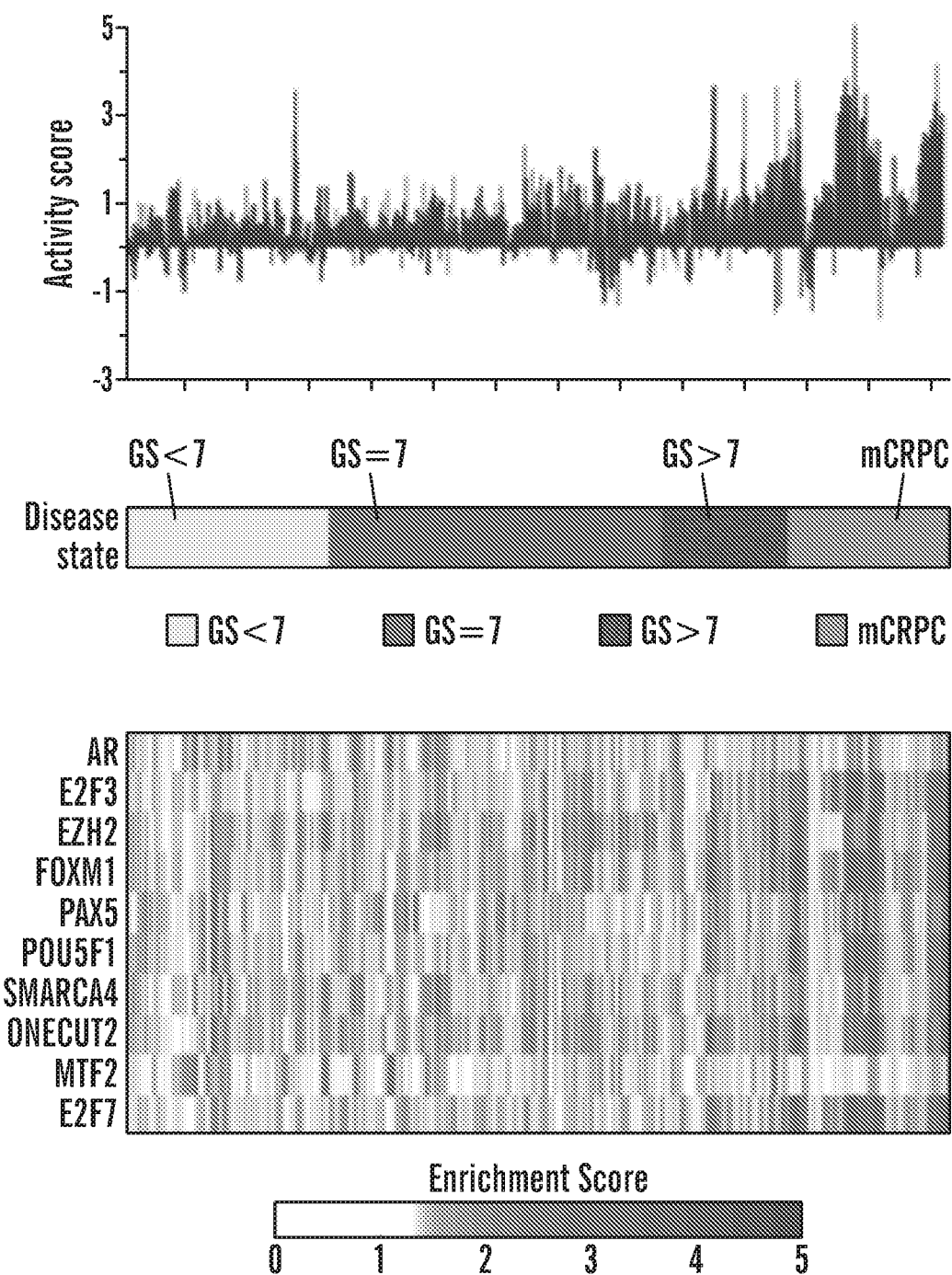
Figure 18C:
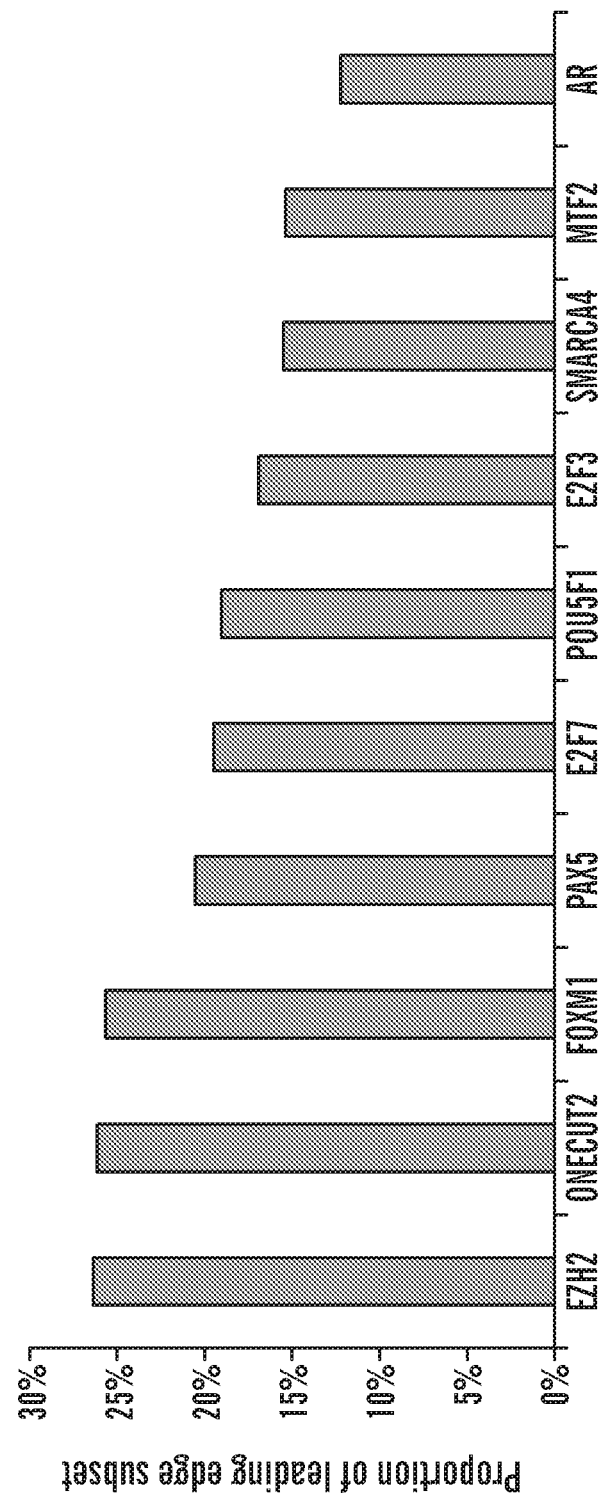
Figure 25B:
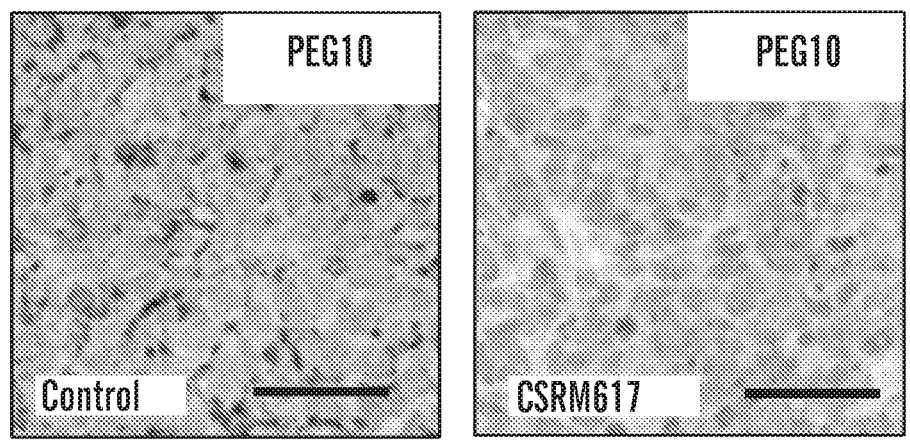
Figure 25C:
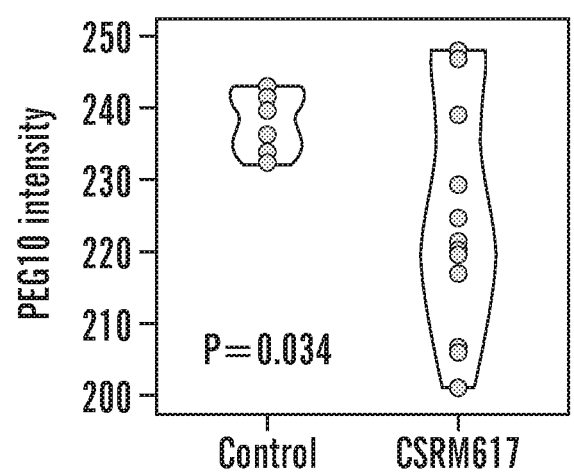

Compound CSRM617 inhibited cell proliferation in vitro against LNCaP, C4-2 and 22Rv1 cells. Compound CSRM617 also inhibited subcutaneous growth of established 22Rv1 xenografts at a dose of 50 mg/Kg/d (FIG. 14D). Compound CSRM617 did not affect body weight (FIG. 14E), feeding patterns or behavior of the mice. To determine whether Compound CSRM617 is effective against CRPC metastases, 22Rv1 cells were injected intracardially in SCID mice, and the animals were subsequently treated with the above dose of the compound for several weeks. Compound CSRM617 inhibited onset and growth of diffuse metastases in the treated mice in comparison to the control group (FIG. 15). To test for evidence of bioactivity of Compound CSRM617 in situ, PEG10 protein levels were measured using IHC followed by digital imaging in adrenal gland tumors. PEG10 protein was significantly down-regulated in tumors treated with Compound CSRM617 (FIG. 25B and FIG. 25C).

These findings demonstrate that OC2 is a master regulator operating to drive NE differentiation within adenocarcinoma. It can cooperate with the AR, but also acts to repress AR activity across the genome. We have demonstrated that this protein is targetable with a drug-like small molecule, Compound CSRM617, which binds directly to OC2 and inhibits its function. We have synthesized and tested derivatives of Compound CSRM617 and have identified analogs with similar potency but improved solubility. These analogs are Compound 122, Compound 123, Compound 843, Compound 844 and Compound 848 as shown in Table 1. We have demonstrated that OC2 activity can be detected in the diagnostic biopsies of untreated primary tumors, raising the possibility that OC2 could be targeted in patients with de novo metastatic disease and/or signs of early CRPC in order to thwart metastatic progression.

As provided herein, we have identified a small molecule, Compound CSRM617, that binds to OC2 and inhibits its activity. We have synthesized derivatives of Compound CSRM617 and these derivatives have demonstrated comparable activity and improved solubility to Compound CSRM617. These analogs are Compound 122, Compound 123, Compound 843, Compound 844 and Compound 848 as shown in Table 1. Compounds 122, 123 and 843 directly bind OC2.

Figure 26:
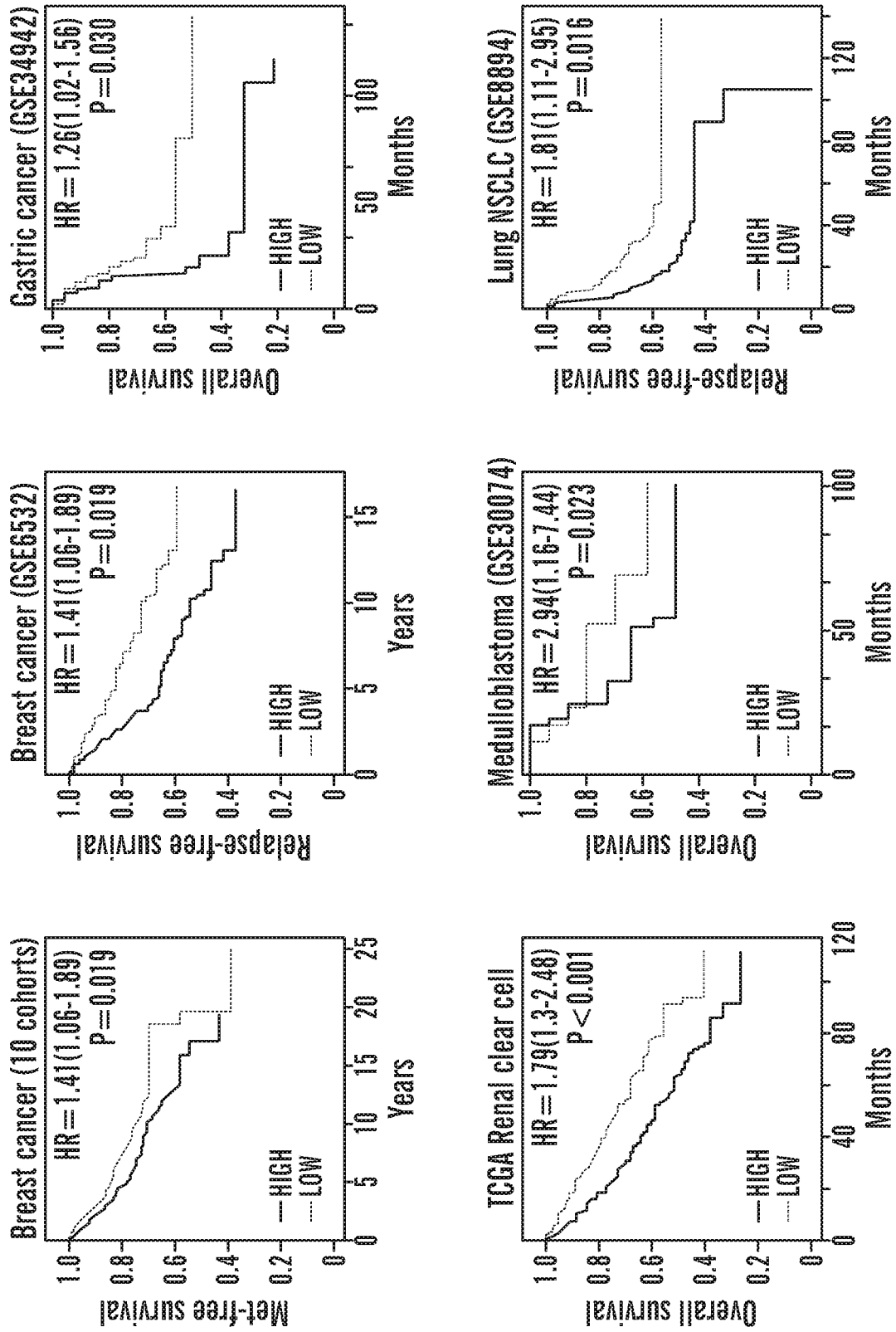
FIG. 26 depicts in accordance with various embodiments of the invention, the relationships between the OC2 expression and BCR-free survival, metastasis-free survival, overall survival, and relapse-free survival in cancer types. SurvExpress and PROGgeneV2 tools were used to perform Kaplan-Meier analysis and Cox proportional hazard regression. OC2 expression and survival outcomes were correlated to assess significant associations. Samples were stratified by OC2 expression level at median value of all the samples in each cohort. 'Breast cancer 10 cohorts' indicates the breast metabase build from SurvExpress database, which merges 10 breast cancer cohorts generated by the same Affymetrix microarray platform. For every comparison, a corresponding P-value<0.05 was considered significant. OC2 expression is significantly associated with poor clinical outcome in cancer types other than prostate, including breast, gastric, colon, clear cell renal, brain, and lung cancer.
Figure 26:
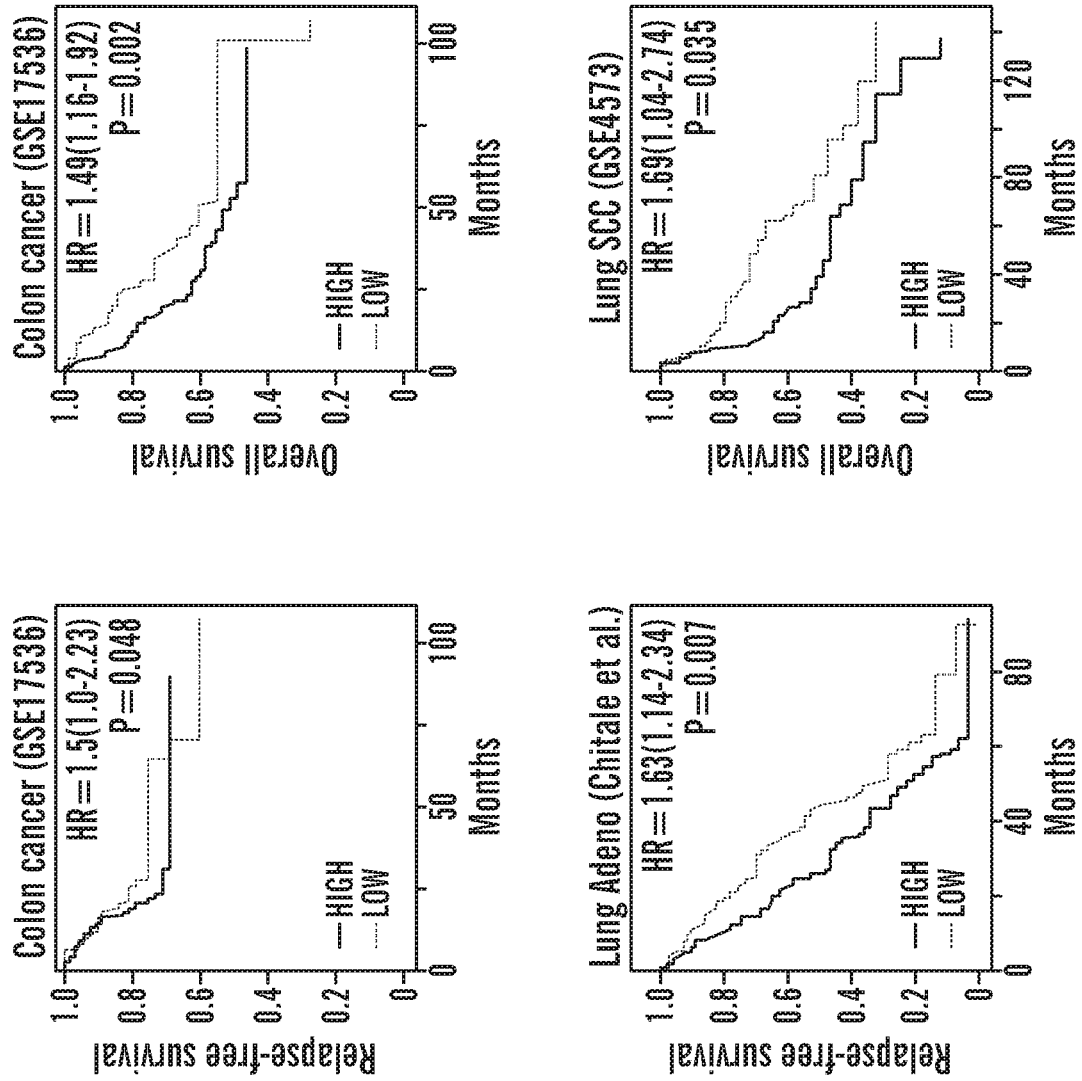

There is a correlation between ONECUT2 expression and cancer prognosis. In cancer patients with increased ONECUT2, the prognosis is poor (FIG. 26). Specifically, FIG. 26 shows the relationships between the OC2 expression and BCR-free survival, metastasis-free survival, overall survival, and relapse-free survival in cancer types. SurvExpress and PROGgeneV2 tools were used to perform Kaplan-Meier analysis and Cox proportional hazard regression. OC2 expression and survival outcomes were correlated to assess significant associations. Samples were stratified by OC2 expression level at median value of all the samples in each cohort. 'Breast cancer 10 cohorts' indicates the breast metabase build from SurvExpress database, which merges 10 breast cancer cohorts generated by the same Affymetrix microarray platform. For every comparison, a corresponding P-value<0.05 was considered significant. OC2 expression is significantly associated with poor clinical outcome in cancer types other than prostate, including breast, gastric, colon, clear cell renal, brain, and lung cancer Example 4

Additional derivatives of Compound CSRM617 are prepared. These additional derivatives of Compound CSRM617 are studied to assess specificity of the chemical analogs for OC2 and effectiveness in inhibiting the actions of this protein. Various studies we perform include in silico and high throughput screening using the UCLA Molecular Shared Screening Resource (MSSR), followed by optimization using homology modeling.

As shown in Scheme 10, in various embodiments we prepare and test several analogs of Compound 122 in which the 2,3,4-trihydroxylphenyl unit is replaced with other substituted phenyl units, wherein the substituents include, but are not limited to, one or more of F, Cl, OMe, OH, and/or combinations thereof. In the various embodiments of Scheme 1, the phenethylamine (2) is reacted with a protected serine (3) to give, after deprotection, the desired amide (4). We test various embodiments of amide (4) for inhibiting expression or activity of ONECUT2. Tests for biological activity and selectivity include growth inhibition assays, gene expression profiling, and SPR.

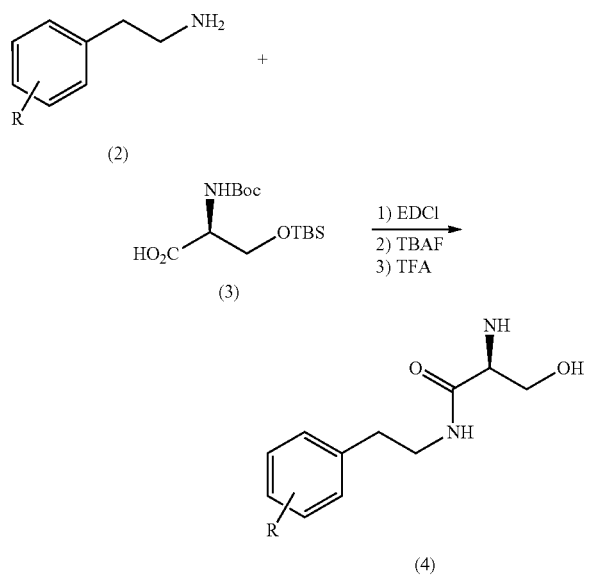

R=independently one or more of hydrogen or optionally substituted substituent

As shown in Scheme 11, in various embodiments we prepare and test various other compounds based on phenethylamine (2). In the various embodiments of Scheme 11, the phenethylamine (2) is reacted with various carboxylic acids to give, after deprotection, the desired amide (5). We test various embodiments of amide (5) for inhibiting expression or activity of ONECUT2. Tests for biological activity and selectivity include growth inhibition assays, gene expression profiling, and SPR.

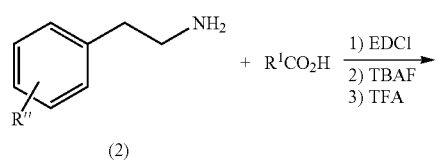

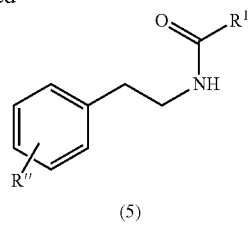

$R''$=independently one or more of hydrogen or optionally substituted substituent $R^1$=hydrogen or optionally substituted substituent As shown in Scheme 12, in various embodiments we prepare and test various compounds having the structure of amide (6). We test various embodiments of amide (6) for inhibiting expression or activity of ONECUT2. Tests for biological activity and selectivity include growth inhibition assays, gene expression profiling, and SPR.

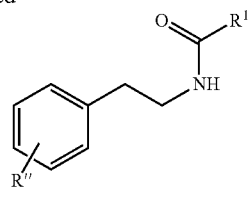

$R'''$=independently one or more of hydrogen or optionally substituted substituent $R^2$=hydrogen or optionally substituted substituent X=NHC(O), C(O)NH, OC(O), C(O)O, C(O), or CH=N As shown in Scheme 13, in various embodiments we prepare and test various compounds having the structure of amide (7). We test various embodiments of amide (7) for inhibiting expression or activity of ONECUT2. Tests for biological activity and selectivity include growth inhibition assays, gene expression profiling, and SPR.

$R^3$=hydrogen or optionally substituted substituent $R^4$=hydrogen or optionally substituted substituent X=O or S As shown in Scheme 14, we prepared dimer (8) which was identified by LC/MS. In various embodiments we test the compound having the structure of dimer (8). We test various embodiments of dimer (8) for inhibiting expression or activity of ONECUT2. Tests for biological activity and selectivity include growth inhibition assays, gene expression profiling, and SPR.

201

Scheme 14.

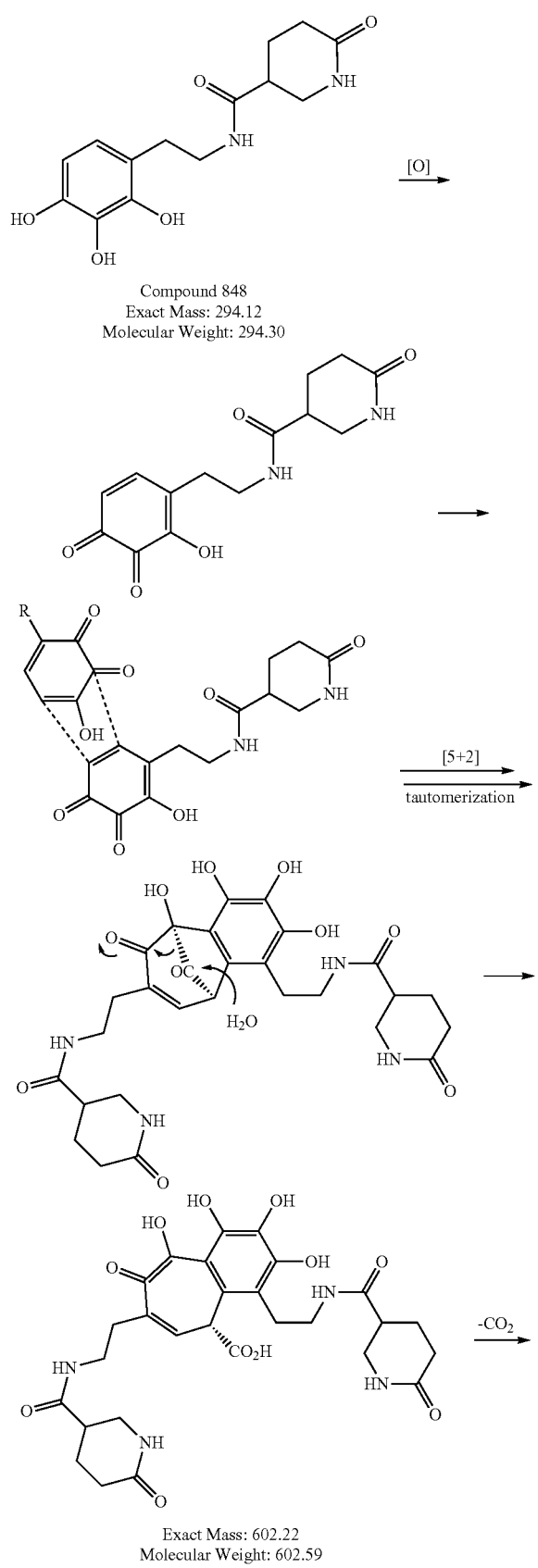

Compound 848
Exact Mass: 294.12
Molecular Weight: 294.30

Exact Mass: 602.22
Molecular Weight: 602.59

202

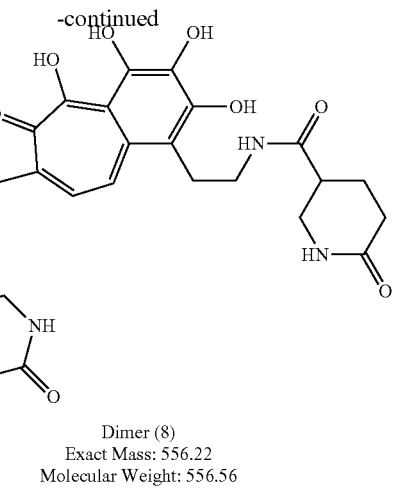

Dimer (8)
Exact Mass: 556.22
Molecular Weight: 556.56

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A compound selected from:

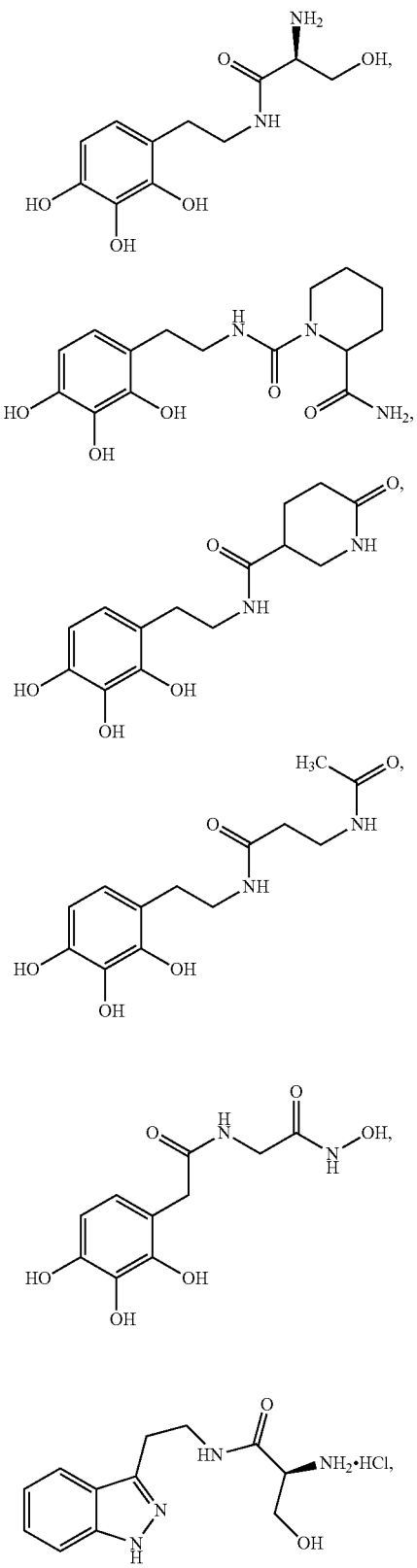

-continued

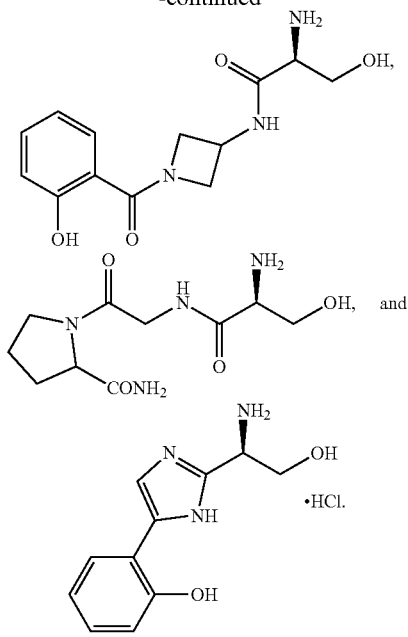

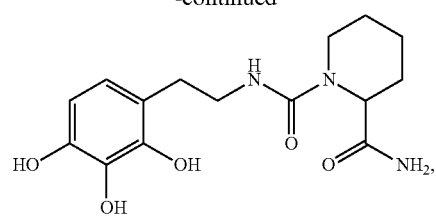

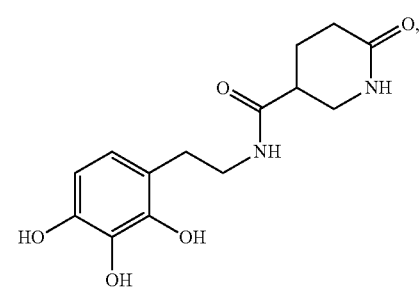

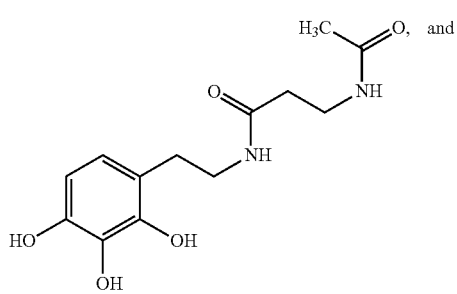

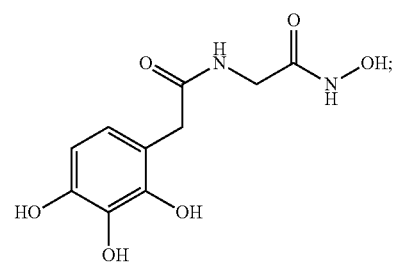

or a pharmaceutically acceptable salt thereof.

2. A pharmaceutical composition, comprising: a compound of claim 1; and a pharmaceutically acceptable excipient or carrier.

3. A method for treating, inhibiting, or reducing the severity of cancer that overexpress ONECUT2 in a subject in need thereof comprising administering a therapeutically effective amount of a compound of claim 1, wherein the compound inhibits expression or activity of ONECUT2, so as to treat, inhibit, or reduce the severity of cancer that overexpress ONECUT2 in the subject.

4. The method of claim 3 wherein the cancer is castration resistant prostate cancer (CRPC), breast cancer, lung cancer, colon cancer, renal cancer, gastric cancer, brain cancer, or medulloblastoma.

5. The method of claim 3 wherein the method further comprises administration or treatment with an additional anti-cancer therapy to the subject in need thereof.

6. The method of claim 5 wherein the additional anti-cancer therapy is surgery, chemotherapy, radiation therapy, thermotherapy, immunotherapy, hormone therapy, laser therapy, biotherapy, anti-angiogenic therapy, photodynamic therapy, or a combination thereof.

7. The method of claim 6 wherein the agent and the additional anti-cancer therapy are administered sequentially.

8. The method of claim 6 wherein the agent and the additional anti-cancer therapy are administered simultaneously.

9. A compound selected from:

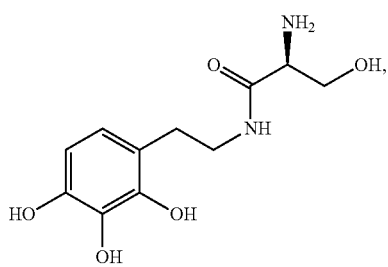

10. A pharmaceutical composition comprising a compound of claim 9 and a pharmaceutically acceptable excipient or carrier.

11. A method for treating, inhibiting, or reducing the severity of cancer that overexpress ONECUT2 in a subject in need thereof comprising administering a therapeutically effective amount of a compound of claim 9, wherein the compound inhibits expression or activity of ONECUT2, so as to treat, inhibit, or reduce the severity of cancer that overexpress ONECUT2 in the subject.

12. The method of claim 11 wherein the cancer is castration resistant prostate cancer (CRPC), breast cancer, lung cancer, colon cancer, renal cancer, gastric cancer, brain cancer, or medulloblastoma.

13. A compound represented by formula 843:

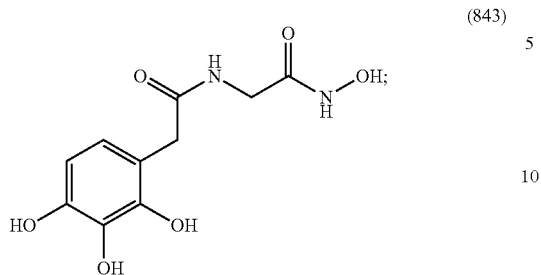

(843)

or a pharmaceutically acceptable salt thereof.

14. A pharmaceutical composition comprising the compound of claim 13 and a pharmaceutically acceptable excipient or carrier.

15. A method for treating, inhibiting, or reducing the severity of cancer that overexpress ONECUT2 in a subject in need thereof comprising administering a therapeutically effective amount of the compound of claim 13, wherein the compound inhibits expression or activity of ONECUT2, so as to treat, inhibit, or reduce the severity of cancer that overexpress ONECUT2 in the subject.

16. The method of claim 15 wherein the cancer is castration resistant prostate cancer (CRPC), breast cancer, lung cancer, colon cancer, renal cancer, gastric cancer, brain cancer, or medulloblastoma.

* * * * *

UNITED STATES PATENT AND TRADEMARK OFFICE
CERTIFICATE OF CORRECTION

| | | |
|---|---|---|
| PATENT NO. | : 10,927,070 B2 | Page 1 of 1 |
| APPLICATION NO. | : 16/307702 | |
| DATED | : February 23, 2021 | |
| INVENTOR(S) | : Michael Freeman et al. | |

It is certified that error appears in the above-identified patent and that said Letters Patent is hereby corrected as shown below:

In the Specification

At Column 1, Lines 17-21, please delete:
"This invention was made with government support under Grant Nos. DK087806 and CA143777 awarded by National Institutes of Health and Grant No. W81XWH-14-1-0152 awarded by Department of Defense. The government has certain rights in the invention."

And insert:
-- This invention was made with government support under Grant Numbers CA143777, CA220327, DK087806, and HL155346, awarded by the National Institutes of Health, and W81XWH-14-1-0152, awarded by the Department of the Army. The Government has certain rights in the invention. --
therefor.

Signed and Sealed this
Twenty-first Day of January, 2025

Coke Morgan Stewart
*Acting Director of the United States Patent and Trademark Office*